US008980865B2

(12) United States Patent
Wang et al.

(10) Patent No.: US 8,980,865 B2
(45) Date of Patent: Mar. 17, 2015

(54) SUBSTITUTED NUCLEOTIDE ANALOGS

(71) Applicant: Alios BioPharma, Inc., South San Francisco, CA (US)

(72) Inventors: Guangyi Wang, Carlsbad, CA (US); Leonid Beigelman, San Mateo, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 15 days.

(21) Appl. No.: 13/722,472

(22) Filed: Dec. 20, 2012

(65) Prior Publication Data

US 2013/0164261 A1 Jun. 27, 2013

Related U.S. Application Data

(60) Provisional application No. 61/579,533, filed on Dec. 22, 2011.

(51) Int. Cl.
*A01N 43/04* (2006.01)
*A61K 31/70* (2006.01)
*C07H 19/04* (2006.01)
*C07H 19/00* (2006.01)
*C07H 19/20* (2006.01)
*C07H 19/10* (2006.01)
*C07H 19/048* (2006.01)
*A61K 31/7072* (2006.01)
*A61K 31/7056* (2006.01)
*A61K 31/7076* (2006.01)
*A61K 31/708* (2006.01)
*A61K 38/21* (2006.01)
*A61K 45/06* (2006.01)
*C07H 19/207* (2006.01)

(52) U.S. Cl.
CPC .......... *A61K 31/7072* (2013.01); *A61K 31/7056* (2013.01); *A61K 31/7076* (2013.01); *A61K 31/708* (2013.01); *A61K 38/21* (2013.01); *A61K 45/06* (2013.01); *C07H 19/10* (2013.01); *C07H 19/20* (2013.01); *C07H 19/207* (2013.01)
USPC .............. 514/47; 514/48; 514/51; 536/26.23; 536/26.26; 536/26.7; 536/26.8

(58) Field of Classification Search
CPC .......... A61K 31/7072; A61K 31/7076; A61K 31/7056; A61K 31/708; A61K 38/21; A61K 45/06; C07H 19/10; C07H 19/20; C07H 19/207
See application file for complete search history.

(56) References Cited

U.S. PATENT DOCUMENTS

| | | |
|---|---|---|
| 2,844,579 A | 7/1958 | Turner et al. |
| 3,180,859 A | 4/1965 | Hoeksema |
| 3,431,252 A | 3/1969 | Walton |
| 3,816,399 A | 6/1974 | Shaw et al. |
| 3,872,084 A | 3/1975 | Jones et al. |
| 3,872,098 A | 3/1975 | Jones et al. |
| 4,093,714 A | 6/1978 | Tolman et al. |
| 5,378,825 A | 1/1995 | Cook et al. |
| 5,432,272 A | 7/1995 | Benner |
| 5,552,311 A | 9/1996 | Sorscher et al. |
| 5,578,718 A | 11/1996 | Cook et al. |
| 5,580,967 A | 12/1996 | Joyce |
| 5,602,240 A | 2/1997 | De Mesmaeker et al. |
| 5,610,289 A | 3/1997 | Cook et al. |
| 5,616,488 A | 4/1997 | Sullivan et al. |
| 5,625,056 A | 4/1997 | Genieser et al. |
| 5,631,359 A | 5/1997 | Chowrira et al. |
| 5,631,360 A | 5/1997 | Usman et al. |
| 5,639,647 A | 6/1997 | Usman et al. |
| 5,646,128 A | 7/1997 | Firestein et al. |
| 5,658,780 A | 8/1997 | Stinchcomb et al. |
| 5,677,437 A | 10/1997 | Teng et al. |
| 5,681,940 A | 10/1997 | Wang et al. |
| 5,686,599 A | 11/1997 | Tracz |
| 5,693,532 A | 12/1997 | McSwiggen et al. |
| 5,714,383 A | 2/1998 | Thompson |
| 5,721,350 A | 2/1998 | Chattopadhyaya |
| 5,728,684 A | 3/1998 | Cheng et al. |
| 5,744,595 A | 4/1998 | Srivastava et al. |
| 5,767,097 A | 6/1998 | Tam |

(Continued)

FOREIGN PATENT DOCUMENTS

| | | |
|---|---|---|
| CA | 2252144 | 4/2000 |
| CN | 1290707 A | 12/2001 |

(Continued)

OTHER PUBLICATIONS (R) Porter et al. (eds.), Chapter 28 ("Hepatitis") and Chapter 128 ("Transplantation") in The Merck Manual of Diagnosis and Therapy, 19th Edition, Merck & Co., Inc., Rahway, NJ, 2011, only title page and text pp. 249-258 and 1136 supplied.*
Aivazashvili et al., Use of 5'-C-methylnucleoside triphosphates in the synthesis of RNA catalyzed by RNA-polymerase of *Escherichia coli*, MOLBBJ, 1987, vol. 21, Issue 4, pp. 898-908.
Aivasashvilli et al., Utilization of 5'-C-methylnucleoside triphosphates in RNA synthesis reaction catalyzed by *Escherichia coli* RNA-polymerase, Molekulyarnaya Biologiya (Moscow), 1987, vol. 21, Issue 4, pp. 1080-1091.
Aspelund et al., 5-Isopropyl- and 5-propyl-1-methyl-3-phenyldialuric acids, Acta Acad. Aboensis, Math. & Phys., 1958, vol. 21, Issue 11, pp. 3-11.

(Continued)

*Primary Examiner* — Lawrence E Crane
(74) *Attorney, Agent, or Firm* — Knobbe Martens Olson & Bear LLP

(57) ABSTRACT

Disclosed herein are phosphorothioate nucleotide analogs, such as thiophosphoroamidate prodrugs and thiophosphates (including α-thiomonophosphates, α-thiodiphosphates, and α-thiotriphosphates), methods of synthesizing phosphorothioate nucleotide analogs, such as thiophosphoramidate prodrugs, and thiophosphates and methods of treating viral infections, such as HCV, cancer, and/or parasitic diseases with the phosphorothioate nucleotide analogs, such as thiophosphoramidate prodrugs, and thiophosphates.

24 Claims, 34 Drawing Sheets

(56) References Cited

U.S. PATENT DOCUMENTS

| | | |
|---|---|---|
| 5,783,425 A | 7/1998 | Dudycz et al. |
| 5,804,683 A | 9/1998 | Usman et al. |
| 5,807,718 A | 9/1998 | Joyce et al. |
| 5,811,300 A | 9/1998 | Sullivan et al. |
| 5,831,071 A | 11/1998 | Usman et al. |
| 5,837,542 A | 11/1998 | Grimm et al. |
| 5,837,855 A | 11/1998 | Chowrira et al. |
| 5,871,918 A | 2/1999 | Thorp et al. |
| 5,892,024 A | 4/1999 | Chaturvedula et al. |
| 5,902,880 A | 5/1999 | Thompson |
| 5,952,478 A | 9/1999 | Baxter et al. |
| 5,965,721 A | 10/1999 | Cook et al. |
| 5,968,745 A | 10/1999 | Thorp et al. |
| 5,977,343 A | 11/1999 | Tracz |
| 5,985,621 A | 11/1999 | Usman et al. |
| 6,017,896 A | 1/2000 | Sorscher et al. |
| 6,022,962 A | 2/2000 | Chowrira et al. |
| 6,030,957 A | 2/2000 | Uckun et al. |
| 6,063,566 A | 5/2000 | Joyce |
| 6,063,628 A | 5/2000 | Loeb et al. |
| 6,087,482 A | 7/2000 | Teng et al. |
| 6,130,326 A | 10/2000 | Ramasamy et al. |
| 6,132,971 A | 10/2000 | Thorp et al. |
| 6,156,501 A | 12/2000 | McGall et al. |
| 6,191,266 B1 | 2/2001 | Wang |
| 6,232,463 B1 | 5/2001 | Cook et al. |
| 6,326,174 B1 | 12/2001 | Joyce et al. |
| 6,353,098 B1 | 3/2002 | Usman et al. |
| 6,361,951 B1 | 3/2002 | Thorp et al. |
| 6,365,374 B1 | 4/2002 | Usman et al. |
| 6,437,117 B1 | 8/2002 | Usman et al. |
| 6,440,705 B1 | 8/2002 | Stanton, Jr. et al. |
| 6,455,513 B1 | 9/2002 | McGuigan et al. |
| 6,458,945 B1 | 10/2002 | Stanton, Jr. et al. |
| 6,469,158 B1 | 10/2002 | Usman et al. |
| 6,482,932 B1 | 11/2002 | Beigelman et al. |
| 6,491,905 B1 | 12/2002 | Sorscher et al. |
| 6,495,677 B1 | 12/2002 | Ramasamy et al. |
| 6,503,890 B1 | 1/2003 | Uckun |
| 6,528,640 B1 | 3/2003 | Beigelman et al. |
| 6,552,183 B1 | 4/2003 | Ramasamy et al. |
| 6,566,059 B1 | 5/2003 | Stanton, Jr. et al. |
| 6,569,630 B1 | 5/2003 | Vivekananda et al. |
| 6,573,248 B2 | 6/2003 | Ramasamy et al. |
| 6,582,923 B2 | 6/2003 | Stanton, Jr. et al. |
| 6,589,941 B1 | 7/2003 | Fahrig et al. |
| 6,596,700 B2 | 7/2003 | Sommadossi et al. |
| 6,617,438 B1 | 9/2003 | Beigelman et al. |
| 6,642,206 B2 | 11/2003 | Ramasamy et al. |
| 6,649,750 B1 | 11/2003 | Capaldi et al. |
| 6,649,751 B2 | 11/2003 | Usman et al. |
| 6,670,461 B1 | 12/2003 | Wengel et al. |
| 6,677,314 B2 | 1/2004 | Klecker et al. |
| 6,677,315 B2 | 1/2004 | Klecker et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,777,395 B2 | 8/2004 | Bhat et al. |
| 6,784,161 B2 | 8/2004 | Ismaili et al. |
| 6,787,526 B1 | 9/2004 | Bryant et al. |
| 6,794,499 B2 | 9/2004 | Wengel et al. |
| 6,812,219 B2 | 11/2004 | LaColla et al. |
| 6,815,542 B2 | 11/2004 | Hong et al. |
| 6,831,069 B2 | 12/2004 | Tam et al. |
| 6,875,752 B2 | 4/2005 | Aszodi et al. |
| 6,887,707 B2 | 5/2005 | Loeb et al. |
| 6,914,054 B2 | 7/2005 | Sommadossi et al. |
| 6,958,318 B2 | 10/2005 | Sorscher et al. |
| 6,974,865 B2 | 12/2005 | Cook et al. |
| 6,995,148 B2 | 2/2006 | Jones et al. |
| 7,018,989 B2 | 3/2006 | McGuigan et al. |
| 7,034,133 B2 | 4/2006 | Wengel et al. |
| 7,037,718 B2 | 5/2006 | Ealick et al. |
| 7,041,817 B2 | 5/2006 | Usman et al. |
| 7,049,068 B2 | 5/2006 | Thorp et al. |
| 7,064,114 B2 | 6/2006 | Yiv et al. |
| 7,081,449 B2 | 7/2006 | Pietrzkowski et al. |
| 7,091,315 B1 | 8/2006 | Ruben et al. |
| 7,101,861 B2 | 9/2006 | Sommadossi et al. |
| 7,105,493 B2 | 9/2006 | Sommadossi et al. |
| 7,105,499 B2 | 9/2006 | Carroll et al. |
| 7,112,406 B2 | 9/2006 | Behlke et al. |
| 7,125,855 B2 | 10/2006 | Bhat et al. |
| 7,138,501 B2 | 11/2006 | Ruben et al. |
| 7,141,574 B2 | 11/2006 | Beaulieu et al. |
| 7,141,665 B1 | 11/2006 | Joyce et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,235,649 B2 | 6/2007 | Gewirth et al. |
| 7,268,119 B2 | 9/2007 | Cook et al. |
| 7,285,658 B2 | 10/2007 | Cook et al. |
| 7,335,648 B2 | 2/2008 | Plourde, Jr. et al. |
| 7,339,054 B2 | 3/2008 | Xu et al. |
| 7,351,841 B2 | 4/2008 | Owada et al. |
| 7,365,057 B2 | 4/2008 | LaColla et al. |
| 7,368,438 B2 | 5/2008 | Plourde, Jr. et al. |
| 7,378,402 B2 | 5/2008 | Martin |
| 7,384,924 B2 | 6/2008 | LaColla et al. |
| 7,407,965 B2 | 8/2008 | Chen et al. |
| 7,427,636 B2 | 9/2008 | Cannizzaro et al. |
| 7,429,565 B2 | 9/2008 | Booojamra et al. |
| 7,432,261 B2 | 10/2008 | Cannizzaro et al. |
| 7,452,901 B2 | 11/2008 | Boojamra et al. |
| 7,470,724 B2 | 12/2008 | Cannizzaro et al. |
| 7,547,704 B2 | 6/2009 | LaColla et al. |
| 7,582,618 B2 | 9/2009 | Sommadossi et al. |
| 7,598,230 B2 | 10/2009 | Cook et al. |
| 7,598,373 B2 | 10/2009 | Storer et al. |
| 7,608,597 B2 | 10/2009 | Sommadossi et al. |
| 7,608,600 B2 | 10/2009 | Storer et al. |
| 7,625,875 B2 | 12/2009 | Gosselin et al. |
| 7,635,689 B2 | 12/2009 | LaColla et al. |
| 7,645,747 B2 | 1/2010 | Boojamra et al. |
| 7,713,941 B2 | 5/2010 | Cook et al. |
| 7,718,790 B2 | 5/2010 | Stuyver et al. |
| 7,749,983 B2 | 7/2010 | Hostetler et al. |
| 7,953,557 B2 | 5/2011 | Johnson et al. |
| 2001/0011075 A1 | 8/2001 | Townsend et al. |
| 2002/0132237 A1 | 9/2002 | Algate et al. |
| 2002/0150922 A1 | 10/2002 | Stolk et al. |
| 2003/0004122 A1 | 1/2003 | Beigelman et al. |
| 2003/0008841 A1 | 1/2003 | Devos et al. |
| 2003/0073144 A1 | 4/2003 | Benson et al. |
| 2003/0144489 A1 | 7/2003 | Burgin et al. |
| 2003/0166064 A1 | 9/2003 | King et al. |
| 2003/0207271 A1 | 11/2003 | Holwitt |
| 2004/0009491 A1 | 1/2004 | Birse |
| 2004/0023265 A1 | 2/2004 | Vivekananda et al. |
| 2004/0023266 A1 | 2/2004 | Vivekananda et al. |
| 2004/0063658 A1 | 4/2004 | Roberts et al. |
| 2004/0127436 A1 | 7/2004 | Daifuku et al. |
| 2004/0171028 A1 | 9/2004 | Baker et al. |
| 2004/0171032 A1 | 9/2004 | Baker et al. |
| 2004/0229839 A1 | 11/2004 | Babu et al. |
| 2004/0259934 A1 | 12/2004 | Olsen et al. |
| 2005/0031588 A1 | 2/2005 | Sommadossi et al. |
| 2005/0032067 A1 | 2/2005 | Prakash et al. |
| 2005/0042632 A1 | 2/2005 | Radka |
| 2005/0042647 A1 | 2/2005 | Baker et al. |
| 2005/0186568 A1 | 8/2005 | Bandman et al. |
| 2005/0203044 A1 | 9/2005 | Zinnen |
| 2005/0214901 A1 | 9/2005 | Ealick et al. |
| 2005/0233358 A1 | 10/2005 | Thorp et al. |
| 2005/0239733 A1 | 10/2005 | Jurk et al. |
| 2005/0245463 A1 | 11/2005 | Pham et al. |
| 2005/0256073 A1 | 11/2005 | Lipford |
| 2005/0261237 A1 | 11/2005 | Boojamra et al. |
| 2006/0003952 A1 | 1/2006 | Ravikumar et al. |
| 2006/0014689 A1 | 1/2006 | Vesely |

(56) References Cited

U.S. PATENT DOCUMENTS

| | | |
|---|---|---|
| 2006/0058254 A1 | 3/2006 | Dina et al. |
| 2006/0074035 A1 | 4/2006 | Hong et al. |
| 2006/0094678 A1 | 5/2006 | Vornlocher et al. |
| 2006/0100166 A1 | 5/2006 | De Koning et al. |
| 2006/0105976 A1 | 5/2006 | Soutschek et al. |
| 2006/0121086 A1 | 6/2006 | Boyer et al. |
| 2006/0122146 A1 | 6/2006 | Chun et al. |
| 2006/0142238 A1 | 6/2006 | McGuigan |
| 2006/0193869 A1 | 8/2006 | Barrat et al. |
| 2006/0217330 A1 | 9/2006 | Hartmann et al. |
| 2006/0229265 A1 | 10/2006 | Milburn et al. |
| 2006/0240462 A1 | 10/2006 | Todd et al. |
| 2006/0264404 A1 | 11/2006 | Boojamra et al. |
| 2006/0269517 A1 | 11/2006 | Blatt et al. |
| 2006/0287260 A1 | 12/2006 | Manoharan et al. |
| 2007/0027116 A1 | 2/2007 | Cho et al. |
| 2007/0032448 A1 | 2/2007 | Hong et al. |
| 2007/0037773 A1 | 2/2007 | Sommadossi et al. |
| 2007/0042350 A1 | 2/2007 | Li et al. |
| 2007/0066552 A1 | 3/2007 | Clarke et al. |
| 2007/0093446 A1 | 4/2007 | Douglass, III et al. |
| 2007/0105122 A1 | 5/2007 | Ota et al. |
| 2007/0105806 A1 | 5/2007 | Sah et al. |
| 2007/0123544 A1 | 5/2007 | Plourde, Jr. et al. |
| 2007/0135372 A1 | 6/2007 | MacLachlan et al. |
| 2007/0196824 A1 | 8/2007 | Stuyver et al. |
| 2007/0197463 A1 | 8/2007 | Chun et al. |
| 2007/0207973 A1 | 9/2007 | Daifuku et al. |
| 2007/0213292 A1 | 9/2007 | Stoffel et al. |
| 2007/0219365 A1 | 9/2007 | Joyce et al. |
| 2007/0231810 A1 | 10/2007 | Todd et al. |
| 2007/0238099 A1 | 10/2007 | Cohen et al. |
| 2007/0238678 A1 | 10/2007 | Barrat et al. |
| 2007/0258921 A1 | 11/2007 | Dalko |
| 2007/0259832 A1 | 11/2007 | Cook et al. |
| 2007/0265224 A1 | 11/2007 | Cook et al. |
| 2007/0275912 A1 | 11/2007 | Bhat et al. |
| 2007/0281899 A1 | 12/2007 | Bumcrot et al. |
| 2007/0299068 A1 | 12/2007 | Karp et al. |
| 2008/0009462 A1 | 1/2008 | Hostetler et al. |
| 2008/0015161 A1 | 1/2008 | Vornlocher et al. |
| 2008/0026362 A1 | 1/2008 | Ho et al. |
| 2008/0027068 A1 | 1/2008 | Owada et al. |
| 2008/0064753 A1 | 3/2008 | Palladino et al. |
| 2008/0070935 A1 | 3/2008 | Huang et al. |
| 2008/0152621 A1 | 6/2008 | Johansson et al. |
| 2008/0161246 A1 | 7/2008 | Klein et al. |
| 2008/0161324 A1 | 7/2008 | Johansen et al. |
| 2008/0199870 A1 | 8/2008 | Guenther et al. |
| 2008/0200423 A1 | 8/2008 | Cook et al. |
| 2008/0207542 A1 | 8/2008 | McSwiggen et al. |
| 2008/0207554 A1 | 8/2008 | Beigelman et al. |
| 2008/0261913 A1 | 10/2008 | Sommadossi et al. |
| 2008/0286230 A1 | 11/2008 | Sommadossi et al. |
| 2008/0293665 A1 | 11/2008 | Undheim et al. |
| 2009/0131372 A1 | 5/2009 | Chen et al. |
| 2009/0169504 A1 | 7/2009 | Sommadossi et al. |
| 2009/0176732 A1 | 7/2009 | Beigelman et al. |
| 2009/0181921 A1 | 7/2009 | Blatt et al. |
| 2009/0220950 A1 | 9/2009 | Stuyver et al. |
| 2009/0221684 A1 | 9/2009 | Grinstaff et al. |
| 2009/0227543 A1 | 9/2009 | Cannizzaro et al. |
| 2009/0233872 A1 | 9/2009 | Ariga et al. |
| 2009/0238790 A2 | 9/2009 | Sommadossi et al. |
| 2009/0247488 A1 | 10/2009 | Cannizzaro et al. |
| 2009/0275535 A1 | 11/2009 | Boojamra et al. |
| 2009/0280084 A1 | 11/2009 | Schinazi et al. |
| 2009/0280086 A1 | 11/2009 | Sommadossi et al. |
| 2009/0318380 A1 | 12/2009 | Sofia et al. |
| 2010/0016251 A1 | 1/2010 | Sofia et al. |
| 2010/0022467 A1 | 1/2010 | Boojamra et al. |
| 2010/0035835 A1 | 2/2010 | Narjes et al. |
| 2010/0081628 A1 | 4/2010 | Du et al. |
| 2010/0093656 A1 | 4/2010 | Adelfinskaya et al. |
| 2010/0137237 A1 | 6/2010 | Undheim et al. |
| 2010/0137576 A1 | 6/2010 | Stec et al. |
| 2010/0152128 A1 | 6/2010 | Attenni et al. |
| 2010/0249068 A1 | 9/2010 | Beigelman et al. |
| 2010/0297079 A1 | 11/2010 | Almond et al. |
| 2010/0305060 A1 | 12/2010 | Hecker et al. |
| 2010/0311684 A1 | 12/2010 | Cook et al. |
| 2010/0331397 A1 | 12/2010 | Beigelman et al. |
| 2011/0015383 A1 | 1/2011 | Stec et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0165286 A1 | 6/2012 | Beigelman et al. |
| 2013/0165400 A1 | 6/2013 | Beigelman et al. |
| 2013/0252920 A1 | 9/2013 | Blatt et al. |
| 2013/0253181 A1 | 9/2013 | Serebryany et al. |
| 2013/0281687 A1 | 10/2013 | Serebryany et al. |
| 2014/0179627 A1 | 6/2014 | Beigelman et al. |
| 2014/0179910 A1 | 6/2014 | Beigelman et al. |
| 2014/0303108 A1 | 10/2014 | Beigelman et al. |
| 2014/0303113 A1 | 10/2014 | Krop et al. |

FOREIGN PATENT DOCUMENTS

| | | |
|---|---|---|
| CN | 1337401 A | 2/2002 |
| CN | 1343673 A | 4/2002 |
| CN | 101108870 A | 1/2008 |
| DE | 3824110 A1 | 1/1990 |
| DE | 279247 A1 | 5/1990 |
| DE | 4341161 A1 | 6/1995 |
| EP | 0547008 A1 | 6/1993 |
| EP | 0629633 A2 | 12/1994 |
| EP | 0799834 A1 | 10/1997 |
| EP | 0742287 B1 | 1/2006 |
| GB | 1209654 A | 10/1970 |
| GB | 1319303 A | 6/1973 |
| JP | 04-046124 | 2/1992 |
| JP | 06-228186 A | 8/1994 |
| JP | 2006-248949 A | 9/2006 |
| JP | 2006-248975 A | 9/2006 |
| NZ | 216172 | 8/1989 |
| NZ | 224189 | 9/1991 |
| NZ | 226844 | 10/1991 |
| NZ | 231444 | 9/1992 |
| NZ | 505531 | 7/2001 |
| PL | 144471 B1 | 5/1988 |
| WO | WO 84/04748 A1 | 12/1984 |
| WO | WO 88/03147 A1 | 5/1988 |
| WO | WO 92/12718 A1 | 8/1992 |
| WO | WO 92/20822 A1 | 11/1992 |
| WO | WO 94/17803 A1 | 8/1994 |
| WO | WO 94/22890 A1 | 10/1994 |
| WO | WO 95/18139 A1 | 7/1995 |
| WO | WO 96/07666 A1 | 3/1996 |
| WO | WO 96/23506 A1 | 8/1996 |
| WO | WO 96/29336 A1 | 9/1996 |
| WO | WO 96/30383 A1 | 10/1996 |
| WO | WO 97/26270 A2 | 7/1997 |
| WO | WO 98/00434 A1 | 1/1998 |
| WO | WO 99/10365 A2 | 3/1999 |
| WO | WO 99/46362 A1 | 9/1999 |
| WO | WO 99/55857 A2 | 11/1999 |
| WO | WO 00/00501 A1 | 1/2000 |
| WO | WO 00/14263 A2 | 3/2000 |
| WO | WO 00/56366 A1 | 9/2000 |
| WO | WO 01/27114 A1 | 4/2001 |
| WO | WO 01/49701 A1 | 7/2001 |
| WO | WO 01/68663 A1 | 9/2001 |
| WO | WO 01/72779 A1 | 10/2001 |
| WO | WO 01/90121 A2 | 11/2001 |
| WO | WO 02/03997 A1 | 1/2002 |
| WO | WO 02/22660 A2 | 3/2002 |
| WO | WO 02/26930 A2 | 4/2002 |
| WO | WO 02/29103 A2 | 4/2002 |
| WO | WO 02/069903 A2 | 9/2002 |
| WO | WO 02/088385 A1 | 11/2002 |
| WO | WO 02/090526 A2 | 11/2002 |
| WO | WO 02/092006 A2 | 11/2002 |
| WO | WO 02/096927 A2 | 12/2002 |
| WO | WO 02/097031 A2 | 12/2002 |

(56) References Cited

FOREIGN PATENT DOCUMENTS

| | | |
|---|---|---|
| WO | WO 02/100415 A2 | 12/2002 |
| WO | WO 03/016475 A2 | 2/2003 |
| WO | WO 03/016497 A2 | 2/2003 |
| WO | WO 03/016572 A1 | 2/2003 |
| WO | WO 03/019189 A1 | 3/2003 |
| WO | WO 03/029271 A2 | 4/2003 |
| WO | WO 03/031419 A1 | 4/2003 |
| WO | WO 03/035012 A2 | 5/2003 |
| WO | WO 03/038052 A2 | 5/2003 |
| WO | WO 03/039348 A2 | 5/2003 |
| WO | WO 03/039523 A2 | 5/2003 |
| WO | WO 03/042357 A2 | 5/2003 |
| WO | WO 03/051896 A1 | 6/2003 |
| WO | WO 03/054152 A2 | 7/2003 |
| WO | WO 03/054219 A2 | 7/2003 |
| WO | WO 03/062257 A1 | 7/2003 |
| WO | WO 03/062376 A2 | 7/2003 |
| WO | WO 03/062379 A2 | 7/2003 |
| WO | WO 03/062385 A2 | 7/2003 |
| WO | WO 03/062391 A2 | 7/2003 |
| WO | WO 03/063688 A2 | 8/2003 |
| WO | WO 03/072602 A2 | 9/2003 |
| WO | WO 03/072729 A2 | 9/2003 |
| WO | WO 03/072757 A2 | 9/2003 |
| WO | WO 03/076586 A2 | 9/2003 |
| WO | WO 03/077875 A2 | 9/2003 |
| WO | WO 03/083082 A2 | 10/2003 |
| WO | WO 03/083084 A2 | 10/2003 |
| WO | WO 03/083085 A2 | 10/2003 |
| WO | WO 03/087300 A2 | 10/2003 |
| WO | WO 03/090674 A2 | 11/2003 |
| WO | WO 03/093439 A2 | 11/2003 |
| WO | WO 03/094848 A2 | 11/2003 |
| WO | WO 04/001008 A2 | 12/2003 |
| WO | WO 2004/003000 A2 | 1/2004 |
| WO | WO 2004/003162 A1 | 1/2004 |
| WO | WO 2004/009797 A2 | 1/2004 |
| WO | WO 2004/026890 A1 | 4/2004 |
| WO | WO 2004/028454 A2 | 4/2004 |
| WO | WO 2004/041924 A2 | 5/2004 |
| WO | WO 2004/050899 A2 | 6/2004 |
| WO | WO 2004/080466 A1 | 9/2004 |
| WO | WO 2004/106356 A1 | 12/2004 |
| WO | WO 2005/003766 A2 | 1/2005 |
| WO | WO 2005/010150 A1 | 2/2005 |
| WO | WO 2005/020885 A2 | 3/2005 |
| WO | WO 2005/039552 A2 | 5/2005 |
| WO | WO 2005/040174 A1 | 5/2005 |
| WO | WO 2005/047255 A1 | 5/2005 |
| WO | WO 2005/077966 A1 | 8/2005 |
| WO | WO 2005/123755 A2 | 12/2005 |
| WO | WO 2006/034373 A2 | 3/2006 |
| WO | WO 2006/038865 A1 | 4/2006 |
| WO | WO 2006/062240 A1 | 6/2006 |
| WO | WO 2006/066080 A1 | 6/2006 |
| WO | WO 2006/094347 A1 | 9/2006 |
| WO | WO 2006/105440 A2 | 10/2006 |
| WO | WO 2006/106169 A1 | 10/2006 |
| WO | WO 2006/116512 A1 | 11/2006 |
| WO | WO 2006/119507 A2 | 11/2006 |
| WO | WO 2006/121820 A1 | 11/2006 |
| WO | WO 2007/006544 A2 | 1/2007 |
| WO | WO 2007/020018 A1 | 2/2007 |
| WO | WO 2007/027248 A2 | 3/2007 |
| WO | WO 2007/028051 A2 | 3/2007 |
| WO | WO 2007/056191 A2 | 5/2007 |
| WO | WO 2007/089731 A2 | 8/2007 |
| WO | WO 2007/149554 A2 | 12/2007 |
| WO | WO 2008/033432 A2 | 3/2008 |
| WO | WO 2008/033466 A2 | 3/2008 |
| WO | WO 2008/039267 A2 | 4/2008 |
| WO | WO 2008/052770 A2 | 5/2008 |
| WO | WO 2008/073661 A2 | 6/2008 |
| WO | WO 2008/083949 A2 | 7/2008 |
| WO | WO 2008/101157 A1 | 8/2008 |
| WO | WO 2008/103276 A2 | 8/2008 |
| WO | WO 2008/104408 A2 | 9/2008 |
| WO | WO 2008/106803 A2 | 9/2008 |
| WO | WO 2009/005382 A2 | 1/2009 |
| WO | WO 2009/073506 A3 | 6/2009 |
| WO | WO 2009/127230 A1 | 10/2009 |
| WO | WO 2010/019954 A2 | 2/2010 |
| WO | WO 2010/020786 A1 | 2/2010 |
| WO | WO 2010/048552 A3 | 4/2010 |
| WO | WO 2010/091386 A2 | 8/2010 |
| WO | WO 2010/108140 A1 | 9/2010 |
| WO | WO 2011/005860 A2 | 1/2011 |
| WO | WO 2011/094489 A1 | 8/2011 |
| WO | WO 2011/156757 A1 | 12/2011 |
| WO | WO 2012/040126 A1 | 3/2012 |
| WO | WO 2012/040127 A1 | 3/2012 |
| WO | WO 2012/088155 A1 | 6/2012 |
| WO | WO 2012/142085 | 10/2012 |
| WO | WO 2013/142124 | 9/2013 |
| WO | WO 2013/142159 | 9/2013 |
| WO | WO 2013/142525 | 9/2013 |
| WO | WO 2014/100498 | 6/2014 |

OTHER PUBLICATIONS

Bajwa et al., Thymidine nucleoside 3',5'-cyclic phosphoramidites and phosphites—configuration at phosphorus in trivalent and pentavalent cyclic nucleotides by phosphorus-31 and carbon-13 NMR, Tetrahedron Letters, 1978, vol. 5, pp. 421-424.

Baker et al., Synthesis of potential anticancer agents. VI. Use of the O-benzoyl blocking group from synthesis of 6-chloropurine nucleosides, Journal of Organic Chemistry, 1957, vol. 22, pp. 954-959.

Baker et al., Synthesis of potential anticancer agents. VII. Nucleosides derived from L-rhamnofuranose, Journal of Organic Chemistry, 1957, vol. 22, pp. 959-966.

Baker et al., Synthesis of potential anticancer agents. VIII. Nucleosides derived from L-rhamnofuranose, Journal of Organic Chemistry, 1957, vol. 22, pp. 966-971.

Baraniak et al., Ribonucleoside cyclic 3',5'-phosphoramidates: Synthesis, stereochemistry, and conversion into ribonucleoside cyclic 3',5'-phosphorothioates and -[180] phosphates, Journal of the Chemical Society, Perkin Transactions 1: Organic and Bio-Organic Chemistry, 1987, vol. 8, pp. 1645-1656.

Baraniak et al., Synthesis of adenosine cyclic 3',5'-phosphorofuoridate (cAMP-F), Tetrahedron Letters, 1995, vol. 36, Issue 44, Elsevier, pp. 8119-8122.

Baraniak, Deoxyribonucleoside cyclic 3',5'-phosphorofluoridates phosphorus, Sulfur Silicon Relat. Elem., 1996, vol. 111, p. 80.

Beaulieu et al., Inhibitors of the HCV NS5B polymerase: New hope for the treatment of hepatitis C infections, Curr. Opin. Invest. Drugs, 2004, vol. 5, Issue 8, pp. 838-850.

Beigelman et al., Synthesis of 5'-C-methyl-D-allo- & L-talo-ribonucleoside 3'-O-phosphoramidites & their incorporation into hammerhead ribozymes, Nucleosides & Nucleotides, 1995, vol. 14, Issue 5, pp. 901-905.

Bergstrom, Nucleoside phosphorylation and related modifications, Current Protocols in Nucleic Acid Chemistry, Chapter 13, John Wiley & Sons, 2008, Suppl. 33, pp. 13.0.1-13.0.2.

Bennett et al., Designer gene therapy using an *Escherichia coli* purine nucleoside phosphorylase/prodrug system, Chemistry & Biology, 2003, vol. 10, Issue 12, pp. 1173-1181.

Billich et al., Synthesis, conformation and enzymatic properties of 1-(β-D-allofuranosyl) uracil and some derivatives, Nucleic Acids Research, 1983, vol. 11, Issue 21, pp. 7611-7624.

Bindal et al., The relationship of vasodilator activity of adenosine analogs with molecular connectivity and van der Waals volume, Arzneimittel-Forschung, 1980, vol. 30, Issue 6, pp. 924-928.

Botelho et al, Inhibition of cAMP-dependent protein kinase by adenosine cyclic 3',5'-phosphorodithioate, a second cAMP antagonist, Journal of Biological Chemistry, 1988, vol. 263, Issue 11, pp. 5301-5305.

Bottka et al., Evidence for the stereoelectronic control of the acid hydrolysis of adenosine cyclic 3', 5'-phosphoramidate diastereoisomers, Nucleosides & Nucleotides, 1989, vol. 8, Issue 7, pp. 1217-1229.

(56) References Cited

OTHER PUBLICATIONS

Bruns, Adenosine receptor activation in human fibroblasts: nucleoside agonists and antagonists, Canadian Journal of Physiology and Pharmacology, 1980, vol. 58, Issue 6, pp. 673-691.
Bundgaard, "Design of prodrugs", Elsevier Science Publishers B.V. (1985), Table of Contents only.
Cahard et al., Aryloxy phosphoramidate triesters as pro-tides, Mini-Reviews in Medicinal Chemistry, 2004, vol. 4, pp. 371-381.
Cappuccino et al., Growth inhibition of *Clostridium feseri* by carcinostatic purine and pyrimidine analogs. I. Effect of medium on growth inhibition, Cancer Research, 1964, vol. 24, pp. 1243-1248.
Carroll et al , Inhibition of hepatitis C virus RNA replication by 2'-modified nucleoside analogs, Journal of Biological Chemistry, 2003, vol. 278, Issue 14, pp. 11979-11984.
Carey, Francis, Organic Chemistry, 2nd ed., McGraw Hill, Inc., New York (1992), pp. 328-331.
CAS Reg. No. 18883-94-8.
CAS RN 486446-48-4, STNEasy, Entry Date Feb. 6, 2003, (https://stneasy.cas.org), retrieved on Nov. 17, 2011.
CAS Reg. No. 71738-02-8.
CAS Reg. No. 80875-87-2.
Cass et al., Mediated transport of nucleosides by human erythrocytes. Specificity toward purine nucleosides as permeants, Biochemica et Biophysica Acta, Biomembranes,1973, vol. 291, Issue 3, pp. 734-746.
Chidgeavadze et al., Synthesis and substrate properties of C-methyl-2'-deoxynucleoside 5'-triphosphates in DNA synthesis reactions catalyzed by DNA polymerases, Bioorganicheskaya Khimiya, 1991, vol. 17, Issue 5, pp. 678-684.
Chidgeavadze et al., 5'-C- and 3'-C-Methyl-2'-deoxynucleoside 5'-triphosphates and their substrate properties in DNA-polymerase-catalyzed DNA synthesis reactions, Soviet Journal of Bioorganic Chemistry (a translation of Bioorganicheskaya Khimiya), 1992, vol. 17, Issue 5, pp. 389-395.
Cullis, The stereospecific conversion of p-chiral dialkyl phosphorothioates into $^{18}$O-phosphates, Tetrahedron Letters, 1983, vol. 24, Issue 50, pp. 5677-5680.
Cusack et al., Simple syntheses of glycofuranosylamines derived from D-xylose, D-mannose, and L-rhamnose, intermediates in the preparation of some N-glycofuranosyl uracils, Chemical Communications, 1971, vol. 4, pp. 190-191.
David et al., Synthesis of the two epimeric 5'-methylcytidines, their 5'-phosphates and [5-$^3$H]-5'-pyrophosphates, and the two 5'-methyldeoxycytidines. A novel cytosine anhydronucleoside with two oxygen bridges between the base and the sugar, Journal of the Chemical Society, Perkin Transactions 1: Organic and Bio-Organic Chemistry, 1982, vol. 1, pp. 385-393.
De Vroom et al., Synthesis of ribonucleoside 3' ,5'-cyclic phosphorothioates using a modified hydroxybenzotriazole phosphotriester approach, Recueil des Travaux Chimiques des Pays-Bas, 1987, vol. 106, Issue 11, pp. 577-580.
Del Vecchio et al., Small molecule and biologic inhibitors of hepatitis C virus: A symbiotic approach, Mini-Reviews in Medicinal Chemistry, Nov. 2006, vol. 6, Issue 11, pp. 1263-1268.
Deval et al., Pyrophosphorolytic excision of nonobligate chain terminators by hepatitis C virus NS5B polymerase, Antimicrobial Agents and Chemotherapy, Aug. 2007, vol. 51, Issue 8, pp. 2920-2928.
De Zwart et al., A functional screening of adenosine analogs at the adenosine A2B receptor: A search for potent agonists, Nucleosides & Nucleotides, 1998, vol. 17, Issue 6, pp. 969-985.
Dutartre et al., General catalytic deficiency of hepatitis C virus RNA polymerase with an S282T mutation and mutually exclusive resistance towards 2'-modified nucleotide analogues, Antimicro. Agts. Chemother., 2006, vol. 50, Issue 12, pp. 4161-4169.
Dzhavadova et al., Molecular and crystal structures of 1-(6-desoxy-β-D-allofuranosyl) cytosine and 1-(6-desoxy-α-L-talofuranosyl) cytosine, Sov. Phys. Crystallog., 1988, vol. 33, Issue 6, pp. 837-841.

Dzhavadova et al., The molecular and crystal structures of 1-(6-deoxy-β-D-allofuranosyl) cytosine and 1-(6-deoxy-α-L-talofuranosyl) cytosine, Kristallografiya, 1988, vol. 33, Issue 6, pp. 1408-1414.
Dzhavadova et al., The molecular and crystal structure of 1-(2, 6-dideoxy-α-L-lyxo-hexofuranosyl) thymine, Bioorganicheskaya Khimiya, 1989, vol. 15, Issue 7, pp. 976-982.
Eliahu, S. et al, A Novel Insulin Secretagogue Based on a Dinucleoside Polyphosphate Scaffold, Journal of Medicinal Chemistry, 2010, vol. 53, No. 6, pp. 2472-2481.
Eppacher et al., Synthesis and incorporation of C(5')-ethynylated uracil-derived phosphoramidites into RNA, Helvetica Chimica Acta, 2004, vol. 87, pp. 3004-3020.
Estrada et al., In silico studies toward the discovery of new anti-HIV nucleoside compounds with the use of TOPS-MODE and 2D/3D connectivity indices. 1. Pyrimidyl derivatives, Journal of Chemical Information and Computer Sciences, 2002, vol. 42, Issue 5, pp. 1194-1203.
Feldwisch et al., Purification & characterization of a cAMP-binding protein of *Volvox carteri* f. nagariensis iyengar, European Journal of Biochemistry, 1995, vol. 228, Issue 2, pp. 480-489.
Ferrini et al., Free amino acids in the egg of *Ciona intestinalis* during some development stages, Ricerca Scientifica, Parte 2: Rendiconti, Sezione B: Biologica, 1964, vol. 5, Issue 3, pp. 213-217.
Fingl et al., The Pharmacological Basis of Therapeutics, 5th ed., MacMillan Publishing Co., Inc. (1975) Chapter 1, General Principles, pp. 1-46.
Fischer, B. et al., 2-Thioether 5'-o-(1-Thiotriphosphate)adenosine Derivatives as New Insulin Secretagogues Acting through P2Y-Receptors, Journal of Medicinal Chemistry, 1999, vol. 42, No. 18, pp. 3636-3646.
Follman et al., Novel nucleosides derived from 5'-C-methyl adenosine, Eur. Biophys. Congr., Proc., 1$^{st}$, 1971, vol. 1, pp. 285-287.
Follman et al., Adenine nucleosides in solution. Stabilization of the anti-conformation by C-5' substituents, European Journal of Biochemistry, 1974, vol. 47, Issue 1, pp. 187-197.
Follman et al., Adenine nucleosides in solution: Circular dichroism studies and base conformation, European Journal of Biochemistry, 1975, vol. 58, Issue 1, pp. 31-41.
Gangjee et al., Vasodilator activity of adenosine analogs, Journal of Pharmaceutical Sciences, 1978, vol. 67, Issue 1, pp. 121-123.
Gardner et al. "Comparative Kinetics of Nucleotide Analog Incorporation by Vent DNA Polymerase" *J. Bio. Chem.* (2004) 279(12):11834-11842.
Gimisis et al., Tuning the reactivity of O-tert-butyldimethylsilylimidazolyl aminals towards organolithium reagents, Synlett, 2003, vol. 10, pp. 1451-1454.
Girardet et al., Synthesis and cytotoxicity of 4-amino-5-oxopyrido [2, 3-d] pyrimidine nucleosides, Journal of Medicinal Chemistry, 2000, vol. 43, Issue 20, pp. 3704-3713.
Gonzalez et al., A radial distribution function approach to predict A2B agonist effect of adenosine analogues, Bioorganic & Medicinal Chemistry, 2005, vol. 13, Issue 3, pp. 601-608.
Gopalakrishnan et al., A virtual screening approach for thymidine monophosphate kinase inhibitors as antitubercular agents based on docking and pharmacophore models, Journal of Chemical Information and Modeling, 2005, vol. 45, pp. 1101-1108.
Grant et al., Binding specificities of adenosine aminohydrolase from calf intestinal mucosa with dialdehydes derived from hexofuranosyladenine nucleosides, Journal of Medicinal Chemistry, 1980, vol. 23, Issue 1, pp. 39-42.
Grant et al., Hexofuranosyladenine nucleosides as substrates and inhibitors of calf intestinal adenosine deaminase, Journal of Medicinal Chemistry, 1979, vol. 22, Issue 8, pp. 1016-1018.
Greene et al., Protective Groups in Organic Synthesis, 3. Ed., John Wiley & Sons, (1999) Cover & Contents pages.
Gunic et al., Synthesis & cytotoxicity of 4'-C- and 5'-C-substituted toyocamycins, Bioorganic & Medicinal Chemistry, 2001, vol. 9, Issue 1, pp. 163-170.
Gurskaya et al., X-ray crystallographic studies of nucleoside analogs. I. The crystal structure of 1-(6-deoxy-β-D-allofuranosyl) cytosine, $C_{10}H_{15}N_3O_5$, Crystal Structure Communications, 1982, vol. 11, Issue 4, pp. 1245-1252.

(56) References Cited

OTHER PUBLICATIONS

Hai et al., Species- or isozyme-specific enzyme inhibitors. 9. Selective effects in inhibitions of rat pyruvate kinase isozymes by adenosine 5'-diphosphate derivatives, Journal of Medicinal Chemistry, 1982, vol. 25, Issue 10, pp. 1184-1188.

Hai et al., Species- or isozyme-specific enzyme inhibitors. 7. Selective effects in inhibitions of rat adenylate kinase isozymes by adenosine 5'-phosphate derivatives, Journal of Medicinal Chemistry, 1982, vol. 25, Issue 7, pp. 806-812.

Hampton et al., Substrate properties of cycloadenosines with adenosine aminohydrolase as evidence for the conformation of enzyme-bound adenosine, Biochemistry, 1972, vol. 11, Issue 25, pp. 4736-4739.

Hampton et al., Interactions of epimeric 5'-C-methyl and 5'-C-carbamyl derivatives of adenosine monophosphate with adenosine monophosphate utilizing enzymes, Biochemistry, 1973, vol. 12, Issue 17, pp. 3328-3332.

Hayakawa et al., A strategy for the stereoselective preparation of thymidine phosphorothioates with the (R) or the (S) configuration at the stereogenic oligodeoxyribonucleotides with stereochemically pure phosphate/phosphorothioate chimeric backbones, European Journal of Organic Chemistry, 2006, vol. 17, pp. 3834-3844.

Hayatshahi et al., QSARs and activity predicting models for competitive inhibitors of adenosine deaminase, FEBS Letters, 2007, vol. 581, Issue 3, pp. 506-514.

Hebert et al., Structural features of the noncatalytic cGMP binding sites of frog photoreceptor phosphodiesterase using cGMP analogs, Journal of Biological Chemistry, 1998, vol. 273, Issue 10, pp. 5557-5565.

Heinemann et al., Comparison of the cellular pharmacokinetics and toxicity of 2'.2'-difluorodeoxycytidine and 1-beta-D-arabinofuranosylcytosine, Cancer Research, 1988, vol. 48, pp. 4024-4031.

Henderson et al, Inhibitors of adenine phosphoribosyltransferase, Cancer Chemotherapy Reports Supplement, 1968, vol. 1, Issue 2, pp. 363-373.

Henderson et al., Mechanisms of inhibition of adenine phosphoribosyltransferase by adenine nucleosides and nucleotides, Canadian Journal of Biochemistry, 1970, vol. 48, Issue 5, pp. 573-579.

Hiebl et al., Side-chain derivatives of biologically active nucleosides. Part 1. Side-chain analogs of 3'-azido-3'-deoxythymidine (AZT), Journal of Medicinal Chemistry, 1992, vol. 35, Issue 16, pp. 3016-3023.

Hiebl et al., Side-chain derivatives of biologically active nucleosides. Part 2: Synthesis and anti-HIV activity of 5'-C-methyl derivatives of 3'-fluoro-3'-deoxythymidine, Antiviral Chemistry and Chemotherapy, 1996, vol. 7, Issue 3, pp. 173-177.

Higuchi et al., "Pro-drugs as novel drug delivery systems", A.C.S. Symposium Series, American Chemical Society, 1975, vol. 14, pp. 154-183.

Hillaire-Buys, D. et al., Pharmacological Evaluation and Chemical Stability of 2-benzylthieoether-5'-O-(1-thiotriphosphate)-Adenosine, A New Insulin Secretagogue Acting Through P2Y Receptors, Drug Development Research, 2001, vol. 53, No. 1, pp. 33-43.

Hong, J. A. et al., Identification of Critical Ligand Binding Determinants in *Mycrobacterium tuberculosis* Adenosine-5'-phosphosulfate Reductase, Journal of Medicinal Chemistry, 2009, vol. 52, No. 17, pp. 5485-5495.

Howgate et al., Conversion of 2',3'-O-isopropylideneadenosine into 9-(6-deoxy-β-D-allofuranosyl)- and 9-(6-deoxy-α-L-talofuranosyl) adenines, Carbohydrate Research, 1972, vol. 2, pp. 309-315.

Hrdlicka et al., Synthesis and biological evaluation of branched and conformationally restricted analogs of the anticancer compounds 3'-C-ethynyluridine (EUrd) and 3'-C-ethynylcytidine (ECyd), Bioorganic & Medicinal Chemistry, 2005, vol. 13, vol. 7, pp. 2597-2621.

Hrebabecky et al., Synthesis of 1-(3-azido-2,3-dideoxy-B-D-allofuranosyl)thymine, 1-(2,3-dideoxy-B-D-allofuranosyl)thymine, and 1-(2,3-dideoxy-B-D-erythro-hex-2-enofuranosyl)thymine, Carbohydrate Research, 1991, vol. 216, pp. 179-186.

Huang et al., Recent development of therapeutics for chronic HCV infection, Antiviral Research, 2006, vol. 71, Issue 2&3, pp. 351-362.

Hung et al., A New Nonhydrolyzable Reactive cGMP Analogue, (Rp)-Guanosine-3' ,5'-cyclic-S-(4-bromo-2,3-dioxobutyl) monophosphorothioate Which Targets the cGMP Binding Site of Human Platelet PDE3A, Bioorganic Chemistry, 2008, vol. 36, Issue 3, Elsevier Inc., pp. 141-147.

Hung et al., A new nonhydrolyzable reactive cAMP analog, (Sp)-adenosine-3' ,5' -cyclic-S-(4-bromo-2,3-dioxobutyl) monophosphorothioate irreversibly inactivates human platelet cGMP-inhibited cAMP phosphodiesterase, Bioorganic Chemistry, 2002, vol. 30, vol. 1, pp. 16-31.

Hung et al., New insights from the structure-function analysis of the catalytic region of human platelet phosphodiesterase 3A: A role for the unique 44-amino acid insert, Journal of Biological Chemistry, 2006, vol. 281, Issue 39, pp. 29236-29244.

Hung et al., A nonhydrolyzable reactive cAMP analogue, (Sp)-8-[4-bromo-2,3-dioxobutyl) thio]adenosine 3', 5'-cyclic S-(methyl) monophosphorothioate, irreversibly inactivates human platelet cGMP-inhibited cAMP phosphodiesterase at micromolar concentrations, Biochemistry, 2002, vol. 41, Issue 9, pp. 2962-2969.

Iimori et al., A study on conformationally restricted sangivamycins and their inhibitory abilities of protein kinases, Nucleic Acids Symposium Series, 1992, vol. 27, pp. 169-170.

Iimori et al., 2'-C-, 3'-C-, and 5'-C-Methylsangivamycins: Conformational lock with the methyl group, Tetrahedron Letters, 1991, vol. 32, Issue 49, pp. 7273-7276.

IUPAC-IUB Commission on Biochemical Nomenclature, Biochemistry, 1972, vol. 11, pp. 942-944.

Jacobson et al., Structure-activity relationships of 9-alkyladenine and ribose-modified adenosine derivatives at rat A3 adenosine receptors, Journal of Medicinal Chemistry, 1995, vol. 38, Issue 10, pp. 1720-1735.

Kappler et al., Isozyme-specific enzyme inhibitors. 10. Adenosine 5'-triphosphate derivatives as substrates or inhibitors of methionine adenosyltransferases of rat normal and hepatoma tissues, Journal of Medicinal Chemistry, 1986, vol. 29, Issue 3, pp. 318-322.

Kappler et al., Species- or isozyme-selective enzyme inhibitors. 8. Synthesis of disubstituted two-substrate condensation products as inhibitors of rat adenylate kinases, Journal of Medicinal Chemistry, 1982, vol. 25, Issue 10, pp. 1179-1184.

Karpeiskii et al., Conformational analogs of nucleotides. V. Synthesis of 5'-C-methylnucleosides from 6-deoxy-D-allose, Bioorganicheskaya Khimiya, 1979, vol. 5, No. 6, pp. 895-905.

Karpeiskii et al., Conformational analogs of nucleotides. V. Synthesis of 5'-C-methylnucleosides from 6-deoxy-D-allose, Soviet Journal of Bioorganic Chemistry (a translation of Bioorganicheskaya Khimiya), 1979, vol. 5, No. 1, pp. 672-680.

Karpeiskii et al., Study of substrate specificity of nuclease S1 from *Aspergillus oryzae* in the hydrolysis of low molecular weight substrates, Bioorganicheskaya Khimiya, 1982, vol. 8, Issue 3, pp. 385-395.

Karpeiskii et al., A study of substrate specificity of nuclease S1 from *Aspergillus oryzae* in the hydrolysis of low-molecular-weight substrates, Soviet Journal of Bioorganic Chemistry (a translation of Bioorganicheskaya Khimiya), 1983, vol. 8, Issue 3, pp. 196-204.

Karpeiskii et al., Snthesis of 5'-C-methyluridines (D-allo and L-talo), 5'-mono-, di- and triphosphates, and dinucleoside phosphates on their basis, Nucleic Acids Symposium Series, 1981, Issue 9, pp. 157-160.

Karpeiskii et al., Synthesis of 5'-mono-, di- and triphosphates of 5'-C-methyluridines, Bioorganicheskaya Khimiya, 1982, vol. 8, Issue 7, pp. 933-939.

Karpeiskii et al., Synthesis of 5'-mono-, 5'-di- and 5'-triphosphates of 5'-C-methyluridines, Soviet Journal of Bioorganic Chemistry (a translation of Bioorganicheskaya Khimiya), 1983, vol. 8, Issue 7, pp. 498-504.

Kett et al., Heterocyclic derivatives of sugars: An NMR study of the formation of 1-glycosyl-3, 5-dimethyl-1H-pyrazoles from hydrazones, Carbohydrate Research, 1997, vol. 299, Issue 3, pp. 129-141.

(56) References Cited

OTHER PUBLICATIONS

Kim et al., The effect of thalidomide and its derivatives on thyroxine-induced metamorphosis of tadpole, Canadian Journal of Biochemistry and Physiology, 1965, vol. 43, Issue 6, pp. 769-779.
Klumpp et al., The novel nucleoside analog R1479 (4'-azidocytidine) is a potent inhibitor of NS5B-dependent RNA synthesis and hepatitis C virus replication in cell culture, Journal of Biological Chemistry, 2006, vol. 281, Issue 7, pp. 3793-3799.
Krakowiak et al., Stereochemistry of rHint1 hydrolase assisted cleavage of P-N bond in nucleoside 5'-O-phosphoramidothioates, Chemical Communications, 2007, vol. 21, pp. 2163-2165.
Kiuru et al., Synthesis and enzymatic deprotection of biodegradably protected dinucleoside-2',5'-monophosphates: 3-(acetyloxy)-2,2-bis(ethoxycarbonyl)propyl phosphoesters of 3'-O-(acyloxymethyl)adenylyl-2',5'-adenosines, Chemistry and Biodiversity, 2011, vol. 8, Issue 2, pp. 266-286.
Lau et al., Synthesis and evaluation of antiviral activity of L-acosamine and L-ristosamine nucleosides of furanose configuration, Acta Chemica Scandinavica, 1991, vol. 45, Issue 6, pp. 616-620.
Leisvouri et al., Chemical and enzymatic stability of amino acid derived phosphoramidates of antiviral nucleoside 5'-monophosphates bearing a biodegradable protecting group, Organic and Biomolecular Chemistry, 2010, vol. 8, Issue 9, pp. 2131-2141.
Lepage et al., Metabolism of purine nucleoside analogs, Cancer Research, 1965, vol. 25, pp. 46-52.
Lerner, 9-α-L-Rhamnofuranosyladenine. An improved synthesis of a 6-deoxyhexofuranosyl nucleoside, Nucleic Acid Chem., 1991, vol. 4, pp. 274-280.
Lerner, 9-(6-Deoxyhexofuranosyl) adenine nucleosides. Further studies on the acetolysis of hexofuranosides, Journal of Organic Chemistry, 1978, vol. 43, Issue 5, pp. 962-965.
Lerner, Adenine nucleosides derived from 6-deoxyhexofuranoses, Journal of Organic Chemistry, 1976, vol. 41, Issue 2, pp. 306-310.
Lerner, Interconversions of hexofuranosyl nucleosides. IV. Synthesis of nucleosides derived from 6-deoxy-L-glucose, Journal of Organic Chemistry, 1972, Issue 37, vol. 26, pp. 4386-4391.
Lerner, Interconversions of hexofuranosyl nucleosides. V. Synthesis and reexamination of the structure of 9-(6-deoxy-α-L-mannofuranosyl) adenine, Journal of Organic Chemistry, 1973, vol. 21, pp. 3704-3709.
Lerner et al., Preparation and antileukemic screening of some new 6'-deoxyhexopyranosyladenine nucleosides, J. Med. Chem., 1987, vol. 30, Issue 8, pp. 1521-1525.
Lerner, Preparation of nucleosides via isopropylidene sugar derivatives. V. Coupling reactions using the titanium tetrachloride method, Carbohydrate Research, 1970, vol. 14, Issue 3, pp. 297-303.
Lerner, Synthesis of 9-α-D-rhamofuranosyladenine, Carbohydrate Research, 1974, vol. 38, pp. 328-332.
Lesiak et al., A new approach to syntheses of organic phosphoroselenoates and phosphorodiselenoates. Proof of absolute configuration assignment in diastereomers of cTMPS [thymidine cyclic 3',5'-phosphorothioates], Polish Journal of Chemistry, 1979, vol. 53, Issue 10, pp. 2041-2050.
Lesnikowski et al., A simple procedure for synthesis of diastereoisomers of thymidine cyclic 3',5'-phosphate derivatives, Nucleic Acids Symposium Series, 1987, vol. 18, pp. 273-276.
Lesnikowski et al., Some aspects of the electron impact induced fragmentation of diastereoisomeric thymidine cyclic 3',5'-phosphoranilidothioates, Organic Mass Spectrometry, 1980, vol. 15, Issue 9, pp. 454-455.
Lin, C. et al. Synthesis of Dinucleotide Thiophosphoramidates as Anti-HIV New Prodrugs, Synthesis, 2003, No. 13, pp. 1989-1994.
Lin et al., Novel 3', 5'-cyclic nucleotide analog. Adenosine 3' ,5'-cyclic boranomonophosphate, Organic Letters, 2001, vol. 3, pp. 795-797.
Long et al., Structure-activity relationship for adenosine kinase from *Mycobacterium tuberculosis*. II. Modifications to the ribofuranosyl moiety, Biochemical Pharmacology, 2008, vol. 75, Issue 8, pp. 1588-1600.

Malmsjo et al., "Characterization of Contractile P2 Receptors in Human Coronary Arteries by Use of the Stable Pyrimidine Uridine 5'-O-Thiodisphosphate and Uridine 5'-O-3-Thiotriphosphate" *J. Pharmcology and Experimental Therapeutics* (2000), 293(3):755-760.
Markiewicz et al., The reaction of 1,3-dichloro-1,1,3,3-tetraisopropyldisiloxane with cytosine arabinoside and 1-(6-deoxy-α-L-talofuranosyl) uracil, Collection of Czechoslovak Chemical Communications, 1980, vol. 45, Issue 6, pp. 1860-1865.
Marx et al., Synthesis of 4'-C-acylated thymidines, Helvetica Chimica Acta, 1996, vol. 79, Issue 7, pp. 1980-1994.
McGuigan et al., Phosphate prodrugs derived from N-acetyglucosamine have enhanced chondroprotective activity in explant cultures and represent a new lead in antiosteoarthritis drug discovery, Journal of Medicinal Chemistry, 2008, vol. 51, Issue 18, pp. 5807-5812.
McKenzie et al., Characteristics of the relaxant response of adenosine and its analogs in intestinal smooth muscle, European Journal of Pharmacology, 1977, vol. 41, Issue 2, pp. 183-191.
McKenzie et al., Effects of adenosine and related compounds on adenylate cyclase and cyclic AMP levels in smooth muscle, European Journal of Pharmacology, 1977, vol. 41, Issue 2, pp. 193-203.
McKenzie et al., Hepatic failure and lactic acidosis due to fialuridine (FIAU), an investigational nucleoside analogue for chronic hepatitis B, New England Journal of Medicine, 1995, vol. 333, pp. 1099-1105.
McMurry, Organic Chemistry, 5th ed., Brooks/Cole, Pacific Grove, CA (2000), Chapter 11.5, pp. 398 & 408.
McOmie, Protective Groups in Organic Chemistry, Plenum Press (1973), Cover & Contents pages only.
Miao et al., One pot synthesis of aryl thiophosphoramidate derivatives of AZT, Synthetic Communications, 2002, vol. 32, Issue 21, pp. 3301-3309.
Miao et al., A stepwise one pot synthesis of alkyl thiophosphoramidate derivitaves of nucleosides, Synthetic Communications, 2002, vol. 32, Issue 8, pp. 1159-1167.
Miao et al., One pot synthesis of nucleoside 5'-thiophosphoramidates, Synthetic Communications, 2002, vol. 32, Issue 7, pp. 1069-1076.
Mikhailov, Conformational analogs of nucleotides. Synthesis of 5'-C-methyl nucleosides, Sint. Issled. Biol. Soedin., Tezisy Dokl. Konf. Molodykh Uch., 1978, vol. 6, pp. 38-39.
Mikhailov et al., Conformational peculiarities of 5'-C-methylnucleosides, Bioorganicheskaya Khimiya, 1989, vol. 15, Issue 7, pp. 969-975.
Mikhailov et al., Conformational features of 5'-C-methylnucleosides, Soviet Journal of Bioorganic Chemistry (a translation of Bioorganicheskaya Khimiya), 1990, vol. 15, Issue 7, pp. 532-538.
Misiura et al., Synthesis, chemical and enzymatic reactivity, and toxicity of dithymidylyl-3',5'-phosphorofluoridate and -phosphorothiofluoridate, Bioorganic & Medicinal Chemistry, 2001, vol. 9, Issue 6, pp. 1525-1532.
Murai et al., A synthesis and an x-ray analysis of 2'-C-, 3'-C- and 5'-C-methylsangivamycins, Heterocycles, 1992, vol. 33, Issue 1, pp. 391-404.
Myers et al., Synthetic studies of the tunicamycin antibiotics. Preparation of (+)-tunicaminyluracil, (+)-tunicamycin-V, and 5'-epi-tunicamycin-V, Journal of the American Chemical Society, 1994, vol. 116, Issue 11, pp. 4697-4718.
Nelson et al., Synthesis and antitumor activity of 7- and 9-(6'-deoxy-α-L-talofuranosyl)-hypoxathine and 9-(6'-deoxy-α-L-talofuranosyl)-6-thiopurine, Journal of Medicinal Chemistry, 1983, vol. 26, Issue 10, pp. 1527-1530.
Nelson et al., Synthesis of hypoxanthine, guanine, and 6-thiopurine nucleosides of 6-deoxy-D-allofuranose, Journal of Medicinal Chemistry, 1983, vol. 26, Issue 7, pp. 1071-1074.
Nelson et al., Synthesis of methyl 3,5-di-O-benzoyl-2,6-dideoxy-β-L-lyxo-hexofuranoside, a nucleoside precursor, Carbohydrate Research, 1983, vol. 124, Issue 1, pp. 161-165.
Nutt et al., Branched-chain sugar nucleosides. II. 5',5'-Di-C-methyladenosine, Journal of Medicinal Chemistry, 1968, vol. 11, Issue 1, pp. 151-153.

(56) References Cited

OTHER PUBLICATIONS

Oivanen et al., Hydrolysis of isomeric cytidyl-(3',5')-5'-C-methyluridines by acids, bases and metal ions: Steric effects in the hydrolysis of the phosphodiester bonds of RNA, Acta Chemica Scandinavica, 1995, vol. 49, Issue 4, pp. 307-310.

Ora et al., Hydrolytic stability of nucleoside phosphotriesters derived from bis(hydroxymethyl)-1,3-dicarbonyl compounds and their congeners: Towards a novel pro-drug strategy for antisense oligonucleotides, J. Chem. Soc. Perkin Trans. 2, 2001, vol. 6, pp. 881-885.

Ora et al., Biodegradable protections for nucleoside 5'-monophosphates: Comparative study on the removal of O-acetyl and O-acetyloxymethyl protected 3-hydroxy-2,2-bis(ethoxycarbonyl)propyl groups, Journal of Organic Chemistry, 2009, vol. 74, Issue 14, pp. 4992-5001.

Padyukova et al., Synthesis of thymidine 5'-derivatives, Bioorganicheskaya Khimiya, 1990, vol. 16, Issue 5, pp. 668-673.

Padyukova et al., Synthesis of 5'-derivatives of thymidine, Soviet Journal of Bioorganic Chemistry (a translation of Bioorganicheskaya Khimiya), 1991, vol. 16, Issue 5, pp. 370-375.

Padyukova et al., Synthesis of dinucleoside phosphates containing 5'-O-bonded 1-(6-deoxy-β-D-allofuranosyl) uracil and 1-(6-deoxy-α-L-talofuranosyl) uracil, Collection of Czechoslovak Chemical Communications, 1980, vol. 45, Issue 9, pp. 2550-2557.

Panova et al., Substrate specificity of *Escherichia coli* thymidine phosphorylase, Biochemistry, 2007, vol. 72, Issue 1, pp. 21-28.

Parker et al., Design and evaluation of 5'-modified nucleoside analogs as prodrugs for an *E. coli* purine nucleoside phosphorylase mutant, Nucleosides Nucleotides and Nucleic Acids, 2005, vol. 24, Issues 5/6/7, pp. 387-392.

Poijärvi et al., Towards nucleotide prodrugs derived from 2,2-bis(hydroxymethyl)malonate and its congeners: Hydrolytic cleavage of 2-cyano-2-(hydroxymethyl)-3-methoxy-3-oxopropyl and 3-(alkylamino)-2-cyano-2-(hydroxymethyl)-3-oxopropyl protections from the internucleosidic phosphodiester and phosphorothioate linkages, Hely. Chim Acta., 2002, vol. 85, pp. 1869-1876.

Poijärvi et al., Towards oligonucleotide pro-drugs: 2,2-Bis(ethoxycarbonyl) and 2-(alkylaminocarbonyl)-2-cyano substituted 3-(pivaloyloxy)propyl groups as biodegradable protecting groups for internucleosidic phosphoromonothioate linkages, Lett. Org. Chem., 2004, vol. 1, pp. 183-188.

Poijärvi et al., 2,2-Bis(ethoxycarbonyl)- and 2-(alkylaminocarbonyl)-2-cyano-substituted 3-(pivaloyloxy)propyl groups as biodegradable phosphate protections of oligonucleotides, Bioconjugate Chem., 2005, vol. 16, pp. 1564-1571.

Prakash et al., Synthesis and evaluation of S-acyl-2-thioethyl esters of modified nucleoside 5'-monophosphates as inhibitors of hepatitis C virus RNA replication, Journal of Medicinal Chemistry, 2005, vol. 48, Issue 4, pp. 1199-1210.

Pravdina et al., Inhibition by nucleoside 5'-triphosphate analogs of RNA synthesis catalyzed by RNA polymerase of influenza A virus, Molekulyarnaya Genetika, Mikrobiologiya I Virusologiya, 1990, vol. 11, pp. 22-25.

Ranganathan et al., Model analogs of nucleoside 3', 5'-cyclic phosphates. I. 5'-Mono- and dimethyl analogs of adenosine 3',5'-cyclic phosphate, Journal of Organic Chemistry, 1974, vol. 39, Issue 3, pp. 290-298.

Reimer et al., Inhibition of hepatitis B virus DNA polymerase by thymidine triphosphate analogs in vitro, Antiviral Chemistry and Chemotherapy, 1991, vol. 2, Issue 4, pp. 249-253.

Reist et al., Potential anticancer agents. LXXVII. Synthesis of nucleosides of purine-6-thiol (6-mercaptopurine) containing "fraudulent" sugars, Journal of Organic Chemistry, 1962, vol. 27, pp. 3279-3283.

Reist et al., Potential anticancer agents. VIII. Synthesis of nucleosides derived from L-talofuranose, Journal of the American Chemical Society, 1958, vol. 80, pp. 5775-5779.

Reist et al., Potential anticancer agents. IV. Synthesis of nucleosides derived from 6-deoxy-D-allofuranose, Journal of the American Chemical Society, 1958, vol. 80, pp. 3962-3966.

Reist et al., Potential anticancer agents. XI. Synthesis of nucleosides derived from 6-deoxy-L-idofuranose, Journal of Organic Chemistry, 1958, vol. 23, pp. 1757-1760.

Reist et al., Potential anticancer agents. X. Synthesis of nucleosides derived from 6-deoxy-D-glucofuranose, Journal of Organic Chemistry, 1958, vol. 23, pp. 1753-1757.

Roche, Bioreversible carriers in drug design: Theory and application, Pergamon Press: New York, 1987, pp. 14-21.

Saha et al., 5'-Methyl-DNA—A new oligonucleotide analog. Synthesis and biochemical properties, Journal of Organic Chemistry, 1995, vol. 60, Issue 4, pp. 788-789.

Sakai et al., Isolation from *Nocardioides* sp. strain CT16, purification, and characterization of a deoxycytidine deaminase extremely thermostable in the presence of D,L-dithiothreitol, Biosci. Biotechnol. Biochem., 2002, vol. 66, Issue 8, pp. 1646-1651.

Scott et al., Mapping ligand interactions with the hyperpolarization activated cyclic nucleotide modulated (HCN) ion channel binding domain using a soluble construct, Biochemistry, 2007, vol. 46, Issue 33, pp. 9417-9431.

Secrist et al., Gene therapy of cancer: Activation of nucleoside prodrugs with *E. coli* purine nucleoside phosphorylase, Nucleosides & Nucleotides, 1999, vol. 18, Issue 4&5, pp. 745-757.

Severe Toxicity of Fialuridine (letters to the editor), New England Journal of Medicine, 1996, vol. 334, pp. 1135-1138.

Shaw et al., Mass spectrometry of nucleic acid components Analogs of adenosine, Journal of the American Chemical Society, 1970, vol. 92, Issue 8, pp. 2510-2522.

Sheid et al., Enzymatic formation of potential anticancer and antiviral inosine analogs, Experientia, 1996, vol. 52, Issue 9, pp. 878-881.

Shigeura et al., Structural basis for phosphorylation of adenosine congeners, Nature, 1967, vol. 215, Issue 5099, pp. 419-420.

Shuto et al., Stereo- and regioselective introduction of 1- or 2-hydroxyethyl group via intramolecular radical cyclization reaction with a novel silicon-containing tether. An efficient synthesis of 4'α-branched 2'-deoxyadenosines, Journal of Organic Chemistry, 1998, vol. 63, Issue 3, pp. 746-754.

Smith et al., The design, synthesis, and antiviral activity of monofluoro and difluoro analogues of 4'-azidocytidine and against hepatitis C virus replication: The discovery of 4'-azido-2'-deoxy-2'-fluorocytidine and 4'-azido-2'-dideoxy-2',2'-difluorocytidine, Journal of Medicinal Chemistry, 2009, vol. 52, pp. 2971-2978.

Sopchik et al., Facile preparation of the individual diastereoisomers of thymidine 3',5'-cyclic phosphorothioate (cTMPS), Tetrahedron Letters, 1981, vol. 22, Issue 4, pp. 307-310.

Spormann et al., Synthesis and photoreaction of 4'-pivaloyl guanosides, Synthesis, 2001, vol. 14, pp. 2156-2164.

Srivastava et al., Enantiomeric forms of 9-(5,6-dideoxy-α-D-arabino-hex-5-enofuranosyl) adenine and preparation of 9-(6-deoxy-β-D-galactofuranosyl) adenine. Further results with the acetolysis of hexofuranosides, Tetrahedron, 1978, vol. 34, Issue 17, pp. 2627-2631.

Streitwieser et al., Introduction to Organic Chemistry, 3rd ed., Macmillan Publishing Co. Inc., New York, NY, 1985, pp. 113-139.

Streitwieser et al., Introduction to Organic Chemistry, 2nd ed., Macmillan Publishing Co. Inc., New York, NY, 1981, pp. 169-171.

Sun et al., Effects of cGMP, cAMP and two other cAMP derivatives on the transcription system of isolated rat liver nuclei, Shengwu Huaxue Zazhi, 1987, vol. 3, Issue 5, pp. 455-461.

Tian et al., Synthesis of 8-chloroadenosine 3',5'-cyclophosphotriesters and phosphoramidates, Progress in Natural Science, 1994, vol. 4, Issue 6, pp. 726-731.

Tomassini et al., Inhibitory effect of 2'-substituted nucleosides on hepatitis C virus replication correlates with metabolic properties in replicon cells, Antimicrobial Agents and Chemotherapy, 2005, vol. 49, Issue 5, pp. 2050-2058.

Tomei et al., HCV antiviral resistance: The impact of in vitro studies on the development of antiviral agents targeting the viral NS5B polymerase, Antiviral Chemistry and Chemotherapy, 2005, vol. 16, Issue 4, pp. 225-245.

Trafelet et al., Synthesis of (5'S)-5'-C-alkyl-2'-deoxynucleosides, Helvetica Chimica Acta, 2001, vol. 84, Issue 1, pp. 87-105.

(56) References Cited

OTHER PUBLICATIONS

Tunitskaya et al., Substrate properties of C'-methyl UTP derivatives in T7 RNA polymerase reactions. Evidence for N-type NTP conformation, FEBS Letters, 1997, vol. 400, Issue 3, pp. 263-266.

Ueno et al., Nucleosides and nucleotides. 174. Synthesis of oligodexynucleotides containing 4'-C-[2-[[N-(2-aminoethyl)carbamoyl]oxy]ethyl]thymidine and their thermal stability and nuclease-resistance properties, Journal of Organic Chemistry, 1998, vol. 63, Issue 5, pp. 1660-1667.

Venkatachalam et al., A comparative study of the hydrolysis pathways of substituted aryl phosphoramidate versus aryl thiophosphoramidate derivatives of stavudine, European Journal of Medicinal Chemistry, 2004, vol. 39, pp. 665-683.

Vilar et al., Probabilistic neural network model for the in silico evaluation of anti-HIV activity and mechanism of action, Journal of Medicinal Chemistry, 2006, vol. 49, Issue 3, pp. 1118-1124.

Walczak et al., Synthesis of 1-(3-(1,2,4-triazol-1-yl)-2,3,6-trideoxy-L-arabino-hexofuranosyl) uracils via an α, β-unsaturated aldehydohexose, Monatshefte für Chemie, 1992, vol. 123, Issue 4, pp. 349-354.

Wang et al., Study on the structure-activity relationship of new anti-HIV nucleoside derivatives based on the Support Vector Machine method, QSAR & Combinatorial Science, 2007, vol. 26, Issue 2, pp. 161-172.

Wang et al., Synthesis and cytokine modulation properties of pyrrolo [2,3-d]-4-pyrimidone nucleosides, Journal of Medicinal Chemistry, 2000, vol. 43, Issue 13, pp. 2566-2574.

Wu et al., The cyclophosphorylation of adenosine, Huaxue Xuebao, 1986, vol. 44, Issue 6, pp. 635-638.

Yakovlev et al., Stereoelectronic effects in the enzymatic cleavage of dinucleoside phosphates by Rnases, Bioorganicheskaya Khimiya, 1985, vol. 11, Issue 2, pp. 205-210.

Yakovlev et al., Stereoelectronic effects in the reactions involved in the enzymatic cleavage of dinucleoside phosphates by Rnases, Soviet Journal of Bioorganic Chemistry (a translation of Bioorganicheskaya Khimiya), 1985, vol. 11, Issue 2, pp. 107-112.

Yakovlev et al., Stereoelectronic effects in Rnase-catalyzed reactions of dinucleoside phosphate cleavage, FEBS Letters, 1985, vol. 179, Issue 2, pp. 217-220.

Zinchenko et al., 2'-, 3'- and 5'-C-Methyl derivatives of uridine in the reaction of microbiological transglycosylation, Doklady Akademii Nauk SSSR, 1987, vol. 297, Issue 3, pp. 731-734.

Zinchenko et al., Substrate specificity of uridine and purine nucleoside phosphorylases of *Escherichia coli* whole cells, Biopolimery I Kletka, 1988, vol. 4, Issue 6, pp. 298-302.

Zinchenko et al., Substrate specificity of uridine and purine nucleoside phosphorylases of the whole cells of *Escherichia coli*, Nucleic Acids Symposium Series, 1987, vol. 18, Issue 7, pp. 137-140.

International Search Report and Written Opinion issued on Mar. 15, 2013 in PCT Application No. PCT/US2012/071064, filed on Dec. 20, 2012.

Reutenauer, J. et al., "Investigation of Debio 025, a cyclophilin inhibitor, in the dystrophic *mdx* mouse, a model for Duchenne muscular dystrophy" British J. Pharmacology (2008) 155:574-584.

\* cited by examiner

Figure 1: HCV Protease Inhibitors

| # | Name | Structure |
|---|---|---|
| 1001 | Telaprevir VX-950 | 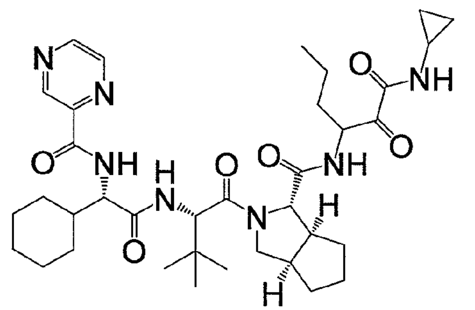 |
| 1002 | MK-5172 | 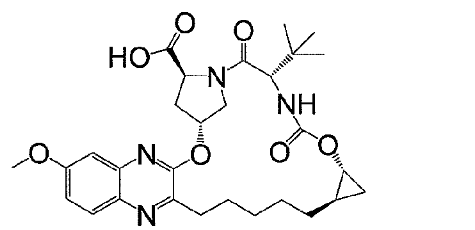 |
| 1003 | ABT-450 | |
| 1004 | BILN-2061 | |
| 1005 | BI-201335 BI335 | |

Figure 1 (cont.): HCV Protease Inhibitors

| # | Name | Structure |
|---|---|---|
| 1013 | TMC-435<br>TMC-435350 | 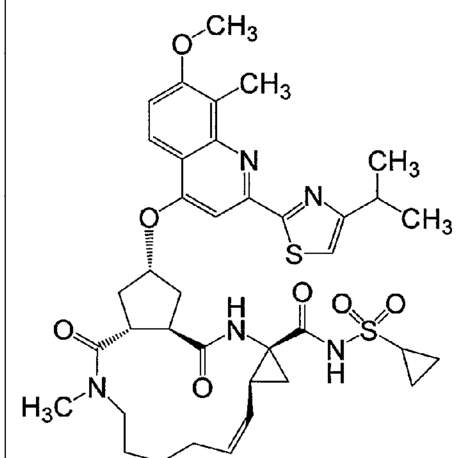 |
| 1014 | Danoprevir<br>ITMN-191<br>RG7227<br>RO5190591 | 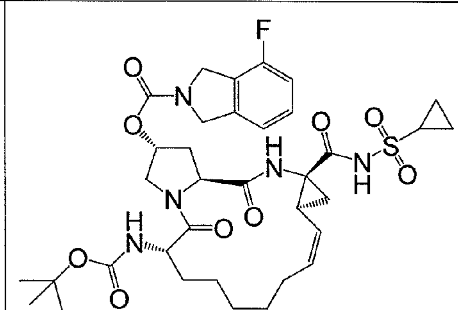 |

| # | Name | Structure |
|---|---|---|
| 1006 | BMS-650032<br>BMS032<br>Asunaprevir | 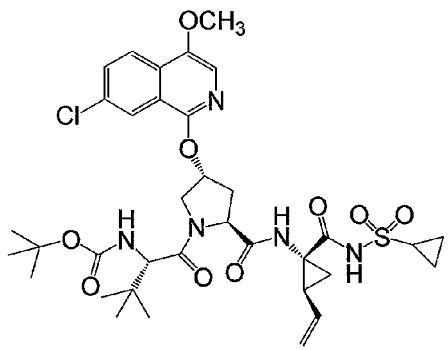 |
| 1007 | Boceprevir<br>SCH 503034 | 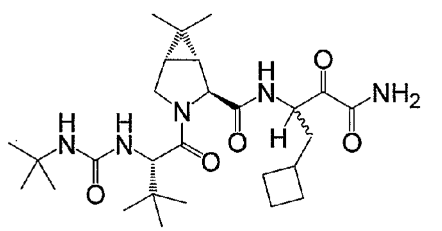 |
| 1008 | GS-9256 | |
| 1009 | GS-9451 | |
| 1010 | IDX-320 | |
| 1011 | ACH-1625 | |
| 1012 | ACH-2684 | |

Figure 1 (cont.): HCV Protease Inhibitors

| # | Name | Structure |
|---|---|---|
| 1015 | MK-7009 Vaniprevir | *(structure shown)* |
| 1016 | PHX1766 | |

Figure 2: HCV Polymerase Inhibitors – Nucleosides, Nucleotides and Analogs Thereof
| # | Name | Structure |
|---|---|---|
| 2001 | RG7128 Mericitabine | 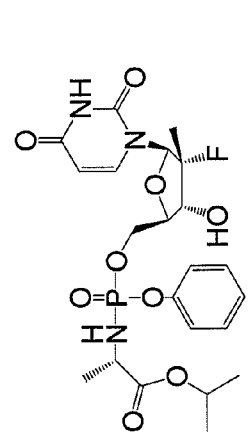 |
| 2002 | PSI-7851 | 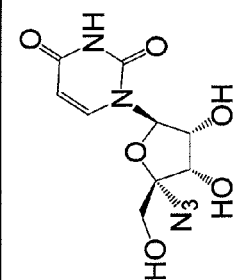 |
| 2003 | PSI-7977 GS-7977, Sofosbuvir | 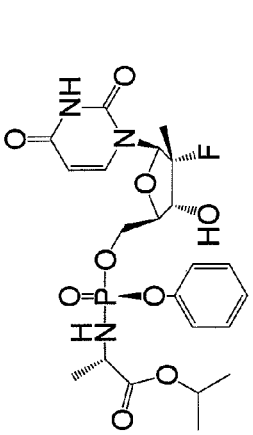 |
| 2004 | PSI-352938 GS-938 | 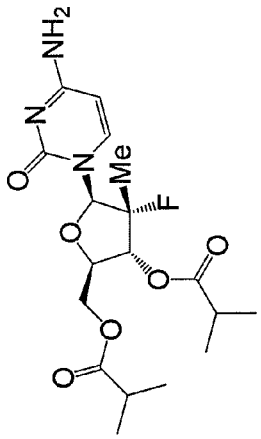 |
| 2005 | 4'-azidouridine and its prodrugs | 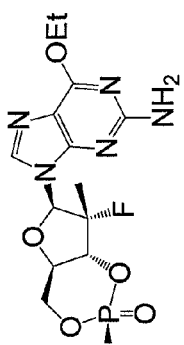 |
| 2006 | PSI-661 | |
| 2007 | GS-6620 | |
| 2008 | TMC649128 | |

Figure 2 (cont.): HCV Polymerase Inhibitors – Nucleosides, Nucleotides and Analogs Thereof

| # | Name | Structure |
|---|---|---|
| 2009 | NM283 | ![structure with NH2, Me, OH, ValO, HO groups on cytidine-like nucleoside] |
| 2010 | BCX5191 | |
| 2011 | IDX19368 | |
| 2012 | IDX19370 | |

Figure 3: HCV Polymerase Inhibitors – Non-Nucleosides

| # | Name | Structure |
|---|---|---|
| 3001 | ABT-333 | |
| 3002 | ANA-598 Setrobuvir | 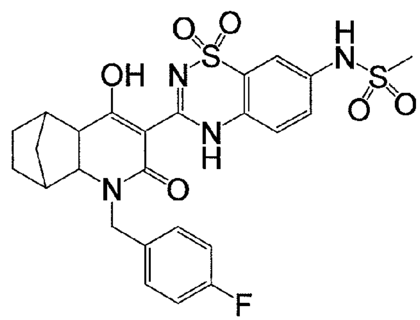 |
| 3003 | VX-222 S1480 VCH-222 | 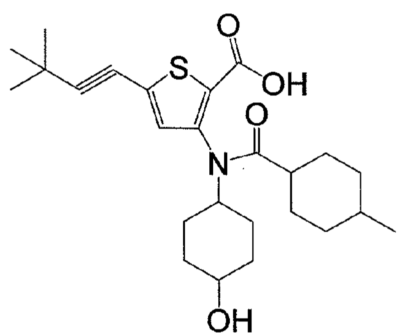 |
| 3004 | HCV-796 | 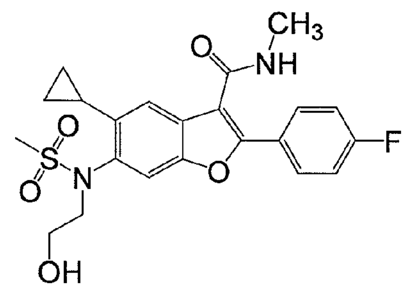 |
| 3005 | BI-207127 | |
| 3006 | GS-9190 | 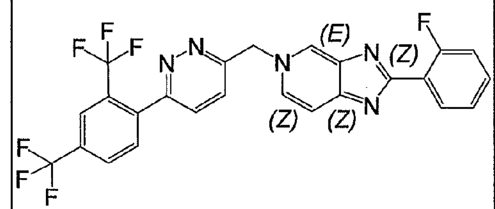 |
| 3007 | Filibuvir PF-00868554 | 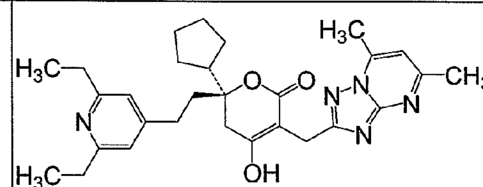 |

Figure 3 (cont.): HCV Polymerase Inhibitors – Non-Nucleosides

| # | Name | Structure |
|---|------|-----------|
| 3008 | VX-497 | (structure shown) |
| 3009 | ABT-072 | |
| 3010 | MK-3281 | |

| # | Name | Structure |
|---|------|-----------|
| 3011 | TMC647055 | |
| 3012 | BMS-791325 | |
| 3013 | PPI-383 | |
| 3014 | GS9669 | |

Figure 4: NS5A Inhibitors

| # | Name | Structure |
|---|---|---|
| 4001 | BMS-790052 BMS052 S1482 Daclatasvir | [structure shown] |
| 4002 | PPI-461 | |
| 4003 | ACH-2928 | |
| 4004 | GS-5885 | |
| 4005 | BMS-824393 | |
| 4006 | ABT 267 | |
| 4007 | ACH-3102 | |
| 4008 | AZD-7295 | |
| 4009 | IDX719 | |
| 4010 | PPI-668 | |
| 4011 | MK8742 | |
| 4012 | GSK805 | |

Figure 5: Other Antivirals
| # | Name | Structure |
|---|---|---|
| 5001 | Debio-025 Alisporivir | |
| 5002 | MIR-122 | |
| 5003 | clemizole | |
| 5004 | ITX 5061 | |
| 5005 | BIT225 | |
| 5006 | NIM811 | |
| 5007 | SCY-635 | |
| 5008 | Nitazoxanide | 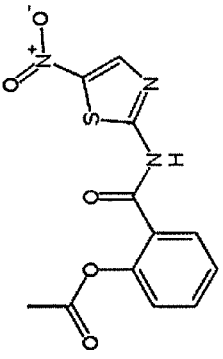 |
| 5009 | Miravirsen | |
| 5010 | Celgosivir | 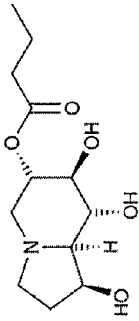 |
| 5011 | GS9620 | |

Figure 6: Compounds of Formula (CC) and alpha-thiotriphosphates thereof

Figure 6 (cont.): Compounds of Formula (CC) and alpha-thiotriphosphates thereof

| # | Structure |
|---|---|
| 6006 | (structure) |
| 6007 | (structure) |
| 6008 | (structure) |
| 6009 | (structure) |

Figure 6 (cont.): Compounds of Formula (CC) and alpha-thiotriphosphates thereof
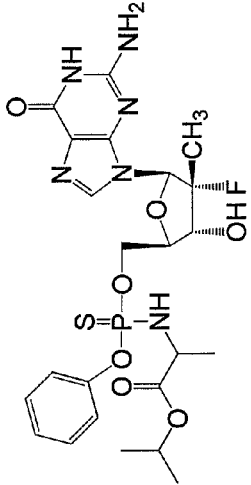

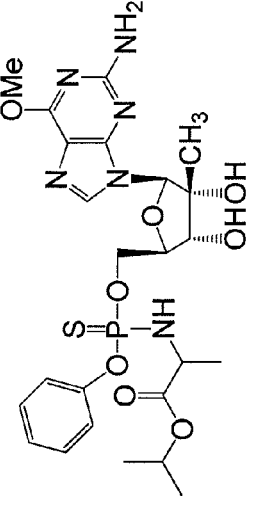
Figure 6 (cont.): Compounds of Formula (CC) and alpha-thiotriphosphates thereof Figure 6 (cont.): Compounds of Formula (CC) and alpha-thiotriphosphates thereof

Figure 6 (cont.): Compounds of Formula (CC) and alpha-thiotriphosphates thereof

Figure 6 (cont.): Compounds of Formula (CC) and alpha-thiotriphosphates thereof

| # | Structure |
|---|---|
| 6037 | 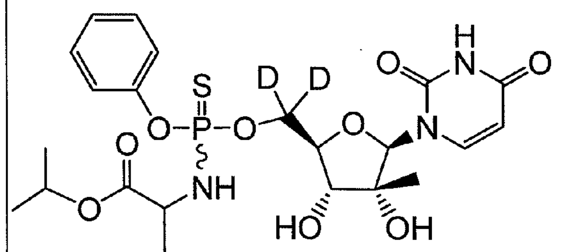 |
| 6038 | 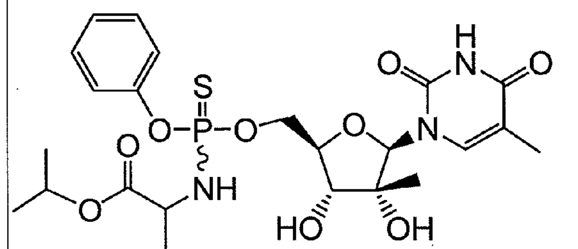 |
| 6039 | 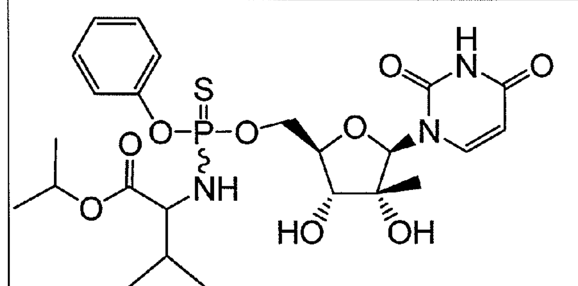 |

| # | Structure |
|---|---|
| 6034 | 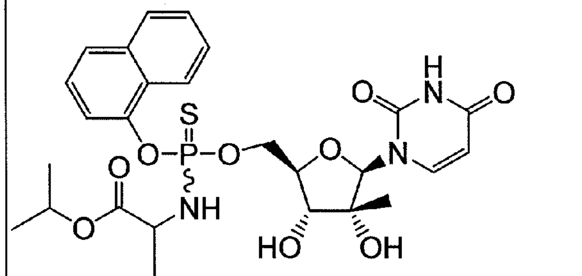 |
| 6035 | 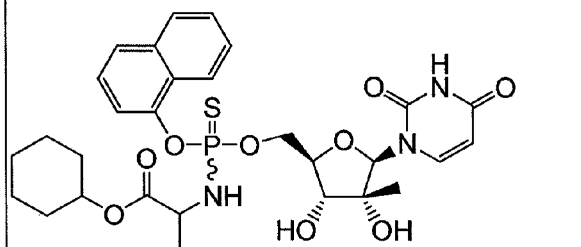 |
| 6036 | 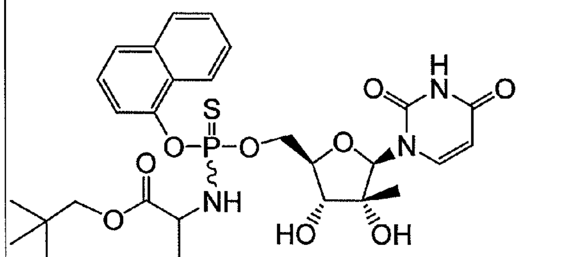 |

Figure 6 (cont.): Compounds of Formula (CC) and alpha-thiotriphosphates thereof
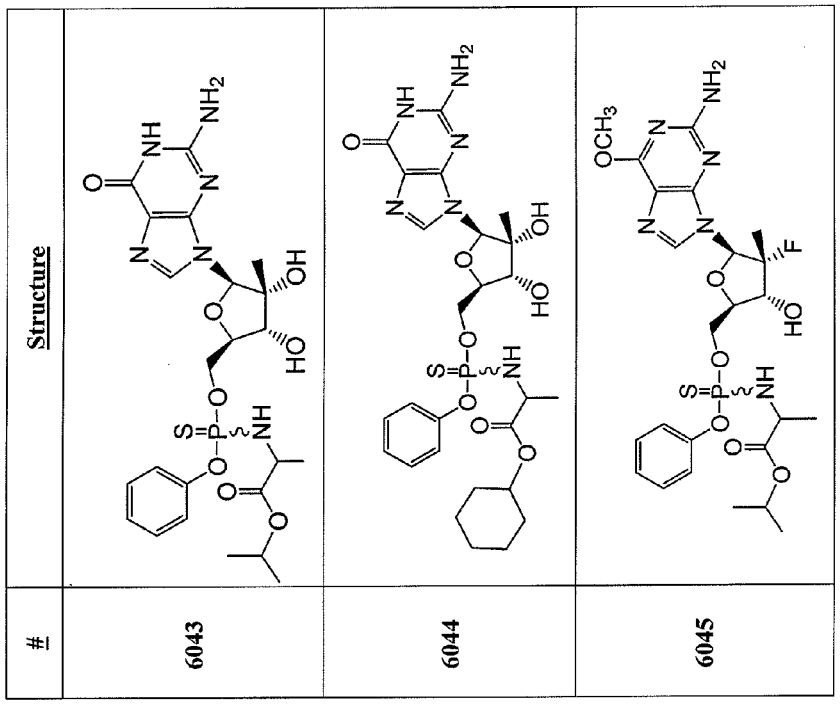
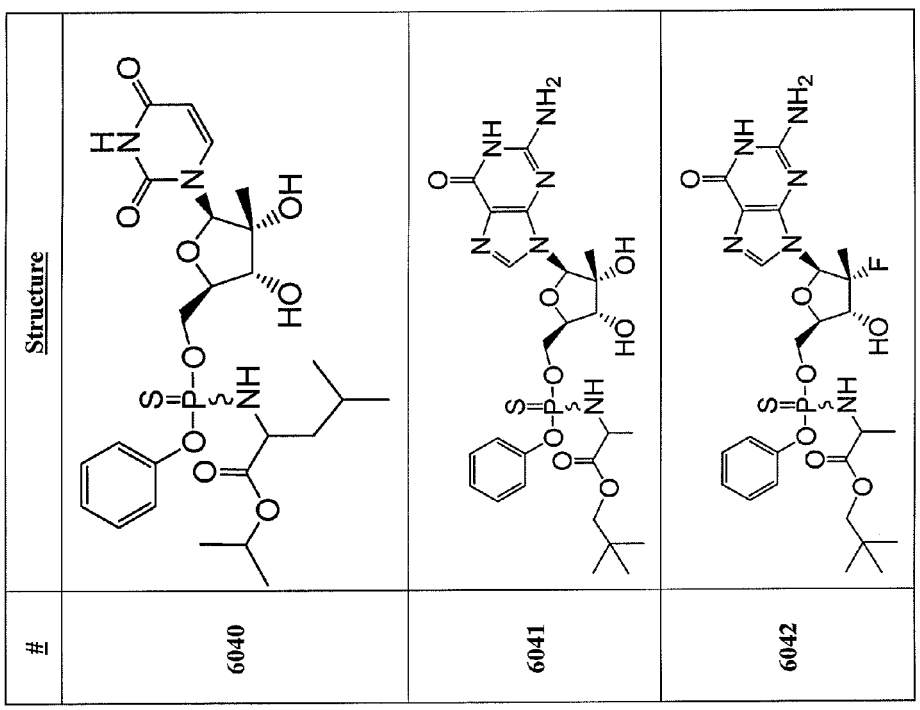

Figure 6 (cont.): Compounds of Formula (CC) and alpha-thiotriphosphates thereof

| # | Structure |
|---|---|
| 6049 | (structure) |
| 6050 | (structure) |
| 6051 | (structure) |

| # | Structure |
|---|---|
| 6046 | (structure) |
| 6047 | (structure) |
| 6048 | (structure) |

Figure 6 (cont.): Compounds of Formula (CC) and alpha-thiotriphosphates thereof

| # | Structure | # | Structure |
|---|---|---|---|
| 6052 | (2-amino-6-aminopurine nucleoside with 2'-methyl, 3'-OH, 5'-O-phosphoramidate: P(=S)(OPh)(NH-CH(CH₃)-C(=O)-O-iPr)) | 6054 | (2-amino-6-chloropurine nucleoside with 2'-methyl, 3'-OH, 5'-O-phosphoramidate: P(=S)(OPh)(NH-CH(CH₃)-C(=O)-O-iPr)) |
| 6053 | (2-amino-6-(allylamino)purine nucleoside with 2'-methyl, 3'-OH, 5'-O-phosphoramidate: P(=S)(OPh)(NH-CH(CH₃)-C(=O)-O-iPr)) | 6055 | (adenine nucleoside with 2'-methyl, 3'-OH, 5'-O-phosphoramidate: P(=S)(OPh)(NH-CH(CH₃)-C(=O)-O-neopentyl)) |

Figure 6 (cont.): Compounds of Formula (CC) and alpha-thiotriphosphates thereof

Figure 6 (cont.): Compounds of Formula (CC) and alpha-thiotriphosphates thereof

Figure 6 (cont.): Compounds of Formula (CC) and alpha-thiotriphosphates thereof

Figure 6 (cont.): Compounds of Formula (CC) and alpha-thiotriphosphates thereof
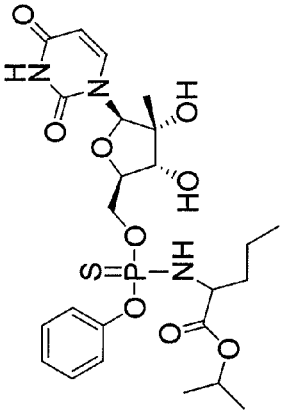

Figure 6 (cont.): Compounds of Formula (CC) and alpha-thiotriphosphates thereof

| # | Structure |
|---|---|
| 6078 | (structure) |

Figure 7: Compounds of Formula (BB)

Figure 7 (cont.): Compounds of Formula (BB)

| # | Structure |
|---|---|
| 7009 | |
| 70010 | |
| 7011 | |
| 7006 | 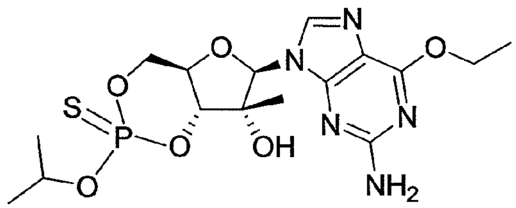 |
| 7007 | 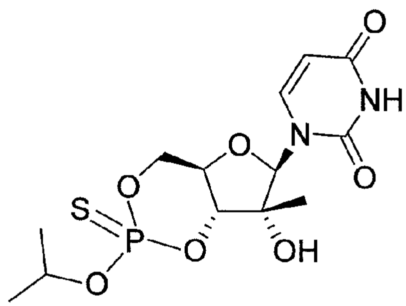 |
| 7008 | 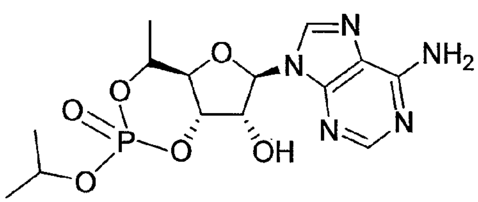 |

Figure 7 (cont.): Compounds of Formula (BB)

| # | Structure |
|---|---|
| 7015 | |
| 7016 | |
| 7012 | 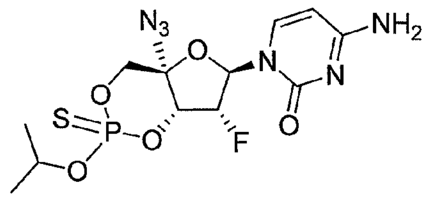 |
| 7013 | 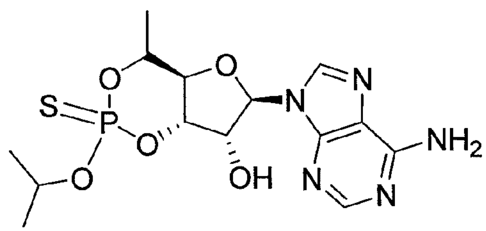 |
| 7014 | 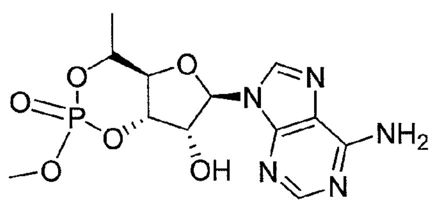 |

Figure 8: Compounds of Formula (I)
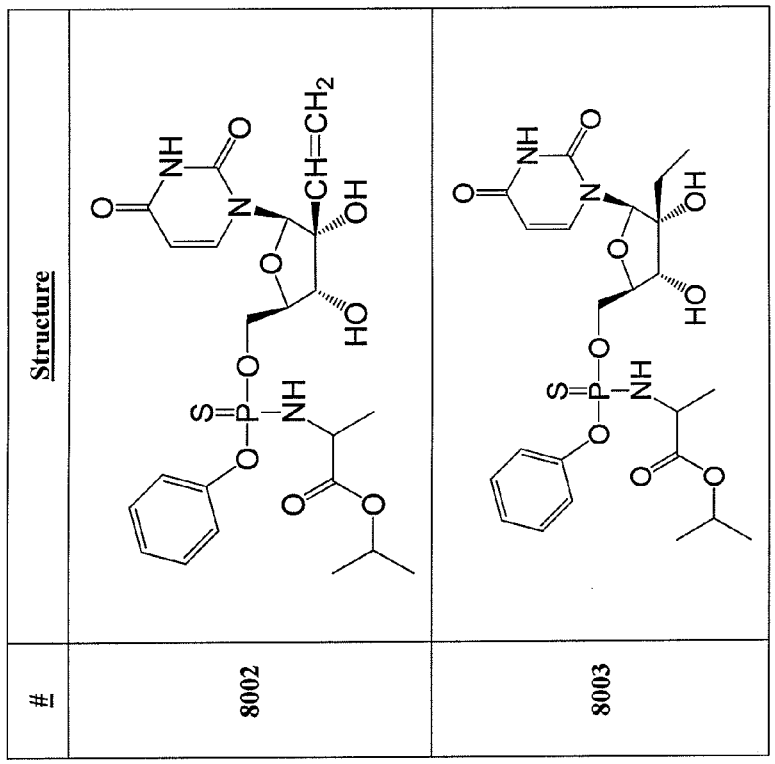
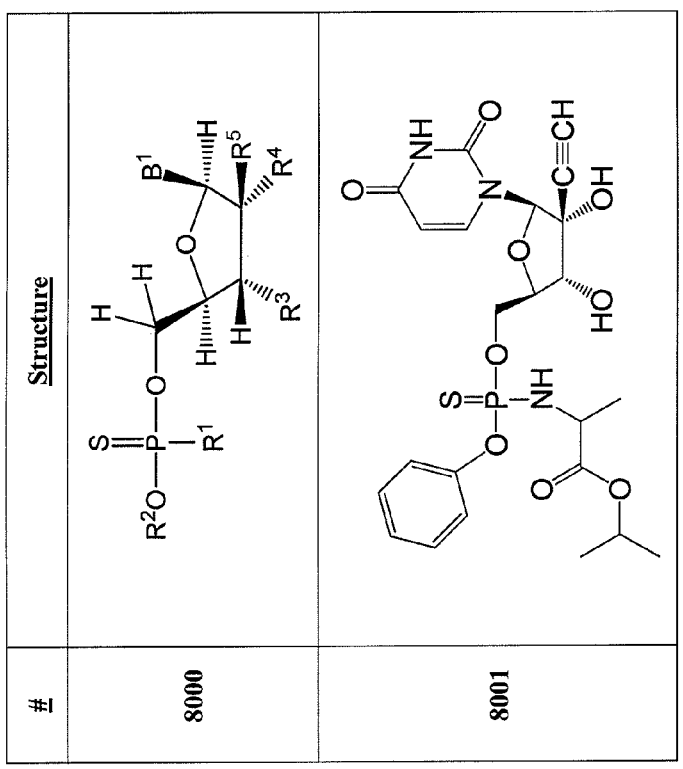

Figure 8 (cont.): Compounds of Formula (I)
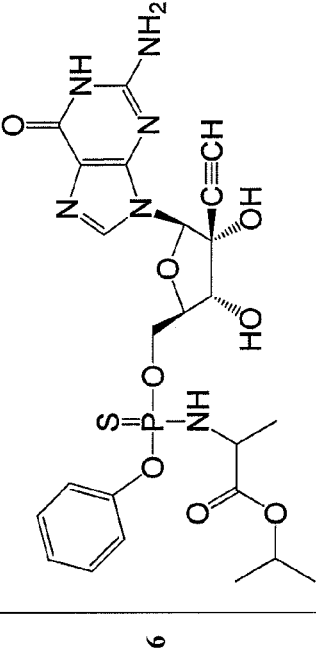

Figure 8 (cont.): Compounds of Formula (I)
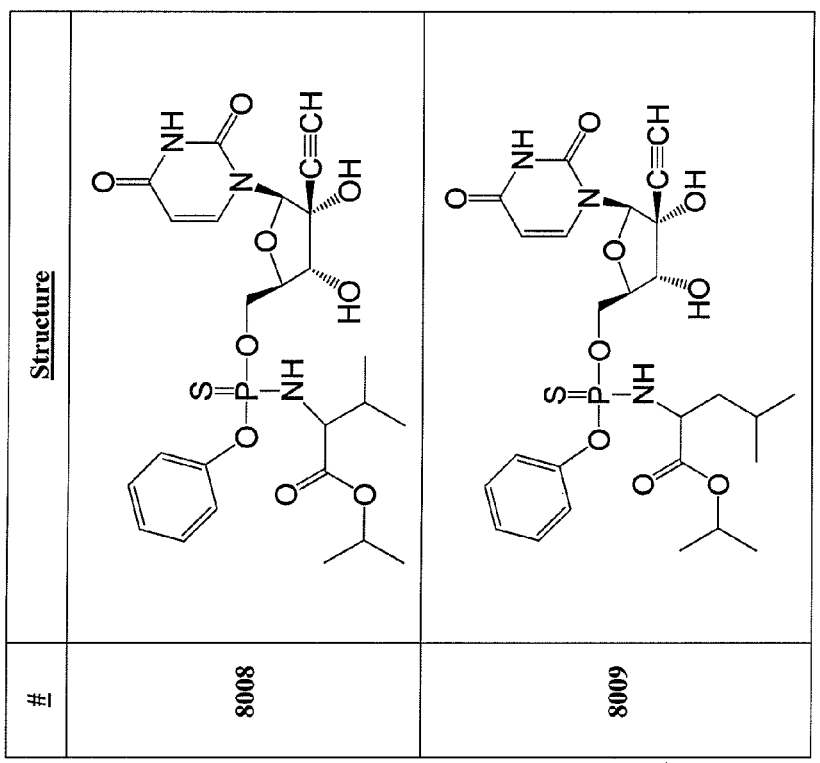
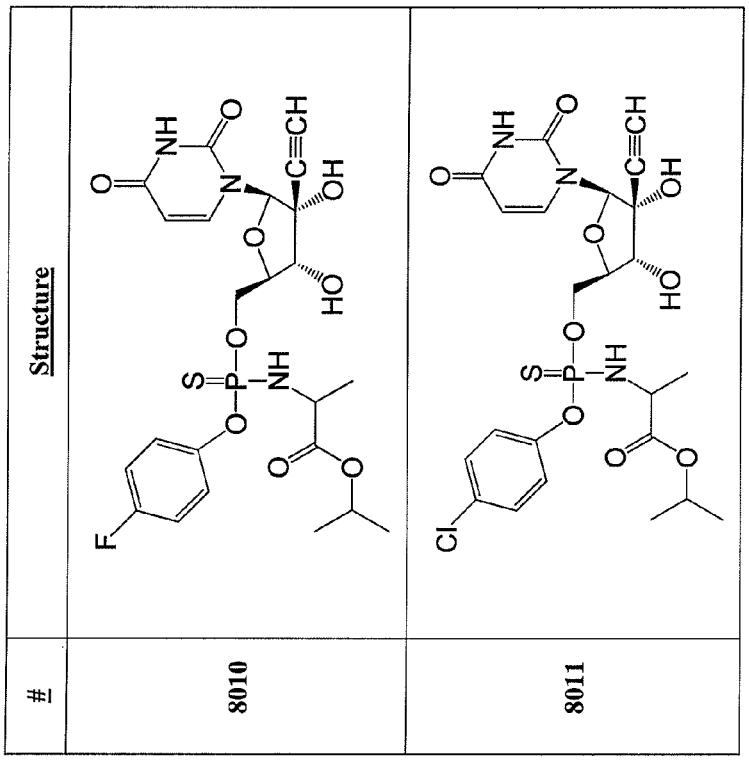

Figure 8 (cont.): Compounds of Formula (I)
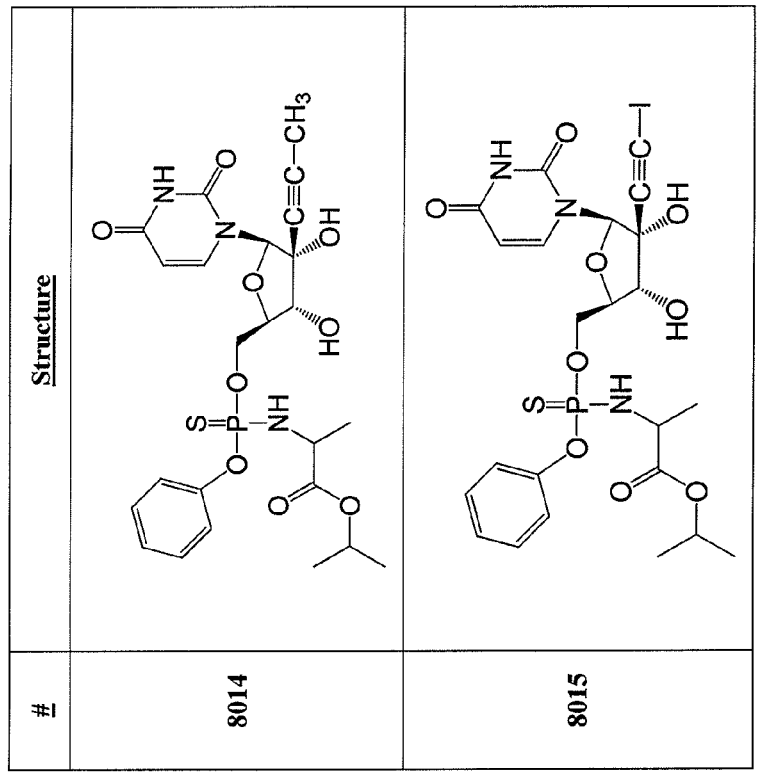
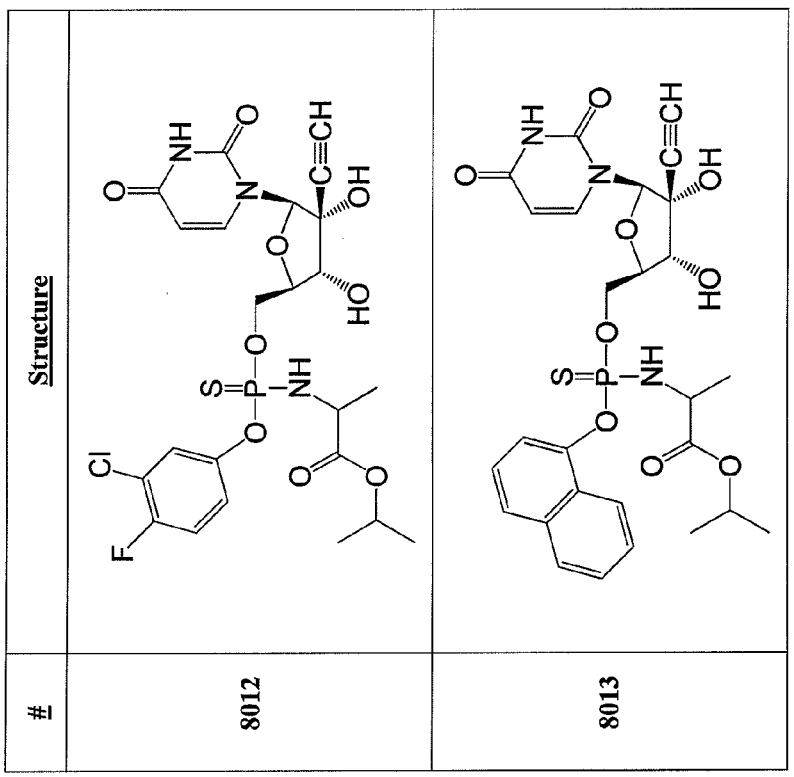

Figure 8 (cont.): Compounds of Formula (I)
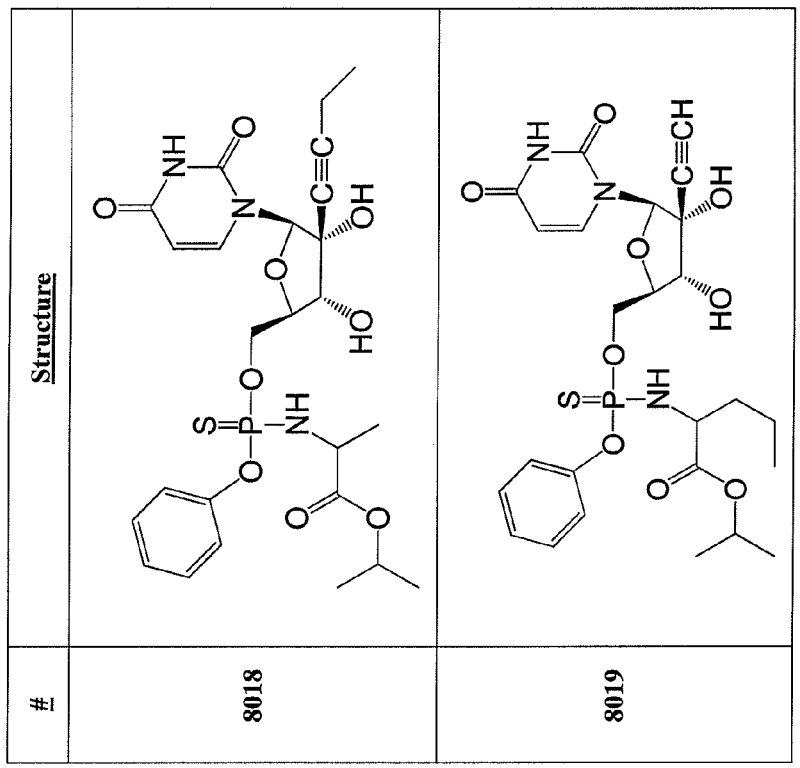
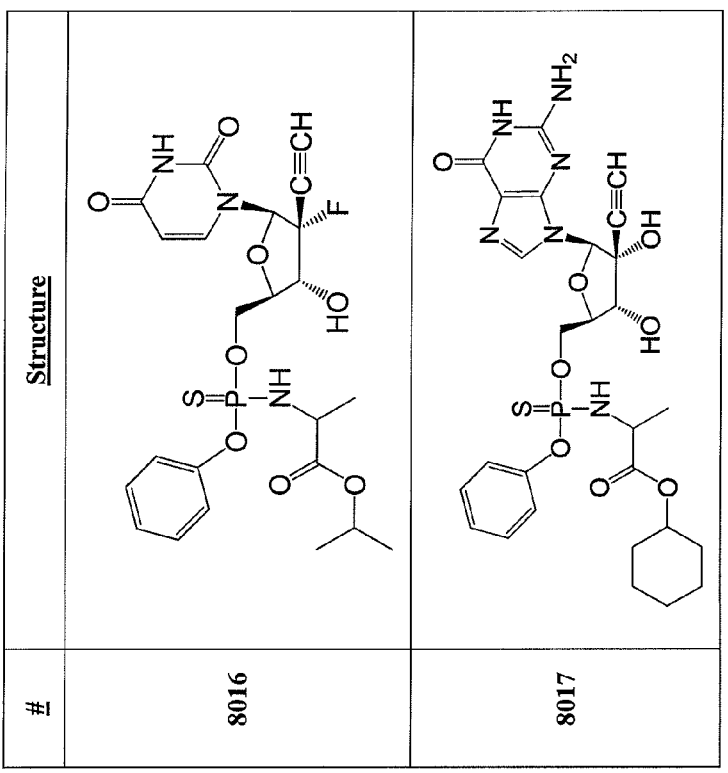

Figure 8 (cont.): Compounds of Formula (I)
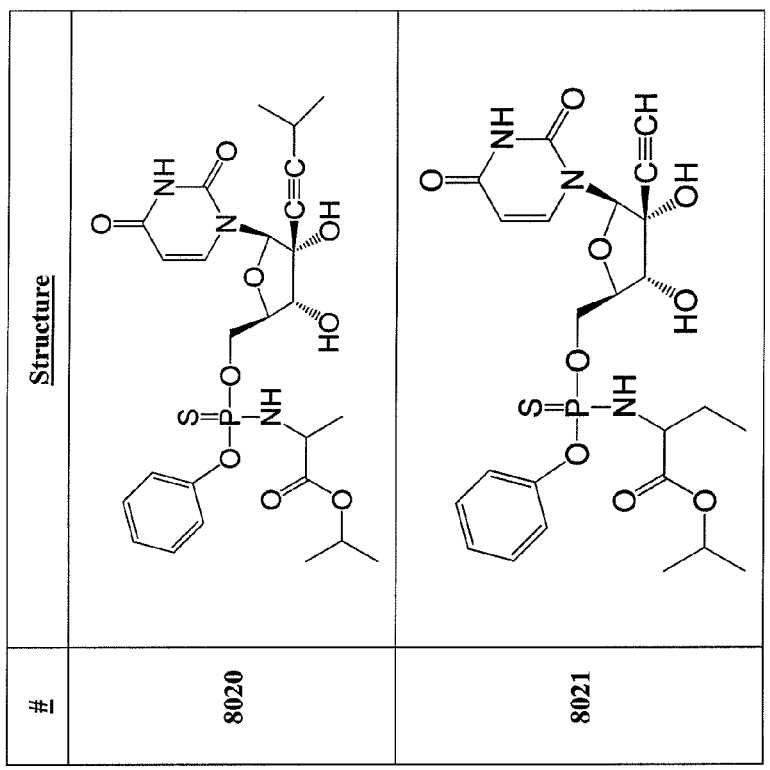
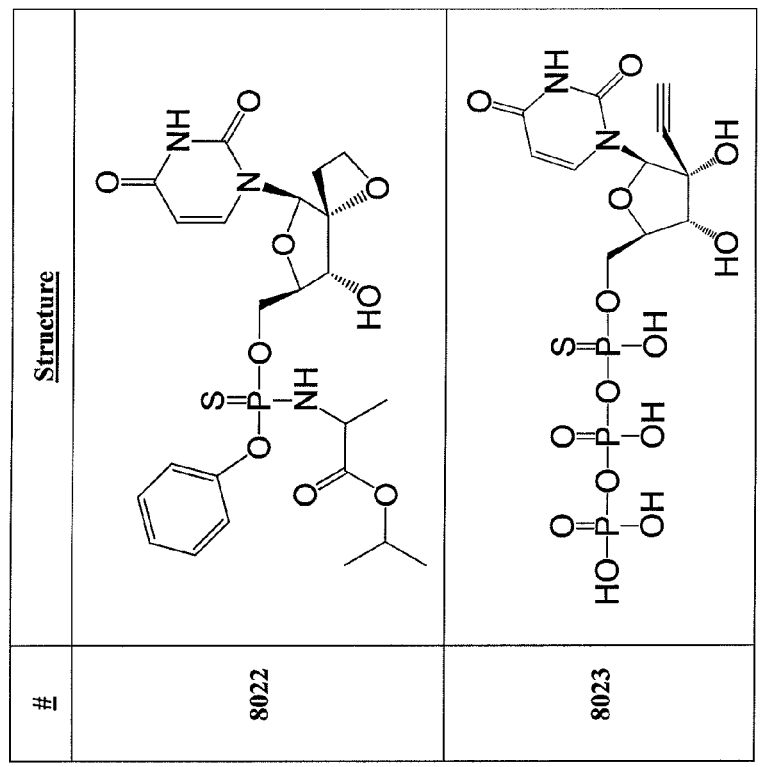

Figure 8 (cont.): Compounds of Formula (I)

| # | Structure |
|---|---|
| 8024 | (structure) |
| 8025 | (structure) |
| 8026 | (structure) |
| 8027 | (structure) |

SUBSTITUTED NUCLEOTIDE ANALOGS

This application claims the benefit of U.S. Provisional Application No. 61/579,533, filed Dec. 22, 2011; which are incorporated herein by reference in its entirety; including any drawings.

BACKGROUND

1. Field

The present application relates to the fields of chemistry, biochemistry and medicine. More particularly, disclosed herein are phosphorothioate nucleotide analogs, pharmaceutical compositions that include one or more phosphorothioate nucleotide analogs and methods of synthesizing the same. Also disclosed herein are methods of treating diseases and/or conditions with a phosphorothioate nucleotide analog, alone or in combination therapy with other agents.

2. Description

Nucleoside analogs are a class of compounds that have been shown to exert antiviral and anticancer activity both in vitro and in vivo, and thus, have been the subject of widespread research for the treatment of viral infections and cancer. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I) or a pharmaceutically acceptable salt thereof.

Some embodiments disclosed herein relate to a method of ameliorating and/or treating a neoplastic disease that can include administering to a subject suffering from the neoplastic disease a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a neoplastic disease. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a neoplastic disease.

Some embodiments disclosed herein relate to a method of inhibiting the growth of a tumor that can include administering to a subject having a tumor a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for inhibiting the growth of a tumor. Still other embodiments described herein relate to one or more compounds of Formula (I), or a pharmaceutically acceptable salt of thereof, or a pharmaceutical composition that includes one or more compounds of Formula (I), or a pharmaceutically acceptable salt thereof, that can be used for inhibiting the growth of a tumor.

Some embodiments disclosed herein relate to a method of ameliorating and/or treating a viral infection that can include administering to a subject identified as suffering from the viral infection a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a viral infection. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a viral infection.

Some embodiments disclosed herein relate to a method of ameliorating and/or treating a viral infection that can include contacting a cell infected with the virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for ameliorating and/or treating a viral infection that can include contacting a cell infected with the virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for ameliorating and/or treating a viral infection by contacting a cell infected with the virus with an effective amount of said compound(s).

Some embodiments disclosed herein relate to a method of inhibiting replication of a virus that can include contacting a cell infected with the virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for inhibiting replication of a virus that can include contacting a cell infected with the virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for inhibiting replication of a virus by contacting a cell infected with the virus with an effective amount of said compound(s).

Some embodiments disclosed herein relate to a method of ameliorating and/or treating a parasitic disease that can include administering to a subject suffering from the parasitic disease a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a parasitic disease. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a parasitic disease.

Some embodiments disclosed herein relate to a method of ameliorating and/or treating a viral infection that can include administering to a subject identified as suffering from the viral infection a therapeutically effective amount of a compound described herein or a pharmaceutically acceptable salt thereof (for example, one or more compounds of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, an other antiviral compound, a compound of Formula (BB) and a compound of Formula (CC), or a pharmaceutically acceptable salt of any of the foregoing. Some embodiments disclosed herein relate to a method of ameliorating and/or treating a viral infection that can include contacting a cell infected with the viral infection with a therapeutically effective amount of a compound described herein or a pharmaceutically acceptable salt thereof (for example, one or more compounds of Formula (I), or a pharmaceutically acceptable salt thereof), or a pharmaceutical composition that includes a compound described herein, in combination with an agent selected from an interferon, ribavirin, a HCV protease inhibitor, a HCV polymerase inhibitor, a NS5A inhibitor, an other antiviral compound, a compound of Formula (BB) and a compound of Formula (CC), or a pharmaceutically acceptable salt of any of the foregoing. Some embodiments disclosed herein relate to a method of inhibiting replication of a virus that can include administering to a subject identified as being infected with the virus a therapeutically effective amount of a compound described herein or a pharmaceutically acceptable salt thereof (for example, a compound of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, an other antiviral compound, or a pharmaceutically acceptable salt of any of the foregoing. In some embodiments, the agent can be a compound, or a pharmaceutically acceptable salt thereof, selected from Compound 1001-1016, 2001-2012, 3001-3014, 4001-4012, 5001-5011, 6001-6078 and 7000-7016, or a pharmaceutical composition that includes one or more of the aforementioned compounds, or pharmaceutically acceptable salt thereof. In some embodiments, the method can include administering a second agent selected from an interferon, ribavirin, a HCV protease inhibitor, a HCV polymerase inhibitor, a NS5A inhibitor, an other antiviral compound, a compound of Formula (BB) and a compound of Formula (CC), or a pharmaceutically acceptable salt of any of the foregoing. In some embodiments, the viral infection can be HCV.

BRIEF DESCRIPTION OF THE DRAWINGS

FIG. 1 shows example HCV protease inhibitors.
FIG. 2 shows example nucleoside HCV polymerase inhibitors.
FIG. 3 shows example non-nucleoside HCV polymerase inhibitors.
FIG. 4 shows example NS5A inhibitors.
FIG. 5 shows example other antivirals.
FIG. 6 shows example compounds of Formula (CC), and alpha-thiotriphosphates thereof.
FIG. 7 shows example compounds of Formula (BB).
FIG. 8 shows example compounds of Formula (I).

DETAILED DESCRIPTION

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{3A}$, $R^{4A}$ and $R^{5A}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

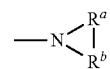

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring of the cycloalkyl, ring of the cycloalkenyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1, 2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl and their benzo-fused analogs.

A "(heteroalicyclyl)alkyl" and "(heterocyclyl)alkyl" refer to a heterocyclic or a heteroalicylylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heteroalicyclyl, aralkyl, (heteroaryl)alkyl or (heteroalicyclyl)alkyl is defined herein. A non-limiting list of alkoxys are methoxy, ethoxy, n-propoxy, 1-methylethoxy(isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

As used herein, "arylthio" refers to RS—, in which R is an aryl, such as, but not limited to, phenyl. An arylthio may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl, as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl.

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An N-carbamyl may be substituted or unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, aryl, heteroaryl, heteroalicyclyl, aralkyl, (hetero aryl)alkyl or (heteroalicyclyl)alkyl. An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, aryl, heteroaryl, heteroalicyclyl, aralkyl, (hetero aryl)alkyl or (heteroalicyclyl)alkyl. An N-thiocarbamyl may be substituted or unsubstituted.

A "C-amido" group refers to a "—C(=O)N($R_AR_B$)" group in which $R_A$ and $R_B$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)—)—, and naphthyl-O—C(=O)—. N-linked amino acid ester derivatives can be substituted or unsubstituted.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' preferred, 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

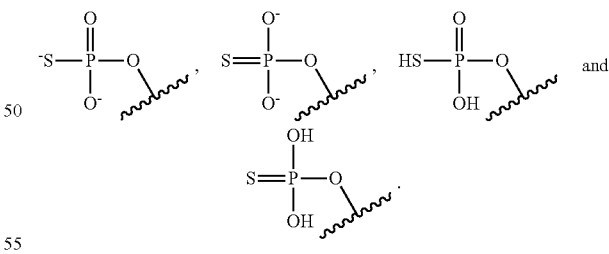

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Some embodiments disclosed herein relate to a compound of Formula (I) or a pharmaceutically acceptable salt thereof:

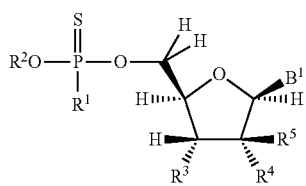
(I)

wherein: $B^1$ can be an optionally substituted heterocyclic base or an optionally substituted heterocyclic base with a protected amino group; $R^1$ can be selected from $O^-$, OH, an optionally substituted N-linked amino acid and an optionally substituted N-linked amino acid ester derivative; $R^2$ can be absent or selected from hydrogen, an optionally substituted aryl, an optionally substituted heteroaryl, an optionally substituted heterocyclyl and

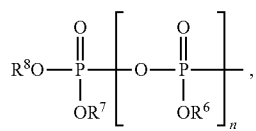

wherein $R^6$, $R^7$ and $R^8$ can be independently absent or hydrogen, and n can be 0 or 1; provided that when $R^1$ is $O^-$ or OH, then $R^2$ can be absent, hydrogen or

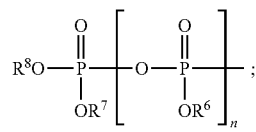

$R^3$ can be selected from hydrogen, halogen, $-OR^9$ and $-OC(=O)R^{10}$; $R^4$ can be selected from halogen, $-OR^{11}$ and $-OC(=O)R^{12}$; or $R^3$ and $R^4$ can both be oxygen atoms and linked together by a carbonyl group; $R^5$ can be selected from an optionally substituted $C_{2-6}$ alkyl, an optionally substituted $C_{2-6}$ alkenyl, an optionally substituted $C_{2-6}$ alkynyl and an optionally substituted $C_{3-6}$ cycloalkyl; or $R^4$ and $R^5$ together can form $-(C_{1-6}$ alkyl)-O$-$ or $-O-(C_{1-6}$ alkyl)-; $R^9$ and $R^{11}$ can be independently hydrogen or an optionally substituted $C_{1-6}$ alkyl; and $R^{10}$ and $R^{12}$ can be independently an optionally substituted $C_{1-6}$ alkyl or an optionally substituted $C_{3-6}$ cycloalkyl.

The substituents attached to the 2'-carbon can vary. In some embodiments, $R^5$ can be an optionally substituted $C_{2-6}$ alkyl. Suitable alkyl groups include, but are not limited to optionally substituted variants of the following: ethyl, n-propyl, isopropyl, n-butyl, isobutyl, tert-butyl, pentyl (branched and straight-chained), and hexyl (branched and straight-chained). In some embodiments, $R^5$ can be a substituted $C_{2-6}$ alkyl. In some embodiments, $R^5$ can be an unsubstituted $C_{2-6}$ alkyl.

In some embodiments, $R^5$ can be an optionally substituted $C_{2-6}$ alkenyl or an optionally substituted $C_{2-6}$ alkynyl. In other embodiments, $R^5$ can be an optionally substituted $C_{2-6}$ alkenyl. Suitable alkenyl groups include, but are not limited to optionally substituted variants of the following: ethenyl, n-propenyl, isopropenyl, n-butenyl, isobutenyl, tert-butenyl, pentenyl (branched and straight-chained), and hexenyl (branched and straight-chained). The double bond(s) can be at any position(s) within the alkenyl group. The alkenyl group can have one, two, or more than two double bonds. In some embodiments, $R^5$ can be a substituted $C_{2-6}$ alkenyl. In other embodiments, $R^5$ can be an unsubstituted $C_{2-6}$ alkenyl.

In still other embodiments, $R^5$ can be an optionally substituted $C_{2-6}$ alkynyl. Suitable alkynyl groups include, but are not limited to optionally substituted variants of the following: ethynyl, n-propynyl, isopropynyl, n-butynyl, isobutynyl, tert-butynyl, pentynyl (branched and straight-chained), and hexynyl (branched and straight-chained). The triple bond(s) can be at any position(s) within the alkynyl group. The alkynyl group can have one, two, or more than two triple bonds. In some embodiments, $R^5$ can be a substituted $C_{2-6}$ alkynyl, such as a 2-haloethynyl or 2-($C_{1-6}$ alkyl)-ethynyl. In some embodiments, $R^5$ can be 2-fluoroethynyl, 2-chloroethynyl, 2-bromoethynyl, 2-iodoethynyl, 2-methylethynyl, 2-ethylethynyl or 2-isopropylethynyl. In some embodiments, $R^5$ can be an unsubstituted $C_{2-6}$ alkynyl.

In some embodiments, $R^5$ can be an optionally substituted $C_{3-6}$ cycloalkyl. Suitable cycloalkyl groups include, but are not limited to optionally substituted variants of the following: cyclopropyl, cyclobutyl, cyclopentyl, and cyclohexyl. In some embodiments, $R^5$ can be a substituted $C_{3-6}$ cycloalkyl. In some embodiments, $R^5$ can be an unsubstituted $C_{3-6}$ cycloalkyl.

In some embodiments, $R^4$ can be halogen. For example, $R^4$ can be chloro or fluoro. In other embodiments, $R^4$ can be $-OR^{11}$. In some embodiments, when $R^{11}$ is hydrogen, $R^4$ can be a hydroxy group. In still other embodiments, when $R^{11}$ is an optionally substituted $C_{1-6}$ alkyl, $R^4$ can be an optionally substituted $C_{1-6}$ alkoxy. Examples of $R^4$ being $-OR^{11}$, wherein $R^{11}$ can be an optionally substituted $C_{1-6}$ alkyl include, but are not limited to, are methoxy, ethoxy, n-propoxy, isopropoxy, n-butoxy, isobutoxy, tert-butoxy, pentoxy (straight-chained or branched) and hexoxy (straight-chained or branched). In yet still other embodiments, $R^4$ can be —OC(=O)$R^{12}$, wherein $R^{12}$ can be an optionally substituted $C_{1-6}$ alkyl, such as optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^4$ can be —OC(=O)$R^{12}$, wherein $R^{12}$ can be an optionally substituted $C_{3-6}$ cycloalkyl, such as those described herein.

In some embodiments, $R^4$ and $R^5$ can together form —($C_{1-6}$ alkyl)-O— or —O—($C_{1-6}$ alkyl)-. In some embodiments, $R^4$ and $R^5$ can together form —($C_{1-6}$ alkyl)-O—, such as —CH$_2$—O—, —CH$_2$CH$_2$—O—, —CH$_2$CH$_2$CH$_2$—O—, —CH$_2$CH$_2$CH$_2$CH$_2$—O—, —CH$_2$CH$_2$CH$_2$CH$_2$CH$_2$—O— or —CH$_2$CH$_2$CH$_2$CH$_2$CH$_2$CH$_2$—O—. In some embodiments, $R^4$ and $R^5$ can together form —O—($C_{1-6}$ alkyl)-, such as —O—CH$_2$—, —O—CH$_2$CH$_2$—, —O—CH$_2$CH$_2$CH$_2$—, —O—CH$_2$CH$_2$CH$_2$CH$_2$—, —O—CH$_2$CH$_2$CH$_2$CH$_2$CH$_2$— or —O—CH$_2$CH$_2$CH$_2$CH$_2$CH$_2$CH$_2$—. The $C_{1-6}$ alkyl group can be an optionally substituted $C_{1-6}$ alkyl, such as optionally substituted variants of the following: methyl, ethyl, n-propyl, isopropyl, n-butyl, isobutyl, tert-butyl, pentyl (branched and straight-chained), and hexyl (branched and straight-chained).

The substituents attached to the 3'-carbon can vary. In some embodiments, $R^3$ can be hydrogen. In other embodiments, $R^3$ can be halogen. In other embodiments, $R^3$ can be —OR$^9$, wherein $R^9$ can be hydrogen. In still other embodiments, $R^3$ can be —OR$^9$, wherein $R^9$ can be an optionally substituted $C_{1-6}$ alkyl. A non-limiting list of examples of $R^3$ being —OR$^9$, wherein $R^9$ can be an optionally substituted $C_{1-6}$ alkyl are methoxy, ethoxy, n-propoxy, isopropoxy, n-butoxy, isobutoxy and tert-butoxy, pentoxy (straight-chained or branched) and hexoxy (straight-chained or branched). In yet still other embodiments, $R^3$ can be —OC(=O)$R^{10}$, wherein $R^{10}$ can be an optionally substituted $C_{1-6}$ alkyl or an optionally substituted $C_{3-6}$ cycloalkyl. Examples of suitable optionally substituted $C_{1-6}$ alkyls include optionally substituted variants of the following: methyl, ethyl, n-propyl, isopropyl, n-butyl, isobutyl, tert-butyl pentyl (branched and straight-chained), and hexyl (branched and straight-chained). Examples of suitable optionally substituted $C_{3-6}$ cycloalkyls include optionally substituted variants of the following: cyclopropyl, cyclobutyl, cyclopentyl and cyclohexyl.

In some embodiments, $R^3$ and $R^4$ can both be hydroxy. In still other embodiments, $R^3$ and $R^4$ can both be oxygen atoms and linked together by a carbonyl group, for example, —O—C(=O)—O—.

In some embodiments, $R^5$ can be an optionally substituted $C_{2-6}$ alkyl and $R^4$ can be a halogen. In some embodiments, $R^5$ can be an optionally substituted $C_{2-6}$ alkyl, $R^4$ can be a halogen, and $R^3$ can be hydrogen. In some embodiments, $R^5$ can be an optionally substituted $C_{2-6}$ alkyl, $R^4$ can be a halogen, and $R^3$ can be a halogen. In some embodiments, $R^5$ can be an optionally substituted $C_{2-6}$ alkyl, $R^4$ can be a halogen, and $R^3$ can be —OR$^9$. In some embodiments, $R^5$ can be an optionally substituted $C_{2-6}$ alkyl, $R^4$ can be a halogen, and $R^3$ can be —OC(=O)$R^{10}$. In some embodiments, $R^5$ can be an optionally substituted $C_{2-6}$ alkyl and $R^4$ can be —OR$^{11}$. In some embodiments, $R^5$ can be an optionally substituted $C_{2-6}$ alkyl, $R^4$ can be —OR$^{11}$, and $R^3$ can be hydrogen. In some embodiments, $R^5$ can be an optionally substituted $C_{2-6}$ alkyl, $R^4$ can be —OR$^{11}$, and $R^3$ can be a halogen. In some embodiments, $R^5$ can be an optionally substituted $C_{2-6}$ alkyl, $R^4$ can be —OR$^{11}$, and $R^3$ can be —OR$^9$. In some embodiments, $R^5$ can be an optionally substituted $C_{2-6}$ alkyl, $R^4$ can be —OR$^{11}$, and $R^3$ can be —OC(=O)$R^{10}$. In some embodiments, $R^5$ can be an optionally substituted $C_{2-6}$ alkyl and $R^4$ can be —OC(=O)$R^{12}$. In some embodiments, $R^5$ can be an optionally substituted $C_{2-6}$ alkyl, $R^4$ can be —OC(=O)$R^{12}$, and $R^3$ can be hydrogen. In some embodiments, $R^5$ can be an optionally substituted $C_{2-6}$ alkyl, $R^4$ can be —OC(=O)$R^{12}$, and $R^3$ can be a halogen. In some embodiments, $R^5$ can be an optionally substituted $C_{2-6}$ alkyl, $R^4$ can be —OC(=O)$R^{12}$, and $R^3$ can be —OR$^9$. In some embodiments, $R^5$ can be an optionally substituted $C_{2-6}$ alkyl, $R^4$ can be —OC(=O)$R^{12}$, and $R^3$ can be —OC(=O)$R^{10}$. In some embodiments, $B^1$ can be an optionally substituted adenine, an optionally substituted guanine, an optionally substituted thymine, an optionally substituted cytosine, or an optionally substituted uracil in any of the embodiments described in this paragraph.

In some embodiments, $R^5$ can be an optionally substituted $C_{2-6}$ alkenyl and $R^4$ can be a halogen. In some embodiments, $R^5$ can be an optionally substituted $C_{2-6}$ alkenyl, $R^4$ can be a halogen, and $R^3$ can be hydrogen. In some embodiments, $R^5$ can be an optionally substituted $C_{2-6}$ alkenyl, $R^4$ can be a halogen, and $R^3$ can be a halogen. In some embodiments, $R^5$ can be an optionally substituted $C_{2-6}$ alkenyl, $R^4$ can be a halogen, and $R^3$ can be —OR$^9$. In some embodiments, $R^5$ can be an optionally substituted $C_{2-6}$ alkenyl, $R^4$ can be a halogen, and $R^3$ can be —OC(=O)$R^{10}$. In some embodiments, $R^5$ can be an optionally substituted $C_{2-6}$ alkenyl and $R^4$ can be —OR$^{11}$. In some embodiments, $R^5$ can be an optionally substituted $C_{2-6}$ alkenyl, $R^4$ can be —OR$^{11}$, and $R^3$ can be hydrogen. In some embodiments, $R^5$ can be an optionally substituted $C_{2-6}$ alkenyl, $R^4$ can be —OR$^{11}$, and $R^3$ can be a halogen. In some embodiments, $R^5$ can be an optionally substituted $C_{2-6}$ alkenyl, $R^4$ can be —OR$^{11}$, and $R^3$ can be —OR$^9$. In some embodiments, $R^5$ can be an optionally substituted $C_{2-6}$ alkenyl, $R^4$ can be —OR$^{11}$, and $R^3$ can be —OC(=O)$R^{10}$. In some embodiments, $R^5$ can be an optionally substituted $C_{2-6}$ alkenyl and $R^4$ can be —OC(=O)$R^{12}$. In some embodiments, $R^5$ can be an optionally substituted $C_{2-6}$ alkenyl, $R^4$ can be —OC(=O)$R^{12}$, and $R^3$ can be hydrogen. In some embodiments, $R^5$ can be an optionally substituted $C_{2-6}$ alkenyl, $R^4$ can be —OC(=O)$R^{12}$, and $R^3$ can be a halogen. In some embodiments, $R^5$ can be an optionally substituted $C_{2-6}$ alkenyl, $R^4$ can be —OC(=O)$R^{12}$, and $R^3$ can be —OR$^9$. In some embodiments, $R^5$ can be an optionally substituted $C_{2-6}$ alkenyl, $R^4$ can be —OC(=O)$R^{12}$, and $R^3$ can be —OC(=O)$R^{10}$. In some embodiments, $B^1$ can be an optionally substituted adenine, an optionally substituted guanine, an optionally substituted thymine, an optionally substituted cytosine, or an optionally substituted uracil in any of the embodiments described in this paragraph.

In some embodiments, $R^5$ can be an optionally substituted $C_{2-6}$ alkynyl and $R^4$ can be a halogen. In some embodiments, $R^5$ can be an optionally substituted $C_{2-6}$ alkynyl, $R^4$ can be a halogen, and $R^3$ can be hydrogen. In some embodiments, $R^5$ can be an optionally substituted $C_{2-6}$ alkynyl, $R^4$ can be a halogen, and $R^3$ can be a halogen. In some embodiments, $R^5$ can be an optionally substituted $C_{2-6}$ alkynyl, $R^4$ can be a halogen, and $R^3$ can be —OR$^9$. In some embodiments, $R^5$ can be an optionally substituted $C_{2-6}$ alkynyl, $R^4$ can be a halogen, and $R^3$ can be —OC(=O)$R^{10}$. In some embodiments, $R^5$ can be an optionally substituted $C_{2-6}$ alkynyl and $R^4$ can be —OR$^{11}$. In some embodiments, $R^5$ can be an optionally substituted $C_{2-6}$ alkynyl, $R^4$ can be —OR$^{11}$, and $R^3$ can be hydrogen. In some embodiments, $R^5$ can be an optionally substituted $C_{2-6}$ alkynyl, $R^4$ can be —OR$^{11}$, and $R^3$ can be a halogen. In some embodiments, $R^5$ can be an optionally substituted $C_{2-6}$ alkynyl, $R^4$ can be —OR$^{11}$, and $R^3$ can be —OR$^9$. In some embodiments, R$^5$ can be an optionally substituted C$_{2-6}$ alkynyl, R$^4$ can be —OR$^{11}$, and R$^3$ can be —OC(=O)R$^{10}$. In some embodiments, R$^5$ can be an optionally substituted C$_{2-6}$ alkynyl and R$^4$ can be —OC(=O)R$^{12}$. In some embodiments, R$^5$ can be an optionally substituted C$_{2-6}$ alkynyl, R$^4$ can be —OC(=O)R$^{12}$, and R$^3$ can be hydrogen. In some embodiments, R$^5$ can be an optionally substituted C$_{2-6}$ alkynyl, R$^4$ can be —OC(=O)R$^{12}$, and R$^3$ can be a halogen. In some embodiments, R$^5$ can be an optionally substituted C$_{2-6}$ alkynyl, R$^4$ can be —OC(=O)R$^{12}$, and R$^3$ can be —OR$^9$. In some embodiments, R$^5$ can be an optionally substituted C$_{2-6}$ alkynyl, R$^4$ can be —OC(=O)R$^{12}$, and R$^3$ can be —OC(=O)R$^{10}$. In some embodiments, B$^1$ can be an optionally substituted adenine, an optionally substituted guanine, an optionally substituted thymine, an optionally substituted cytosine, or an optionally substituted uracil in any of the embodiments described in this paragraph.

In some embodiments, R$^5$ can be an optionally substituted C$_{3-6}$ cycloalkyl and R$^4$ can be a halogen. In some embodiments, R$^5$ can be an optionally substituted C$_{3-6}$ cycloalkyl, R$^4$ can be a halogen, and R$^3$ can be hydrogen. In some embodiments, R$^5$ can be an optionally substituted C$_{3-6}$ cycloalkyl, R$^4$ can be a halogen, and R$^3$ can be a halogen. In some embodiments, R$^5$ can be an optionally substituted C$_{3-6}$ cycloalkyl, R$^4$ can be a halogen, and R$^3$ can be —OR$^9$. In some embodiments, R$^5$ can be an optionally substituted C$_{3-6}$ cycloalkyl, R$^4$ can be a halogen, and R$^3$ can be —OC(=O)R$^{10}$. In some embodiments, R$^5$ can be an optionally substituted C$_{3-6}$ cycloalkyl and R$^4$ can be —OR$^{11}$. In some embodiments, R$^5$ can be an optionally substituted C$_{3-6}$ cycloalkyl, R$^4$ can be —OR$^{11}$, and R$^3$ can be hydrogen. In some embodiments, R$^5$ can be an optionally substituted C$_{3-6}$ cycloalkyl, R$^4$ can be —OR$^{11}$, and R$^3$ can be a halogen. In some embodiments, R$^5$ can be an optionally substituted C$_{3-6}$ cycloalkyl, R$^4$ can be —OR$^{11}$, and R$^3$ can be —OR$^9$. In some embodiments, R$^5$ can be an optionally substituted C$_{3-6}$ cycloalkyl, R$^4$ can be —OR$^{11}$, and R$^3$ can be —OC(=O)R$^{10}$. In some embodiments, R$^5$ can be an optionally substituted C$_{3-6}$ cycloalkyl and R$^4$ can be —OC(=O)R$^{12}$. In some embodiments, R$^5$ can be an optionally substituted C$_{3-6}$ cycloalkyl, R$^4$ can be —OC(=O)R$^{12}$, and R$^3$ can be hydrogen. In some embodiments, R$^5$ can be an optionally substituted C$_{3-6}$ cycloalkyl, R$^4$ can be —OC(=O)R$^{12}$, and R$^3$ can be a halogen. In some embodiments, R$^5$ can be an optionally substituted C$_{3-6}$ cycloalkyl, R$^4$ can be —OC(=O)R$^{12}$, and R$^3$ can be —OR$^9$. In some embodiments, R$^5$ can be an optionally substituted C$_{3-6}$ cycloalkyl, R$^4$ can be —OC(=O)R$^{12}$, and R$^3$ can be —OC(=O)R$^{10}$. In some embodiments, B$^1$ can be an optionally substituted adenine, an optionally substituted guanine, an optionally substituted thymine, an optionally substituted cytosine, or an optionally substituted uracil in any of the embodiments described in this paragraph.

In some embodiments, R$^4$ and R$^5$ can together form —(C$_{1-6}$ alkyl)-O— or —O—(C$_{1-6}$ alkyl)-, and R$^3$ can be hydrogen. In some embodiments, R$^4$ and R$^5$ can together form —(C$_{1-6}$ alkyl)-O— or —O—(C$_{1-6}$ alkyl)-, and R$^3$ can be a halogen. In some embodiments, R$^4$ and R$^5$ can together form —(C$_{1-6}$ alkyl)-O— or —O—(C$_{1-6}$ alkyl)-, and R$^3$ can be —OR$^9$. In some embodiments, R$^4$ and R$^5$ can together form —(C$_{1-6}$ alkyl)-O— or —O—(C$_{1-6}$ alkyl)-, and R$^3$ can be —OC(=O)R$^{10}$. In some embodiments, R$^4$ and R$^5$ can together form —CH$_2$—O—, —CH$_2$CH$_2$—O—, —CH$_2$CH$_2$CH$_2$—O—, —CH$_2$CH$_2$CH$_2$CH$_2$—O—, —CH$_2$CH$_2$CH$_2$CH$_2$CH$_2$—O— or —CH$_2$CH$_2$CH$_2$CH$_2$CH$_2$CH$_2$—O—, and R$^3$ can be hydrogen. In some embodiments, R$^4$ and R$^5$ can together form —CH$_2$—O—, —CH$_2$CH$_2$—O—, —CH$_2$CH$_2$CH$_2$—O—, —CH$_2$CH$_2$CH$_2$CH$_2$—O—, —CH$_2$CH$_2$CH$_2$CH$_2$CH$_2$—O— or —CH$_2$CH$_2$CH$_2$CH$_2$CH$_2$CH$_2$—O—, and R$^3$ can be a halogen. In some embodiments, R$^4$ and R$^5$ can together form —CH$_2$—O—, —CH$_2$CH$_2$—O—, —CH$_2$CH$_2$CH$_2$—O—, —CH$_2$CH$_2$CH$_2$CH$_2$—O—, —CH$_2$CH$_2$CH$_2$CH$_2$CH$_2$—O— or —CH$_2$CH$_2$CH$_2$CH$_2$CH$_2$CH$_2$—O—, and R$^3$ can be —OR$^9$. In some embodiments, R$^4$ and R$^5$ can together form —CH$_2$—O—, —CH$_2$CH$_2$—O—, —CH$_2$CH$_2$CH$_2$—O—, —CH$_2$CH$_2$CH$_2$CH$_2$—O—, —CH$_2$CH$_2$CH$_2$CH$_2$CH$_2$—O— or —CH$_2$CH$_2$CH$_2$CH$_2$CH$_2$CH$_2$—O—, and R$^3$ can be —OC(=O)R$^{10}$. In some embodiments, R$^4$ and R$^5$ can together form —O—CH$_2$—, —O—CH$_2$CH$_2$—, —O—CH$_2$CH$_2$CH$_2$—, —O—CH$_2$CH$_2$CH$_2$CH$_2$—, —O—CH$_2$CH$_2$CH$_2$CH$_2$CH$_2$— or —O—CH$_2$CH$_2$CH$_2$CH$_2$CH$_2$CH$_2$—, and R$^3$ can be hydrogen. In some embodiments, R$^4$ and R$^5$ can together form —O—CH$_2$—, —O—CH$_2$CH$_2$—, —O—CH$_2$CH$_2$CH$_2$—, —O—CH$_2$CH$_2$CH$_2$CH$_2$—, —O—CH$_2$CH$_2$CH$_2$CH$_2$CH$_2$— or —O—CH$_2$CH$_2$CH$_2$CH$_2$CH$_2$CH$_2$—, and R$^3$ can be a halogen. In some embodiments, R$^4$ and R$^5$ can together form —O—CH$_2$—, —O—CH$_2$CH$_2$—, —O—CH$_2$CH$_2$CH$_2$—, —O—CH$_2$CH$_2$CH$_2$CH$_2$—, —O—CH$_2$CH$_2$CH$_2$CH$_2$CH$_2$— or —O—CH$_2$CH$_2$CH$_2$CH$_2$CH$_2$CH$_2$—, and R$^3$ can be —OR$^9$. In some embodiments, R$^4$ and R$^5$ can together form —O—CH$_2$—, —O—CH$_2$CH$_2$—, —O—CH$_2$CH$_2$CH$_2$—, —O—CH$_2$CH$_2$CH$_2$CH$_2$—, —O—CH$_2$CH$_2$CH$_2$CH$_2$CH$_2$— or —O—CH$_2$CH$_2$CH$_2$CH$_2$CH$_2$CH$_2$—, and R$^3$ can be —OC(=O)R$^{10}$.

In some embodiments, R$^4$ can be a halogen and R$^3$ can be a hydrogen. In some embodiments, R$^4$ can be a halogen and R$^3$ can be a halogen. In some embodiments, R$^4$ can be a halogen and R$^3$ can be —OR$^9$. In some embodiments, R$^4$ can be a halogen and R$^3$ can be —OC(=O)R$^{10}$. In some embodiments, R$^4$ can be —OR$^{11}$ and R$^3$ can be a hydrogen. In some embodiments, R$^4$ can be —OR$^{11}$ and R$^3$ can be a halogen. In some embodiments, R$^4$ can be —OR$^{11}$ and R$^3$ can be —OR$^9$. In some embodiments, R$^4$ can be —OR$^{11}$ and R$^3$ can be —OC(=O)R$^{10}$. In some embodiments, R$^4$ can be —OC(=O)R$^{12}$ and R$^3$ can be a hydrogen. In some embodiments, R$^4$ can be —OC(=O)R$^{12}$ and R$^3$ can be a halogen. In some embodiments, R$^4$ can be —OC(=O)R$^{12}$ and R$^3$ can be —OR$^9$. In some embodiments, R$^4$ can be —OC(=O)R$^{12}$ and R$^3$ can be —OC(=O)R$^{10}$.

With respect to R$^2$, in some embodiments, R$^2$ can be absent. In some embodiments, R$^2$ can be hydrogen. Those skilled in the art understand that when R$^2$ is absent, the oxygen atom that is associated with R$^2$ will have a negative charge. In some embodiments, R$^2$ can be an optionally substituted heteroaryl. In other embodiments, R$^2$ can be an optionally substituted heterocyclyl. In still other embodiments, R$^2$ can be an optionally substituted aryl. For example, R$^2$ can be an optionally substituted phenyl or an optionally substituted naphthyl. If R$^2$ is a substituted phenyl or a substituted naphthyl, the phenyl ring and the naphthyl ring(s) can be substituted one or more times. Suitable substituents that can be present on optionally substituted phenyl and an optionally substituted naphthyl include electron-donating groups and electron-withdrawing groups. In some embodiments, R$^2$ can be a substituted phenyl or a substituted naphthyl that is substituted one or more times with a halogen, such as chloro, fluoro, bromo, or iodo. In some embodiments, R$^2$ can be a para-substituted phenyl, such as para-chlorophenyl, para-fluorophenyl, para-bromophenyl, or para-iodophenyl. In some embodiments, R$^2$ can be a meta-substituted phenyl, such as meta-chlorophenyl, meta-fluorophenyl, meta-bromophenyl, or meta-iodophenyl. In some embodiments, R$^2$ can be an ortho-substituted phenyl, such as ortho-chlorophenyl, ortho-fluorophenyl, ortho-bromophenyl, or ortho-iodophenyl. In some embodiments, $R^2$ can be a meta-para-disubstituted phenyl, such as meta-para-dichlorophenyl, meta-para-difluorophenyl, meta-para-dibromophenyl, meta-para-diiodophenyl, meta-chloro-para-bromophenyl, meta-bromo-para-chlorophenyl, meta-bromo-para-fluorophenyl, meta-fluoro-para-bromophenyl, meta-chloro-para-fluorophenyl, or meta-fluoro-para-chlorophenyl. In some embodiments, $R^2$ can be an ortho-para-disubstituted phenyl, such as ortho-para-dichlorophenyl, ortho-para-difluorophenyl, ortho-para-dibromophenyl, ortho-para-diiodophenyl, ortho-chloro-para-bromophenyl, ortho-bromo-para-chlorophenyl, ortho-bromo-para-fluorophenyl, ortho-fluoro-para-bromophenyl, ortho-chloro-para-fluorophenyl, or ortho-fluoro-para-chlorophenyl. In some embodiments, $R^2$ can be an ortho-meta-disubstituted phenyl, such as ortho-meta-dichlorophenyl, ortho-meta-difluorophenyl, ortho-meta-dibromophenyl, ortho-meta-diiodophenyl, ortho-chloro-meta-bromophenyl, ortho-bromo-meta-chlorophenyl, ortho-bromo-meta-fluorophenyl, ortho-fluoro-meta-bromophenyl, ortho-chloro-meta-fluorophenyl, or ortho-fluoro-meta-chlorophenyl. In other embodiment, $R^2$ can be an unsubstituted phenyl or an unsubstituted naphthyl.

In some embodiments, $R^2$ can be absent or hydrogen, and $R^1$ can be OH or O$^-$. In some embodiment,

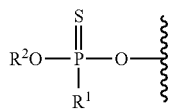

can be a monothiophosphate. In other embodiments, $R^2$ can be

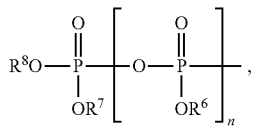

wherein $R^6$, $R^7$ and $R^8$ can be independently absent or hydrogen, and n can be 0 or 1. In some embodiments, n can be 0. In other embodiments, n can be 1. Those skilled in the art understand when n is 0, $R^2$ can be an α-thiodiphosphate. Similarly, those skilled in the art understand when n is 1, $R^2$ can be an α-thiotriphosphate. In some embodiments, at least one of $R^6$, $R^7$ and $R^8$ can be absent. In other embodiments, at least one of $R^6$, $R^7$ and $R^8$ can be hydrogen. In some embodiments, $R^7$ and $R^8$ can be absent. In other embodiments, $R^7$ and $R^8$ can be hydrogen. In some embodiments, $R^6$, $R^7$ and $R^8$ can be absent. In some embodiments, $R^6$, $R^7$ and $R^8$ can be hydrogen. Those skilled in the art understand that when any of $R^6$, $R^7$ and $R^8$ are absent the oxygen atom to which $R^6$, $R^7$ and $R^8$ are associated with can have a negative charge. For example, when $R^7$ is absent, the oxygen atom to which $R^7$ is associated with can be O$^-$. Depending upon the substituents attached to each phosphorus atoms, one or more the phosphorus atoms can be a chiral center. For example, when n is 1, the alpha-phosphorus (the phosphorus nearest to the pentose ring) can be a chiral center. In some embodiments, the alpha-phosphorus can be a (R)-stereocenter. In other embodiments, the alpha-phosphorus can be a (S)-stereocenter.

In some embodiments, $R^1$ can be O$^-$. In other embodiments, $R^1$ can be OH. In still other embodiments, $R^1$ can be an optionally substituted N-linked α-amino acid. In yet still other embodiments, $R^1$ can be an optionally substituted N-linked α-amino acid ester derivative. Various amino acids and amino acid ester derivatives can be used, including those described herein. Suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional suitable amino acids include, but are not limited to, alpha-ethyl-glycine, alpha-propyl-glycine and beta-alanine. Examples of an N-linked amino acid ester derivatives include, but are not limited to, an ester derivatives of any of the following amino acids: alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of N-linked amino acid ester derivatives include, but are not limited to, an ester derivative of any of the following amino acids: alpha-ethyl-glycine, alpha-propyl-glycine and beta-alanine.

In an embodiment, $R^1$ can be an ester derivative of alanine. In an embodiment, $R^1$ can be selected from alanine methyl ester, alanine ethyl ester, alanine isopropyl ester, alanine cyclohexyl ester, alanine neopentyl ester, valine isopropyl ester, isoleucine isopropyl ester, methionine isopropyl ester, and leucine isopropyl ester. In some embodiments, $R^1$ can be 2-aminobutane isopropyl ester. In some embodiments, the optionally substituted N-linked amino acid or the optionally substituted N-linked amino acid ester derivative can be in the L-configuration. In other embodiments, the optionally substituted N-linked amino acid or the optionally substituted N-linked amino acid ester derivative can be in the D-configuration.

In some embodiments, when $R^1$ is an optionally substituted N-linked cc amino acid or an optionally substituted N-linked α-amino acid ester derivative, then $R^2$ can be selected from optionally substituted aryl, an optionally substituted heteroaryl and an optionally substituted heterocyclyl. In some embodiments, when $R^1$ is an optionally substituted N-linked α-amino acid ester derivative, then $R^2$ can be an optionally substituted aryl. In other embodiments, when $R^1$ is an optionally substituted N-linked α-amino acid ester derivative, then $R^2$ can be an optionally substituted heteroaryl. In still other embodiments, when $R^1$ is an optionally substituted N-linked α-amino acid ester derivative, then $R^2$ can be an optionally substituted heterocyclyl.

In some embodiments, $R^1$ can have the structure

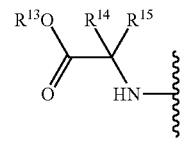

wherein $R^{13}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted $C_{1-6}$ haloalkyl; and $R^{14}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{15}$ can be hydrogen or an optionally substituted $C_{1-4}$-alkyl; or $R^{14}$ and $R^{15}$ can be taken together to form an optionally substituted $C_{3-6}$ cycloalkyl.

When $R^1$ has the structure shown above, $R^{14}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). When $R^{14}$ is substituted, $R^{14}$ can be substituted with one or more substituents selected from N-amido, mercapto, alkylthio, an optionally substituted aryl, hydroxy, an optionally substituted heteroaryl, O-carboxy, and amino. In some embodiment, $R^{14}$ can be an unsubstituted $C_{1-6}$-alkyl, such as methyl, ethyl, n-propyl, isopropyl, n-butyl, isobutyl, tert-butyl, pentyl (branched and straight-chained), and hexyl (branched and straight-chained). In an embodiment, $R^{14}$ can be methyl.

As to $R^{13}$, in some embodiments, $R^{13}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{13}$ can be methyl or isopropyl. In some embodiments, $R^{13}$ can be ethyl or neopentyl. In other embodiments, $R^{13}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{13}$ can be an optionally substituted cyclohexyl. In still other embodiments, $R^{13}$ can be an optionally substituted aryl, such as phenyl and naphthyl. In yet still other embodiments, $R^{13}$ can be an optionally substituted aryl($C_{1-6}$ alkyl). In some embodiments, $R^{13}$ can be an optionally substituted benzyl. In some embodiments, $R^{13}$ can be an optionally substituted $C_{1-6}$haloalkyl, for example, $CF_3$.

In some embodiments, $R^{15}$ can be hydrogen. In other embodiments, $R^{15}$ can be an optionally substituted $C_{1-4}$-alkyl, such as methyl, ethyl, n-propyl, isopropyl, n-butyl, isobutyl and tert-butyl. In an embodiment, $R^{15}$ can be methyl. In some embodiments, $R^{14}$ and $R^{15}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{14}$ and $R^{15}$, the carbon to which $R^{14}$ and $R^{15}$ are attached may be a chiral center. In some embodiment, the carbon to which $R^{14}$ and $R^{15}$ are attached may be a (R)-chiral center. In other embodiments, the carbon to which $R^{14}$ and $R^{15}$ are attached may be a (S)-chiral center.

Examples of suitable

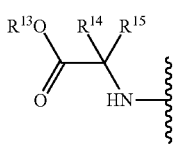

groups include the following:

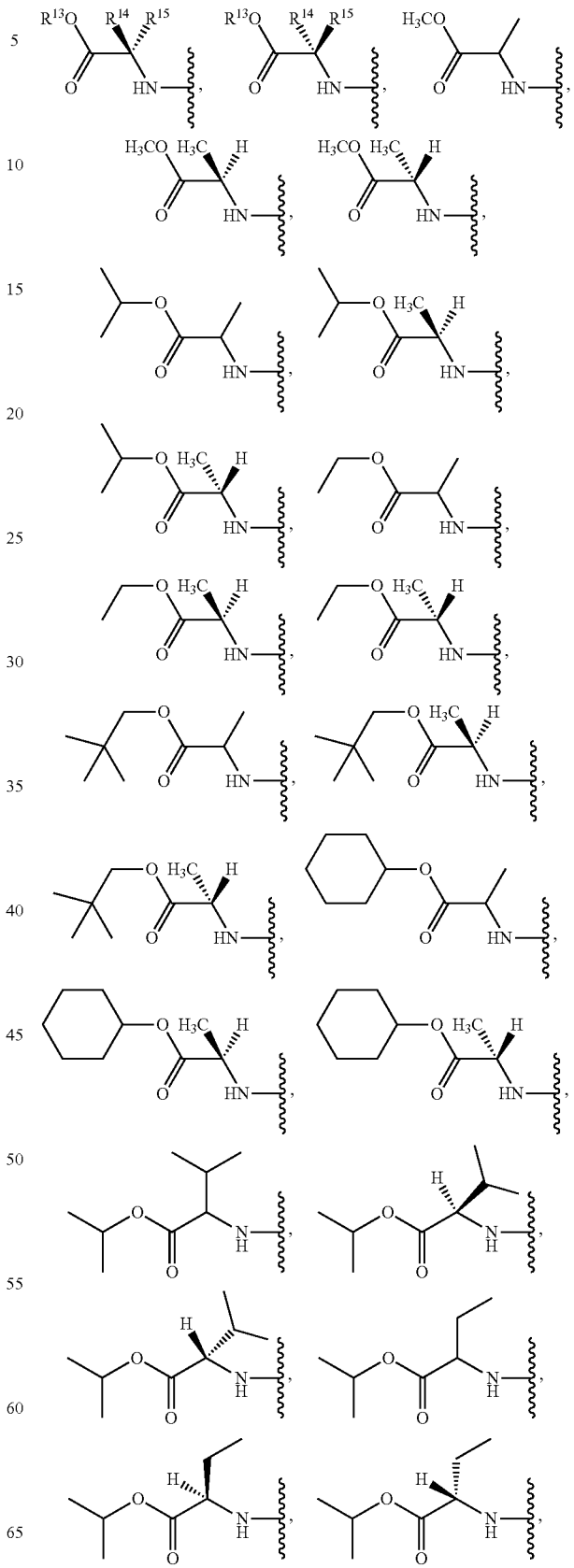

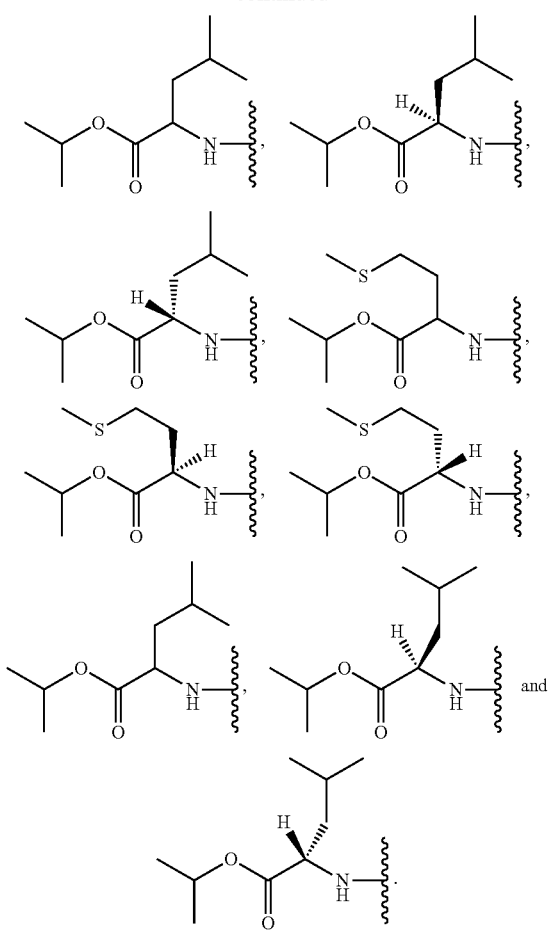

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

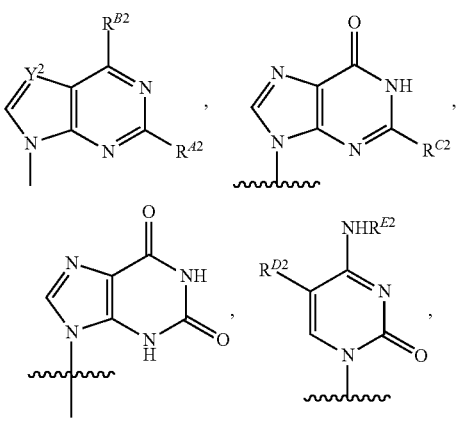

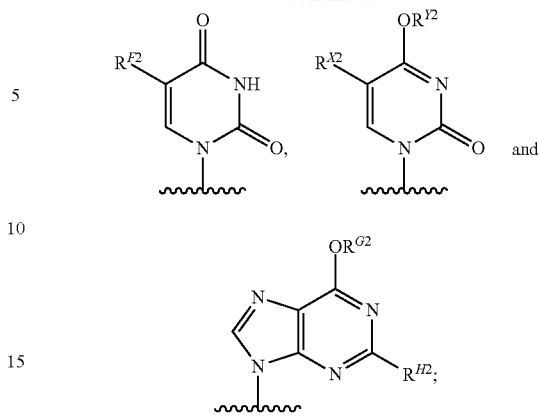

wherein: $R^{A2}$ can be selected from hydrogen, halogen and $NHR^{J2}$, wherein $R^{J2}$ can be selected from hydrogen, —C(=O)$R^{K2}$ and —C(=O)O$R^{L2}$; $R^{B2}$ can be halogen or $NHR^{W2}$, wherein $R^{W2}$ is selected from hydrogen, an optionally substituted $C_{1-6}$ alkyl, an optionally substituted $C_{2-6}$ alkenyl, an optionally substituted $C_{3-8}$ cycloalkyl, —C(=O)$R^{M2}$ and —C(=O)O$R^{N2}$; $R^{C2}$ can be hydrogen or $NHR^{O2}$, wherein $R^{O2}$ can be selected from hydrogen, —C(=O)$R^{P2}$ and —C(=O)O$R^{Q2}$; $R^{D2}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{E2}$ can be selected from hydrogen, an optionally substituted $C_{1-6}$ alkyl, an optionally substituted $C_{3-8}$ cycloalkyl, —C(=O)$R^{R2}$ and —C(=O)O$R^{S2}$; $R^{F2}$ and $R^{X2}$ can be independently selected from hydrogen, halogen, an optionally substituted $C_{1-6}$ alkyl, an optionally substituted $C_{2-6}$ alkenyl and an optionally substituted $C_{2-6}$ alkynyl; $Y^2$ can be N (nitrogen) or C$R^{T2}$, wherein $R^{T2}$ can be selected from hydrogen, halogen, an optionally substituted $C_{1-6}$-alkyl, an optionally substituted $C_{2-6}$-alkenyl and an optionally substituted $C_{2-6}$-alkynyl; $R^{G2}$ can be an optionally substituted $C_{1-6}$ alkyl; $R^{H2}$ can be hydrogen or $NHR^{T2}$, wherein $R^{T2}$ can be independently selected from hydrogen, —C(=O)$R^{U2}$ and —C(=O)O$R^{V2}$, $R^{K2}$, $R^{L2}$, $R^{M2}$, $R^{N2}$, $R^{P2}$, $R^{Q2}$, $R^{R2}$, $R^{S2}$, $R^{U2}$ and $R^{V2}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl); and $R^{Y2}$ can be an optionally substituted $C_{1-6}$ alkyl or an optionally substituted $C_{3-6}$ cycloalkyl. In some embodiments, the structures shown above can be modified by replacing one or more hydrogens with substituents selected from the list of substituents provided for the definition of "substituted."Suitable optionally substituted $C_{1-6}$ alkyl groups that can be present on an optionally substituted heterocyclic base or an optionally substituted heterocyclic base with one or more protected amino groups are described herein, and include, optionally substituted variants of the following: methyl, ethyl, n-propyl, isopropyl, n-butyl, isobutyl, tert-butyl, pentyl (branched and straight-chained), and hexyl (branched and straight-chained). In some embodiments, $B^1$ can be a naturally occurring nucleobase. In other embodiments, $B^1$ can be a non-naturally occurring nucleobase. In some embodiments, $B^1$ can be selected from adenine, guanine, thymine, cytosine and uracil.

In some embodiments, $R^{B2}$ can be $NH_2$. In other embodiments, $R^{E2}$ can be hydrogen. In some embodiments, $B^1$ can be

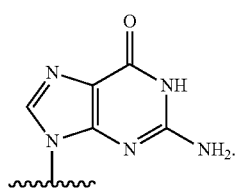 [SMILES: *n1cnc2c(=O)[nH]c(N)nc21]

In other embodiments, $B^1$ can be

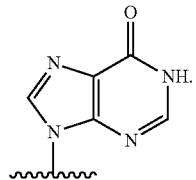 [SMILES: *n1cnc2c(=O)[nH]cnc21]

In some embodiments, $B^1$ can be

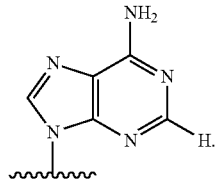

In some embodiments, $B^1$ can be

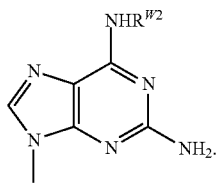

In some embodiments, $R^{W2}$ can be hydrogen. In still other embodiments, $B^1$ can be

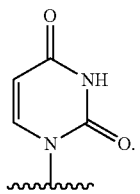 [SMILES: *n1ccc(=O)[nH]c1=O]

In some embodiments, $B^1$ can be

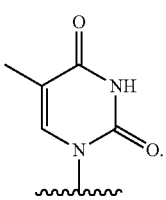 [SMILES: *n1cc(C)c(=O)[nH]c1=O]

In yet still other embodiments, $B^1$ can be

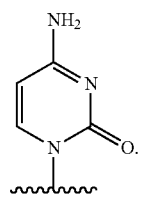 [SMILES: *n1ccc(N)nc1=O]

In some embodiments, $B^1$ can be

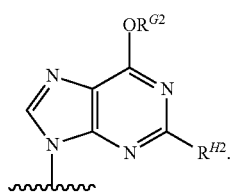

In other embodiments, $B^1$ can be

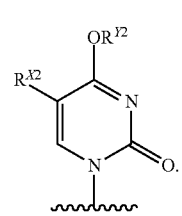

In still other embodiments, $B^1$ can be

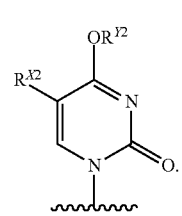

wherein $R^{x2}$ is hydrogen.

In some embodiments, $R^5$ cannot be an optionally substituted $C_{2-6}$ alkyl. In some embodiments, $R^4$ cannot be halogen. In some embodiments, when $R^4$ is halogen, then $R^3$ cannot be hydrogen or halogen. In some embodiments, when $R^4$ is halogen, then $R^3$ can be —$OR^9$ or —$OC(=O)R^{10}$. In some embodiments, $R^2$ cannot be hydrogen. In some embodiments, when $R^2$ is hydrogen, then $R^1$ cannot be $O^-$ or OH. In some embodiments, when $R^2$ is hydrogen, then $R^1$ can be an optionally substituted N-linked amino acid and an optionally substituted N-linked amino acid ester derivative. In some embodiments, when $R^1$ is $O^-$ or OH, then $R^2$ cannot be

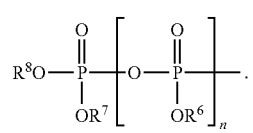

In some embodiments, at least one of $R^3$ and $R^4$ cannot be hydroxy. For example, $R^3$ cannot be hydroxy, $R^4$ cannot be hydroxy, or both of $R^3$ and $R^4$ cannot be hydroxy.

Some embodiments disclosed herein relate to a compound of Formula (I) or a pharmaceutically acceptable salt thereof, wherein: $B^1$ can be an optionally substituted heterocyclic base as described in paragraph [0110]; $R^1$ can be selected from $O^-$, OH, an optionally substituted N-linked amino acid and an optionally substituted N-linked amino acid ester derivative; $R^2$ can be absent or selected from hydrogen, an optionally substituted aryl, an optionally substituted heteroaryl, an optionally substituted heterocyclyl and

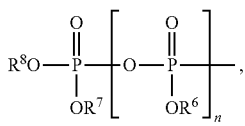

wherein $R^6$, $R^7$ and $R^8$ can be independently absent or hydrogen, and n can be 0 or 1; provided that when $R^1$ is $O^-$ or OH, then $R^2$ can be absent, hydrogen or

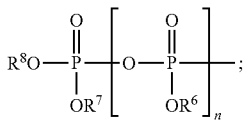

$R^3$ can be selected from hydrogen, halogen and $—OR^9$; $R^4$ can be halogen or $—OR^{11}$; $R^5$ can be selected from an optionally substituted $C_{2-6}$ alkyl, an optionally substituted $C_{2-6}$ alkenyl and an optionally substituted $C_{2-6}$ alkynyl; and $R^9$ and $R^{11}$ can be independently hydrogen or an optionally substituted $C_{1-6}$ alkyl.

Some embodiments disclosed herein relate to a compound of Formula (I) or a pharmaceutically acceptable salt thereof, wherein: $B^1$ can be an optionally substituted heterocyclic base or an optionally substituted heterocyclic base with a protected amino group selected from

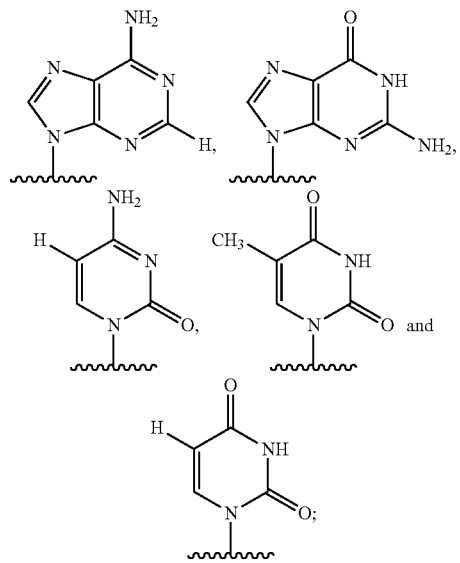

$R^1$ can be selected from $O^-$, OH, an optionally substituted N-linked amino acid and an optionally substituted N-linked amino acid ester derivative; $R^2$ can be absent or selected from hydrogen, an optionally substituted aryl, an optionally substituted heteroaryl, an optionally substituted heterocyclyl and

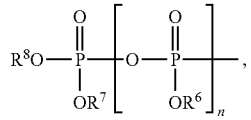

wherein $R^6$, $R^7$ and $R^8$ can be independently absent or hydrogen, and n can be 0 or 1; provided that when $R^1$ is $O^-$ or OH, then $R^2$ can be absent, hydrogen or

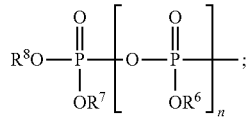

$R^3$ can be selected from hydrogen, halogen and $—OR^9$; $R^4$ can be halogen or $—OR^{11}$; $R^5$ can be selected from an optionally substituted $C_{2-6}$ alkyl, an optionally substituted $C_{2-6}$ alkenyl and an optionally substituted $C_{2-6}$ alkynyl; and $R^9$ and $R^{11}$ can be independently hydrogen or an optionally substituted $C_{1-6}$ alkyl.

Some embodiments relate to a compound of Formula (I) or a pharmaceutically acceptable salt thereof, wherein: $B^1$ can be an optionally substituted heterocyclic base or an optionally substituted heterocyclic base with a protected amino group; $R^1$ can be selected from $O^-$, OH, an optionally substituted N-linked amino acid and an optionally substituted N-linked amino acid ester derivative; $R^2$ can be absent or selected from hydrogen, an optionally substituted aryl, an optionally substituted heteroaryl, an optionally substituted heterocyclyl and

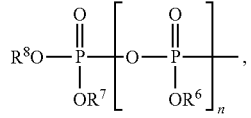

wherein $R^6$, $R^7$ and $R^8$ can be independently absent or hydrogen, and n can be 0 or 1; provided that when $R^1$ is $O^-$ or OH, then $R^2$ can be absent, hydrogen or

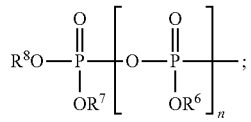

$R^3$ can be selected from hydrogen, halogen, $—OR^9$ and $—OC(=O)R^{10}$; $R^4$ can be selected from halogen, $—OR^{11}$ and $—OC(=O)R^{12}$; or $R^3$ and $R^4$ can both be oxygen atoms and linked together by a carbonyl group; $R^5$ can be an optionally substituted $C_{2-6}$ alkenyl or an optionally substituted $C_{2-6}$ alkynyl; $R^9$ and $R^{11}$ can be independently hydrogen or an optionally substituted $C_{1-6}$ alkyl; and $R^{10}$ and $R^{12}$ can be independently an optionally substituted $C_{1-6}$ alkyl or an optionally substituted $C_{3-6}$ cycloalkyl.

In some embodiments, a compound of Formula (I) can be a single diastereomer. In other embodiments, a compound of Formula (I) can be a mixture of diastereomers. In some embodiments, a compound of Formula (I) can be a 1:1 mixture of two diastereomers. In some embodiments, a compound of Formula (I) can be diasteriometrically enriched (for example, one diastereomer can be present at a concentration of >55%, ≥75%, ≥80%, ≥90%, ≥95%, ≥98%, or ≥99% as compared to the total concentration of the other diastereomers).
Examples of compounds of Formula (I) include, but are not limited to the following:
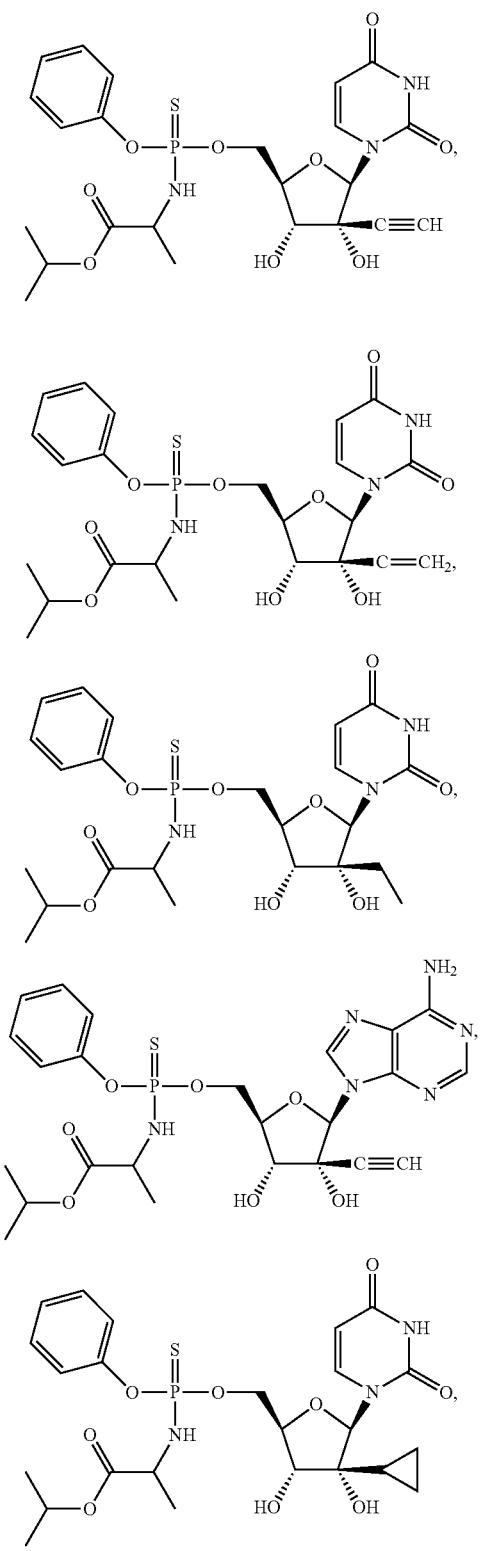
-continued
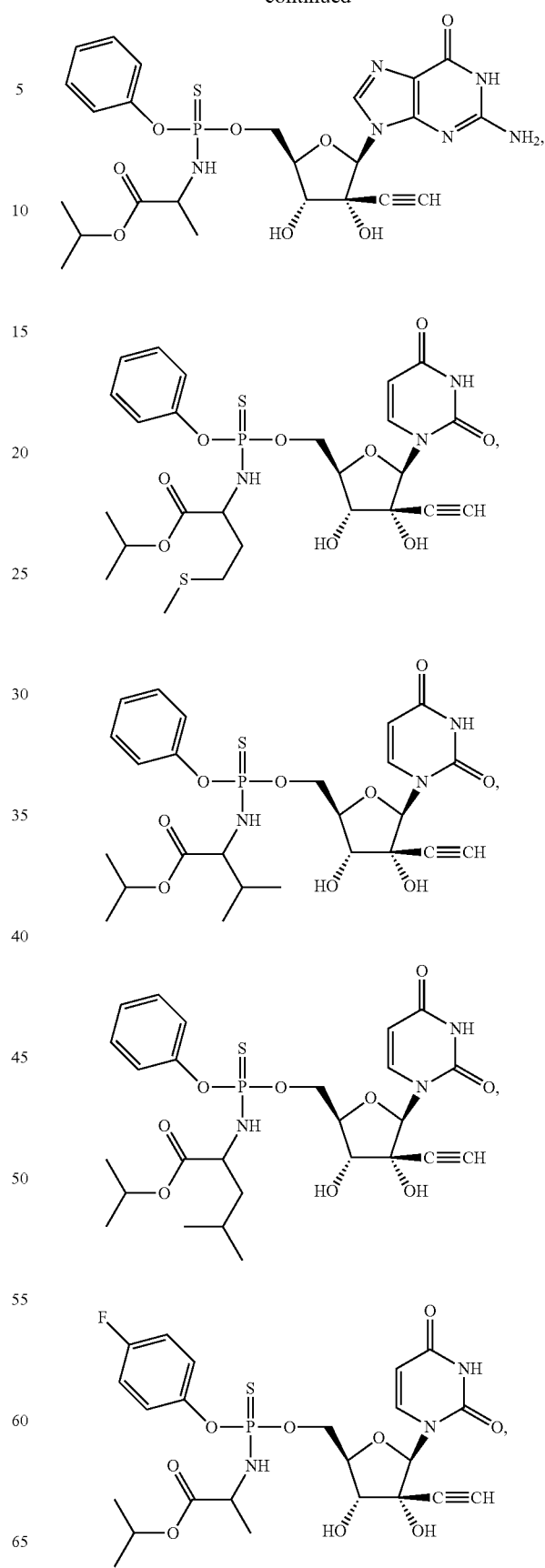

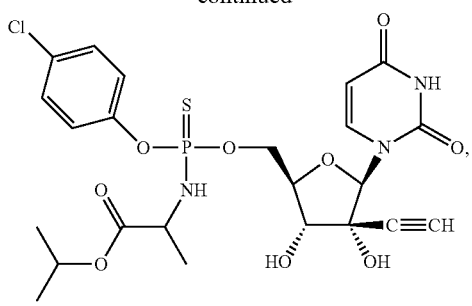
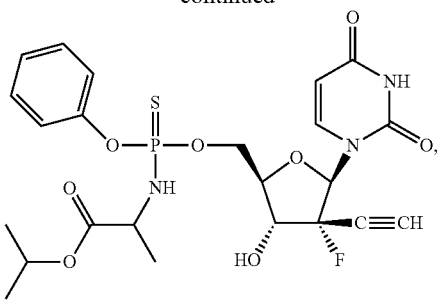
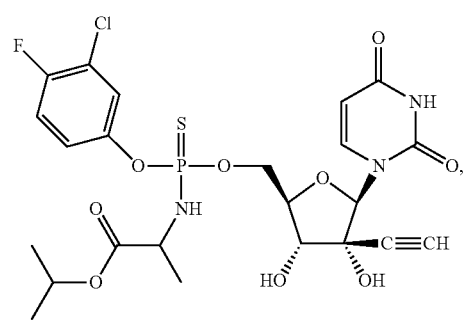
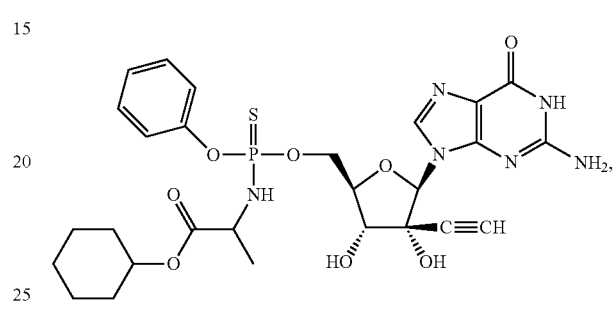
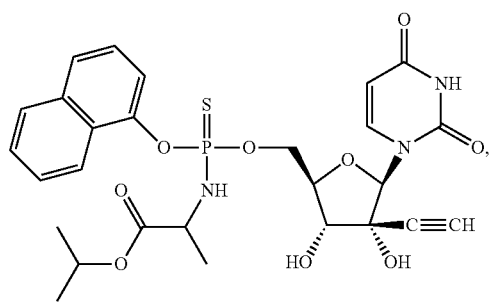
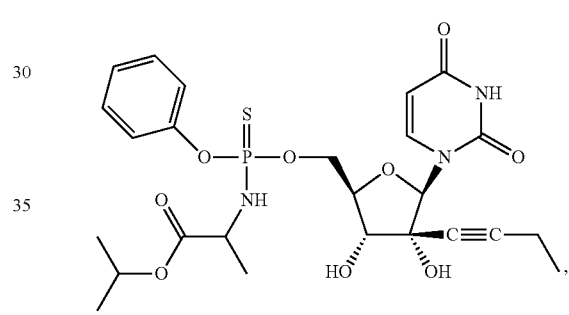
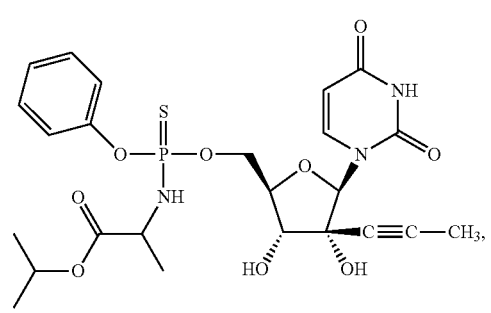
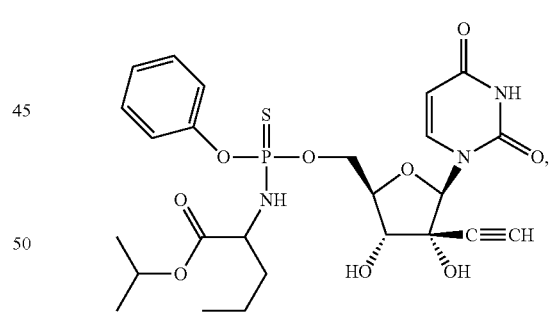
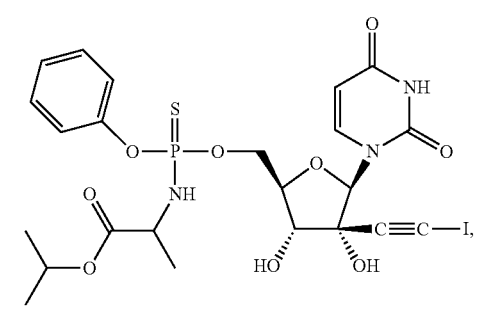
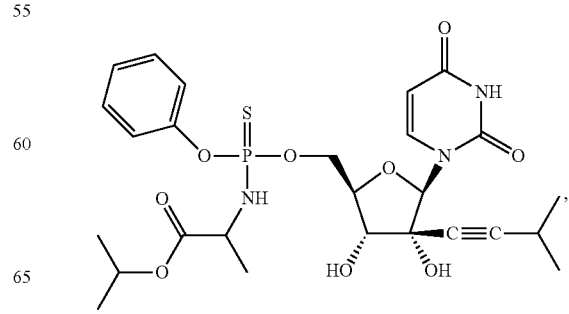

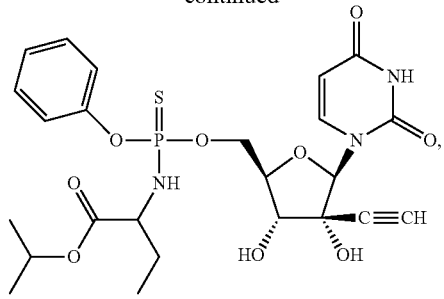

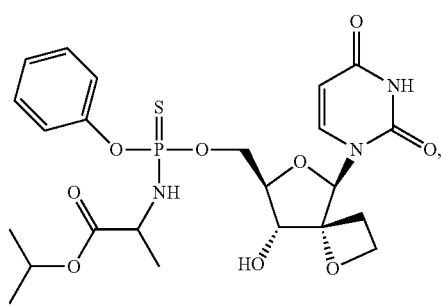

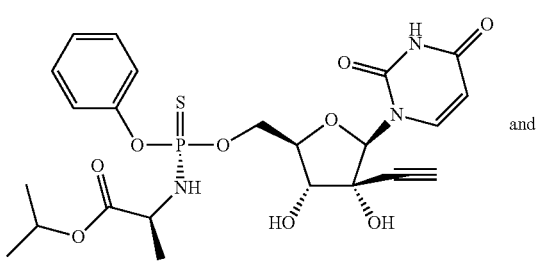

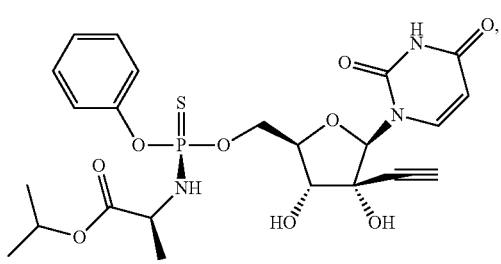 [SMILES: C#C[C@@]1(O)[C@H](O)[C@@H](CO[P@](=S)(N[C@@H](C)C(=O)OC(C)C)Oc2ccccc2)O[C@H]1n1ccc(=O)[nH]c1=O]

or a pharmaceutical acceptable salt of the foregoing.

Additional examples of compounds of Formula (I) include the following:

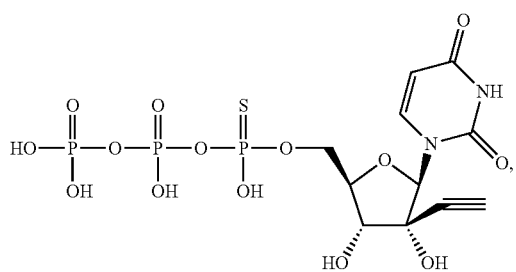

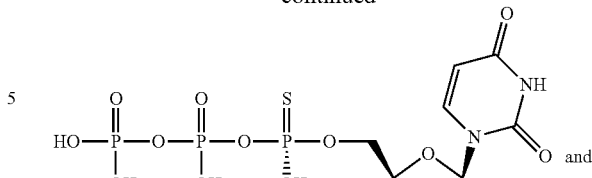

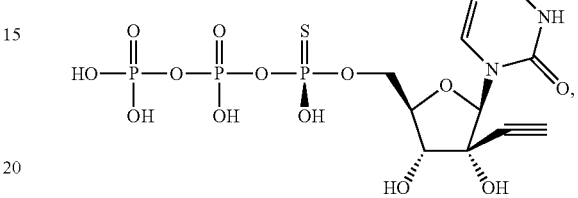

or a pharmaceutical acceptable salt of the foregoing.

In some embodiments, neutralizing the charge on the thiophosphate group may facilitate the penetration of the cell membrane by a compound of Formula (I), or a pharmaceutically acceptable salt thereof, by making the compound more lipophilic compared to a thionucleotide having a comparable structure with one or more charges present on the phosphate. Once absorbed and taken inside the cell, the groups attached to the thiophosphate can be easily removed by esterases, proteases, or other enzymes. In some embodiments, the groups attached to the thiophosphate can be removed by simple hydrolysis. Inside the cell, the thio-monophosphate thus released may then be metabolized by cellular enzymes to the thio-diphosphate or the active thio-triphosphate. Furthermore, in some embodiments, varying the substituents on a compound described herein, such as compound of Formula (I), can help maintain the efficacy of such the compound by reducing undesirable effects, such as isomerization.

In some embodiments, the phosphorylation of a thio-monophosphate of a compound of Formula (I), or pharmaceutically acceptable salt thereof, can be stereoselective. For example, a thio-monophosphate of a compound of Formula (I) can be phosphorylated to give an alpha-thiodiphosphate and/or an alpha-thiotriphosphate compound that can be enriched in the (R) or (S) diastereomer with respect to the 5'-O-phosphorous atom. For example, one of the (R) and (S) configuration with respect to the 5'-O-phosphorous atom of the alpha-thiodiphosphate and/or the alpha-thiotriphosphate compound can be present in an amount>50%, ≥75%, ≥90%, ≥95% or ≥99% compared to the amount of the other of the (R) or (S) configuration with respect to the 5'-O-phosphorous atom. In some embodiments, phosphorylation of a compound of Formula (I), or pharmaceutically acceptable salt thereof, can result in the formation of a compound that has the (R)-configuration at the 5'-O-phosphorous atom. In some embodiments, phosphorylation of a compound of Formula (I), or pharmaceutically acceptable salt thereof, can result in formation of a compound that has the (S)-configuration at the 5'-O-phosphorous atom.

In some embodiments, a compound of Formula (I), or a pharmaceutically acceptable salt thereof, can act as a chain terminator of HCV replication. For example, compounds of Formula (I) can contain a moiety at the 2'-carbon position such that once the compound is incorporated into an RNA chain of HCV no further elongation is observed to occur. For example, a compound of Formula (I) can contain a 2'-carbon modification wherein $R^5$ is a non-hydrogen group selected from an optionally substituted $C_{2-6}$ alkyl, an optionally substituted $C_{2-6}$ alkenyl and an optionally substituted $C_{2-6}$ alkynyl.

In some embodiments, a compound of Formula (I), or a pharmaceutically acceptable salt thereof, can have increased metabolic and/or plasma stability. In some embodiments, a compound of Formula (I), or a pharmaceutically acceptable salt thereof, can be more resistant to hydrolysis and/or more resistant to enzymatic transformations. For example, a compound of Formula (I), or a pharmaceutically acceptable salt thereof, can have increased metabolic stability, increased plasma stability, can be more resistant to hydrolysis and/or can be more resistant to enzymatic transformations compared to a compound that is identical in structure but for having a phosphate attached to the 5'-carbon of the ribose ring. In some embodiments, a compound of Formula (I), or a pharmaceutically acceptable salt thereof, can have improved properties. In previous studies, replacing a sulfur with an oxygen on the alpha-phosphate of a nucleotide phosphoroamidate has resulted in more than a 1000-fold decrease in potency. See Venkatachalam et al. *European Journal of Medicinal Chemistry* (2004) 39:665-683. A non-limiting list of example properties include, but are not limited to, increased biological half-life, increased bioavailability, increase potency, a sustained in vivo response, increased dosing intervals, decreased dosing amounts, decreased cytotoxicity, reduction in required amounts for treating disease conditions, reduction in viral load, reduction in time to seroconversion (i.e., the virus becomes undetectable in patient serum), increased sustained viral response, a reduction of morbidity or mortality in clinical outcomes, increased subject compliance, decreased liver conditions (such as liver fibrosis, liver cirrohis and/or liver cancer), and compatibility with other medications. In some embodiments, a compound of Formula (I), or a pharmaceutically acceptable salt thereof, can have a biological half-life of greater than 24 hours. In some embodiments, a compound of Formula (I), or a pharmaceutically acceptable salt thereof, can have a biological half-life in the range of about 40 hours to about 46 hours. In some embodiments, a compound of Formula (I), or a pharmaceutically acceptable salt thereof, can have a biological half-life greater than a compound that has a phosphate attached to the 5'-carbon of the ribose ring (for example, a compound that is identical in structure but for having a phosphate attached to the 5'-carbon of the ribose ring). In some embodiments, a compound of Formula (I), or a pharmaceutically acceptable salt thereof, can have more potent antiviral activity (for example, a lower $EC_{50}$ in an HCV replicon assay) as compared to the current standard of care.

Additionally, in some embodiments, the presence of a phosphorothioamidate in a compound of Formula (I) can increase the stability of the compound by inhibiting its degradation. Also, in some embodiments, the presence of a phosphorothioamidate can make the compound more resistant to cleavage in vivo and provide sustained, extended efficacy. In some embodiments, a phosphorothioamidate can facilitate the penetration of the cell membrane by a compound of Formula (I) by making the compound more lipophilic.

Synthesis

Compounds of Formula (I) and those described herein may be prepared in various ways. General synthetic routes to the compound of Formula (I), and some examples of starting materials used to synthesize the compounds of Formula (I) are shown in Scheme 1, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

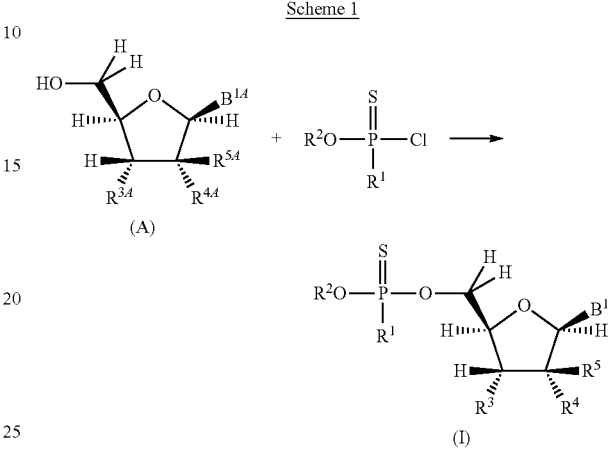

Scheme 1

One method for forming a compound of Formula (I) is shown in Scheme 1. In Scheme 1, $R^{3A}$, $R^{4A}$, $R^{5A}$ and $B^{1A}$ can be the same as $R^3$, $R^4$, $R^5$ and $B^1$ as described herein for Formula (I); and $R^1$ and $R^2$ can be the same as described herein for Formula (I). As shown in Scheme 1, a compound of Formula (A) can be reacted with a compound having the formula $R^2O—P(=S)(R^1)—Cl$ to form a compound of Formula (I).

To reduce the formation of side products, one or more the groups attached to the pentose ring can be protected with one or more suitable protecting groups. As an example, if $R^{3A}$ and/or $R^{4A}$ is/are hydroxy group(s), the hydroxy group(s) can be protected with suitable protecting groups, such as triarylmethyl and/or silyl groups. Examples of triarylmethyl groups include but are not limited to, trityl, monomethoxytrityl (MMTr), 4,4'-dimethoxytrityl (DMTr), 4,4',4''-trimethoxytrityl (TMTr), 4,4',4''-tris-(benzoyloxy)trityl (TBTr), 4,4',4''-tris(4,5-dichlorophthalimido)trityl (CPTr), 4,4',4''-tris(levulinyloxy)trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4''-tris-(tert-butylphenyl)methyl (TTTr) and 4,4'-di-3,5-hexadienoxytrityl. Examples of suitable silyl groups are described herein. Alternatively, $R^{3A}$ and/or $R^{4A}$ can be protected by a single achiral or chiral protecting group, for example, by forming an orthoester, a cyclic acetal or a cyclic ketal. Suitable orthoesters include methoxymethylene acetal, ethoxymethylene acetal, 2-oxacyclopentylidene orthoester, dimethoxymethylene orthoester, 1-methoxyethylidene orthoester, 1-ethoxyethylidene orthoester, methylidene orthoester, phthalide orthoester 1,2-dimethoxyethylidene orthoester, and alpha-methoxybenzylidene orthoester; suitable cyclic acetals include methylene acetal, ethylidene acetal, t-butylmethylidene acetal, 3-(benzyloxy) propyl acetal, benzylidene acetal, 3,4-dimethoxybenzylidene acetal and p-acetoxybenzylidene acetal; and suitable cyclic ketals include 1-t-butylethylidene ketal, 1-phenylethylidene ketal, isopropylidene ketal, cyclopentylidene ketal, cyclohexylidene ketal, cycloheptylidene ketal and 1-(4-methoxyphenyl)ethylidene ketal.

If desired, any —NH and/or NH$_2$ groups present on the B$^{1A}$ can also be protected with one or more suitable protecting groups. Examples of suitable protecting groups include triarylmethyl groups and silyl groups. Examples of silyl groups include, but are not limited to, trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl.

Suitable thiophosphorochloridates can be synthetically prepared. An example of a general structure of a thiophosphorochloridate is shown in Scheme 1. In some embodiments, the thiophosphorochloridate can be coupled to a compound of Formula (A). In some embodiments, to facilitate the coupling, a Grignard reagent can be used. Suitable Grignard reagents are known to those skilled in the art and include, but are not limited to, alkylmagnesium chlorides and alkylmagnesium bromides. In other embodiments, the thiophosphorochloridate can be added to a compound of Formula (A) using a base. Suitable bases are known to those skilled in the art. Examples of bases include, but are not limited to, an amine base, such as an alkylamine (including mono-, di- and tri-alkylamines (e.g., triethylamine)), optionally substituted pyridines (e.g. collidine) and optionally substituted imidazoles (e.g., N-methylimidazole)).

As described herein, in some embodiments, R$^3$ and R$^4$ can be both oxygen atoms linked together by a carbonyl groups. The —O—C(=O)—O— group can be formed using methods known to those skilled in the art. For example, a compound of Formula (I), wherein R$^3$ and R$^4$ are both hydroxy groups, can be treated with 1,1'-carbonyldiimidazole (CDI).

In some embodiments, R$^3$ and/or R$^4$ can be —OC(=O)R$^{10}$ and —OC(=O)R$^{12}$, respectively. The —OC(=O)R$^{10}$ and —OC(=O)R$^{12}$ groups can be formed at the 2'- and 3'-positions using various methods known to those skilled in the art. As an example, a compound of Formula (I), wherein R$^3$ and R$^4$ are both hydroxy groups, can be treated with an alkyl anhydride (e.g., acetic anhydride and propionic anhydride) or an alkyl acid chloride (e.g., acetylchloride). If desired, a catalyst can be used to facilitate the reaction. An example of suitable catalyst is 4-dimethylaminopyridine (DMAP). Alternatively, the —OC(=O)R$^{10}$ and —OC(=O)R$^{12}$ groups can be formed at the 2'- and 3'-positions by reacting an alkyl acid (e.g. acetic acid and propionic acid) in the presences of a carbodiimide or a coupling reagent. Examples of carbodiimides include, but are not limited to, N,N'-dicyclohexylcarbodiimide (DCC), N,N'-diisopropylcarbodiimide (DIC) and 1-ethyl-3-(3-dimethylaminopropyl)carbodiimide (EDC).

As described herein, B$^{1A}$ can include a carbamate and/or an amide. Those skilled in the art know methods for forming a carbamate and/or an amide on B$^{1A}$. In some embodiments, the carbamate can be formed using 1,1'-carbonyldiimidazole and an alcohol.

B$^{1A}$ can be added to the pentose ring using various methods known to those skilled in the art. In some embodiments, a compound of Formula (B) can be reacted with a nitrogenous base. In some embodiments, R$^{3A}$, R$^{4A}$, R$^{5A}$ and B$^{1A}$ of a compound of Formula (B) can be the same as disclosed herein, with respect to R$^3$, R$^4$, R$^5$ and B$^1$; and PG$^1$ can be an appropriate protecting group. In some embodiments, PG$^1$ can be p-nitrobenzyl group. In some embodiments, any hydroxy groups attached to the pentose ring can be protected with one or more suitable protecting groups. In some embodiments, any hydroxy groups attached to the pentose ring can be protected with benzoyl groups. Examples of nitrogenous bases include an optionally substituted heterocyclic bases described herein, wherein the nitrogen atom (—N) connected to the pentose ring is —NH. If desired, any —NH and/or NH$_2$ groups present on the nitrogenous base can be protected with one or more suitable protecting groups. Suitable protecting groups are described herein. In some embodiments, the nitrogenous base can be added via a coupling reaction in the presence of a Lewis acid or TMSOTf. Suitable Lewis acids are known to those skilled in the art.

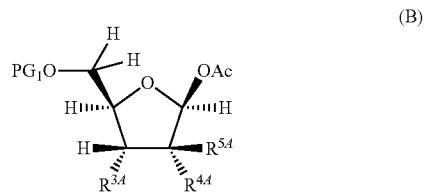

(B)

Various methods can be used to make a compound of Formula (I), wherein R$^1$ is

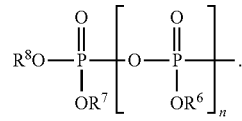

For example, a thiophosphorochloridate having the general formula of (P(=S)Cl$_3$) can be transformed into a phosphorus reagent having the general formula, P(=S)LG$_3$, wherein each LG can be amine-based leaving group. In some embodiments, each LG can be a triazole. The phosphorus reagent having the general formula, P(=S)LG$_3$, can be reacted with a compound of Formula (I). Using a suitable pyrophosphorylation reagent, the β and γ phosphates can be added. An example of a suitable pyrophosphorylation reagent is tris (tetrabutylammonium)hydrogen pyrophosphate.

During the synthesis of any of the compounds described herein, if desired, any hydroxy groups attached to the pentose ring, and any —NH and/or NH$_2$ groups present on the B$^{1A}$ can be protected with one or more suitable protecting groups. Suitable protecting groups are described herein. Those skilled in the art will appreciate that groups attached to the pentose ring and any —NH and/or NH$_2$ groups present on the B$^{1A}$ can be protected with various protecting groups, and any protecting groups present can be exchanged for other protecting groups. The selection and exchange of the protecting groups is within the skill of those of ordinary skill in the art. Any protecting group(s) can also be removed by methods known in the art, for example, with an acid (e.g., a mineral or an organic acid), a base or a fluoride source.

Pharmaceutical Compositions

Some embodiments described herein relates to a pharmaceutical composition, that can include a therapeutically effective amount of one or more compounds described herein (e.g., a compound of Formula (I)), or a pharmaceutically acceptable salt thereof) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments disclosed herein relate to a method of treating and/or ameliorating a disease or condition that can include administering to a subject a therapeutically effective amount of one or more compounds described herein, such as a compound of Formula (I), or a pharmaceutically acceptable salt thereof, or a pharmaceutical composition that includes a compound described herein, or a pharmaceutically acceptable salt thereof.

Some embodiments disclosed herein relate to a method of ameliorating or treating a neoplastic disease that can include administering to a subject suffering from a neoplastic disease a therapeutically effective amount of one or more compounds described herein (e.g., a compound of Formula (I)), or a pharmaceutically acceptable salt thereof), or a pharmaceutical composition that includes a compound described herein, or a pharmaceutically acceptable salt thereof. In some embodiments, the neoplastic disease can be cancer. In some embodiments, the neoplastic disease can be a tumor such as a solid tumor. In an embodiment, the neoplastic disease can be leukemia. Exemplary leukemias include, but are not limited to, acute lymphoblastic leukemia (ALL), acute myeloid leukemia (AML) and juvenile myelomonocytic leukemia (JMML).

Some embodiments disclosed herein relate to a method of inhibiting the growth of a tumor that can include administering to a subject having a tumor a therapeutically effective amount of one or more compounds described herein (for example, a compound of Formula (I)), or a pharmaceutical composition that includes one or more compounds described herein, or a pharmaceutically acceptable salt thereof.

Other embodiments disclosed herein relates to a method of ameliorating or treating a viral infection that can include administering to a subject suffering from a viral infection a therapeutically effective amount of one or more compounds described herein (for example, a compound of Formula (I)), or a pharmaceutical composition that includes one or more compounds described herein, or a pharmaceutically acceptable salt thereof. In some embodiments, the viral infection can be caused by a virus selected from an adenovirus, an Alphaviridae, an Arbovirus, an Astrovirus, a Bunyaviridae, a Coronaviridae, a Filoviridae, a Flaviviridae, a Hepadnaviridae, a Herpesviridae, an Alphaherpesvirinae, a Betaherpesvirinae, a Gammaherpesvirinae, a Norwalk Virus, an Astroviridae, a Caliciviridae, an Orthomyxoviridae, a Paramyxoviridae, a Paramyxoviruses, a Rubulavirus, a Morbillivirus, a Papovaviridae, a Parvoviridae, a Picornaviridae, an Aphthoviridae, a Cardioviridae, an Enteroviridae, a Coxsackie virus, a Polio Virus, a Rhinoviridae, a Phycodnaviridae, a Poxyiridae, a Reoviridae, a Rotavirus, a Retroviridae, an A-Type Retrovirus, an Immunodeficiency Virus, a Leukemia Viruses, an Avian Sarcoma Viruses, a Rhabdoviruses, a Rubiviridae, a Togaviridae an Arenaviridae and/or a Bornaviridae. In some embodiments, the viral infection can be a hepatitis C viral (HCV) infection. In still other embodiments, the viral infection can be HIV.

Some embodiments disclosed herein relate to methods of ameliorating and/or treating a viral infection that can include contacting a cell infected with the virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a viral infection that can include contacting a cell infected with the virus with an effective amount of said compound(s). Still other embodiments described herein relate to one or more compounds described herein, or a pharmaceutically acceptable salt of a compound described herein, that can be used for ameliorating and/or treating a viral infection by contacting a cell infected with the virus with an effective amount of said compound(s). In some embodiments, the compound can be a compound of Formula (I), or a pharmaceutical acceptable salt thereof. In other embodiments, the compound can be a mono-, di- and/or tri-phosphate of a compound of Formula (I), or a pharmaceutically acceptable salt of the foregoing. In some embodiments, the virus can be a HCV virus.

Some embodiments disclosed herein relate to methods of inhibiting replication of a virus that can include contacting a cell infected with the virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for inhibiting replication of a virus that can include contacting a cell infected with the virus with an effective amount of said compound(s). Still other embodiments described herein relate to a compound described herein, or a pharmaceutically acceptable salt of a compound described herein, that can be used for inhibiting replication of a virus by contacting a cell infected with the virus with an effective amount of said compound(s). In some embodiments, the compound can be a compound of Formula (I), or a pharmaceutical acceptable salt thereof. In other embodiments, the compound can be a mono-, di- and/or triphosphate of a compound of Formula (I), or a pharmaceutically acceptable salt of the foregoing. In some embodiments, the virus can be a HCV virus.

HCV is an enveloped positive strand RNA virus in the Flaviviridae family. There are various nonstructural proteins of HCV, such as NS2, NS3, NS4, NS4A, NS4B, NS5A, and NS5B. NS5B is believed to be an RNA-dependent RNA polymerase involved in the replication of HCV RNA.

Some embodiments described herein relate to a method of inhibiting NS5B polymerase activity that can include contacting a cell (for example, a cell infected with HCV) with an effective amount of a compound of Formula (I), or a pharmaceutical acceptable salt thereof. Some embodiments described herein relate to a method of inhibiting NS5B polymerase activity that can include administering a cell (for example, a cell infected with HCV) with an effective amount of a compound of Formula (I), or a pharmaceutical acceptable salt thereof. In some embodiments, a compound of Formula (I), or a pharmaceutically acceptable salt thereof, can inhibit a RNA dependent RNA polymerase. In some embodiments, a compound of Formula (I), or a pharmaceutically acceptable salt thereof, can inhibit a HCV polymerase (for example, NS5B polymerase).

Some embodiments described herein relate to a method of treating HCV infection in a subject suffering from a HCV infection that can include administering to the subject an effective amount of a compound of Formula (I), or a pharmaceutical acceptable salt thereof, or a pharmaceutical composition that includes an effective amount of a compound of Formula (I), or a pharmaceutical acceptable salt thereof. Some embodiments described herein relate to a method of treating a condition selected from liver fibrosis, liver cirrhosis, and liver cancer in a subject suffering from one or more of the aforementioned liver conditions that can include administering to the subject an effective amount of a compound or a pharmaceutical composition described herein (for example, a compound of Formula (I), or a pharmaceutical acceptable salt thereof). One cause of liver fibrosis, liver cirrohis, and/or liver cancer can be a HCV infection. Some embodiments described herein relate to a method of increasing liver function in a subject having a HCV infection that can include administering to the subject an effective amount of a compound or a pharmaceutical composition described herein (for example, a compound of Formula (I), or a pharmaceutical acceptable salt thereof). Also contemplated is a method for reducing or eliminating further virus-caused liver damage in a subject having an HCV infection by administering to the subject an effective amount of a compound or a pharmaceutical composition described herein (for example, a compound of Formula (I), or a pharmaceutical acceptable salt thereof). In some embodiments, this method can include slowing or halting the progression of liver disease. In other embodiments, the course of the disease can be reversed, and stasis or improvement in liver function is contemplated.

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4-e; 5a; 6a; 7a-7b; 8a-8b; 9a; 10a; and 11a). In some embodiments, an effective amount of a compound of Formula (I), or a pharmaceutical acceptable salt thereof, or a pharmaceutical composition that includes an effective amount of a compound of Formula (I), or a pharmaceutical acceptable salt thereof, can be effective to treat at least one genotype of HCV. In some embodiments, a compound described herein (for example, a compound of Formula (I), or a pharmaceutical acceptable salt thereof) can be effective to treat all 11 genotypes of HCV. In some embodiments, a compound described herein (for example, a compound of Formula (I), or a pharmaceutical acceptable salt thereof) can be effective to treat 3 or more, 5 or more, 7 or more, or 9 or more genotypes of HCV. In some embodiments, a compound of Formula (I), or a pharmaceutical acceptable salt thereof can be more effective against a larger number of HCV genotypes than the standard of care. In some embodiments, a compound of Formula (I), or a pharmaceutical acceptable salt thereof, can be more effective against a particular HCV genotype than the standard of care (such as genotype 1, 2, 3, 4, 5 and/or 6).

Various indicators for determining the effectiveness of a method for treating a HCV infection are known to those skilled in the art. Examples of suitable indicators include, but are not limited to, a reduction in viral load, a reduction in viral replication, a reduction in time to seroconversion (virus undetectable in patient serum), an increase in the rate of sustained viral response to therapy, a reduction of morbidity or mortality in clinical outcomes, a reduction in the rate of liver function decrease; stasis in liver function; improvement in liver function; reduction in one or more markers of liver dysfunction, including alanine transaminase, aspartate transaminase, total bilirubin, conjugated bilirubin, gamma glutamyl transpeptidase, and/or other indicator of disease response. Similarly, successful therapy with an effective amount of a compound or a pharmaceutical composition described herein (for example, a compound of Formula (I), or a pharmaceutical acceptable salt thereof) can reduce the incidence of liver cancer in HCV infected subjects.

In some embodiments, an effective amount of a compound of Formula (I), or a pharmaceutically acceptable salt thereof, is an amount that is effective to reduce viral titers to undetectable levels, for example, to about 100 to about 500, to about 50 to about 100, to about 10 to about 50, or to about 15 to about 25 international units/mL serum. In some embodiments, an effective amount of a compound of Formula (I), or a pharmaceutically acceptable salt thereof, is an amount that is effective to reduce viral load compared to the viral load before administration of the compound of Formula (I), or a pharmaceutically acceptable salt thereof. For example, wherein the viral load is measured before administration of the compound of Formula (I), or a pharmaceutically acceptable salt thereof, and again after completion of the treatment regime with the compound of Formula (I), or a pharmaceutically acceptable salt thereof (for example, 1 month after completion). In some embodiments, an effective amount of a compound of Formula (I), or a pharmaceutically acceptable salt thereof, can be an amount that is effective to reduce viral load to lower than about 25 international units/mL serum. In some embodiments, an effective amount of a compound of Formula (I), or a pharmaceutically acceptable salt thereof, is an amount that is effective to achieve a reduction in viral titer in the serum of the subject in the range of about 1.5-log to about a 2.5-log reduction, about a 3-log to about a 4-log reduction, or a greater than about 5-log reduction compared to the viral load before administration of the compound of Formula (I), or a pharmaceutically acceptable salt thereof. For example, the viral load can be measured before administration of the compound of Formula (I), or a pharmaceutically acceptable salt thereof, and again after completion of the treatment regime with the compound of Formula (I), or a pharmaceutically acceptable salt thereof (for example, 1 month after completion).

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of HCV relative to pre-treatment levels in a subject, as determined after completion of the treatment regime (for example 1 month after completion). In some embodiments, a compound of Formula (I), or a pharmaceutically acceptable salt thereof, can result in a reduction of the replication of HCV relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of HCV replication in the range of 1 to 1.5 log, 1.5 log to 2 log, 2 log to 2.5 log, 2.5 to 3 log, 3 log to 3.5 log or 3.5 to 4 log more reduction of HCV replication compared to the reduction of HCV reduction achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, an effective amount of a compound of Formula (I), or a pharmaceutically acceptable salt thereof, is an amount that is effective to achieve a sustained viral response, for example, non-detectable or substantially non-detectable HCV RNA (e.g., less than about 500, less than about 400, less than about 200, or less than about 100 genome copies per milliliter serum) is found in the subject's serum for a period of at least about one month, at least about two months, at least about three months, at least about four months, at least about five months, or at least about six months following cessation of therapy.

In some embodiments, a therapeutically effective amount of a compound of Formula (I), or a pharmaceutically acceptable salt thereof, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of a markers includes measuring the levels of serum alanine aminotransferase (ALT), aspartate aminotransferase (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of a compound of Formula (I), or a pharmaceutically acceptable salt thereof, can be an amount effective to reduce ALT, AST, ALP, GGT and/or TBIL levels to with what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, a compound of Formula (I), or a pharmaceutically acceptable salt thereof, can be administered to a treatment failure subject suffering from HCV. In some embodiments, a compound of Formula (I), or a pharmaceutically acceptable salt thereof, can be administered to a non-responder subject suffering from HCV. In some embodiments, a compound of Formula (I), or a pharmaceutically acceptable salt thereof, can be administered to a relapsed subject suffering from HCV.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with an HCV strain that is resistant to one or more different anti-HCV agents. In some embodiments, development of resistant HCV strains is delayed when a subject is treated with a compound of Formula (I), or a pharmaceutically acceptable salt thereof, compared to the development of HCV strains resistant to other HCV drugs.

In some embodiments, an effective amount of a compound of Formula (I), or a pharmaceutically acceptable salt thereof, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of current therapy. In some embodiments, a compound of Formula (I), or a pharmaceutically acceptable salt thereof, can be provided to a subject that is hypersensitive to interferon and/or ribavirin.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a compound of Formula (I), or a pharmaceutically acceptable salt thereof, can be administered to a subject experiencing viral load rebound, or can prevent such viral load rebound when used to treat the subject.

The standard of care for treating HCV has been associated with several side effects (adverse events). In some embodiments, a compound of Formula (I), or a pharmaceutically acceptable salt thereof, can decrease the number and/or severity of side effects that can be observed in HCV patients being treated with ribavirin and pegylated interferon according to the standard of care. Examples of side effects include, but are not limited to fever, malaise, tachycardia, chills, headache, arthralgias, myalgias, fatigue, apathy, loss of appetite, nausea, vomiting, cognitive changes, asthenia, drowsiness, lack of initiative, irritability, confusion, depression, severe depression, suicidal ideation, anemia, low white blood cell counts, and thinning of hair. In some embodiments, a compound of Formula (I), or a pharmaceutically acceptable salt thereof, can be provided to a subject that discontinued a HCV therapy because of one or more adverse effects or side effects associated with one or more other HCV agents.

Table 1 provides some embodiments of the percentage improvement obtained using a compound of Formula (I), or a pharmaceutically acceptable salt thereof, as compared to the standard of care. Examples include the following: in some embodiments, a compound of Formula (I), or a pharmaceutically acceptable salt thereof, results in a percentage of non-responders that is 10% less than the percentage of non-responders receiving the standard of care; in some embodiments, a compound of Formula (I), or a pharmaceutically acceptable salt thereof, results in a number of side effects that is in the range of about 10% to about 30% less than compared to the number of side effects experienced by a subject receiving the standard of care; and in some embodiments, a compound of Formula (I), or a pharmaceutically acceptable salt thereof, results in a severity of a side effect (such as one of those described herein) that is 25% less than compared to the severity of the same side effect experienced by a subject receiving the standard of care. Methods of quantifying the severity of a side effect are known to those skilled in the art.

TABLE 1

| Percentage of non-responders | Percentage of relapsers | Percentage of resistance | Percentage of viral load rebound | Number of side effects | Severity of side effects |
|---|---|---|---|---|---|
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

Yet still other embodiments disclosed herein relates to a method of ameliorating or treating a parasitic disease that can include administering to a subject suffering from a parasitic disease a therapeutically effective amount of one or more compounds described herein (for example, a compound of Formula (I)), or a pharmaceutical composition that includes one or more compounds described herein. In some embodiments, the parasite disease can be Chagas' disease.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of an agent within the standard of care. In some embodiments, a compound of Formula (I), or a pharmaceutically acceptable salt thereof, can be administered one time per day. For example, a compound of Formula (I), or a pharmaceutically acceptable salt thereof, can be administered one time per day to a subject suffering from a HCV infection. In some embodiments, the total time of the treatment regime with a compound of Formula (I), or a pharmaceutically acceptable salt thereof, can less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ED_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, the compounds disclosed herein, such as a compound of Formula (I), or a pharmaceutically acceptable salt thereof, or a pharmaceutical composition that includes a compound described herein, or a pharmaceutically acceptable salt thereof, can be used in combination with one or more additional agent(s). Examples of additional agents that can be used in combination with a compound of Formula (I), or a pharmaceutically acceptable salt thereof, or a pharmaceutical composition that includes a compound of Formula (I), or a pharmaceutically acceptable salt thereof, include, but are not limited to, agents currently used in a conventional standard of care for treating HCV, HCV protease inhibitors, HCV polymerase inhibitors, NS5A inhibitors, other antiviral compounds, pharmaceutically acceptable salts and pharmaceutical compositions that can include compounds of Formula (BB) (including pharmaceutically acceptable salts and pharmaceutical compositions that can include a compound of Formula (BB), or a pharmaceutically acceptable salt thereof), compounds of Formula (CC) (including pharmaceutically acceptable salts and pharmaceutical compositions that can include a compound of Formula (CC), or a pharmaceutically acceptable salt thereof), and/or combinations thereof. In some embodiments, a compound of Formula (I), or a pharmaceutically acceptable salt thereof, or a pharmaceutical composition that includes a compound of Formula (I), or a pharmaceutically acceptable salt thereof, can be used with one, two, three or more additional agents described herein. A non-limiting list of examples of combinations of a compound of Formula (I), or a pharmaceutically acceptable salt thereof, or a pharmaceutical composition that includes a compound of Formula (I), or a pharmaceutically acceptable salt thereof, is provided in Tables A, B, C and D.

In some embodiments, a compound of Formula (I), or a pharmaceutically acceptable salt thereof, or a pharmaceutical composition that includes a compound of Formula (I), or a pharmaceutically acceptable salt thereof, can be used in combination with an agent(s) currently used in a conventional standard of care therapy. For example, for the treatment of HCV, a compound disclosed herein can be used in combination with Pegylated interferon-alpha-2a (brand name PEGASYS®) and ribavirin, or Pegylated interferon-alpha-2b (brand name PEG-INTRON®) and ribavirin. As another example, a compound disclosed herein can be used in combination with oseltamivir (TAMIFLU®) or zanamivin (RELENZA®) for treating an influenza infection.

In some embodiments, a compound of Formula (I), or a pharmaceutically acceptable salt thereof, or a pharmaceutical composition that includes a compound of Formula (I), or a pharmaceutically acceptable salt thereof, can be substituted for an agent currently used in a conventional standard of care therapy. For example, for the treatment of HCV, a compound of Formula (I), or a pharmaceutically acceptable salt thereof, or a pharmaceutical composition that includes a compound of Formula (I), or a pharmaceutically acceptable salt thereof, can be used in place of ribavirin.

In some embodiments, a compound of Formula (I), or a pharmaceutically acceptable salt thereof, or a pharmaceutical composition that includes a compound of Formula (I), or a pharmaceutically acceptable salt thereof, can be used in combination with an interferon, such as a pegylated interferon. Examples of suitable interferons include, but are not limited to, Pegylated interferon-alpha-2a (brand name PEGASYS®), Pegylated interferon-alpha-2b (brand name PEG-INTRON®), interferon alfacon-1 (brand name INFERGEN®), pegylated interferon lambda and/or a combination thereof.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV protease inhibitor. A non-limiting list of example HCV protease inhibitors include the following: VX-950 (TELAPREVIR®), MK-5172, ABT-450, BILN-2061, BI-201335, BMS-650032, SCH 503034 (BOCEPREVIR®), GS-9256, GS-9451, IDX-320, ACH-1625, ACH-2684, TMC-435, ITMN-191 (DANOPREVIR®) and/or a combination thereof. Additional HCV protease inhibitors suitable for use in combination with a compound of Formula (I), or a pharmaceutically acceptable salt thereof, or a pharmaceutical composition that includes a compound of Formula (I), or a pharmaceutically acceptable salt thereof, include VP-19744, PSI-879, VCH-759/VX-759, HCV-371, IDX-375, GL-60667, JTK-109, PSI-6130, R1479, R-1626, R-7182, MK-0608, INX-8014, INX-8018, A-848837, A-837093, BILB-1941, VCH-916, VCH-716, GSK-71185, GSK-625433, XTL-2125 and those disclosed in PCT Publication No. WO 2012/142085. A non-limiting list of example HCV protease inhibitors includes the compounds numbered 1001-1016 in FIG. 1.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV polymerase inhibitor. In some embodiments, the HCV polymerase inhibitor can be a nucleoside inhibitor. In other embodiments, the HCV polymerase inhibitor can be a non-nucleoside inhibitor. Examples of suitable nucleoside inhibitors include, but are not limited to, RG7128, PSI-7851, PSI-7977, INX-189, PSI-352938, PSI-661, 4'-azidouridine (including known prodrugs of 4'-azidouridine), GS-6620, IDX-184, and TMC649128 and/or combinations thereof. A non-limiting list of example nucleoside inhibitors includes compounds numbered 2001-2012 in FIG. 2. Examples of suitable non-nucleoside inhibitors include, but are not limited to, ABT-333, ANA-598, VX-222, HCV-796, BI-207127, GS-9190, PF-00868554 (FILIBUVIR®), VX-497 and/or combinations thereof. A non-limiting list of example non-nucleoside inhibitors includes the compounds numbered 3001-3014 in FIG. 3. Further HCV polymerase inhibitors suitable for use in combination with a compound of Formula (I), or a pharmaceutically acceptable salt thereof, or a pharmaceutical composition that includes a compound of Formula (I), or a pharmaceutically acceptable salt thereof, include VX-500, VX-813, VBY-376, TMC-435350, EZ-058, EZ-063, GS-9132, ACH-1095, IDX-136, IDX-316, ITMN-8356, ITMN-8347, ITMN-8096, ITMN-7587, VX-985, and those disclosed in PCT Publication No. WO 2012/142085.

In some embodiments, a compound of Formula (I), or a pharmaceutically acceptable salt thereof, or a pharmaceutical composition that includes a compound of Formula (I), or a pharmaceutically acceptable salt thereof, can be used in combination with a NS5A inhibitor. A non-limiting list of example NS5A inhibitors include BMS-790052, PPI-461, ACH-2928, GS-5885, BMS-824393 and/or combinations thereof. A non-limiting list of example NS5A inhibitors includes the compounds numbered 4001-4012 in FIG. 4. Additional NS5A inhibitors suitable for use in combination with a compound of Formula (I), or a pharmaceutically acceptable salt thereof, or a pharmaceutical composition that includes a compound of Formula (I), or a pharmaceutically acceptable salt thereof, include A-832, PPI-1301 and those disclosed in PCT Publication No. WO 2012/142085, which is hereby incorporated by reference for the limited purpose of its disclosure of HCV protease inhibitors, HCV polymerase inhibitors and NS5A inhibitors.

In some embodiments, a compound of Formula (I), or a pharmaceutically acceptable salt thereof, or a pharmaceutical composition that includes a compound of Formula (I), or a pharmaceutically acceptable salt thereof, can be used in combination with other antiviral compounds. Examples of other antiviral compounds include, but are not limited to, Debio-025, MIR-122 and/or combinations thereof. A non-limiting list of example other antiviral compounds includes the compounds numbered 5001-5011 in FIG. 5.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (BB), or a pharmaceutically acceptable salt thereof, or a pharmaceutical composition that includes a compound of Formula (BB), or a pharmaceutically acceptable salt thereof (see, U.S. Publication No. 2012/0165286, published Jun. 28, 2012, the contents of which are incorporated by reference in their entireties):

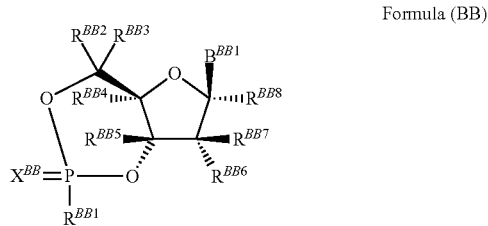

Formula (BB)

wherein $B^{BB1}$ can be an optionally substituted heterocyclic base or an optionally substituted heterocyclic base with a protected amino group; $X^{BB}$ can be O (oxygen) or S (sulfur); $R^{BB1}$ can be selected from $-Z^{BB}-R^{BB9}$, an optionally substituted N-linked amino acid and an optionally substituted N-linked amino acid ester derivative; $Z^{BB}$ can be selected from O (oxygen), S (sulfur) and $N(R^{BB10})$; $R^{BB2}$ and $R^{BB3}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl); or $R^{BB2}$ and $R^{BB3}$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl; $R^{BB4}$ can be selected from hydrogen, halogen, azido, cyano, an optionally substituted $C_{1-6}$ alkyl, an optionally substituted $C_{2-6}$ alkenyl, an optionally substituted $C_{2-6}$ alkynyl and an optionally substituted allenyl; $R^{BB5}$ can be hydrogen or an optionally substituted $C_{1-6}$ alkyl; $R^{BB6}$ can be selected from hydrogen, halogen, azido, amino, cyano, an optionally substituted $C_{1-6}$ alkyl, $-OR^{BB11}$ and $-OC(=O)R^{BB12}$; $R^{BB7}$ can be selected from hydrogen, halogen, azido, cyano, an optionally substituted $C_{1-6}$ alkyl, $-OR^{BB13}$ and $-OC(=O)R^{BB14}$; $R^{BB8}$ can be selected from hydrogen, halogen, azido, cyano, an optionally substituted $C_{1-6}$ alkyl, $-OR^{BB15}$ and $-OC(=O)R^{BB16}$; $R^{BB9}$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl); $R^{BB10}$ can be selected from hydrogen, an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl); $R^{BB11}$, $R^{BB13}$ and $R^{BB15}$ can be independently hydrogen or an optionally substituted $C_{1-6}$ alkyl; and $R^{BB12}$, $R^{BB14}$ and $R^{BB16}$ can be independently an optionally substituted $C_{1-6}$ alkyl or an optionally substituted $C_{3-6}$ cycloalkyl. In some embodiments, at least one of $R^{BB2}$ and $R^{BB3}$ is not hydrogen. A non-limiting list of example compounds of Formula (BB) includes the compound numbered 7000-7016 in FIG. 7.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (CC), or a pharmaceutically acceptable salt thereof, or a pharmaceutical composition that includes a compound of Formula (CC), or a pharmaceutically acceptable salt thereof (see, U.S. Publication No. 2012/0071434, published Mar. 22, 2012, the contents of which are incorporated by reference in its entirety):

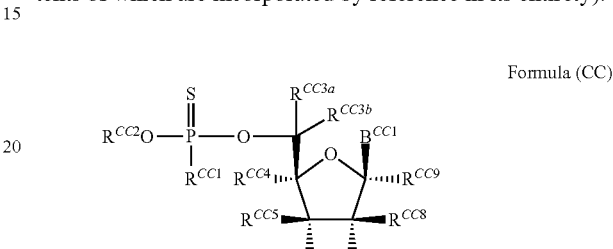

Formula (CC)

wherein $B^{CC1}$ can be an optionally substituted heterocyclic base or an optionally substituted heterocyclic base with a protected amino group; $R^{CC1}$ can be selected from $O^-$, OH, an optionally substituted N-linked amino acid and an optionally substituted N-linked amino acid ester derivative; $R^{CC2}$ can be selected from an optionally substituted aryl, an optionally substituted heteroaryl, an optionally substituted heterocyclyl and

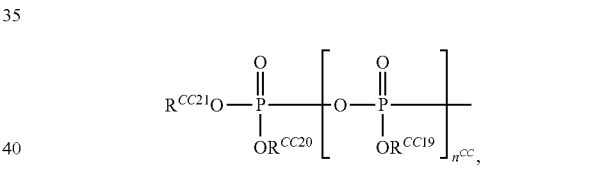

wherein $R^{CC19}$, $R^{CC20}$, and $R^{CC21}$ can be independently absent or hydrogen, and $n^{CC}$ can be 0 or 1; provided that when $R^{CC1}$ is $O^-$ or OH, then $R^{CC2}$ is

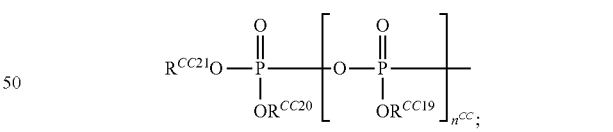

$R^{CC3a}$ and $R^{CC3b}$ can be independently selected from hydrogen, deuterium, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{CC3a}$ and $R^{CC3b}$ can be taken together to form an optionally substituted $C_{3-6}$ cycloalkyl; $R^{CC4}$ can be selected from hydrogen, azido, an optionally substituted $C_{1-6}$ alkyl, an optionally substituted $C_{2-6}$ alkenyl and an optionally substituted $C_{2-6}$ alkynyl; $R^{CC5}$ can be selected from hydrogen, halogen, azido, cyano, an optionally substituted $C_{1-6}$ alkyl, $-OR^{CC10}$ and $-OC(=O)R^{CC11}$; $R^{CC6}$ can be selected from hydrogen, halogen, azido, cyano, an optionally substituted $C_{1-6}$ alkyl, $-OR^{CC12}$ and $-OC(=O)R^{CC13}$; $R^{CC7}$ can be selected from hydrogen, halogen, azido, cyano, an optionally substituted $C_{1-6}$ alkyl, $-OR^{CC14}$ and $-OC(=O)R^{CC15}$; or $R^{CC6}$ and $R^{CC7}$ can be both oxygen atoms and linked together by a carbonyl group; $R^{CC8}$ can be selected from hydrogen, halogen, azido, cyano, an optionally substituted $C_{1-6}$ alkyl, $-OR^{CC16}$ and $-OC(=O)R^{CC17}$; $R^{CC9}$ can be selected from hydrogen, azido, cyano, an optionally substituted $C_{1-6}$ alkyl and $-OR^{CC18}$; $R^{CC10}$, $R^{CC12}$, $R^{CC14}$, $R^{CC16}$ and $R^{CC18}$ can be independently selected from hydrogen and an optionally substituted $C_{1-6}$ alkyl; and $R^{CC11}$, $R^{CC13}$, $R^{CC15}$ and $R^{CC17}$ can be independently selected from an optionally substituted $C_{1-6}$ alkyl and an optionally substituted $C_{3-6}$ cycloalkyl. In some embodiments, when $R^{CC3a}$, $R^{CC3b}$, $R^{CC4}$, $R^{CC5}$, $R^{CC7}$, $R^{CC8}$, and $R^{CC9}$ are all hydrogen, then $R^{CC6}$ is not azido. In some embodiments, $R^{CC2}$ cannot be

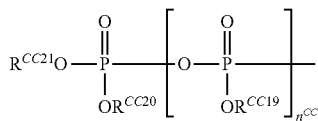

when $R^{CC3a}$ is hydrogen, $R^{CC3b}$ is hydrogen, $R^{CC4}$ is H, $R^{CC5}$ is OH or H, $R^{CC6}$ is hydrogen, OH, or $-OC(=O)CH_3$, $R^{CC7}$ is hydrogen, OH, $OCH_3$ or $-OC(=O)CH_3$, $R^{CC8}$ is hydrogen, OH or $OCH_3$, $R^{CC9}$ is H and $B^{CC1}$ is an optionally substituted adenine, an optionally substituted guanine, an optionally substituted uracil or an optionally substituted hypoxanthine. In some embodiments, $R^{CC2}$ cannot be

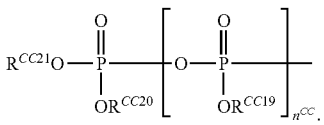

A non-limiting list of examples of compounds of Formula (CC) includes the compounds numbered 6000-6078 in FIG. 6.

Some embodiments described herein relate to a method of ameliorating or treating a viral infection that can include contacting a cell infected with the viral infection with a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (BB) and a compound of Formula (CC), or a pharmaceutically acceptable salt of any of the aforementioned compounds.

Some embodiments described herein relate to a method of ameliorating or treating a viral infection that can include administering to a subject suffering from the viral infection a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (BB) and a compound of Formula (CC), or a pharmaceutically acceptable salt of any of the aforementioned compounds.

Some embodiments described herein relate to a method of inhibiting viral replication of a virus that can include contacting a cell infected with the virus with an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (BB) and a compound of Formula (CC), or a pharmaceutically acceptable salt of any of the aforementioned compounds.

Some embodiments described herein relate to a method of ameliorating or treating a viral infection that can include contacting a cell infected with the viral infection with a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (BB) and a compound of Formula (CC), or a pharmaceutically acceptable salt of any of the aforementioned compounds.

Some embodiments described herein relate to a method of ameliorating or treating a viral infection that can include administering to a subject suffering from the viral infection a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (BB) and a compound of Formula (CC), or a pharmaceutically acceptable salt of any of the aforementioned compounds.

Some embodiments described herein relate to a method of inhibiting viral replication of a virus that can include contacting a cell infected with the virus with an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (BB) and a compound of Formula (CC), or a pharmaceutically acceptable salt of any of the aforementioned compounds.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt the thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. For example, when performing a conventional standard of care therapy using art-recognized dosing amounts and dosing schedules, a compound of Formula (I), or a pharmaceutically acceptable salt thereof, or a pharmaceutical composition that includes a compound of Formula (I), or a pharmaceutically acceptable salt thereof, can be administered in addition to that therapy, or in place of one of the agents of a combination therapy, using effective amounts and dosing protocols as described herein.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) in FIGS. 1-7 (including pharmaceutically acceptable salts and prodrugs thereof) can result in an additive effect. In some embodiments, the combination of a compound of Formula (I), or a pharmaceutically acceptable salt thereof, in combination with one or more additional agent(s) in FIGS. 1-7 (including pharmaceutically acceptable salts and prodrugs thereof) can result in a synergistic effect. In some embodiments, the combination of a compound of Formula (I), or a pharmaceutically acceptable salt thereof, in combination with one or more additional agent(s) in FIGS. 1-7 (including pharmaceutically acceptable salts and prodrugs thereof) can result in a strongly synergistic effect. In some embodiments, the combination of a compound of Formula (I), or a pharmaceutically acceptable salt thereof, in combination with one or more additional agent(s) in FIGS. 1-7 (including pharmaceutically acceptable salts and prodrugs thereof) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) in FIGS. 1-7 (including pharmaceutically acceptable salts and prodrugs thereof) may be a reduction in the required amount(s) of one or more compounds of FIGS. 1-7 (including pharmaceutically acceptable salts and prodrugs thereof) that is effective in treating a disease condition disclosed herein (for example, HCV), as compared to the amount required to achieve same therapeutic result when one or more compounds of FIGS. 1-7 (including pharmaceutically acceptable salts and prodrugs thereof) are administered without a compound of Formula (I), or a pharmaceutically acceptable salt thereof. For example, the amount of a compound in FIGS. 1-7 (including a pharmaceutically acceptable salt and prodrug thereof), can be less compared to the amount of the compound in FIGS. 1-7 (including a pharmaceutically acceptable salt and prodrug thereof), needed to achieve the same viral load reduction when administered as a monotherapy. Another potential advantage of utilizing a compound of Formula (I), or a pharmaceutically acceptable salt thereof, in combination with one or more additional agent(s) in FIGS. 1-7 (including pharmaceutically acceptable salts and prodrugs thereof) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) in FIGS. 1-7 (including pharmaceutically acceptable salts and prodrugs thereof) may include little to no cross resistance between a compound of Formula (I), or a pharmaceutically acceptable salt thereof, and one or more additional agent(s) in FIGS. 1-7 (including pharmaceutically acceptable salts and prodrugs thereof) thereof; different routes for elimination of a compound of Formula (I), or a pharmaceutically acceptable salt thereof, and one or more additional agent(s) in FIGS. 1-7 (including pharmaceutically acceptable salts and prodrugs thereof); little to no overlapping toxicities between a compound of Formula (I), or a pharmaceutically acceptable salt thereof, and one or more additional agent(s) in FIGS. 1-7 (including pharmaceutically acceptable salts and prodrugs thereof); little to no significant effects on cytochrome P450; and/or little to no pharmacokinetic interactions between a compound of Formula (I), or a pharmaceutically acceptable salt thereof, and one or more additional agent(s) in FIGS. 1-7 (including pharmaceutically acceptable salts and prodrugs thereof).

A non-limiting list of example combination of compounds of Formula (I), or a pharmaceutically acceptable salt thereof, or a pharmaceutical composition that includes a compound described herein, with one or more additional agent(s) are provided in Tables A, B, C and D. Each numbered X and Y compound in Tables A, B, C and D has a corresponding name and/or structure provided in FIGS. 1-7. The numbered compounds in Tables A, B, C and D includes pharmaceutically acceptable salts of the compounds and pharmaceutical compositions containing the compounds or a pharmaceutically acceptable salt thereof. For example, 1001 includes the compound corresponding to 1001, pharmaceutically acceptable salts thereof, and pharmaceutical compositions that include compound 1001 and/or a pharmaceutically acceptable salt thereof. The combinations exemplified in Tables A, B, C and D are designated by the formula X:Y, which represents a combination of a compound X with a compound Y. For example, the combination designated as 1001:8001 in Table A represents a combination of compound 1001 with compound 8001, including pharmaceutically acceptable salts of compound 1001 and/or 8001, and pharmaceutical compositions including compound 1001 and 8001 (including pharmaceutical compositions that include pharmaceutically acceptable salts of compound 1001 and/or compound 8001). Thus, the combination designated as 1001:8001 in Table A represents the combination of Telaprevir (compound 1001, as shown in FIG. 1) and

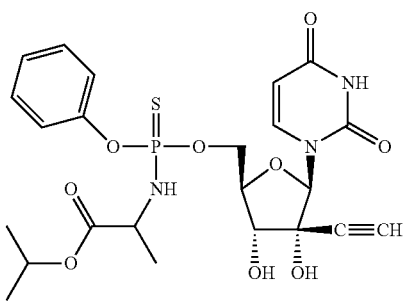 [SMILES: C#C[C@@]1(O)[C@H](O)[C@@H](COP(=S)(NC(C)C(=O)OC(C)C)Oc2ccccc2)O[C@H]1n1ccc(=O)[nH]c1=O]

(compound 8001, as shown in FIG. 8), including pharmaceutically acceptable salts of compound 1001 and/or 8001, and pharmaceutical compositions including compound 1001 and 8001 (including pharmaceutical compositions that include pharmaceutically acceptable salts of compound 1001 and/or compound 8001). Each of the combinations provided in Tables A, B, C and D can be used with one, two, three or more additional agents described herein. In some embodiments described herein, the combination of agents can be used to treat, ameliorate and/or inhibit a virus and/or a viral infection, wherein the virus can be HCV and the viral infection can be an HCV viral infection.

TABLE A

Example combinations of a compound X with a compound Y.

| X:Y | X:Y | X:Y | X:Y | X:Y | X:Y |
|---|---|---|---|---|---|
| 1001:8000 | 1001:8001 | 1001:8002 | 1001:8003 | 1001:8004 | 1001:8005 |
| 1002:8000 | 1002:8001 | 1002:8002 | 1002:8003 | 1002:8004 | 1002:8005 |
| 1003:8000 | 1003:8001 | 1003:8002 | 1003:8003 | 1003:8004 | 1003:8005 |
| 1004:8000 | 1004:8001 | 1004:8002 | 1004:8003 | 1004:8004 | 1004:8005 |
| 1005:8000 | 1005:8001 | 1005:8002 | 1005:8003 | 1005:8004 | 1005:8005 |
| 1006:8000 | 1006:8001 | 1006:8002 | 1006:8003 | 1006:8004 | 1006:8005 |
| 1007:8000 | 1007:8001 | 1007:8002 | 1007:8003 | 1007:8004 | 1007:8005 |
| 1008:8000 | 1008:8001 | 1008:8002 | 1008:8003 | 1008:8004 | 1008:8005 |
| 1009:8000 | 1009:8001 | 1009:8002 | 1009:8003 | 1009:8004 | 1009:8005 |
| 1010:8000 | 1010:8001 | 1010:8002 | 1010:8003 | 1010:8004 | 1010:8005 |
| 1011:8000 | 1011:8001 | 1011:8002 | 1011:8003 | 1011:8004 | 1011:8005 |
| 1012:8000 | 1012:8001 | 1012:8002 | 1012:8003 | 1012:8004 | 1012:8005 |
| 1013:8000 | 1013:8001 | 1013:8002 | 1013:8003 | 1013:8004 | 1013:8005 |
| 1014:8000 | 1014:8001 | 1014:8002 | 1014:8003 | 1014:8004 | 1014:8005 |
| 1015:8000 | 1015:8001 | 1015:8002 | 1015:8003 | 1015:8004 | 1015:8005 |
| 1016:8000 | 1016:8001 | 1016:8002 | 1016:8003 | 1016:8004 | 1016:8005 |
| 2001:8000 | 2001:8001 | 2001:8002 | 2001:8003 | 2001:8004 | 2001:8005 |
| 2002:8000 | 2002:8001 | 2002:8002 | 2002:8003 | 2002:8004 | 2002:8005 |
| 2003:8000 | 2003:8001 | 2003:8002 | 2003:8003 | 2003:8004 | 2003:8005 |
| 2004:8000 | 2004:8001 | 2004:8002 | 2004:8003 | 2004:8004 | 2004:8005 |
| 2005:8000 | 2005:8001 | 2005:8002 | 2005:8003 | 2005:8004 | 2005:8005 |
| 2006:8000 | 2006:8001 | 2006:8002 | 2006:8003 | 2006:8004 | 2006:8005 |
| 2007:8000 | 2007:8001 | 2007:8002 | 2007:8003 | 2007:8004 | 2007:8005 |
| 2008:8000 | 2008:8001 | 2008:8002 | 2008:8003 | 2008:8004 | 2008:8005 |
| 2009:8000 | 2009:8001 | 2009:8002 | 2009:8003 | 2009:8004 | 2009:8005 |
| 2010:8000 | 2010:8001 | 2010:8002 | 2010:8003 | 2010:8004 | 2010:8005 |
| 2011:8000 | 2011:8001 | 2011:8002 | 2011:8003 | 2011:8004 | 2011:8005 |
| 2012:8000 | 2012:8001 | 2012:8002 | 2012:8003 | 2012:8004 | 2012:8005 |
| 3001:8000 | 3001:8001 | 3001:8002 | 3001:8003 | 3001:8004 | 3001:8005 |
| 3002:8000 | 3002:8001 | 3002:8002 | 3002:8003 | 3002:8004 | 3002:8005 |
| 3003:8000 | 3003:8001 | 3003:8002 | 3003:8003 | 3003:8004 | 3003:8005 |
| 3004:8000 | 3004:8001 | 3004:8002 | 3004:8003 | 3004:8004 | 3004:8005 |
| 3005:8000 | 3005:8001 | 3005:8002 | 3005:8003 | 3005:8004 | 3005:8005 |
| 3006:8000 | 3006:8001 | 3006:8002 | 3006:8003 | 3006:8004 | 3006:8005 |
| 3007:8000 | 3007:8001 | 3007:8002 | 3007:8003 | 3007:8004 | 3007:8005 |
| 3008:8000 | 3008:8001 | 3008:8002 | 3008:8003 | 3008:8004 | 3008:8005 |
| 3009:8000 | 3009:8001 | 3009:8002 | 3009:8003 | 3009:8004 | 3009:8005 |
| 3010:8000 | 3010:8001 | 3010:8002 | 3010:8003 | 3010:8004 | 3010:8005 |
| 3011:8000 | 3011:8001 | 3011:8002 | 3011:8003 | 3011:8004 | 3011:8005 |
| 3012:8000 | 3012:8001 | 3012:8002 | 3012:8003 | 3012:8004 | 3012:8005 |
| 3013:8000 | 3013:8001 | 3013:8002 | 3013:8003 | 3013:8004 | 3013:8005 |
| 3014:8000 | 3014:8001 | 3014:8002 | 3014:8003 | 3014:8004 | 3014:8005 |

TABLE A-continued

Example combinations of a compound X with a compound Y.

| X:Y | X:Y | X:Y | X:Y | X:Y | X:Y |
|---|---|---|---|---|---|
| 1001:8006 | 1001:8007 | 1001:8008 | 1001:8009 | 1001:8010 | 1001:8011 |
| 1002:8006 | 1002:8007 | 1002:8008 | 1002:8009 | 1002:8010 | 1002:8011 |
| 1003:8006 | 1003:8007 | 1003:8008 | 1003:8009 | 1003:8010 | 1003:8011 |
| 1004:8006 | 1004:8007 | 1004:8008 | 1004:8009 | 1004:8010 | 1004:8011 |
| 1005:8006 | 1005:8007 | 1005:8008 | 1005:8009 | 1005:8010 | 1005:8011 |
| 1006:8006 | 1006:8007 | 1006:8008 | 1006:8009 | 1006:8010 | 1006:8011 |
| 1007:8006 | 1007:8007 | 1007:8008 | 1007:8009 | 1007:8010 | 1007:8011 |
| 1008:8006 | 1008:8007 | 1008:8008 | 1008:8009 | 1008:8010 | 1008:8011 |
| 1009:8006 | 1009:8007 | 1009:8008 | 1009:8009 | 1009:8010 | 1009:8011 |
| 1010:8006 | 1010:8007 | 1010:8008 | 1010:8009 | 1010:8010 | 1010:8011 |
| 1011:8006 | 1011:8007 | 1011:8008 | 1011:8009 | 1011:8010 | 1011:8011 |
| 1012:8006 | 1012:8007 | 1012:8008 | 1012:8009 | 1012:8010 | 1012:8011 |
| 1013:8006 | 1013:8007 | 1013:8008 | 1013:8009 | 1013:8010 | 1013:8011 |
| 1014:8006 | 1014:8007 | 1014:8008 | 1014:8009 | 1014:8010 | 1014:8011 |
| 1015:8006 | 1015:8007 | 1015:8008 | 1015:8009 | 1015:8010 | 1015:8011 |
| 1016:8006 | 1016:8007 | 1016:8008 | 1016:8009 | 1016:8010 | 1016:8011 |
| 2001:8006 | 2001:8007 | 2001:8008 | 2001:8009 | 2001:8010 | 2001:8011 |
| 2002:8006 | 2002:8007 | 2002:8008 | 2002:8009 | 2002:8010 | 2002:8011 |
| 2003:8006 | 2003:8007 | 2003:8008 | 2003:8009 | 2003:8010 | 2003:8011 |
| 2004:8006 | 2004:8007 | 2004:8008 | 2004:8009 | 2004:8010 | 2004:8011 |
| 2005:8006 | 2005:8007 | 2005:8008 | 2005:8009 | 2005:8010 | 2005:8011 |
| 2006:8006 | 2006:8007 | 2006:8008 | 2006:8009 | 2006:8010 | 2006:8011 |
| 2007:8006 | 2007:8007 | 2007:8008 | 2007:8009 | 2007:8010 | 2007:8011 |
| 2008:8006 | 2008:8007 | 2008:8008 | 2008:8009 | 2008:8010 | 2008:8011 |
| 2009:8006 | 2009:8007 | 2009:8008 | 2009:8009 | 2009:8010 | 2009:8011 |
| 2010:8006 | 2010:8007 | 2010:8008 | 2010:8009 | 2010:8010 | 2010:8011 |
| 2011:8006 | 2011:8007 | 2011:8008 | 2011:8009 | 2011:8010 | 2011:8011 |
| 2012:8006 | 2012:8007 | 2012:8008 | 2012:8009 | 2012:8010 | 2012:8011 |
| 3001:8006 | 3001:8007 | 3001:8008 | 3001:8009 | 3001:8010 | 3001:8011 |
| 3002:8006 | 3002:8007 | 3002:8008 | 3002:8009 | 3002:8010 | 3002:8011 |
| 3003:8006 | 3003:8007 | 3003:8008 | 3003:8009 | 3003:8010 | 3003:8011 |
| 3004:8006 | 3004:8007 | 3004:8008 | 3004:8009 | 3004:8010 | 3004:8011 |
| 3005:8006 | 3005:8007 | 3005:8008 | 3005:8009 | 3005:8010 | 3005:8011 |
| 3006:8006 | 3006:8007 | 3006:8008 | 3006:8009 | 3006:8010 | 3006:8011 |
| 3007:8006 | 3007:8007 | 3007:8008 | 3007:8009 | 3007:8010 | 3007:8011 |
| 3008:8006 | 3008:8007 | 3008:8008 | 3008:8009 | 3008:8010 | 3008:8011 |
| 3009:8006 | 3009:8007 | 3009:8008 | 3009:8009 | 3009:8010 | 3009:8011 |
| 3010:8006 | 3010:8007 | 3010:8008 | 3010:8009 | 3010:8010 | 3010:8011 |
| 3011:8006 | 3011:8007 | 3011:8008 | 3011:8009 | 3011:8010 | 3011:8011 |
| 3012:8006 | 3012:8007 | 3012:8008 | 3012:8009 | 3012:8010 | 3012:8011 |
| 3013:8006 | 3013:8007 | 3013:8008 | 3013:8009 | 3013:8010 | 3013:8011 |
| 3014:8006 | 3014:8007 | 3014:8008 | 3014:8009 | 3014:8010 | 3014:8011 |
| 1001:8012 | 1001:8013 | 1001:8014 | 1001:8015 | 1001:8016 | 1001:8017 |
| 1002:8012 | 1002:8013 | 1002:8014 | 1002:8015 | 1002:8016 | 1002:8017 |
| 1003:8012 | 1003:8013 | 1003:8014 | 1003:8015 | 1003:8016 | 1003:8017 |
| 1004:8012 | 1004:8013 | 1004:8014 | 1004:8015 | 1004:8016 | 1004:8017 |
| 1005:8012 | 1005:8013 | 1005:8014 | 1005:8015 | 1005:8016 | 1005:8017 |
| 1006:8012 | 1006:8013 | 1006:8014 | 1006:8015 | 1006:8016 | 1006:8017 |
| 1007:8012 | 1007:8013 | 1007:8014 | 1007:8015 | 1007:8016 | 1007:8017 |
| 1008:8012 | 1008:8013 | 1008:8014 | 1008:8015 | 1008:8016 | 1008:8017 |
| 1009:8012 | 1009:8013 | 1009:8014 | 1009:8015 | 1009:8016 | 1009:8017 |
| 1010:8012 | 1010:8013 | 1010:8014 | 1010:8015 | 1010:8016 | 1010:8017 |
| 1011:8012 | 1011:8013 | 1011:8014 | 1011:8015 | 1011:8016 | 1011:8017 |
| 1012:8012 | 1012:8013 | 1012:8014 | 1012:8015 | 1012:8016 | 1012:8017 |
| 1013:8012 | 1013:8013 | 1013:8014 | 1013:8015 | 1013:8016 | 1013:8017 |
| 1014:8012 | 1014:8013 | 1014:8014 | 1014:8015 | 1014:8016 | 1014:8017 |
| 1015:8012 | 1015:8013 | 1015:8014 | 1015:8015 | 1015:8016 | 1015:8017 |
| 1016:8012 | 1016:8013 | 1016:8014 | 1016:8015 | 1016:8016 | 1016:8017 |
| 2001:8012 | 2001:8013 | 2001:8014 | 2001:8015 | 2001:8016 | 2001:8017 |
| 2002:8012 | 2002:8013 | 2002:8014 | 2002:8015 | 2002:8016 | 2002:8017 |
| 2003:8012 | 2003:8013 | 2003:8014 | 2003:8015 | 2003:8016 | 2003:8017 |
| 2004:8012 | 2004:8013 | 2004:8014 | 2004:8015 | 2004:8016 | 2004:8017 |
| 2005:8012 | 2005:8013 | 2005:8014 | 2005:8015 | 2005:8016 | 2005:8017 |
| 2006:8012 | 2006:8013 | 2006:8014 | 2006:8015 | 2006:8016 | 2006:8017 |
| 2007:8012 | 2007:8013 | 2007:8014 | 2007:8015 | 2007:8016 | 2007:8017 |
| 2008:8012 | 2008:8013 | 2008:8014 | 2008:8015 | 2008:8016 | 2008:8017 |
| 2009:8012 | 2009:8013 | 2009:8014 | 2009:8015 | 2009:8016 | 2009:8017 |
| 2010:8012 | 2010:8013 | 2010:8014 | 2010:8015 | 2010:8016 | 2010:8017 |
| 2011:8012 | 2011:8013 | 2011:8014 | 2011:8015 | 2011:8016 | 2011:8017 |
| 2012:8012 | 2012:8013 | 2012:8014 | 2012:8015 | 2012:8016 | 2012:8017 |
| 3001:8012 | 3001:8013 | 3001:8014 | 3001:8015 | 3001:8016 | 3001:8017 |
| 3002:8012 | 3002:8013 | 3002:8014 | 3002:8015 | 3002:8016 | 3002:8017 |
| 3003:8012 | 3003:8013 | 3003:8014 | 3003:8015 | 3003:8016 | 3003:8017 |
| 3004:8012 | 3004:8013 | 3004:8014 | 3004:8015 | 3004:8016 | 3004:8017 |
| 3005:8012 | 3005:8013 | 3005:8014 | 3005:8015 | 3005:8016 | 3005:8017 |

TABLE A-continued

Example combinations of a compound X with a compound Y.

| X:Y | X:Y | X:Y | X:Y | X:Y | X:Y |
|---|---|---|---|---|---|
| 3006:8012 | 3006:8013 | 3006:8014 | 3006:8015 | 3006:8016 | 3006:8017 |
| 3007:8012 | 3007:8013 | 3007:8014 | 3007:8015 | 3007:8016 | 3007:8017 |
| 3008:8012 | 3008:8013 | 3008:8014 | 3008:8015 | 3008:8016 | 3008:8017 |
| 3009:8012 | 3009:8013 | 3009:8014 | 3009:8015 | 3009:8016 | 3009:8017 |
| 3010:8012 | 3010:8013 | 3010:8014 | 3010:8015 | 3010:8016 | 3010:8017 |
| 3011:8012 | 3011:8013 | 3011:8014 | 3011:8015 | 3011:8016 | 3011:8017 |
| 3012:8012 | 3012:8013 | 3012:8014 | 3012:8015 | 3012:8016 | 3012:8017 |
| 3013:8012 | 3013:8013 | 3013:8014 | 3013:8015 | 3013:8016 | 3013:8017 |
| 3014:8012 | 3014:8013 | 3014:8014 | 3014:8015 | 3014:8016 | 3014:8017 |
| 1001:8018 | 1001:8019 | 1001:8020 | 1001:8021 | 1001:8022 | 1001:8023 |
| 1002:8018 | 1002:8019 | 1002:8020 | 1002:8021 | 1002:8022 | 1002:8023 |
| 1003:8018 | 1003:8019 | 1003:8020 | 1003:8021 | 1003:8022 | 1003:8023 |
| 1004:8018 | 1004:8019 | 1004:8020 | 1004:8021 | 1004:8022 | 1004:8023 |
| 1005:8018 | 1005:8019 | 1005:8020 | 1005:8021 | 1005:8022 | 1005:8023 |
| 1006:8018 | 1006:8019 | 1006:8020 | 1006:8021 | 1006:8022 | 1006:8023 |
| 1007:8018 | 1007:8019 | 1007:8020 | 1007:8021 | 1007:8022 | 1007:8023 |
| 1008:8018 | 1008:8019 | 1008:8020 | 1008:8021 | 1008:8022 | 1008:8023 |
| 1009:8018 | 1009:8019 | 1009:8020 | 1009:8021 | 1009:8022 | 1009:8023 |
| 1010:8018 | 1010:8019 | 1010:8020 | 1010:8021 | 1010:8022 | 1010:8023 |
| 1011:8018 | 1011:8019 | 1011:8020 | 1011:8021 | 1011:8022 | 1011:8023 |
| 1012:8018 | 1012:8019 | 1012:8020 | 1012:8021 | 1012:8022 | 1012:8023 |
| 1013:8018 | 1013:8019 | 1013:8020 | 1013:8021 | 1013:8022 | 1013:8023 |
| 1014:8018 | 1014:8019 | 1014:8020 | 1014:8021 | 1014:8022 | 1014:8023 |
| 1015:8018 | 1015:8019 | 1015:8020 | 1015:8021 | 1015:8022 | 1015:8023 |
| 1016:8018 | 1016:8019 | 1016:8020 | 1016:8021 | 1016:8022 | 1016:8023 |
| 2001:8018 | 2001:8019 | 2001:8020 | 2001:8021 | 2001:8022 | 2001:8023 |
| 2002:8018 | 2002:8019 | 2002:8020 | 2002:8021 | 2002:8022 | 2002:8023 |
| 2003:8018 | 2003:8019 | 2003:8020 | 2003:8021 | 2003:8022 | 2003:8023 |
| 2004:8018 | 2004:8019 | 2004:8020 | 2004:8021 | 2004:8022 | 2004:8023 |
| 2005:8018 | 2005:8019 | 2005:8020 | 2005:8021 | 2005:8022 | 2005:8023 |
| 2006:8018 | 2006:8019 | 2006:8020 | 2006:8021 | 2006:8022 | 2006:8023 |
| 2007:8018 | 2007:8019 | 2007:8020 | 2007:8021 | 2007:8022 | 2007:8023 |
| 2008:8018 | 2008:8019 | 2008:8020 | 2008:8021 | 2008:8022 | 2008:8023 |
| 2009:8018 | 2009:8019 | 2009:8020 | 2009:8021 | 2009:8022 | 2009:8023 |
| 2010:8018 | 2010:8019 | 2010:8020 | 2010:8021 | 2010:8022 | 2010:8023 |
| 2011:8018 | 2011:8019 | 2011:8020 | 2011:8021 | 2011:8022 | 2011:8023 |
| 2012:8018 | 2012:8019 | 2012:8020 | 2012:8021 | 2012:8022 | 2012:8023 |
| 3001:8018 | 3001:8019 | 3001:8020 | 3001:8021 | 3001:8022 | 3001:8023 |
| 3002:8018 | 3002:8019 | 3002:8020 | 3002:8021 | 3002:8022 | 3002:8023 |
| 3003:8018 | 3003:8019 | 3003:8020 | 3003:8021 | 3003:8022 | 3003:8023 |
| 3004:8018 | 3004:8019 | 3004:8020 | 3004:8021 | 3004:8022 | 3004:8023 |
| 3005:8018 | 3005:8019 | 3005:8020 | 3005:8021 | 3005:8022 | 3005:8023 |
| 3006:8018 | 3006:8019 | 3006:8020 | 3006:8021 | 3006:8022 | 3006:8023 |
| 3007:8018 | 3007:8019 | 3007:8020 | 3007:8021 | 3007:8022 | 3007:8023 |
| 3008:8018 | 3008:8019 | 3008:8020 | 3008:8021 | 3008:8022 | 3008:8023 |
| 3009:8018 | 3009:8019 | 3009:8020 | 3009:8021 | 3009:8022 | 3009:8023 |
| 3010:8018 | 3010:8019 | 3010:8020 | 3010:8021 | 3010:8022 | 3010:8023 |
| 3011:8018 | 3011:8019 | 3011:8020 | 3011:8021 | 3011:8022 | 3011:8023 |
| 3012:8018 | 3012:8019 | 3012:8020 | 3012:8021 | 3012:8022 | 3012:8023 |
| 3013:8018 | 3013:8019 | 3013:8020 | 3013:8021 | 3013:8022 | 3013:8023 |
| 3014:8018 | 3014:8019 | 3014:8020 | 3014:8021 | 3014:8022 | 3014:8023 |
| 1001:8024 | 1001:8025 | 1001:8026 | 1001:8027 | — | — |
| 1002:8024 | 1002:8025 | 1002:8026 | 1002:8027 | | |
| 1003:8024 | 1003:8025 | 1003:8026 | 1003:8027 | | |
| 1004:8024 | 1004:8025 | 1004:8026 | 1004:8027 | | |
| 1005:8024 | 1005:8025 | 1005:8026 | 1005:8027 | | |
| 1006:8024 | 1006:8025 | 1006:8026 | 1006:8027 | | |
| 1007:8024 | 1007:8025 | 1007:8026 | 1007:8027 | | |
| 1008:8024 | 1008:8025 | 1008:8026 | 1008:8027 | | |
| 1009:8024 | 1009:8025 | 1009:8026 | 1009:8027 | | |
| 1010:8024 | 1010:8025 | 1010:8026 | 1010:8027 | | |
| 1011:8024 | 1011:8025 | 1011:8026 | 1011:8027 | | |
| 1012:8024 | 1012:8025 | 1012:8026 | 1012:8027 | | |
| 1013:8024 | 1013:8025 | 1013:8026 | 1013:8027 | | |
| 1014:8024 | 1014:8025 | 1014:8026 | 1014:8027 | | |
| 1015:8024 | 1015:8025 | 1015:8026 | 1015:8027 | | |
| 1016:8024 | 1016:8025 | 1016:8026 | 1016:8027 | | |
| 2001:8024 | 2001:8025 | 2001:8026 | 2001:8027 | | |
| 2002:8024 | 2002:8025 | 2002:8026 | 2002:8027 | | |
| 2003:8024 | 2003:8025 | 2003:8026 | 2003:8027 | | |
| 2004:8024 | 2004:8025 | 2004:8026 | 2004:8027 | | |
| 2005:8024 | 2005:8025 | 2005:8026 | 2005:8027 | | |
| 2006:8024 | 2006:8025 | 2006:8026 | 2006:8027 | | |
| 2007:8024 | 2007:8025 | 2007:8026 | 2007:8027 | | |
| 2008:8024 | 2008:8025 | 2008:8026 | 2008:8027 | | |
| 2009:8024 | 2009:8025 | 2009:8026 | 2009:8027 | | |
| 2010:8024 | 2010:8025 | 2010:8026 | 2010:8027 | | |
| 2011:8024 | 2011:8025 | 2011:8026 | 2011:8027 | | |
| 2012:8024 | 2012:8025 | 2012:8026 | 2012:8027 | | |
| 3001:8024 | 3001:8025 | 3001:8026 | 3001:8027 | | |
| 3002:8024 | 3002:8025 | 3002:8026 | 3002:8027 | | |
| 3003:8024 | 3003:8025 | 3003:8026 | 3003:8027 | | |
| 3004:8024 | 3004:8025 | 3004:8026 | 3004:8027 | | |
| 3005:8024 | 3005:8025 | 3005:8026 | 3005:8027 | | |
| 3006:8024 | 3006:8025 | 3006:8026 | 3006:8027 | | |
| 3007:8024 | 3007:8025 | 3007:8026 | 3007:8027 | | |
| 3008:8024 | 3008:8025 | 3008:8026 | 3008:8027 | | |
| 3009:8024 | 3009:8025 | 3009:8026 | 3009:8027 | | |
| 3010:8024 | 3010:8025 | 3010:8026 | 3010:8027 | | |
| 3011:8024 | 3011:8025 | 3011:8026 | 3011:8027 | | |
| 3012:8024 | 3012:8025 | 3012:8026 | 3012:8027 | | |
| 3013:8024 | 3013:8025 | 3013:8026 | 3013:8027 | | |
| 3014:8024 | 3014:8025 | 3014:8026 | 3014:8027 | | |

TABLE B

Example combinations of a compound X with a compound Y.

| X:Y | X:Y | X:Y | X:Y | X:Y | X:Y |
|---|---|---|---|---|---|
| 4001:8000 | 4001:8001 | 4001:8002 | 4001:8003 | 4001:8004 | 4001:8005 |
| 4002:8000 | 4002:8001 | 4002:8002 | 4002:8003 | 4002:8004 | 4002:8005 |
| 4003:8000 | 4003:8001 | 4003:8002 | 4003:8003 | 4003:8004 | 4003:8005 |
| 4004:8000 | 4004:8001 | 4004:8002 | 4004:8003 | 4004:8004 | 4004:8005 |
| 4005:8000 | 4005:8001 | 4005:8002 | 4005:8003 | 4005:8004 | 4005:8005 |
| 4006:8000 | 4006:8001 | 4006:8002 | 4006:8003 | 4006:8004 | 4006:8005 |
| 4007:8000 | 4007:8001 | 4007:8002 | 4007:8003 | 4007:8004 | 4007:8005 |
| 4008:8000 | 4008:8001 | 4008:8002 | 4008:8003 | 4008:8004 | 4008:8005 |
| 4009:8000 | 4009:8001 | 4009:8002 | 4009:8003 | 4009:8004 | 4009:8005 |
| 4010:8000 | 4010:8001 | 4010:8002 | 4010:8003 | 4010:8004 | 4010:8005 |
| 4011:8000 | 4011:8001 | 4011:8002 | 4011:8003 | 4011:8004 | 4011:8005 |
| 4012:8000 | 4012:8001 | 4012:8002 | 4012:8003 | 4012:8004 | 4012:8005 |
| 5001:8000 | 5001:8001 | 5001:8002 | 5001:8003 | 5001:8004 | 5001:8005 |
| 5002:8000 | 5002:8001 | 5002:8002 | 5002:8003 | 5002:8004 | 5002:8005 |
| 5003:8000 | 5003:8001 | 5003:8002 | 5003:8003 | 5003:8004 | 5003:8005 |
| 5004:8000 | 5004:8001 | 5004:8002 | 5004:8003 | 5004:8004 | 5004:8005 |
| 5005:8000 | 5005:8001 | 5005:8002 | 5005:8003 | 5005:8004 | 5005:8005 |
| 5006:8000 | 5006:8001 | 5006:8002 | 5006:8003 | 5006:8004 | 5006:8005 |
| 5007:8000 | 5007:8001 | 5007:8002 | 5007:8003 | 5007:8004 | 5007:8005 |
| 5008:8000 | 5008:8001 | 5008:8002 | 5008:8003 | 5008:8004 | 5008:8005 |
| 5009:8000 | 5009:8001 | 5009:8002 | 5009:8003 | 5009:8004 | 5009:8005 |
| 5010:8000 | 5010:8001 | 5010:8002 | 5010:8003 | 5010:8004 | 5010:8005 |
| 5011:8000 | 5011:8001 | 5011:8002 | 5011:8003 | 5011:8004 | 5011:8005 |
| 4001:8006 | 4001:8007 | 4001:8008 | 4001:8009 | 4001:8010 | 4001:8011 |
| 4002:8006 | 4002:8007 | 4002:8008 | 4002:8009 | 4002:8010 | 4002:8011 |
| 4003:8006 | 4003:8007 | 4003:8008 | 4003:8009 | 4003:8010 | 4003:8011 |
| 4004:8006 | 4004:8007 | 4004:8008 | 4004:8009 | 4004:8010 | 4004:8011 |
| 4005:8006 | 4005:8007 | 4005:8008 | 4005:8009 | 4005:8010 | 4005:8011 |
| 4006:8006 | 4006:8007 | 4006:8008 | 4006:8009 | 4006:8010 | 4006:8011 |
| 4007:8006 | 4007:8007 | 4007:8008 | 4007:8009 | 4007:8010 | 4007:8011 |
| 4008:8006 | 4008:8007 | 4008:8008 | 4008:8009 | 4008:8010 | 4008:8011 |
| 4009:8006 | 4009:8007 | 4009:8008 | 4009:8009 | 4009:8010 | 4009:8011 |
| 4010:8006 | 4010:8007 | 4010:8008 | 4010:8009 | 4010:8010 | 4010:8011 |
| 4011:8006 | 4011:8007 | 4011:8008 | 4011:8009 | 4011:8010 | 4011:8011 |
| 4012:8006 | 4012:8007 | 4012:8008 | 4012:8009 | 4012:8010 | 4012:8011 |
| 5001:8006 | 5001:8007 | 5001:8008 | 5001:8009 | 5001:8010 | 5001:8011 |
| 5002:8006 | 5002:8007 | 5002:8008 | 5002:8009 | 5002:8010 | 5002:8011 |
| 5003:8006 | 5003:8007 | 5003:8008 | 5003:8009 | 5003:8010 | 5003:8011 |
| 5004:8006 | 5004:8007 | 5004:8008 | 5004:8009 | 5004:8010 | 5004:8011 |
| 5005:8006 | 5005:8007 | 5005:8008 | 5005:8009 | 5005:8010 | 5005:8011 |
| 5006:8006 | 5006:8007 | 5006:8008 | 5006:8009 | 5006:8010 | 5006:8011 |
| 5007:8006 | 5007:8007 | 5007:8008 | 5007:8009 | 5007:8010 | 5007:8011 |
| 5008:8006 | 5008:8007 | 5008:8008 | 5008:8009 | 5008:8010 | 5008:8011 |
| 5009:8006 | 5009:8007 | 5009:8008 | 5009:8009 | 5009:8010 | 5009:8011 |
| 5010:8006 | 5010:8007 | 5010:8008 | 5010:8009 | 5010:8010 | 5010:8011 |
| 5011:8006 | 5011:8007 | 5011:8008 | 5011:8009 | 5011:8010 | 5011:8011 |

TABLE B-continued

Example combinations of a compound X with a compound Y.

| X:Y | X:Y | X:Y | X:Y | X:Y | X:Y |
|---|---|---|---|---|---|
| 4001:8012 | 4001:8013 | 4001:8014 | 4001:8015 | 4001:8016 | 4001:8017 |
| 4002:8012 | 4002:8013 | 4002:8014 | 4002:8015 | 4002:8016 | 4002:8017 |
| 4003:8012 | 4003:8013 | 4003:8014 | 4003:8015 | 4003:8016 | 4003:8017 |
| 4004:8012 | 4004:8013 | 4004:8014 | 4004:8015 | 4004:8016 | 4004:8017 |
| 4005:8012 | 4005:8013 | 4005:8014 | 4005:8015 | 4005:8016 | 4005:8017 |
| 4006:8012 | 4006:8013 | 4006:8014 | 4006:8015 | 4006:8016 | 4006:8017 |
| 4007:8012 | 4007:8013 | 4007:8014 | 4007:8015 | 4007:8016 | 4007:8017 |
| 4008:8012 | 4008:8013 | 4008:8014 | 4008:8015 | 4008:8016 | 4008:8017 |
| 4009:8012 | 4009:8013 | 4009:8014 | 4009:8015 | 4009:8016 | 4009:8017 |
| 4010:8012 | 4010:8013 | 4010:8014 | 4010:8015 | 4010:8016 | 4010:8017 |
| 4011:8012 | 4011:8013 | 4011:8014 | 4011:8015 | 4011:8016 | 4011:8017 |
| 4012:8012 | 4012:8013 | 4012:8014 | 4012:8015 | 4012:8016 | 4012:8017 |
| 5001:8012 | 5001:8013 | 5001:8014 | 5001:8015 | 5001:8016 | 5001:8017 |
| 5002:8012 | 5002:8013 | 5002:8014 | 5002:8015 | 5002:8016 | 5002:8017 |
| 5003:8012 | 5003:8013 | 5003:8014 | 5003:8015 | 5003:8016 | 5003:8017 |
| 5004:8012 | 5004:8013 | 5004:8014 | 5004:8015 | 5004:8016 | 5004:8017 |
| 5005:8012 | 5005:8013 | 5005:8014 | 5005:8015 | 5005:8016 | 5005:8017 |
| 5006:8012 | 5006:8013 | 5006:8014 | 5006:8015 | 5006:8016 | 5006:8017 |
| 5007:8012 | 5007:8013 | 5007:8014 | 5007:8015 | 5007:8016 | 5007:8017 |
| 5008:8012 | 5008:8013 | 5008:8014 | 5008:8015 | 5008:8016 | 5008:8017 |
| 5009:8012 | 5009:8013 | 5009:8014 | 5009:8015 | 5009:8016 | 5009:8017 |
| 5010:8012 | 5010:8013 | 5010:8014 | 5010:8015 | 5010:8016 | 5010:8017 |
| 5011:8012 | 5011:8013 | 5011:8014 | 5011:8015 | 5011:8016 | 5011:8017 |
| 4001:8018 | 4001:8019 | 4001:8020 | 4001:8021 | 4001:8022 | 4001:8023 |
| 4002:8018 | 4002:8019 | 4002:8020 | 4002:8021 | 4002:8022 | 4002:8023 |
| 4003:8018 | 4003:8019 | 4003:8020 | 4003:8021 | 4003:8022 | 4003:8023 |
| 4004:8018 | 4004:8019 | 4004:8020 | 4004:8021 | 4004:8022 | 4004:8023 |
| 4005:8018 | 4005:8019 | 4005:8020 | 4005:8021 | 4005:8022 | 4005:8023 |
| 4006:8018 | 4006:8019 | 4006:8020 | 4006:8021 | 4006:8022 | 4006:8023 |
| 4007:8018 | 4007:8019 | 4007:8020 | 4007:8021 | 4007:8022 | 4007:8023 |
| 4008:8018 | 4008:8019 | 4008:8020 | 4008:8021 | 4008:8022 | 4008:8023 |
| 4009:8018 | 4009:8019 | 4009:8020 | 4009:8021 | 4009:8022 | 4009:8023 |
| 4010:8018 | 4010:8019 | 4010:8020 | 4010:8021 | 4010:8022 | 4010:8023 |
| 4011:8018 | 4011:8019 | 4011:8020 | 4011:8021 | 4011:8022 | 4011:8023 |
| 4012:8018 | 4012:8019 | 4012:8020 | 4012:8021 | 4012:8022 | 4012:8023 |
| 5001:8018 | 5001:8019 | 5001:8020 | 5001:8021 | 5001:8022 | 5001:8023 |
| 5002:8018 | 5002:8019 | 5002:8020 | 5002:8021 | 5002:8022 | 5002:8023 |
| 5003:8018 | 5003:8019 | 5003:8020 | 5003:8021 | 5003:8022 | 5003:8023 |
| 5004:8018 | 5004:8019 | 5004:8020 | 5004:8021 | 5004:8022 | 5004:8023 |
| 5005:8018 | 5005:8019 | 5005:8020 | 5005:8021 | 5005:8022 | 5005:8023 |
| 5006:8018 | 5006:8019 | 5006:8020 | 5006:8021 | 5006:8022 | 5006:8023 |
| 5007:8018 | 5007:8019 | 5007:8020 | 5007:8021 | 5007:8022 | 5007:8023 |
| 5008:8018 | 5008:8019 | 5008:8020 | 5008:8021 | 5008:8022 | 5008:8023 |
| 5009:8018 | 5009:8019 | 5009:8020 | 5009:8021 | 5009:8022 | 5009:8023 |
| 5010:8018 | 5010:8019 | 5010:8020 | 5010:8021 | 5010:8022 | 5010:8023 |
| 5011:8018 | 5011:8019 | 5011:8020 | 5011:8021 | 5011:8022 | 5011:8023 |
| 4001:8024 | 4001:8025 | 4001:8026 | 4001:8027 | — | — |
| 4002:8024 | 4002:8025 | 4002:8026 | 4002:8027 | | |
| 4003:8024 | 4003:8025 | 4003:8026 | 4003:8027 | | |
| 4004:8024 | 4004:8025 | 4004:8026 | 4004:8027 | | |
| 4005:8024 | 4005:8025 | 4005:8026 | 4005:8027 | | |
| 4006:8024 | 4006:8025 | 4006:8026 | 4006:8027 | | |
| 4007:8024 | 4007:8025 | 4007:8026 | 4007:8027 | | |
| 4008:8024 | 4008:8025 | 4008:8026 | 4008:8027 | | |
| 4009:8024 | 4009:8025 | 4009:8026 | 4009:8027 | | |
| 4010:8024 | 4010:8025 | 4010:8026 | 4010:8027 | | |
| 4011:8024 | 4011:8025 | 4011:8026 | 4011:8027 | | |
| 4012:8024 | 4012:8025 | 4012:8026 | 4012:8027 | | |
| 5001:8024 | 5001:8025 | 5001:8026 | 5001:8027 | | |
| 5002:8024 | 5002:8025 | 5002:8026 | 5002:8027 | | |
| 5003:8024 | 5003:8025 | 5003:8026 | 5003:8027 | | |
| 5004:8024 | 5004:8025 | 5004:8026 | 5004:8027 | | |
| 5005:8024 | 5005:8025 | 5005:8026 | 5005:8027 | | |
| 5006:8024 | 5006:8025 | 5006:8026 | 5006:8027 | | |
| 5007:8024 | 5007:8025 | 5007:8026 | 5007:8027 | | |
| 5008:8024 | 5008:8025 | 5008:8026 | 5008:8027 | | |
| 5009:8024 | 5009:8025 | 5009:8026 | 5009:8027 | | |
| 5010:8024 | 5010:8025 | 5010:8026 | 5010:8027 | | |
| 5011:8024 | 5011:8025 | 5011:8026 | 5011:8027 | | |

TABLE C

Example combinations of a compound X with a compound Y.

| X:Y | X:Y | X:Y | X:Y | X:Y | X:Y |
|---|---|---|---|---|---|
| 6000:8000 | 6043:8000 | 6000:8001 | 6043:8001 | 6000:8002 | 6043:8002 |
| 6001:8000 | 6044:8000 | 6001:8001 | 6044:8001 | 6001:8002 | 6044:8002 |
| 6002:8000 | 6045:8000 | 6002:8001 | 6045:8001 | 6002:8002 | 6045:8002 |
| 6003:8000 | 6046:8000 | 6003:8001 | 6046:8001 | 6003:8002 | 6046:8002 |
| 6004:8000 | 6047:8000 | 6004:8001 | 6047:8001 | 6004:8002 | 6047:8002 |
| 6005:8000 | 6048:8000 | 6005:8001 | 6048:8001 | 6005:8002 | 6048:8002 |
| 6006:8000 | 6049:8000 | 6006:8001 | 6049:8001 | 6006:8002 | 6049:8002 |
| 6007:8000 | 6050:8000 | 6007:8001 | 6050:8001 | 6007:8002 | 6050:8002 |
| 6008:8000 | 6051:8000 | 6008:8001 | 6051:8001 | 6008:8002 | 6051:8002 |
| 6009:8000 | 6052:8000 | 6009:8001 | 6052:8001 | 6009:8002 | 6052:8002 |
| 6010:8000 | 6053:8000 | 6010:8001 | 6053:8001 | 6010:8002 | 6053:8002 |
| 6011:8000 | 6054:8000 | 6011:8001 | 6054:8001 | 6011:8002 | 6054:8002 |
| 6012:8000 | 6055:8000 | 6012:8001 | 6055:8001 | 6012:8002 | 6055:8002 |
| 6013:8000 | 6056:8000 | 6013:8001 | 6056:8001 | 6013:8002 | 6056:8002 |
| 6014:8000 | 6057:8000 | 6014:8001 | 6057:8001 | 6014:8002 | 6057:8002 |
| 6015:8000 | 6058:8000 | 6015:8001 | 6058:8001 | 6015:8002 | 6058:8002 |
| 6016:8000 | 6059:8000 | 6016:8001 | 6059:8001 | 6016:8002 | 6059:8002 |
| 6017:8000 | 6060:8000 | 6017:8001 | 6060:8001 | 6017:8002 | 6060:8002 |
| 6018:8000 | 6061:8000 | 6018:8001 | 6061:8001 | 6018:8002 | 6061:8002 |
| 6019:8000 | 6062:8000 | 6019:8001 | 6062:8001 | 6019:8002 | 6062:8002 |
| 6020:8000 | 6063:8000 | 6020:8001 | 6063:8001 | 6020:8002 | 6063:8002 |
| 6021:8000 | 6064:8000 | 6021:8001 | 6064:8001 | 6021:8002 | 6064:8002 |
| 6022:8000 | 6065:8000 | 6022:8001 | 6065:8001 | 6022:8002 | 6065:8002 |
| 6023:8000 | 6066:8000 | 6023:8001 | 6066:8001 | 6023:8002 | 6066:8002 |
| 6024:8000 | 6067:8000 | 6024:8001 | 6067:8001 | 6024:8002 | 6067:8002 |
| 6025:8000 | 6068:8000 | 6025:8001 | 6068:8001 | 6025:8002 | 6068:8002 |
| 6026:8000 | 6069:8000 | 6026:8001 | 6069:8001 | 6026:8002 | 6069:8002 |
| 6027:8000 | 6070:8000 | 6027:8001 | 6070:8001 | 6027:8002 | 6070:8002 |
| 6028:8000 | 6071:8000 | 6028:8001 | 6071:8001 | 6028:8002 | 6071:8002 |
| 6029:8000 | 6072:8000 | 6029:8001 | 6072:8001 | 6029:8002 | 6072:8002 |
| 6030:8000 | 6073:8000 | 6030:8001 | 6073:8001 | 6030:8002 | 6073:8002 |
| 6031:8000 | 6074:8000 | 6031:8001 | 6074:8001 | 6031:8002 | 6074:8002 |
| 6032:8000 | 6075:8000 | 6032:8001 | 6075:8001 | 6032:8002 | 6075:8002 |
| 6033:8000 | 6076:8000 | 6033:8001 | 6076:8001 | 6033:8002 | 6076:8002 |
| 6034:8000 | 6077:8000 | 6034:8001 | 6077:8001 | 6034:8002 | 6077:8002 |
| 6035:8000 | 6078:8000 | 6035:8001 | 6078:8001 | 6035:8002 | 6078:8002 |
| 6036:8000 | | 6036:8001 | | 6036:8002 | |
| 6037:8000 | | 6037:8001 | | 6037:8002 | |
| 6038:8000 | | 6038:8001 | | 6038:8002 | |
| 6039:8000 | | 6039:8001 | | 6039:8002 | |
| 6040:8000 | | 6040:8001 | | 6040:8002 | |
| 6041:8000 | | 6041:8001 | | 6041:8002 | |
| 6042:8000 | | 6042:8001 | | 6042:8002 | |
| 6000:8003 | 6043:8003 | 6000:8005 | 6043:8005 | 6000:8005 | 6043:8005 |
| 6001:8003 | 6044:8003 | 6001:8005 | 6044:8005 | 6001:8005 | 6044:8005 |
| 6002:8003 | 6045:8003 | 6002:8005 | 6045:8005 | 6002:8005 | 6045:8005 |
| 6003:8003 | 6046:8003 | 6003:8005 | 6046:8005 | 6003:8005 | 6046:8005 |
| 6004:8003 | 6047:8003 | 6004:8005 | 6047:8005 | 6004:8005 | 6047:8005 |
| 6005:8003 | 6048:8003 | 6005:8005 | 6048:8005 | 6005:8005 | 6048:8005 |
| 6006:8003 | 6049:8003 | 6006:8005 | 6049:8005 | 6006:8005 | 6049:8005 |
| 6007:8003 | 6050:8003 | 6007:8005 | 6050:8005 | 6007:8005 | 6050:8005 |
| 6008:8003 | 6051:8003 | 6008:8005 | 6051:8005 | 6008:8005 | 6051:8005 |
| 6009:8003 | 6052:8003 | 6009:8005 | 6052:8005 | 6009:8005 | 6052:8005 |
| 6010:8003 | 6053:8003 | 6010:8005 | 6053:8005 | 6010:8005 | 6053:8005 |
| 6011:8003 | 6054:8003 | 6011:8005 | 6054:8005 | 6011:8005 | 6054:8005 |
| 6012:8003 | 6055:8003 | 6012:8005 | 6055:8005 | 6012:8005 | 6055:8005 |
| 6013:8003 | 6056:8003 | 6013:8005 | 6056:8005 | 6013:8005 | 6056:8005 |
| 6014:8003 | 6057:8003 | 6014:8005 | 6057:8005 | 6014:8005 | 6057:8005 |
| 6015:8003 | 6058:8003 | 6015:8005 | 6058:8005 | 6015:8005 | 6058:8005 |
| 6016:8003 | 6059:8003 | 6016:8005 | 6059:8005 | 6016:8005 | 6059:8005 |
| 6017:8003 | 6060:8003 | 6017:8005 | 6060:8005 | 6017:8005 | 6060:8005 |
| 6018:8003 | 6061:8003 | 6018:8005 | 6061:8005 | 6018:8005 | 6061:8005 |
| 6019:8003 | 6062:8003 | 6019:8005 | 6062:8005 | 6019:8005 | 6062:8005 |
| 6020:8003 | 6063:8003 | 6020:8005 | 6063:8005 | 6020:8005 | 6063:8005 |
| 6021:8003 | 6064:8003 | 6021:8005 | 6064:8005 | 6021:8005 | 6064:8005 |
| 6022:8003 | 6065:8003 | 6022:8005 | 6065:8005 | 6022:8005 | 6065:8005 |
| 6023:8003 | 6066:8003 | 6023:8005 | 6066:8005 | 6023:8005 | 6066:8005 |
| 6024:8003 | 6067:8003 | 6024:8005 | 6067:8005 | 6024:8005 | 6067:8005 |
| 6025:8003 | 6068:8003 | 6025:8005 | 6068:8005 | 6025:8005 | 6068:8005 |
| 6026:8003 | 6069:8003 | 6026:8005 | 6069:8005 | 6026:8005 | 6069:8005 |
| 6027:8003 | 6070:8003 | 6027:8005 | 6070:8005 | 6027:8005 | 6070:8005 |
| 6028:8003 | 6071:8003 | 6028:8005 | 6071:8005 | 6028:8005 | 6071:8005 |
| 6029:8003 | 6072:8003 | 6029:8005 | 6072:8005 | 6029:8005 | 6072:8005 |
| 6030:8003 | 6073:8003 | 6030:8005 | 6073:8005 | 6030:8005 | 6073:8005 |
| 6031:8003 | 6074:8003 | 6031:8005 | 6074:8005 | 6031:8005 | 6074:8005 |

TABLE C-continued

Example combinations of a compound X with a compound Y.

| X:Y | X:Y | X:Y | X:Y | X:Y | X:Y |
|---|---|---|---|---|---|
| 6032:8003 | 6075:8003 | 6032:8005 | 6075:8005 | 6032:8005 | 6075:8005 |
| 6033:8003 | 6076:8003 | 6033:8005 | 6076:8005 | 6033:8005 | 6076:8005 |
| 6034:8003 | 6077:8003 | 6034:8005 | 6077:8005 | 6034:8005 | 6077:8005 |
| 6035:8003 | 6078:8003 | 6035:8005 | 6078:8005 | 6035:8005 | 6078:8005 |
| 6036:8003 | | 6036:8005 | | 6036:8005 | |
| 6037:8003 | | 6037:8005 | | 6037:8005 | |
| 6038:8003 | | 6038:8005 | | 6038:8005 | |
| 6039:8003 | | 6039:8005 | | 6039:8005 | |
| 6040:8003 | | 6040:8005 | | 6040:8005 | |
| 6041:8003 | | 6041:8005 | | 6041:8005 | |
| 6042:8003 | | 6042:8005 | | 6042:8005 | |
| 6000:8006 | 6043:8006 | 6000:8007 | 6043:8007 | 6000:8008 | 6043:8008 |
| 6001:8006 | 6044:8006 | 6001:8007 | 6044:8007 | 6001:8008 | 6044:8008 |
| 6002:8006 | 6045:8006 | 6002:8007 | 6045:8007 | 6002:8008 | 6045:8008 |
| 6003:8006 | 6046:8006 | 6003:8007 | 6046:8007 | 6003:8008 | 6046:8008 |
| 6004:8006 | 6047:8006 | 6004:8007 | 6047:8007 | 6004:8008 | 6047:8008 |
| 6005:8006 | 6048:8006 | 6005:8007 | 6048:8007 | 6005:8008 | 6048:8008 |
| 6006:8006 | 6049:8006 | 6006:8007 | 6049:8007 | 6006:8008 | 6049:8008 |
| 6007:8006 | 6050:8006 | 6007:8007 | 6050:8007 | 6007:8008 | 6050:8008 |
| 6008:8006 | 6051:8006 | 6008:8007 | 6051:8007 | 6008:8008 | 6051:8008 |
| 6009:8006 | 6052:8006 | 6009:8007 | 6052:8007 | 6009:8008 | 6052:8008 |
| 6010:8006 | 6053:8006 | 6010:8007 | 6053:8007 | 6010:8008 | 6053:8008 |
| 6011:8006 | 6054:8006 | 6011:8007 | 6054:8007 | 6011:8008 | 6054:8008 |
| 6012:8006 | 6055:8006 | 6012:8007 | 6055:8007 | 6012:8008 | 6055:8008 |
| 6013:8006 | 6056:8006 | 6013:8007 | 6056:8007 | 6013:8008 | 6056:8008 |
| 6014:8006 | 6057:8006 | 6014:8007 | 6057:8007 | 6014:8008 | 6057:8008 |
| 6015:8006 | 6058:8006 | 6015:8007 | 6058:8007 | 6015:8008 | 6058:8008 |
| 6016:8006 | 6059:8006 | 6016:8007 | 6059:8007 | 6016:8008 | 6059:8008 |
| 6017:8006 | 6060:8006 | 6017:8007 | 6060:8007 | 6017:8008 | 6060:8008 |
| 6018:8006 | 6061:8006 | 6018:8007 | 6061:8007 | 6018:8008 | 6061:8008 |
| 6019:8006 | 6062:8006 | 6019:8007 | 6062:8007 | 6019:8008 | 6062:8008 |
| 6020:8006 | 6063:8006 | 6020:8007 | 6063:8007 | 6020:8008 | 6063:8008 |
| 6021:8006 | 6064:8006 | 6021:8007 | 6064:8007 | 6021:8008 | 6064:8008 |
| 6022:8006 | 6065:8006 | 6022:8007 | 6065:8007 | 6022:8008 | 6065:8008 |
| 6023:8006 | 6066:8006 | 6023:8007 | 6066:8007 | 6023:8008 | 6066:8008 |
| 6024:8006 | 6067:8006 | 6024:8007 | 6067:8007 | 6024:8008 | 6067:8008 |
| 6025:8006 | 6068:8006 | 6025:8007 | 6068:8007 | 6025:8008 | 6068:8008 |
| 6026:8006 | 6069:8006 | 6026:8007 | 6069:8007 | 6026:8008 | 6069:8008 |
| 6027:8006 | 6070:8006 | 6027:8007 | 6070:8007 | 6027:8008 | 6070:8008 |
| 6028:8006 | 6071:8006 | 6028:8007 | 6071:8007 | 6028:8008 | 6071:8008 |
| 6029:8006 | 6072:8006 | 6029:8007 | 6072:8007 | 6029:8008 | 6072:8008 |
| 6030:8006 | 6073:8006 | 6030:8007 | 6073:8007 | 6030:8008 | 6073:8008 |
| 6031:8006 | 6074:8006 | 6031:8007 | 6074:8007 | 6031:8008 | 6074:8008 |
| 6032:8006 | 6075:8006 | 6032:8007 | 6075:8007 | 6032:8008 | 6075:8008 |
| 6033:8006 | 6076:8006 | 6033:8007 | 6076:8007 | 6033:8008 | 6076:8008 |
| 6034:8006 | 6077:8006 | 6034:8007 | 6077:8007 | 6034:8008 | 6077:8008 |
| 6035:8006 | 6078:8006 | 6035:8007 | 6078:8007 | 6035:8008 | 6078:8008 |
| 6036:8006 | | 6036:8007 | | 6036:8008 | |
| 6037:8006 | | 6037:8007 | | 6037:8008 | |
| 6038:8006 | | 6038:8007 | | 6038:8008 | |
| 6039:8006 | | 6039:8007 | | 6039:8008 | |
| 6040:8006 | | 6040:8007 | | 6040:8008 | |
| 6041:8006 | | 6041:8007 | | 6041:8008 | |
| 6042:8006 | | 6042:8007 | | 6042:8008 | |
| 6000:8009 | 6043:8009 | 6000:8010 | 6043:8010 | 6000:8011 | 6043:8011 |
| 6001:8009 | 6044:8009 | 6001:8010 | 6044:8010 | 6001:8011 | 6044:8011 |
| 6002:8009 | 6045:8009 | 6002:8010 | 6045:8010 | 6002:8011 | 6045:8011 |
| 6003:8009 | 6046:8009 | 6003:8010 | 6046:8010 | 6003:8011 | 6046:8011 |
| 6004:8009 | 6047:8009 | 6004:8010 | 6047:8010 | 6004:8011 | 6047:8011 |
| 6005:8009 | 6048:8009 | 6005:8010 | 6048:8010 | 6005:8011 | 6048:8011 |
| 6006:8009 | 6049:8009 | 6006:8010 | 6049:8010 | 6006:8011 | 6049:8011 |
| 6007:8009 | 6050:8009 | 6007:8010 | 6050:8010 | 6007:8011 | 6050:8011 |
| 6008:8009 | 6051:8009 | 6008:8010 | 6051:8010 | 6008:8011 | 6051:8011 |
| 6009:8009 | 6052:8009 | 6009:8010 | 6052:8010 | 6009:8011 | 6052:8011 |
| 6010:8009 | 6053:8009 | 6010:8010 | 6053:8010 | 6010:8011 | 6053:8011 |
| 6011:8009 | 6054:8009 | 6011:8010 | 6054:8010 | 6011:8011 | 6054:8011 |
| 6012:8009 | 6055:8009 | 6012:8010 | 6055:8010 | 6012:8011 | 6055:8011 |
| 6013:8009 | 6056:8009 | 6013:8010 | 6056:8010 | 6013:8011 | 6056:8011 |
| 6014:8009 | 6057:8009 | 6014:8010 | 6057:8010 | 6014:8011 | 6057:8011 |
| 6015:8009 | 6058:8009 | 6015:8010 | 6058:8010 | 6015:8011 | 6058:8011 |
| 6016:8009 | 6059:8009 | 6016:8010 | 6059:8010 | 6016:8011 | 6059:8011 |
| 6017:8009 | 6060:8009 | 6017:8010 | 6060:8010 | 6017:8011 | 6060:8011 |
| 6018:8009 | 6061:8009 | 6018:8010 | 6061:8010 | 6018:8011 | 6061:8011 |
| 6019:8009 | 6062:8009 | 6019:8010 | 6062:8010 | 6019:8011 | 6062:8011 |
| 6020:8009 | 6063:8009 | 6020:8010 | 6063:8010 | 6020:8011 | 6063:8011 |
| 6021:8009 | 6064:8009 | 6021:8010 | 6064:8010 | 6021:8011 | 6064:8011 |
| 6022:8009 | 6065:8009 | 6022:8010 | 6065:8010 | 6022:8011 | 6065:8011 |
| 6023:8009 | 6066:8009 | 6023:8010 | 6066:8010 | 6023:8011 | 6066:8011 |
| 6024:8009 | 6067:8009 | 6024:8010 | 6067:8010 | 6024:8011 | 6067:8011 |
| 6025:8009 | 6068:8009 | 6025:8010 | 6068:8010 | 6025:8011 | 6068:8011 |
| 6026:8009 | 6069:8009 | 6026:8010 | 6069:8010 | 6026:8011 | 6069:8011 |
| 6027:8009 | 6070:8009 | 6027:8010 | 6070:8010 | 6027:8011 | 6070:8011 |
| 6028:8009 | 6071:8009 | 6028:8010 | 6071:8010 | 6028:8011 | 6071:8011 |
| 6029:8009 | 6072:8009 | 6029:8010 | 6072:8010 | 6029:8011 | 6072:8011 |
| 6030:8009 | 6073:8009 | 6030:8010 | 6073:8010 | 6030:8011 | 6073:8011 |
| 6031:8009 | 6074:8009 | 6031:8010 | 6074:8010 | 6031:8011 | 6074:8011 |
| 6032:8009 | 6075:8009 | 6032:8010 | 6075:8010 | 6032:8011 | 6075:8011 |
| 6033:8009 | 6076:8009 | 6033:8010 | 6076:8010 | 6033:8011 | 6076:8011 |
| 6034:8009 | 6077:8009 | 6034:8010 | 6077:8010 | 6034:8011 | 6077:8011 |
| 6035:8009 | 6078:8009 | 6035:8010 | 6078:8010 | 6035:8011 | 6078:8011 |
| 6036:8009 | | 6036:8010 | | 6036:8011 | |
| 6037:8009 | | 6037:8010 | | 6037:8011 | |
| 6038:8009 | | 6038:8010 | | 6038:8011 | |
| 6039:8009 | | 6039:8010 | | 6039:8011 | |
| 6040:8009 | | 6040:8010 | | 6040:8011 | |
| 6041:8009 | | 6041:8010 | | 6041:8011 | |
| 6042:8009 | | 6042:8010 | | 6042:8011 | |
| 6000:8012 | 6043:8012 | 6000:8013 | 6043:8013 | 6000:8014 | 6043:8014 |
| 6001:8012 | 6044:8012 | 6001:8013 | 6044:8013 | 6001:8014 | 6044:8014 |
| 6002:8012 | 6045:8012 | 6002:8013 | 6045:8013 | 6002:8014 | 6045:8014 |
| 6003:8012 | 6046:8012 | 6003:8013 | 6046:8013 | 6003:8014 | 6046:8014 |
| 6004:8012 | 6047:8012 | 6004:8013 | 6047:8013 | 6004:8014 | 6047:8014 |
| 6005:8012 | 6048:8012 | 6005:8013 | 6048:8013 | 6005:8014 | 6048:8014 |
| 6006:8012 | 6049:8012 | 6006:8013 | 6049:8013 | 6006:8014 | 6049:8014 |
| 6007:8012 | 6050:8012 | 6007:8013 | 6050:8013 | 6007:8014 | 6050:8014 |
| 6008:8012 | 6051:8012 | 6008:8013 | 6051:8013 | 6008:8014 | 6051:8014 |
| 6009:8012 | 6052:8012 | 6009:8013 | 6052:8013 | 6009:8014 | 6052:8014 |
| 6010:8012 | 6053:8012 | 6010:8013 | 6053:8013 | 6010:8014 | 6053:8014 |
| 6011:8012 | 6054:8012 | 6011:8013 | 6054:8013 | 6011:8014 | 6054:8014 |
| 6012:8012 | 6055:8012 | 6012:8013 | 6055:8013 | 6012:8014 | 6055:8014 |
| 6013:8012 | 6056:8012 | 6013:8013 | 6056:8013 | 6013:8014 | 6056:8014 |
| 6014:8012 | 6057:8012 | 6014:8013 | 6057:8013 | 6014:8014 | 6057:8014 |
| 6015:8012 | 6058:8012 | 6015:8013 | 6058:8013 | 6015:8014 | 6058:8014 |
| 6016:8012 | 6059:8012 | 6016:8013 | 6059:8013 | 6016:8014 | 6059:8014 |
| 6017:8012 | 6060:8012 | 6017:8013 | 6060:8013 | 6017:8014 | 6060:8014 |
| 6018:8012 | 6061:8012 | 6018:8013 | 6061:8013 | 6018:8014 | 6061:8014 |
| 6019:8012 | 6062:8012 | 6019:8013 | 6062:8013 | 6019:8014 | 6062:8014 |
| 6020:8012 | 6063:8012 | 6020:8013 | 6063:8013 | 6020:8014 | 6063:8014 |
| 6021:8012 | 6064:8012 | 6021:8013 | 6064:8013 | 6021:8014 | 6064:8014 |
| 6022:8012 | 6065:8012 | 6022:8013 | 6065:8013 | 6022:8014 | 6065:8014 |
| 6023:8012 | 6066:8012 | 6023:8013 | 6066:8013 | 6023:8014 | 6066:8014 |
| 6024:8012 | 6067:8012 | 6024:8013 | 6067:8013 | 6024:8014 | 6067:8014 |
| 6025:8012 | 6068:8012 | 6025:8013 | 6068:8013 | 6025:8014 | 6068:8014 |
| 6026:8012 | 6069:8012 | 6026:8013 | 6069:8013 | 6026:8014 | 6069:8014 |
| 6027:8012 | 6070:8012 | 6027:8013 | 6070:8013 | 6027:8014 | 6070:8014 |
| 6028:8012 | 6071:8012 | 6028:8013 | 6071:8013 | 6028:8014 | 6071:8014 |
| 6029:8012 | 6072:8012 | 6029:8013 | 6072:8013 | 6029:8014 | 6072:8014 |
| 6030:8012 | 6073:8012 | 6030:8013 | 6073:8013 | 6030:8014 | 6073:8014 |
| 6031:8012 | 6074:8012 | 6031:8013 | 6074:8013 | 6031:8014 | 6074:8014 |
| 6032:8012 | 6075:8012 | 6032:8013 | 6075:8013 | 6032:8014 | 6075:8014 |
| 6033:8012 | 6076:8012 | 6033:8013 | 6076:8013 | 6033:8014 | 6076:8014 |
| 6034:8012 | 6077:8012 | 6034:8013 | 6077:8013 | 6034:8014 | 6077:8014 |
| 6035:8012 | 6078:8012 | 6035:8013 | 6078:8013 | 6035:8014 | 6078:8014 |
| 6036:8012 | | 6036:8013 | | 6036:8014 | |
| 6037:8012 | | 6037:8013 | | 6037:8014 | |
| 6038:8012 | | 6038:8013 | | 6038:8014 | |
| 6039:8012 | | 6039:8013 | | 6039:8014 | |
| 6040:8012 | | 6040:8013 | | 6040:8014 | |
| 6041:8012 | | 6041:8013 | | 6041:8014 | |
| 6042:8012 | | 6042:8013 | | 6042:8014 | |
| 6000:8015 | 6043:8015 | 6000:8016 | 6043:8016 | 6000:8017 | 6043:8017 |
| 6001:8015 | 6044:8015 | 6001:8016 | 6044:8016 | 6001:8017 | 6044:8017 |
| 6002:8015 | 6045:8015 | 6002:8016 | 6045:8016 | 6002:8017 | 6045:8017 |
| 6003:8015 | 6046:8015 | 6003:8016 | 6046:8016 | 6003:8017 | 6046:8017 |
| 6004:8015 | 6047:8015 | 6004:8016 | 6047:8016 | 6004:8017 | 6047:8017 |
| 6005:8015 | 6048:8015 | 6005:8016 | 6048:8016 | 6005:8017 | 6048:8017 |
| 6006:8015 | 6049:8015 | 6006:8016 | 6049:8016 | 6006:8017 | 6049:8017 |
| 6007:8015 | 6050:8015 | 6007:8016 | 6050:8016 | 6007:8017 | 6050:8017 |

TABLE C-continued

Example combinations of a compound X with a compound Y.

| X:Y | X:Y | X:Y | X:Y | X:Y | X:Y |
|---|---|---|---|---|---|
| 6008:8015 | 6051:8015 | 6008:8016 | 6051:8016 | 6008:8017 | 6051:8017 |
| 6009:8015 | 6052:8015 | 6009:8016 | 6052:8016 | 6009:8017 | 6052:8017 |
| 6010:8015 | 6053:8015 | 6010:8016 | 6053:8016 | 6010:8017 | 6053:8017 |
| 6011:8015 | 6054:8015 | 6011:8016 | 6054:8016 | 6011:8017 | 6054:8017 |
| 6012:8015 | 6055:8015 | 6012:8016 | 6055:8016 | 6012:8017 | 6055:8017 |
| 6013:8015 | 6056:8015 | 6013:8016 | 6056:8016 | 6013:8017 | 6056:8017 |
| 6014:8015 | 6057:8015 | 6014:8016 | 6057:8016 | 6014:8017 | 6057:8017 |
| 6015:8015 | 6058:8015 | 6015:8016 | 6058:8016 | 6015:8017 | 6058:8017 |
| 6016:8015 | 6059:8015 | 6016:8016 | 6059:8016 | 6016:8017 | 6059:8017 |
| 6017:8015 | 6060:8015 | 6017:8016 | 6060:8016 | 6017:8017 | 6060:8017 |
| 6018:8015 | 6061:8015 | 6018:8016 | 6061:8016 | 6018:8017 | 6061:8017 |
| 6019:8015 | 6062:8015 | 6019:8016 | 6062:8016 | 6019:8017 | 6062:8017 |
| 6020:8015 | 6063:8015 | 6020:8016 | 6063:8016 | 6020:8017 | 6063:8017 |
| 6021:8015 | 6064:8015 | 6021:8016 | 6064:8016 | 6021:8017 | 6064:8017 |
| 6022:8015 | 6065:8015 | 6022:8016 | 6065:8016 | 6022:8017 | 6065:8017 |
| 6023:8015 | 6066:8015 | 6023:8016 | 6066:8016 | 6023:8017 | 6066:8017 |
| 6024:8015 | 6067:8015 | 6024:8016 | 6067:8016 | 6024:8017 | 6067:8017 |
| 6025:8015 | 6068:8015 | 6025:8016 | 6068:8016 | 6025:8017 | 6068:8017 |
| 6026:8015 | 6069:8015 | 6026:8016 | 6069:8016 | 6026:8017 | 6069:8017 |
| 6027:8015 | 6070:8015 | 6027:8016 | 6070:8016 | 6027:8017 | 6070:8017 |
| 6028:8015 | 6071:8015 | 6028:8016 | 6071:8016 | 6028:8017 | 6071:8017 |
| 6029:8015 | 6072:8015 | 6029:8016 | 6072:8016 | 6029:8017 | 6072:8017 |
| 6030:8015 | 6073:8015 | 6030:8016 | 6073:8016 | 6030:8017 | 6073:8017 |
| 6031:8015 | 6074:8015 | 6031:8016 | 6074:8016 | 6031:8017 | 6074:8017 |
| 6032:8015 | 6075:8015 | 6032:8016 | 6075:8016 | 6032:8017 | 6075:8017 |
| 6033:8015 | 6076:8015 | 6033:8016 | 6076:8016 | 6033:8017 | 6076:8017 |
| 6034:8015 | 6077:8015 | 6034:8016 | 6077:8016 | 6034:8017 | 6077:8017 |
| 6035:8015 | 6078:8015 | 6035:8016 | 6078:8016 | 6035:8017 | 6078:8017 |
| 6036:8015 | | 6036:8016 | | 6036:8017 | |
| 6037:8015 | | 6037:8016 | | 6037:8017 | |
| 6038:8015 | | 6038:8016 | | 6038:8017 | |
| 6039:8015 | | 6039:8016 | | 6039:8017 | |
| 6040:8015 | | 6040:8016 | | 6040:8017 | |
| 6041:8015 | | 6041:8016 | | 6041:8017 | |
| 6042:8015 | | 6042:8016 | | 6042:8017 | |
| 6000:8018 | 6043:8018 | 6000:8019 | 6043:8019 | 6000:8020 | 6043:8020 |
| 6001:8018 | 6044:8018 | 6001:8019 | 6044:8019 | 6001:8020 | 6044:8020 |
| 6002:8018 | 6045:8018 | 6002:8019 | 6045:8019 | 6002:8020 | 6045:8020 |
| 6003:8018 | 6046:8018 | 6003:8019 | 6046:8019 | 6003:8020 | 6046:8020 |
| 6004:8018 | 6047:8018 | 6004:8019 | 6047:8019 | 6004:8020 | 6047:8020 |
| 6005:8018 | 6048:8018 | 6005:8019 | 6048:8019 | 6005:8020 | 6048:8020 |
| 6006:8018 | 6049:8018 | 6006:8019 | 6049:8019 | 6006:8020 | 6049:8020 |
| 6007:8018 | 6050:8018 | 6007:8019 | 6050:8019 | 6007:8020 | 6050:8020 |
| 6008:8018 | 6051:8018 | 6008:8019 | 6051:8019 | 6008:8020 | 6051:8020 |
| 6009:8018 | 6052:8018 | 6009:8019 | 6052:8019 | 6009:8020 | 6052:8020 |
| 6010:8018 | 6053:8018 | 6010:8019 | 6053:8019 | 6010:8020 | 6053:8020 |
| 6011:8018 | 6054:8018 | 6011:8019 | 6054:8019 | 6011:8020 | 6054:8020 |
| 6012:8018 | 6055:8018 | 6012:8019 | 6055:8019 | 6012:8020 | 6055:8020 |
| 6013:8018 | 6056:8018 | 6013:8019 | 6056:8019 | 6013:8020 | 6056:8020 |
| 6014:8018 | 6057:8018 | 6014:8019 | 6057:8019 | 6014:8020 | 6057:8020 |
| 6015:8018 | 6058:8018 | 6015:8019 | 6058:8019 | 6015:8020 | 6058:8020 |
| 6016:8018 | 6059:8018 | 6016:8019 | 6059:8019 | 6016:8020 | 6059:8020 |
| 6017:8018 | 6060:8018 | 6017:8019 | 6060:8019 | 6017:8020 | 6060:8020 |
| 6018:8018 | 6061:8018 | 6018:8019 | 6061:8019 | 6018:8020 | 6061:8020 |
| 6019:8018 | 6062:8018 | 6019:8019 | 6062:8019 | 6019:8020 | 6062:8020 |
| 6020:8018 | 6063:8018 | 6020:8019 | 6063:8019 | 6020:8020 | 6063:8020 |
| 6021:8018 | 6064:8018 | 6021:8019 | 6064:8019 | 6021:8020 | 6064:8020 |
| 6022:8018 | 6065:8018 | 6022:8019 | 6065:8019 | 6022:8020 | 6065:8020 |
| 6023:8018 | 6066:8018 | 6023:8019 | 6066:8019 | 6023:8020 | 6066:8020 |
| 6024:8018 | 6067:8018 | 6024:8019 | 6067:8019 | 6024:8020 | 6067:8020 |
| 6025:8018 | 6068:8018 | 6025:8019 | 6068:8019 | 6025:8020 | 6068:8020 |
| 6026:8018 | 6069:8018 | 6026:8019 | 6069:8019 | 6026:8020 | 6069:8020 |
| 6027:8018 | 6070:8018 | 6027:8019 | 6070:8019 | 6027:8020 | 6070:8020 |
| 6028:8018 | 6071:8018 | 6028:8019 | 6071:8019 | 6028:8020 | 6071:8020 |
| 6029:8018 | 6072:8018 | 6029:8019 | 6072:8019 | 6029:8020 | 6072:8020 |
| 6030:8018 | 6073:8018 | 6030:8019 | 6073:8019 | 6030:8020 | 6073:8020 |
| 6031:8018 | 6074:8018 | 6031:8019 | 6074:8019 | 6031:8020 | 6074:8020 |
| 6032:8018 | 6075:8018 | 6032:8019 | 6075:8019 | 6032:8020 | 6075:8020 |
| 6033:8018 | 6076:8018 | 6033:8019 | 6076:8019 | 6033:8020 | 6076:8020 |
| 6034:8018 | 6077:8018 | 6034:8019 | 6077:8019 | 6034:8020 | 6077:8020 |
| 6035:8018 | 6078:8018 | 6035:8019 | 6078:8019 | 6035:8020 | 6078:8020 |
| 6036:8018 | | 6036:8019 | | 6036:8020 | |
| 6037:8018 | | 6037:8019 | | 6037:8020 | |
| 6038:8018 | | 6038:8019 | | 6038:8020 | |
| 6039:8018 | | 6039:8019 | | 6039:8020 | |
| 6040:8018 | | 6040:8019 | | 6040:8020 | |
| 6041:8018 | | 6041:8019 | | 6041:8020 | |
| 6042:8018 | | 6042:8019 | | 6042:8020 | |
| 6000:8021 | 6043:8021 | 6000:8022 | 6043:8022 | 6000:8023 | 6043:8023 |
| 6001:8021 | 6044:8021 | 6001:8022 | 6044:8022 | 6001:8023 | 6044:8023 |
| 6002:8021 | 6045:8021 | 6002:8022 | 6045:8022 | 6002:8023 | 6045:8023 |
| 6003:8021 | 6046:8021 | 6003:8022 | 6046:8022 | 6003:8023 | 6046:8023 |
| 6004:8021 | 6047:8021 | 6004:8022 | 6047:8022 | 6004:8023 | 6047:8023 |
| 6005:8021 | 6048:8021 | 6005:8022 | 6048:8022 | 6005:8023 | 6048:8023 |
| 6006:8021 | 6049:8021 | 6006:8022 | 6049:8022 | 6006:8023 | 6049:8023 |
| 6007:8021 | 6050:8021 | 6007:8022 | 6050:8022 | 6007:8023 | 6050:8023 |
| 6008:8021 | 6051:8021 | 6008:8022 | 6051:8022 | 6008:8023 | 6051:8023 |
| 6009:8021 | 6052:8021 | 6009:8022 | 6052:8022 | 6009:8023 | 6052:8023 |
| 6010:8021 | 6053:8021 | 6010:8022 | 6053:8022 | 6010:8023 | 6053:8023 |
| 6011:8021 | 6054:8021 | 6011:8022 | 6054:8022 | 6011:8023 | 6054:8023 |
| 6012:8021 | 6055:8021 | 6012:8022 | 6055:8022 | 6012:8023 | 6055:8023 |
| 6013:8021 | 6056:8021 | 6013:8022 | 6056:8022 | 6013:8023 | 6056:8023 |
| 6014:8021 | 6057:8021 | 6014:8022 | 6057:8022 | 6014:8023 | 6057:8023 |
| 6015:8021 | 6058:8021 | 6015:8022 | 6058:8022 | 6015:8023 | 6058:8023 |
| 6016:8021 | 6059:8021 | 6016:8022 | 6059:8022 | 6016:8023 | 6059:8023 |
| 6017:8021 | 6060:8021 | 6017:8022 | 6060:8022 | 6017:8023 | 6060:8023 |
| 6018:8021 | 6061:8021 | 6018:8022 | 6061:8022 | 6018:8023 | 6061:8023 |
| 6019:8021 | 6062:8021 | 6019:8022 | 6062:8022 | 6019:8023 | 6062:8023 |
| 6020:8021 | 6063:8021 | 6020:8022 | 6063:8022 | 6020:8023 | 6063:8023 |
| 6021:8021 | 6064:8021 | 6021:8022 | 6064:8022 | 6021:8023 | 6064:8023 |
| 6022:8021 | 6065:8021 | 6022:8022 | 6065:8022 | 6022:8023 | 6065:8023 |
| 6023:8021 | 6066:8021 | 6023:8022 | 6066:8022 | 6023:8023 | 6066:8023 |
| 6024:8021 | 6067:8021 | 6024:8022 | 6067:8022 | 6024:8023 | 6067:8023 |
| 6025:8021 | 6068:8021 | 6025:8022 | 6068:8022 | 6025:8023 | 6068:8023 |
| 6026:8021 | 6069:8021 | 6026:8022 | 6069:8022 | 6026:8023 | 6069:8023 |
| 6027:8021 | 6070:8021 | 6027:8022 | 6070:8022 | 6027:8023 | 6070:8023 |
| 6028:8021 | 6071:8021 | 6028:8022 | 6071:8022 | 6028:8023 | 6071:8023 |
| 6029:8021 | 6072:8021 | 6029:8022 | 6072:8022 | 6029:8023 | 6072:8023 |
| 6030:8021 | 6073:8021 | 6030:8022 | 6073:8022 | 6030:8023 | 6073:8023 |
| 6031:8021 | 6074:8021 | 6031:8022 | 6074:8022 | 6031:8023 | 6074:8023 |
| 6032:8021 | 6075:8021 | 6032:8022 | 6075:8022 | 6032:8023 | 6075:8023 |
| 6033:8021 | 6076:8021 | 6033:8022 | 6076:8022 | 6033:8023 | 6076:8023 |
| 6034:8021 | 6077:8021 | 6034:8022 | 6077:8022 | 6034:8023 | 6077:8023 |
| 6035:8021 | 6078:8021 | 6035:8022 | 6078:8022 | 6035:8023 | 6078:8023 |
| 6036:8021 | | 6036:8022 | | 6036:8023 | |
| 6037:8021 | | 6037:8022 | | 6037:8023 | |
| 6038:8021 | | 6038:8022 | | 6038:8023 | |
| 6039:8021 | | 6039:8022 | | 6039:8023 | |
| 6040:8021 | | 6040:8022 | | 6040:8023 | |
| 6041:8021 | | 6041:8022 | | 6041:8023 | |
| 6042:8021 | | 6042:8022 | | 6042:8023 | |
| 6000:8024 | 6043:8024 | 6000:8025 | 6043:8025 | 6000:8026 | 6043:8026 |
| 6001:8024 | 6044:8024 | 6001:8025 | 6044:8025 | 6001:8026 | 6044:8026 |
| 6002:8024 | 6045:8024 | 6002:8025 | 6045:8025 | 6002:8026 | 6045:8026 |
| 6003:8024 | 6046:8024 | 6003:8025 | 6046:8025 | 6003:8026 | 6046:8026 |
| 6004:8024 | 6047:8024 | 6004:8025 | 6047:8025 | 6004:8026 | 6047:8026 |
| 6005:8024 | 6048:8024 | 6005:8025 | 6048:8025 | 6005:8026 | 6048:8026 |
| 6006:8024 | 6049:8024 | 6006:8025 | 6049:8025 | 6006:8026 | 6049:8026 |
| 6007:8024 | 6050:8024 | 6007:8025 | 6050:8025 | 6007:8026 | 6050:8026 |
| 6008:8024 | 6051:8024 | 6008:8025 | 6051:8025 | 6008:8026 | 6051:8026 |
| 6009:8024 | 6052:8024 | 6009:8025 | 6052:8025 | 6009:8026 | 6052:8026 |
| 6010:8024 | 6053:8024 | 6010:8025 | 6053:8025 | 6010:8026 | 6053:8026 |
| 6011:8024 | 6054:8024 | 6011:8025 | 6054:8025 | 6011:8026 | 6054:8026 |
| 6012:8024 | 6055:8024 | 6012:8025 | 6055:8025 | 6012:8026 | 6055:8026 |
| 6013:8024 | 6056:8024 | 6013:8025 | 6056:8025 | 6013:8026 | 6056:8026 |
| 6014:8024 | 6057:8024 | 6014:8025 | 6057:8025 | 6014:8026 | 6057:8026 |
| 6015:8024 | 6058:8024 | 6015:8025 | 6058:8025 | 6015:8026 | 6058:8026 |
| 6016:8024 | 6059:8024 | 6016:8025 | 6059:8025 | 6016:8026 | 6059:8026 |
| 6017:8024 | 6060:8024 | 6017:8025 | 6060:8025 | 6017:8026 | 6060:8026 |
| 6018:8024 | 6061:8024 | 6018:8025 | 6061:8025 | 6018:8026 | 6061:8026 |
| 6019:8024 | 6062:8024 | 6019:8025 | 6062:8025 | 6019:8026 | 6062:8026 |
| 6020:8024 | 6063:8024 | 6020:8025 | 6063:8025 | 6020:8026 | 6063:8026 |
| 6021:8024 | 6064:8024 | 6021:8025 | 6064:8025 | 6021:8026 | 6064:8026 |
| 6022:8024 | 6065:8024 | 6022:8025 | 6065:8025 | 6022:8026 | 6065:8026 |
| 6023:8024 | 6066:8024 | 6023:8025 | 6066:8025 | 6023:8026 | 6066:8026 |
| 6024:8024 | 6067:8024 | 6024:8025 | 6067:8025 | 6024:8026 | 6067:8026 |
| 6025:8024 | 6068:8024 | 6025:8025 | 6068:8025 | 6025:8026 | 6068:8026 |
| 6026:8024 | 6069:8024 | 6026:8025 | 6069:8025 | 6026:8026 | 6069:8026 |
| 6027:8024 | 6070:8024 | 6027:8025 | 6070:8025 | 6027:8026 | 6070:8026 |

TABLE C-continued

Example combinations of a compound X with a compound Y.

| X:Y | X:Y | X:Y | X:Y | X:Y | X:Y |
|---|---|---|---|---|---|
| 6028:8024 | 6071:8024 | 6028:8025 | 6071:8025 | 6028:8026 | 6071:8026 |
| 6029:8024 | 6072:8024 | 6029:8025 | 6072:8025 | 6029:8026 | 6072:8026 |
| 6030:8024 | 6073:8024 | 6030:8025 | 6073:8025 | 6030:8026 | 6073:8026 |
| 6031:8024 | 6074:8024 | 6031:8025 | 6074:8025 | 6031:8026 | 6074:8026 |
| 6032:8024 | 6075:8024 | 6032:8025 | 6075:8025 | 6032:8026 | 6075:8026 |
| 6033:8024 | 6076:8024 | 6033:8025 | 6076:8025 | 6033:8026 | 6076:8026 |
| 6034:8024 | 6077:8024 | 6034:8025 | 6077:8025 | 6034:8026 | 6077:8026 |
| 6035:8024 | 6078:8024 | 6035:8025 | 6078:8025 | 6035:8026 | 6078:8026 |
| 6036:8024 | | 6036:8025 | | 6036:8026 | |
| 6037:8024 | | 6037:8025 | | 6037:8026 | |
| 6038:8024 | | 6038:8025 | | 6038:8026 | |
| 6039:8024 | | 6039:8025 | | 6039:8026 | |
| 6040:8024 | | 6040:8025 | | 6040:8026 | |
| 6041:8024 | | 6041:8025 | | 6041:8026 | |
| 6042:8024 | | 6042:8025 | | 6042:8026 | |
| 6000:8027 | 6043:8027 | — | — | — | — |
| 6001:8027 | 6044:8027 | | | | |
| 6002:8027 | 6045:8027 | | | | |
| 6003:8027 | 6046:8027 | | | | |
| 6004:8027 | 6047:8027 | | | | |
| 6005:8027 | 6048:8027 | | | | |
| 6006:8027 | 6049:8027 | | | | |
| 6007:8027 | 6050:8027 | | | | |
| 6008:8027 | 6051:8027 | | | | |
| 6009:8027 | 6052:8027 | | | | |
| 6010:8027 | 6053:8027 | | | | |
| 6011:8027 | 6054:8027 | | | | |
| 6012:8027 | 6055:8027 | | | | |
| 6013:8027 | 6056:8027 | | | | |
| 6014:8027 | 6057:8027 | | | | |
| 6015:8027 | 6058:8027 | | | | |
| 6016:8027 | 6059:8027 | | | | |
| 6017:8027 | 6060:8027 | | | | |
| 6018:8027 | 6061:8027 | | | | |
| 6019:8027 | 6062:8027 | | | | |
| 6020:8027 | 6063:8027 | | | | |
| 6021:8027 | 6064:8027 | | | | |
| 6022:8027 | 6065:8027 | | | | |
| 6023:8027 | 6066:8027 | | | | |
| 6024:8027 | 6067:8027 | | | | |
| 6025:8027 | 6068:8027 | | | | |
| 6026:8027 | 6069:8027 | | | | |
| 6027:8027 | 6070:8027 | | | | |
| 6028:8027 | 6071:8027 | | | | |
| 6029:8027 | 6072:8027 | | | | |
| 6030:8027 | 6073:8027 | | | | |
| 6031:8027 | 6074:8027 | | | | |
| 6032:8027 | 6075:8027 | | | | |
| 6033:8027 | 6076:8027 | | | | |
| 6034:8027 | 6077:8027 | | | | |
| 6035:8027 | 6078:8027 | | | | |
| 6036:8027 | | | | | |
| 6037:8027 | | | | | |
| 6038:8027 | | | | | |
| 6039:8027 | | | | | |
| 6040:8027 | | | | | |
| 6041:8027 | | | | | |
| 6042:8027 | | | | | |

TABLE D

Example combinations of a compound X with a compound Y.

| X:Y | X:Y | X:Y | X:Y | X:Y | X:Y |
|---|---|---|---|---|---|
| 7000:8000 | 7000:8001 | 7000:8002 | 7000:8003 | 7000:8004 | 7000:8005 |
| 7001:8000 | 7001:8001 | 7001:8002 | 7001:8003 | 7001:8004 | 7001:8005 |
| 7002:8000 | 7002:8001 | 7002:8002 | 7002:8003 | 7002:8004 | 7002:8005 |
| 7003:8000 | 7003:8001 | 7003:8002 | 7003:8003 | 7003:8004 | 7003:8005 |
| 7004:8000 | 7004:8001 | 7004:8002 | 7004:8003 | 7004:8004 | 7004:8005 |
| 7005:8000 | 7005:8001 | 7005:8002 | 7005:8003 | 7005:8004 | 7005:8005 |
| 7006:8000 | 7006:8001 | 7006:8002 | 7006:8003 | 7006:8004 | 7006:8005 |
| 7007:8000 | 7007:8001 | 7007:8002 | 7007:8003 | 7007:8004 | 7007:8005 |
| 7008:8000 | 7008:8001 | 7008:8002 | 7008:8003 | 7008:8004 | 7008:8005 |
| 7009:8000 | 7009:8001 | 7009:8002 | 7009:8003 | 7009:8004 | 7009:8005 |
| 7010:8000 | 7010:8001 | 7010:8002 | 7010:8003 | 7010:8004 | 7010:8005 |
| 7011:8000 | 7011:8001 | 7011:8002 | 7011:8003 | 7011:8004 | 7011:8005 |
| 7012:8000 | 7012:8001 | 7012:8002 | 7012:8003 | 7012:8004 | 7012:8005 |
| 7013:8000 | 7013:8001 | 7013:8002 | 7013:8003 | 7013:8004 | 7013:8005 |
| 7014:8000 | 7014:8001 | 7014:8002 | 7014:8003 | 7014:8004 | 7014:8005 |
| 7015:8000 | 7015:8001 | 7015:8002 | 7015:8003 | 7015:8004 | 7015:8005 |
| 7016:8000 | 7016:8001 | 7016:8002 | 7016:8003 | 7016:8004 | 7016:8005 |
| 7000:8006 | 7000:8007 | 7000:8008 | 7000:8009 | 7000:8010 | 7000:8011 |
| 7001:8006 | 7001:8007 | 7001:8008 | 7001:8009 | 7001:8010 | 7001:8011 |
| 7002:8006 | 7002:8007 | 7002:8008 | 7002:8009 | 7002:8010 | 7002:8011 |
| 7003:8006 | 7003:8007 | 7003:8008 | 7003:8009 | 7003:8010 | 7003:8011 |
| 7004:8006 | 7004:8007 | 7004:8008 | 7004:8009 | 7004:8010 | 7004:8011 |
| 7005:8006 | 7005:8007 | 7005:8008 | 7005:8009 | 7005:8010 | 7005:8011 |
| 7006:8006 | 7006:8007 | 7006:8008 | 7006:8009 | 7006:8010 | 7006:8011 |
| 7007:8006 | 7007:8007 | 7007:8008 | 7007:8009 | 7007:8010 | 7007:8011 |
| 7008:8006 | 7008:8007 | 7008:8008 | 7008:8009 | 7008:8010 | 7008:8011 |
| 7009:8006 | 7009:8007 | 7009:8008 | 7009:8009 | 7009:8010 | 7009:8011 |
| 7010:8006 | 7010:8007 | 7010:8008 | 7010:8009 | 7010:8010 | 7010:8011 |
| 7011:8006 | 7011:8007 | 7011:8008 | 7011:8009 | 7011:8010 | 7011:8011 |
| 7012:8006 | 7012:8007 | 7012:8008 | 7012:8009 | 7012:8010 | 7012:8011 |
| 7013:8006 | 7013:8007 | 7013:8008 | 7013:8009 | 7013:8010 | 7013:8011 |
| 7014:8006 | 7014:8007 | 7014:8008 | 7014:8009 | 7014:8010 | 7014:8011 |
| 7015:8006 | 7015:8007 | 7015:8008 | 7015:8009 | 7015:8010 | 7015:8011 |
| 7016:8006 | 7016:8007 | 7016:8008 | 7016:8009 | 7016:8010 | 7016:8011 |
| 7000:8012 | 7000:8013 | 7000:8014 | 7000:8015 | 7000:8016 | 7000:8017 |
| 7001:8012 | 7001:8013 | 7001:8014 | 7001:8015 | 7001:8016 | 7001:8017 |
| 7002:8012 | 7002:8013 | 7002:8014 | 7002:8015 | 7002:8016 | 7002:8017 |
| 7003:8012 | 7003:8013 | 7003:8014 | 7003:8015 | 7003:8016 | 7003:8017 |
| 7004:8012 | 7004:8013 | 7004:8014 | 7004:8015 | 7004:8016 | 7004:8017 |
| 7005:8012 | 7005:8013 | 7005:8014 | 7005:8015 | 7005:8016 | 7005:8017 |
| 7006:8012 | 7006:8013 | 7006:8014 | 7006:8015 | 7006:8016 | 7006:8017 |
| 7007:8012 | 7007:8013 | 7007:8014 | 7007:8015 | 7007:8016 | 7007:8017 |
| 7008:8012 | 7008:8013 | 7008:8014 | 7008:8015 | 7008:8016 | 7008:8017 |
| 7009:8012 | 7009:8013 | 7009:8014 | 7009:8015 | 7009:8016 | 7009:8017 |
| 7010:8012 | 7010:8013 | 7010:8014 | 7010:8015 | 7010:8016 | 7010:8017 |
| 7011:8012 | 7011:8013 | 7011:8014 | 7011:8015 | 7011:8016 | 7011:8017 |
| 7012:8012 | 7012:8013 | 7012:8014 | 7012:8015 | 7012:8016 | 7012:8017 |
| 7013:8012 | 7013:8013 | 7013:8014 | 7013:8015 | 7013:8016 | 7013:8017 |
| 7014:8012 | 7014:8013 | 7014:8014 | 7014:8015 | 7014:8016 | 7014:8017 |
| 7015:8012 | 7015:8013 | 7015:8014 | 7015:8015 | 7015:8016 | 7015:8017 |
| 7016:8012 | 7016:8013 | 7016:8014 | 7016:8015 | 7016:8016 | 7016:8017 |
| 7000:8018 | 7000:8019 | 7000:8020 | 7000:8021 | 7000:8022 | 7000:8023 |
| 7001:8018 | 7001:8019 | 7001:8020 | 7001:8021 | 7001:8022 | 7001:8023 |
| 7002:8018 | 7002:8019 | 7002:8020 | 7002:8021 | 7002:8022 | 7002:8023 |
| 7003:8018 | 7003:8019 | 7003:8020 | 7003:8021 | 7003:8022 | 7003:8023 |
| 7004:8018 | 7004:8019 | 7004:8020 | 7004:8021 | 7004:8022 | 7004:8023 |
| 7005:8018 | 7005:8019 | 7005:8020 | 7005:8021 | 7005:8022 | 7005:8023 |
| 7006:8018 | 7006:8019 | 7006:8020 | 7006:8021 | 7006:8022 | 7006:8023 |
| 7007:8018 | 7007:8019 | 7007:8020 | 7007:8021 | 7007:8022 | 7007:8023 |
| 7008:8018 | 7008:8019 | 7008:8020 | 7008:8021 | 7008:8022 | 7008:8023 |
| 7009:8018 | 7009:8019 | 7009:8020 | 7009:8021 | 7009:8022 | 7009:8023 |
| 7010:8018 | 7010:8019 | 7010:8020 | 7010:8021 | 7010:8022 | 7010:8023 |
| 7011:8018 | 7011:8019 | 7011:8020 | 7011:8021 | 7011:8022 | 7011:8023 |
| 7012:8018 | 7012:8019 | 7012:8020 | 7012:8021 | 7012:8022 | 7012:8023 |
| 7013:8018 | 7013:8019 | 7013:8020 | 7013:8021 | 7013:8022 | 7013:8023 |
| 7014:8018 | 7014:8019 | 7014:8020 | 7014:8021 | 7014:8022 | 7014:8023 |
| 7015:8018 | 7015:8019 | 7015:8020 | 7015:8021 | 7015:8022 | 7015:8023 |
| 7016:8018 | 7016:8019 | 7016:8020 | 7016:8021 | 7016:8022 | 7016:8023 |
| 7000:8024 | 7000:8025 | 7000:8026 | 7000:8027 | — | — |
| 7001:8024 | 7001:8025 | 7001:8026 | 7001:8027 | | |
| 7002:8024 | 7002:8025 | 7002:8026 | 7002:8027 | | |
| 7003:8024 | 7003:8025 | 7003:8026 | 7003:8027 | | |
| 7004:8024 | 7004:8025 | 7004:8026 | 7004:8027 | | |
| 7005:8024 | 7005:8025 | 7005:8026 | 7005:8027 | | |
| 7006:8024 | 7006:8025 | 7006:8026 | 7006:8027 | | |
| 7007:8024 | 7007:8025 | 7007:8026 | 7007:8027 | | |
| 7008:8024 | 7008:8025 | 7008:8026 | 7008:8027 | | |
| 7009:8024 | 7009:8025 | 7009:8026 | 7009:8027 | | |
| 7010:8024 | 7010:8025 | 7010:8026 | 7010:8027 | | |

TABLE D-continued

Example combinations of a compound X with a compound Y.

| X:Y | X:Y | X:Y | X:Y | X:Y | X:Y |
|---|---|---|---|---|---|
| 7011:8024 | 7011:8025 | 7011:8026 | 7011:8027 | | |
| 7012:8024 | 7012:8025 | 7012:8026 | 7012:8027 | | |
| 7013:8024 | 7013:8025 | 7013:8026 | 7013:8027 | | |
| 7014:8024 | 7014:8025 | 7014:8026 | 7014:8027 | | |
| 7015:8024 | 7015:8025 | 7015:8026 | 7015:8027 | | |
| 7016:8024 | 7016:8025 | 7016:8026 | 7016:8027 | | |

EXAMPLES

Additional embodiments are disclosed in further detail in the following examples, which are not in any way intended to limit the scope of the claims.

Example 1

Compound 1a

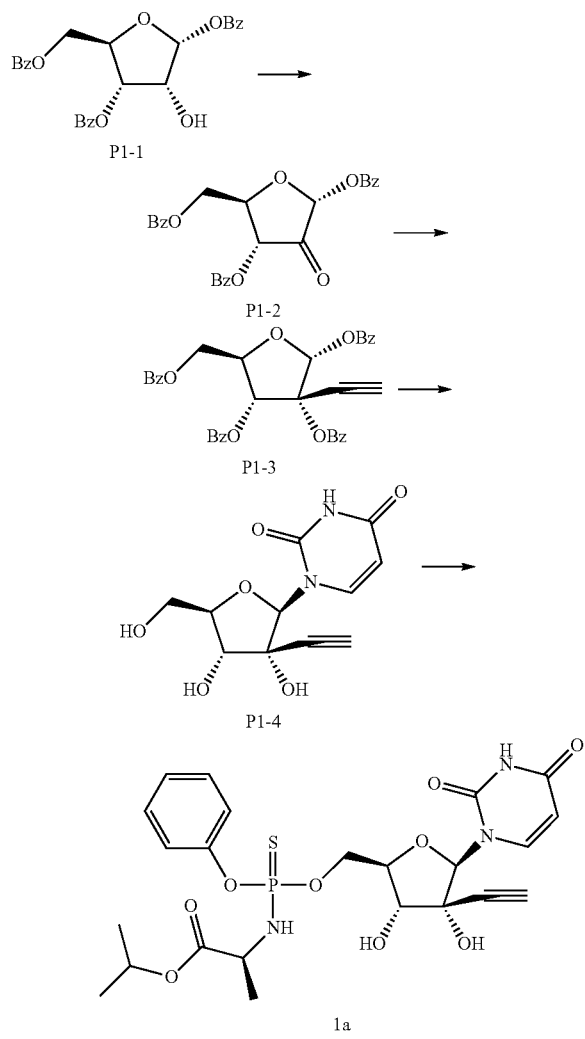

Step 1: Compound P1-2

To a solution of Des s-Martin periodinane (12.0 g, 28.1 mmol) in 500 mL of $CH_2Cl_2$ (DCM) was added P1-1 (8.0 g, 17.3 mmol) at 0° C. The mixture was warmed to room temperature and stirred for 12 hours. The solvent was removed in vacuo, and the residue was triturated with methyl tert-butyl ether (TBME) (150 mL) and filtered through a pad of $MgSO_4$. The filtrate was stirred with an equal volume of $Na_2S_2O_3 \cdot 5H_2O$ in 50 mL of saturated $NaHCO_3$ until the organic layer became clear (~10 minutes). The organic layer was separated, washed with brine, dried over $MgSO_4$, and concentrated to give P1-2 as a white solid (7.3 g, 91%).

Step 2: Compound P1-3

To a solution of P1-2 (39.0 g, 84.9 mmol) in anhydrous THF (450 mL) was added ethynylmagnesium bromide (390 mL, 195 mmol) dropwise over 20 minutes at −78° C. using an ice-acetone cooling bath. The resulting mixture was stirred for 2 hours at −78° C. The ice-acetone cooling bath was removed and saturated $NH_4Cl$ (600 mL) was added with stirring. After warming to room temperature, the mixture was filtered through CELITE™ and washed with saturated aqueous $NH_4Cl$ (300 mL). The combined organic phase was dried with $Na_2SO_4$, filtered, and concentrated to provide a crude product (38.0 g). The crude product was dissolved in anhydrous $CH_2Cl_2$ (DCM) (200 mL), followed by addition of 4-dimethylaminopyridine (DMAP) (19.1 g, 156.4 mmol), benzoyl chloride (23.5 g, 156.4 mmol) and $Et_3N$ (23.7 g, 234.6 mmol). After stirring for 12 hours at room temperature, the reaction mixture was diluted with DCM (100 mL) and then washed with saturated aqueous $NaHCO_3$ (100 mL). The combined aqueous phase was extracted with DCM (100 mL) and the combined organic phase was dried with $Na_2SO_4$, filtered, and evaporated to dryness under reduced pressure to give a yellow oil. The oil was purified by column chromatography (5% ethyl acetate in petroleum ether) to give P1-3 (18.0 g, 39%).

Step 3: Compound P1-4

To a suspension of uracil (4.6 g, 40.6 mmol) in 20 mL of distilled acetonitrile was added N,O-bis(trimethylsilyl)acetamide (16.6 g, 81.3 mmol). The resulting solution was refluxed for 30 minutes and then cooled to ambient temperature. A solution of P1-3 (12.0 g, 20.34 mmol) in 10 mL of acetonitrile was added, followed by dropwise addition of $SnCl_4$ (21.15 g, 81.3 mmol). The reaction mixture was refluxed overnight. The reaction mixture was cooled to room temperature, diluted with 100 mL of ethyl acetate and washed with saturated $NaHCO_3$ and brine. The organic layer was dried with $Na_2SO_4$, filtered, and concentrated. The resulting residue was purified by silica gel column chromatography (ethyl acetate/hexanes 5:1) to give a protected nucleoside intermediate (7.6 g, yield 64%) as a white solid. The nucleoside intermediate was dissolved in methanolic ammonia (70 mL, saturated) and the mixture was stirred at room temperature for 14 hours. The solvent was removed and the residue was purified by silica gel column chromatography (DCM/MeOH=30:1 to 10:1) to give P1-4 as a white solid (1.9 g, 56%). $^1H$ NMR ($CD_3OD$, 400 MHz) δ 8.05 (d, J=8.0 Hz, 1H), 6.02 (s, 1H), 5.68 (d, J=8.0 Hz, 1H), 4.19 (d, J=8.8 Hz, 1H), 3.93 (dd, $J_1$=2.4 Hz, $J_2$=12.4 Hz, 1H), 3.88-3.92 (m, 1H), 3.76 (dd, $J_1$=2.8 Hz, $J_2$=12.8 Hz, 1H), 3.02 (s, 1H); ESI-TOF-MS: m/z 291 [M+Na]$^+$.

Step 4: Compound 1a

To a suspension of P1-4 (110 mg, 0.41 mmol) in dry THF (2 mL) were added N-methylimidazole (NMI) (0.2 mL) and (2S)-isopropyl 2-((chloro(phenoxy)phosphorothioyl)amino)propanoate (389 mg, 1.2 mmol). The reaction mixture was heated to 70° C. and stirred for 1 hour. The solvents were evaporated and the resulting residue was purified by RP HPLC (MeCN and 0.1% HCOOH in water) to give compound 1a as a white solid (a mixture of 2 P-isomers, 100 mg, 44%). $^1$H NMR (MeOD, 400 MHz) δ 7.79, 7.71 (2d, J=8.0 Hz, 1H), 7.15-7.34 (m, 5H), 6.06, 6.03 (2s, 1H), 5.59, 5.56 (2d, J=8.0 Hz, 1H), 4.94-5.01 (m, 1H), 4.46-4.52 (m, 1H), 4.37-4.39 (m, 1H), 4.18-4.32 (m, 1H), 4.05-4.16 (m, 2H), 3.05, 3.27 (2s, 1H), 1.36, 1.31 (2d, J=0.8 Hz, 3H), 1.21-1.24 (m, 6H). $^{31}$P NMR (CD$_3$OD, 162 MHz) δ 8.45, 68.26. ESI-LCMS: m/z 554.0 [M+H]$^+$.

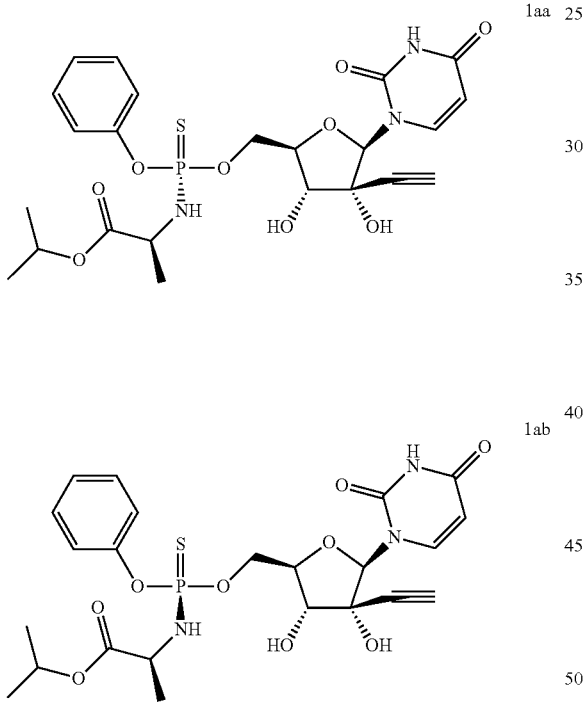

The two diastereomers were separated to provide 1aa and 1ab as follows. A 60:40 diastereomeric mixture of compound 1a (974 mg) was subjected to chromatography using a 30×250 mm 5μ Chiracel OZ-H column and eluted with methanol. There was obtained 522 mg of the faster eluting diastereomer (3.95 min), which was present in slight excess in the mixture. There was obtained 334 mg of the slower eluting diastereomer (5.24 min). Faster eluting diastereomer, major isomer: HPLC purity>99.5%, $^{31}$P NMR 67.1, LC/MS 552 (M−1) Slower eluting diastereomer, minor isomer: HPLC purity>99.3%, $^{31}$P NMR 67.9, LC/MS 552 (M−1).

Example 2

Compound 2a

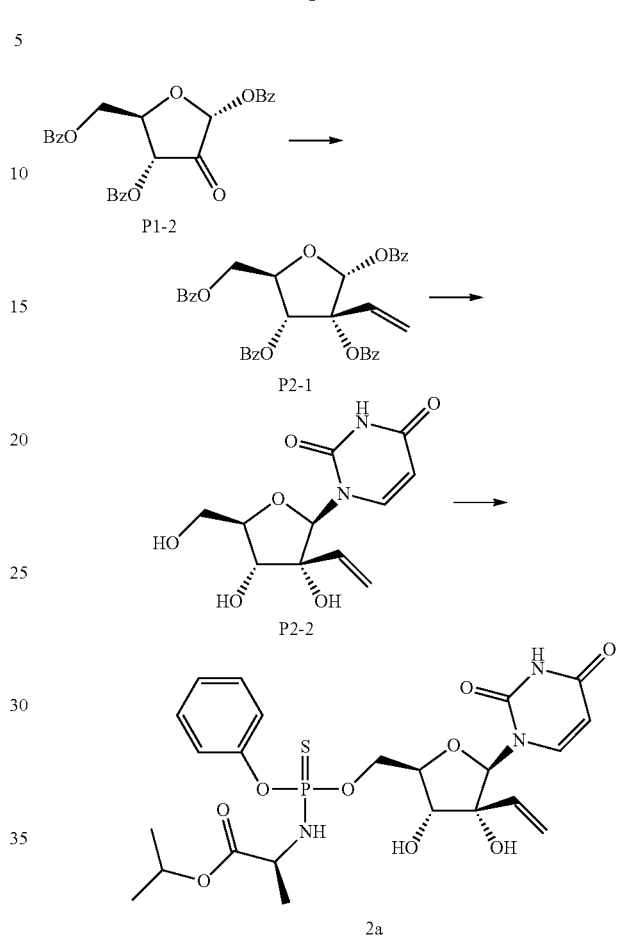

Step 1: Compound P2-1

To a stirred solution of P1-2 (6.0 g, 12.8 mmol) in THF (20 mL) was added vinylmagnesium bromide (44.8 mL, 44.8 mmol) dropwise over 10 minutes and the resulting mixture was stirred at −78° C. for 2 hours. The reaction was quenched with saturated NH$_4$Cl (100 mL), and the mixture was filtered through CELITE™ and extracted with ethyl acetate. The combined organic phase was dried with Na$_2$SO$_4$, filtered, and concentrated to give a crude intermediate. The crude intermediate was dissolved in anhydrous DCM (150 mL), followed by addition of dimethylaminopyridine (DMAP) (3.49 g, 28.6 mmol), benzoyl chloride (6.5 mL, 42.9 mmol) and Et$_3$N (6.0 mL, 42.9 mmol). After stirring at room temperature for 12 hours, the reaction mixture was diluted with DCM (DCM) (100 mL), and washed successively with 1 M aqueous HCl (3×100 mL) and saturated aqueous NaHCO$_3$ (50 mL). The combined organic phase was dried with Na$_2$SO$_4$, filtered, and evaporated to give a residue. The residue was purified by column chromatography (5% ethyl acetate in petroleum ether) to give P2-1 as a white solid (2.3 g, 27%).

Step 3: Compound P2-2

To a suspension of uracil (851 mg, 7.6 mmol) in 20 mL of distilled acetonitrile was added N,O-bis(trimethylsilyl)acetamide (3.1 g, 15.2 mmol). The resulting solution was brought to reflux for 30 minutes. The solution was cooled to ambient temperature. A solution of P2-1 (2.3 g, 3.8 mmol) in 20 mL of acetonitrile was added, followed by slow dropwise addition of SnCl$_4$ (4.0 g, 15.2 mmol). The reaction mixture was refluxed overnight. The reaction mixture was diluted with 200 mL of ethyl acetate, and washed with saturated NaHCO$_3$ and brine. The organic layer was dried with Na$_2$SO$_4$, filtered, and concentrated to give a residue. The residue was purified by silica gel column chromatography (ethyl acetate/hexanes 8:1) to afford the protected nucleoside as a white solid (560 mg, 26%). The protected nucleoside (560 mg, 0.96 mmol) was dissolved in methanolic ammonia (20 mL, saturated) and the mixture was stirred at room temperature for 14 hours. The solvent was removed, and the residue was purified by silica gel column chromatography (DCM/MeOH=30:1 to 10:1) to give P2-2 as a white solid (230 mg, 88%). $^1$H NMR (CD$_3$OD, 400 MHz) δ 8.11 (d, J=8.0 Hz, 1H), 5.94 (s, 1H), 5.65-5.71 (m, 2H), 5.43 (dd, J$_1$=1.2 Hz, J$_2$=17.2 Hz, 1H), 5.24 (d, J$_1$=1.2 Hz, J$_2$=10.8 Hz, 1H), 4.21 (d, J=8.8 Hz, 1H), 3.97-4.01 (m, 2H), 3.78-3.82 (m, 1H). ESI-MS: m/z 271 [M+H]$^+$.

Step 4: Compound 2a

To a suspension of P2-2 (110 mg, 0.41 mmol) in dry tetrahydrofuran (THF) (2 mL) were added N-methylimidazole (NMI) (0.2 mL) and (2S)-isopropyl 2-((chloro(phenoxy)phosphorothioyl)amino)propanoate (389 mg, 1.2 mmol). The reaction mixture was heated to 70° C. and stirred for 1 hour. The solvents were evaporated, and the resulting residue was purified by RP HPLC (MeCN and 0.1% HCOOH in water) to give compound 2a as a white solid (a mixture of 2 P-isomers, 100 mg, 44%). $^1$H NMR (MeOD, 400 MHz) δ 7.81, 7.74 (2d, J=8.0 Hz, 1H), 7.16-7.36 (m, 5H), 5.94, 5.97 (2s, 1H), 5.61-5.69 (m, 1H), 5.54-5.58 (m, 1H), 5.42-5.47 (m, 1H), 5.24-5.39 (m, 1H), 4.86-4.99 (m, 1H), 4.50-4.55 (m, 1H), 4.34-4.42 (m, 1H), 4.17-4.21 (m, 2H), 4.02-4.12 (m, 1H), 1.31-1.38 (m, 3H), 1.21-1.23 (m, 6H). $^{31}$P NMR (CD$_3$OD, 162 MHz) δ 68.43, 68.10. ESI-LCMS: m/z 556.0 [M+H]$^+$.

Example 3

Compound 3a

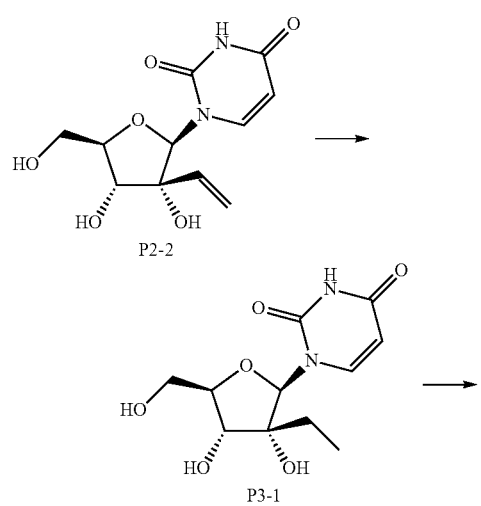

P2-2

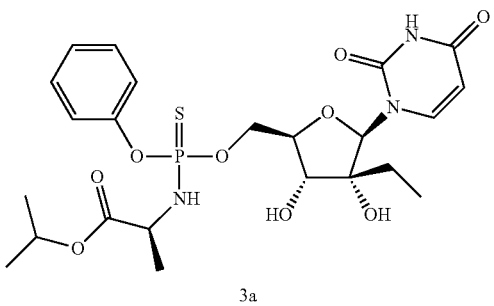

3a

Step 1: Compound P3-1

Compound P2-2 (100 mg, 0.37 mmol) was dissolved in 20 mL of MeOH, and Pd/C (20 mg) was added. The resulting mixture was stirred at room temperature under H$_2$ (balloon) overnight. The reaction mixture was concentrated to give a residue. The resulting residue was purified by silica gel column chromatography (5% MeOH in DCM) to give P3-1 as white solid (90 mg, 94%). $^1$H NMR (MeOD, 400 MHz) δ 7.97 (d, J=8.0 Hz, 1H), 6.01 (s, 1H), 5.69 (d, J=8.0 Hz, 1H), 3.92-3.97 (m, 2H), 3.86-3.89 (m, 1H), 3.76 (dd, J$_1$=2.8 Hz, J$_2$=12.4 Hz, 1H), 1.43-1.54 (m, 2H), 0.95 (t, T=7.6 Hz, 3H). ESI-MS: m/z 273 [M+H]$^+$.

Step 2: Compound 3a

Compound P3-1 (90 mg, 0.33 mmol) was suspended in 2 mL of dry THF, followed by addition of NMI (0.6 mL) and (2S)-isopropyl 2-((chloro(phenoxy)phosphorothioyl)amino)propanoate (318 mg, 1.00 mmol). The reaction mixture was stirred at 70° C. for 1 hour. The solvents were evaporated, and the resulting residue was purified by RP HPLC (MeCN and 0.1% HCOOH in water) to give compound 3a as a white solid (a mixture of two P-isomers, 51 mg, 31%). $^1$H NMR (MeOD, 400 MHz) δ 7.69, 7.63 (2d, J=8.0 Hz, 1H), 7.15-7.35 (m, 5H), 6.00, 6.04 (2s, 1H), 5.59, 5.58 (2d, J=8.0 Hz, 1H), 4.95-4.98 (m, 1H), 4.45-4.50 (m, 1H), 4.25-4.40 (m, 1H), 4.03-4.11 (m, 2H), 3.94, 3.93 (2d, J=9.2 Hz, 1H), 1.41-1.50 (m, 2H), 1.35, 1.31 (2d, J=16.8 Hz, 3H), 1.21, 1.22 (2d, J=6.0 Hz, 6H), 0.92-0.96 (m, 3H). $^{31}$P NMR (CD$_3$OD, 162 MHz) δ 68.35, 67.99. ESI-LCMS: m/z 558.0 [M+H]$^+$.

Example 4

Preparation of additional 2'-C-ethynyluridine 5'-thiophosphoramidates

Compounds 7a-13a, 19a, and 21a as shown in Table 2, were prepared using a similar procedure for preparing compound 1a.

TABLE 2

| Compound # | Structure | $^{31}$P NMR ppm | ESI-LCMS m/z |
|---|---|---|---|
| 7a | 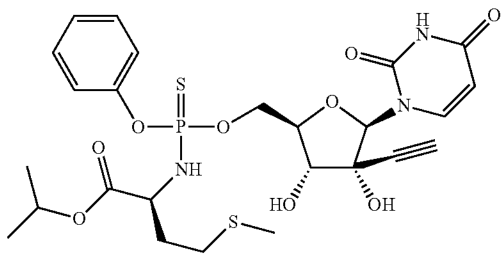 | 68.92, 68.82 | 614.1 (M + 1)$^+$ |
| 8a | 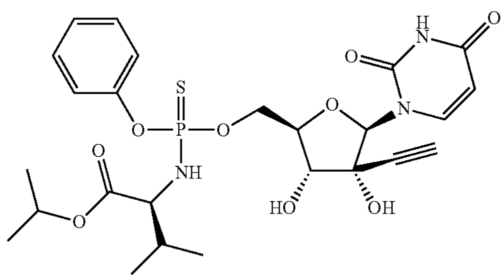 | 70.44, 69.26 | 582.1 (M + 1)$^+$ |
| 9a | 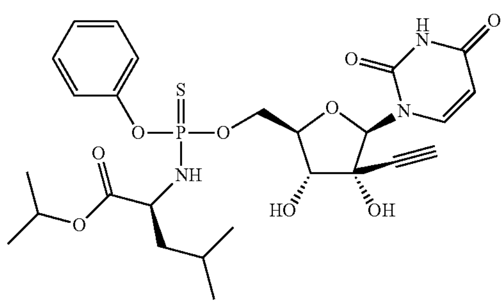 | 69.25, 68.65 | 596.1 (M + 1)$^+$ |
| 10a | 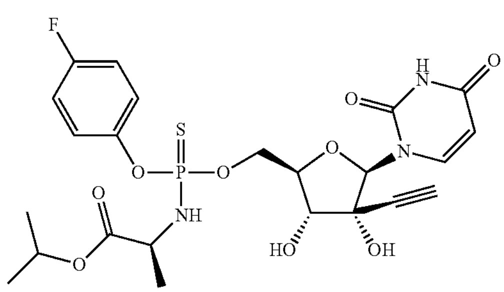 | 69.33, 69.09 | 672.0 (M + 1)$^+$ |
| 11a | 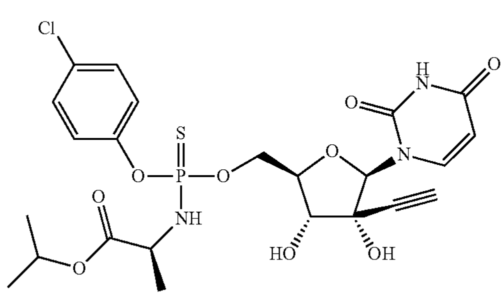 | 68.94, 68.62 | 589.0 (M + 1)$^+$ |

TABLE 2-continued
| Compound # | Structure | 31P NMR ppm | ESI-LCMS m/z |
|---|---|---|---|
| 12a | 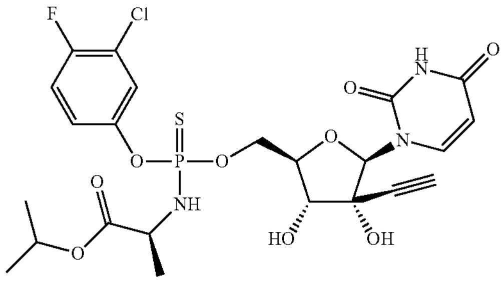 | 69.69 69.28 | 606.0 (M + 1)+ |
| 13a | 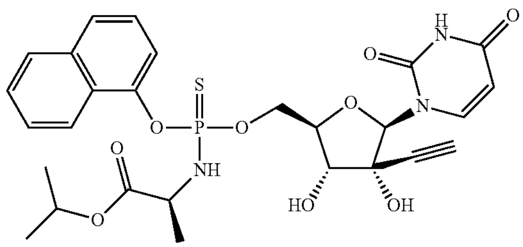 | 68.74 67.82 | 604.1 (M + 1)+ |
| 19a | 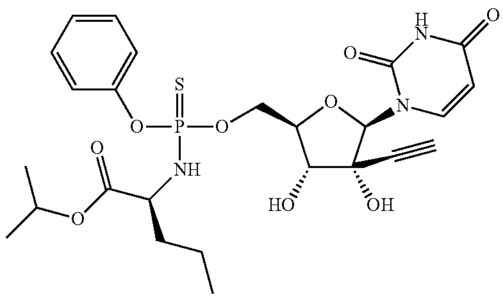 | 69.23 68.52 | 582.0 (M + 1)+ |
| 21a | 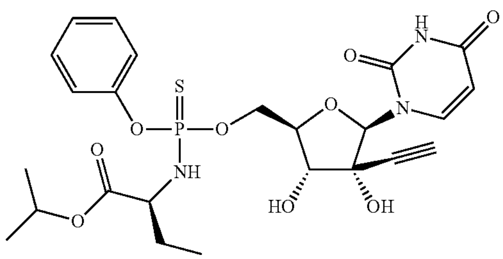 | 69.19 68.52 | 568.1 (M + 1)+ |
Example 5
Compound 5a
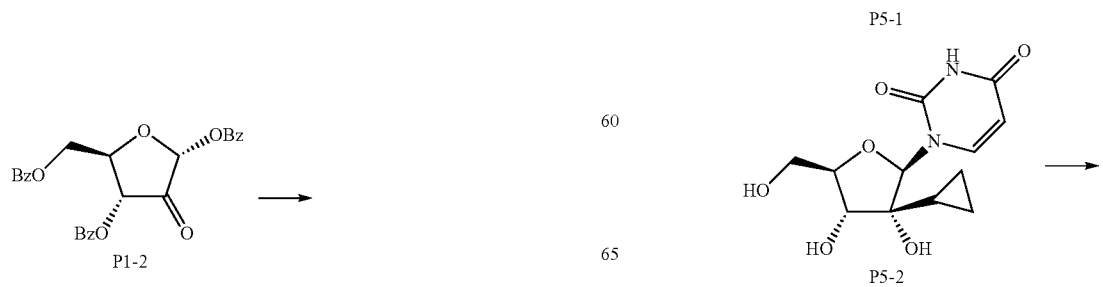

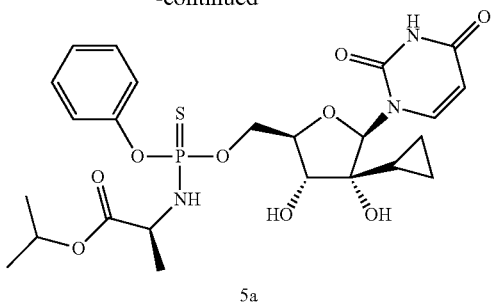

5a

Step 1: Compound P5-1

To a stirred solution of P1-2 (2.0 g, 4.3 mmol) in THF (20 mL) was added 1-propynyl magnesium bromide (17.2 mL, 8.6 mmol) dropwise at −78° C. The resulting mixture was stirred at −78° C. for 2 hours. The reaction was quenched by addition of saturated aqueous NH$_4$Cl (50 mL). The solvent was removed in vacuo, and the resulting residue was diluted with ethyl acetate, washed with brine (100 mL), dried with Na$_2$SO$_4$, filtered, and concentrated to give a crude intermediate as a white solid (2.1 g, yield: 95%). The crude intermediate (2.1 g, 4.2 mmol) was dissolved in anhydrous DCM (150 mL), followed by addition of DMAP (1.0 g, 8.4 mmol), Et$_3$N (1.3 g, 12.6 mmol) and benzoyl chloride (1.76 g 12.6 mmol) at 0° C. The reaction mixture was stirred at room temperature overnight. The reaction mixture was diluted with DCM (100 mL), and washed with saturated aqueous NaHCO$_3$ (100 mL) and brine (100 mL). The organic phase was dried with Na$_2$SO$_4$, filtered, and evaporated to dryness under reduced pressure. The resulting residue was purified by silica gel column chromatography (0-20% petroleum ether in ethyl acetate) to give P5-1 as a yellow solid (1.2 g, yield: 48%).

Step 2: Compound P5-2

To a suspension of uracil (571 mg, 5.1 mmol) in 20 mL of acetonitrile was added N,O-bis(trimethylsilyl)acetamide (1.38 g, 6.8 mmol). The resultant solution was refluxed for 2 hours, and then cooled to ambient temperature. A solution of P5-1 (1.0 g, 1.7 mmol) in 20 mL of acetonitrile was added, followed by slow dropwise addition of SnCl$_4$ (1.76 g, 6.8 mmol). The reaction mixture was refluxed overnight, and then cooled to ambient temperature. Ethyl acetate (200 mL) was added, and the solution was washed with saturated NaHCO$_3$ and brine. The organic layer was dried with Na$_2$SO$_4$, filtered, and concentrated. The resulting residue was purified by silica gel column chromatography (30% petroleum ether in ethyl acetate) to afford the protected nucleoside as a white solid (412 mg, 42%). The protected intermediate (412 mg, 0.69 mmol) was dissolved in methanolic ammonia (100 mL, saturated) and the mixture was stirred at room temperature overnight. The solvent was removed, and the resulting residue was purified by column chromatography (3-~8% MeOH in DCM) to give compound P5-2 as a white solid (171 mg, 87%). $^1$H NMR (MeOD, 400 MHz) δ 8.10 (d, J=8.0 Hz, 1H), 6.03 (s, 1H), 5.72 (d, J=8.0 Hz, 1H), 3.99-4.06 (m, 2H), 3.91-3.94 (m, 1H), 3.82 (dd, J$_1$=2.8 Hz, J$_2$=12.4 Hz, 1H), 0.71-0.75 (m, 1H), 0.53-0.57 (m, 2H), 0.27-0.42 (m, 2H). ESI-TOF-MS: m/z 307 [M+Na]$^+$.

Step 3: Compound 5a

To a stirred solution of P5-2 (110 mg, 0.38 mmol) and NMI (1 mL) in anhydrous acetonitrile (2 mL) was added a solution of (2S)-isopropyl 2-((chloro(phenoxy)phosphorothioyl)amino)propanoate (164 mg, 0.51 mmol) in 0.1 mL acetonitrile dropwise at room temperature under N$_2$. The mixture was stirred at 75° C. for 2 hours. The reaction was quenched with H$_2$O, and extracted ethyl acetate. The organic layer was dried over Na$_2$SO$_4$ and concentrated. The resulting residue was purified by RP HPLC (MeCN and 0.1% HCOOH in water) to give compound 5a as a white solid (a mixture of two P-isomers, 41 mg, 18.6%). $^1$H NMR (MeOD, 400 MHz) δ 7.81, 7.74 (2d, J=8.0 Hz, 1H), 7.18-7.38 (m, 5H), 6.01, 6.04 (2s, 1H), 5.61 (d, J=8.0 Hz, 1H), 4.97-5.03 (m, 1H), 4.48-4.54 (m, 1H), 4.39-4.43 (m, 1H), 4.03-4.16 (m, 2H), 3.94-3.98 (m, 1H), 1.34-1.40 (m, 3H), 1.24-1.26 (m, 6H). $^{31}$P NMR (CD$_3$OD, 162 MHz) δ 68.39, 68.04. ESI-MS: m/z 570.0 [M+H]$^+$.

Example 6

Compound 14a

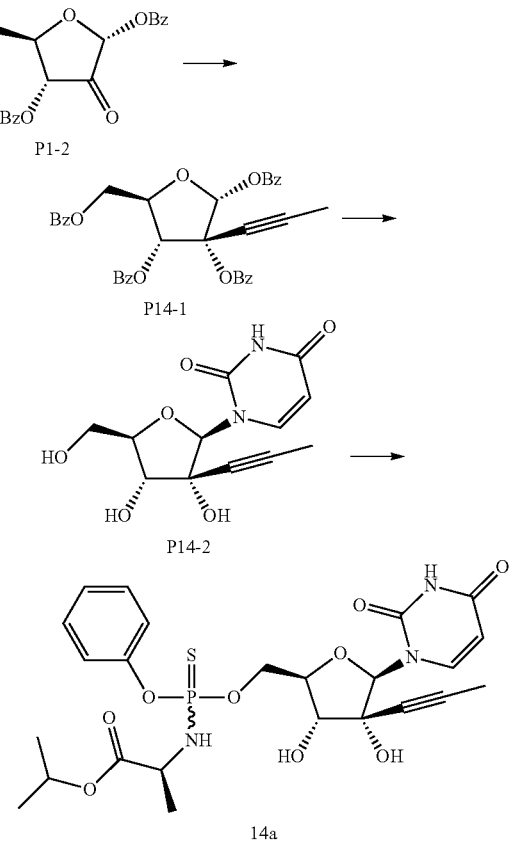

Step 1: Compound P14-1

To a solution of P1-2 (7.6 g, 16.5 mmol) in THF (100 mL) was added 1-propynyl magnesium bromide (105.6 mL, 52.8 mmol) dropwise over 10 minutes at −78° C. The reaction mixture was stirred for 2 hours at −78° C. The reaction was quenched by the addition of saturated aqueous NH$_4$Cl (100 mL). The THF was removed in vacuo, and the resulting residue was diluted with ethyl acetate. The ethyl acetate layer was washed with brine (150 mL), dried with Na$_2$SO$_4$, filtered, and concentrated to give a crude intermediate as a white solid (7.6 g, 92%). The crude intermediate (7.6 g, 15.2 mmol) was dissolved in anhydrous DCM (150 mL), followed by addition of DMAP (3.8 g, 31.1 mmol), benzoyl chloride (7.0 mL, 45.6 mmol) and Et$_3$N (7.6 mL, 45.6 mmol) at 0° C. The reaction mixture was stirred at room temperature overnight. The reaction mixture was diluted with DCM (100 mL), and washed with saturated aqueous NaHCO$_3$ (150 mL) and brine (150 mL). The organic phase was dried with Na$_2$SO$_4$, filtered, and evaporated to dryness under reduced pressure. The resulting residue was purified by silica gel column chromatography (5% ethyl acetate in petroleum ether) to give P14-1 as a yellow solid (8.0 g, 87%).

Step 2: Compound P14-2

To a suspension of uracil (612 mg, 5.5 mmol) in 20 mL of distilled acetonitrile was added N,O-bis(trimethylsilyl)acetamide (1.486 g, 7.3 mmol). The solution was refluxed for 2 hours. The solution was cooled to ambient temperature. A solution of P14-1 (1.1 g, 1.8 mmol) in 20 mL of acetonitrile was added, followed by slow dropwise addition of SnCl$_4$ (1.89 g, 7.3 mmol). The reaction mixture was refluxed overnight. The solution was cooled to ambient temperature, and 200 mL of ethyl acetate was added. The solution was washed with saturated NaHCO$_3$ and brine. The organic layer was dried with Na$_2$SO$_4$, filtered, and concentrated to give a residue. The residue was purified by silica gel column chromatography (petroleum ether:ethyl acetate=100:1 to 3:1) to give the protected intermediate as a brown solid (150 mg, yield 14%). The protected intermediate (500 mg, 0.84 mmol) was dissolved in methanolic ammonia (100 mL, saturated) and the mixture was stirred overnight at room temperature. The solvent was removed, and the resulting residue was purified by column chromatography (DCM/MeOH=30:1 to 10:1) to give P14-2 as a white solid (155 mg, 65%). $^1$H NMR (CD$_3$OD, 400 MHz) δ 8.02 (d, J=8.4 Hz, 1H), 6.00 (s, 1H), 5.68 (d, J=8.4 Hz, 1H), 4.1 (d, J=8.8 Hz, 1H), 3.94 (dd, J$_1$=2.0 Hz, J$_2$=12.4 Hz, 1H), 3.86-3.89 (m, 1H), 3.75 (dd, J$_1$=2.8, J$_2$=12.4 Hz, 1H), 1.75 (s, 3H). ESI-TOF-MS: m/z 305 [M+Na]$^+$.

Step 3: Compound 14a

Compound P14-2 (105 mg, 0.37 mmol) was coevaporated with anhydrous pyridine and toluene three times, and then suspended in distilled acetonitrile (1 mL). NMI (0.5 mL) and a solution of (2S)-isopropyl 2-((chloro(phenoxy)phosphorothioyl)amino)propanoate in distilled acetonitrile (1M, 1 mL, 1.0 mmol) were added to the mixture. The reaction mixture was stirred at room temperature overnight. The solvents were evaporated, and the resulting residue was purified by HPLC (MeCN and 0.1% HCOOH in water) to give compound 14a as white solid (a mixture of two P-isomers, 41 mg, 20%). $^1$H NMR (CD$_3$OD, 400 MHz) δ 7.76, 7.71 (2d, J=8.4 Hz, 1H), 7.15-7.35 (m, 5H), 6.04, 6.01 (2s, 1H), 5.59, 5.57 (2d, J=8.4 Hz, 1H), 4.95-5.01 (m, 1H), 4.44-4.49 (m, 1H), 4.26-4.39 (m, 1H), 4.02-4.13 (m, 3H), 1.76, 1.75 (2s, 3H), 1.36, 1.32 (2d, J=7.2 Hz, 3H), 1.24, 1.22 (2d, J=4.0 Hz, 6H). $^{31}$P NMR (CD$_3$OD, 162 MHz) δ 68.42, 68.30. ESI-LCMS: m/z 568 [M+H]$^+$, 590 [M+Na]$^+$.

Example 7

Compound 15a

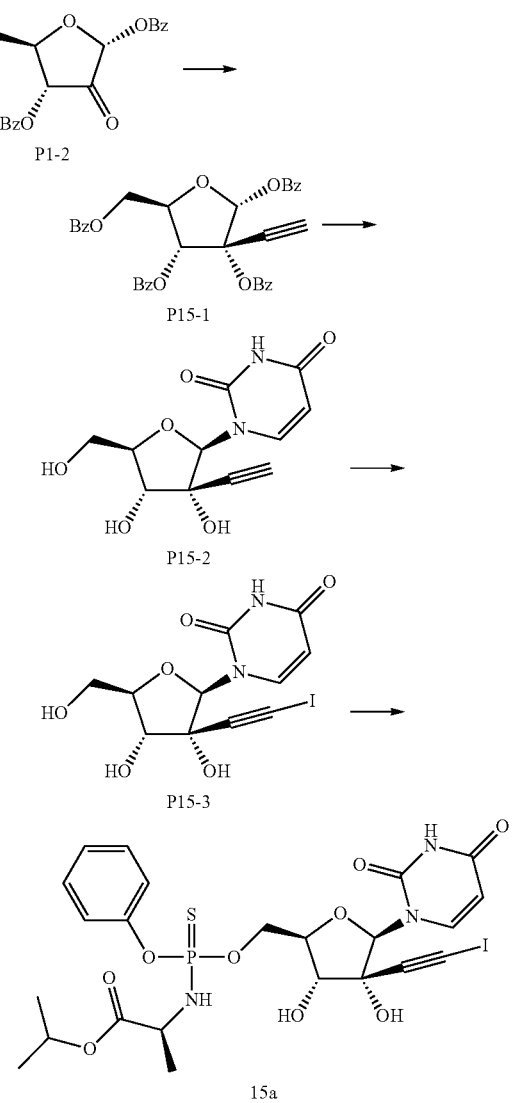

Step 1: Compound P15-1

To a solution of P1-2 (39.0 g, 84.9 mmol) in anhydrous THF (450 mL) was added ethynylmagnesium bromide (390 mL, 195 mmol) dropwise over 20 minutes at −78° C. by cooling with an ice-acetone bath. The resulting mixture was stirred for 2 hours at −78° C. The ice-acetone bath was removed. Saturated NH$_4$Cl (600 mL) was added to the solution with stirring, and allowed to warm to room temperature. The mixture was filtered through CELITE™ and washed with saturated aqueous NH$_4$Cl (300 mL). The combined organic phase was dried with Na$_2$SO$_4$, filtered, and concentrated to provide a crude product (38.0 g). The crude product was dissolved in anhydrous DCM (200 mL), followed by addition of DMAP (19.1 g, 156.4 mmol), benzoyl chloride (23.5 g, 156.4 mmol) and Et₃N (23.7 g, 234.6 mmol). The reaction was stirred for 12 hours at room temperature. The reaction mixture was diluted with DCM (100 mL) and washed with saturated aqueous NaHCO₃ (100 mL). The combined aqueous phase was extracted with DCM (100 mL), and dried with Na₂SO₄, filtered and evaporated to dryness under reduced pressure. The resulting yellow oil was purified by column chromatography (5% ethyl acetate in petroleum ether) to P15-1 (18.0 g, yield: 39%).

Step 2: Compound P15-2

To a suspension of uracil (4.6 g, 40.6 mmol) in 20 mL of distilled acetonitrile was added N,O-bis(trimethylsilyl)acetamide (16.6 g, 81.3 mmol). The resultant solution refluxed for 30 minutes, and then cooled to ambient temperature. A solution of P15-1 (12.0 g, 20.34 mmol) in 10 mL of acetonitrile was added, followed by dropwise addition of SnCl₄ (21.15 g, 81.3 mmol). The reaction mixture was refluxed overnight, and then cooled to room temperature. The reaction mixture was diluted with 100 mL of ethyl acetate, and washed with saturated NaHCO₃ and brine. The organic layer was dried with Na₂SO₄, filtered, and concentrated. The resulting residue was purified via silica gel column chromatography (ethyl acetate/hexanes 5:1) to provide the protected nucleoside (7.6 g, yield 64%) as a white solid. The protected nucleoside was dissolved in methanolic ammonia (70 mL, saturated) and the mixture was stirred at room temperature for 14 hours. The solvent was removed, and the resulting residue was purified via silica gel column chromatography (DCM/MeOH=30:1 to 10:1) to provide P15-2 as a white solid (1.9 g, 56%). ¹H NMR (CD₃OD, 400 MHz) δ 8.05 (d, J=8.0 Hz, 1H), 6.02 (s, 1H), 5.68 (d, J=8.0 Hz, 1H), 4.19 (d, J=8.8 Hz, 1H), 3.93 (dd, J₁=2.4 Hz, J₂=12.4 Hz, 1H), 3.88-3.92 (m, 1H), 3.76 (dd, J₁=2.8 Hz, J₂=12.8 Hz, 1H), 3.02 (s, 1H); ESI-TOF-MS: m/z 291 [M+Na]⁺.

Step 3: Compound P15-3

A solution of P15-2 (200 mg, 074 mmol) in acetone was treated at room temperature with N-iodosuccinimide (NIS) (200 mg, 0.8 mmol) and silver nitrate (61 mg, 3.7 mmol). After 1 hour the reaction mixture was poured with stirring into ice water. The resulting precipitate was filtered and dissolved in ethyl acetate. The resulting solution was washed with water, dried, and evaporated to dryness in vacuo. The resulting residue was purified by column chromatography (DCM/MeOH=20:1) to give P15-3 (115 mg, 52%). ¹H NMR (CD₃OD, 400 MHz) δ 8.00 (d, J=8.0 Hz, 1H), 6.0 (s, 1H), 5.70 (d, J=8.0 Hz, 1H), 4.15 (d, J=9.2 Hz, 1H), 3.85-3.96 (m, 2H), 3.74 (dd, J₁=2.8 Hz, J₂=12.4 Hz, 1H); ESI-TOF-MS: m/z 395 [M+H]⁺.

Step 4: Compound 15a

Compound P15-3 (100 mg, 0.25 mmol) was suspended in 2 ml of dry MeCN, followed by addition of NMI (1 mL) and (2S)-isopropyl 2-((chloro(phenoxy)phosphorothioyl)amino)propanoate (243 mg, 0.75 mmol). The reaction mixture was stirred for 12 hours. The solvents were evaporated, and the resulting residue was purified by RP HPLC (MeCN and 0.1% HCOOH in water) to give compound 15a (a mixture of two P isomers, 62 mg, 38%). ¹H NMR (CD₃OD, 400 MHz) δ 7.73, 7.67 (2d, J=8.0 Hz, 1H), 7.18-7.36 (m, 5H), 6.03, 6.00 (2s, 1H), 5.62, 5.57 (2d, J=8.0 Hz, 1H), 4.95-5.01 (m, 1H), 4.44-4.50 (m, 1H), 4.25-4.37 (m, 1H), 4.05-4.17 (m, 3H), 1.32-1.37 (m, 3H), 1.22-1.24 (m, 3H); ³¹P NMR (CD₃OD, 162 MHz) δ 68.4, 68.2; ESI-LCMS: m/z 680 [M+H]⁺.

Example 8

Compound 16a

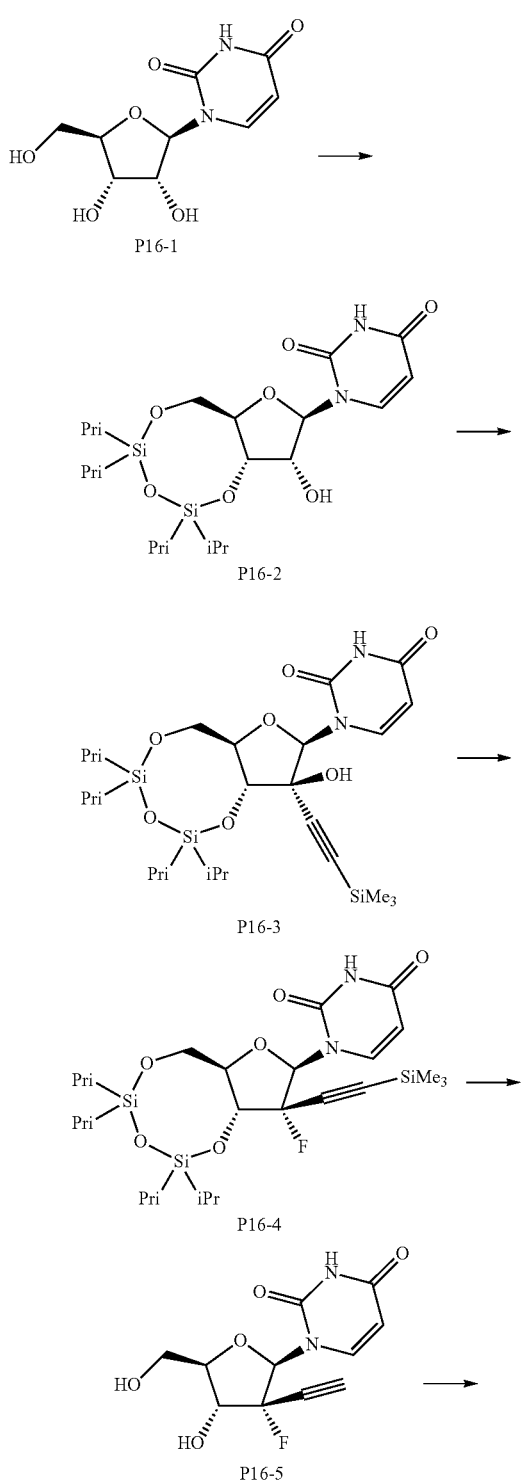

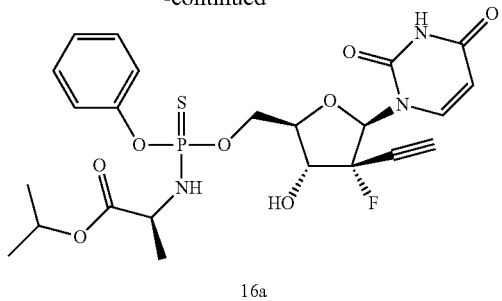

16a

Step 1: Compound P16-2

To an ice-cold solution of P16-1 (2.0 g, 7.6 mmol) in anhydrous pyridine (20 mL) was added 1,3-dichloro-1,1,3,3-tetraisopropyldisiloxane (2.40 g, 7.6 mmol) under $N_2$. The reaction mixture was stirred at room temperature overnight. The solvent was removed under vacuum. The resulting residue was diluted with ethyl acetate (100 mL), and washed with saturated $NaHCO_3$ and brine. The organic layer was separated, dried over anhydrous $Na_2SO_4$, and filtered. The filtrate was concentrated in vacuo to give a residue. The residue was purified by silica gel column chromatography (DCM/MeOH=100/1 to 50/1) to give P16-2 as a white solid (3.2 g, 85%).

Step 2: Compound P16-3

Pyridine (4.5 ml) and acetic anhydride (3.2 mL) were added to a suspension of $CrO_3$ (3.2 g, 32 mmol) in DCM (80 mL) under $N_2$ at 0° C. The mixture was stirred at room temperature for 30 minutes before a solution of P16-2 (3.2 g, 6.6 mmol) in DCM (20 mL) was added at 0° C. The mixture was stirred at room temperature for 1 hour. The mixture was filtered through a silica gel pad, and the filtrate was evaporated to dryness to give a ketone intermediate as a white solid (2.8 g, 90%).

Separately, trimethylsilylacetylene (2.0 g, 20 mmol) was dissolved in anhydrous THF (40 mL), and n-BuLi (8.0 mL, 20 mmol) was added dropwise at −78° C. The reaction mixture was stirred at −78° C. for 30 minutes. The reaction mixture was warmed to room temperature for 10 minutes.

Then, the ketone intermediate (2.0 g, 4.0 mmol) in THF (10 mL) was added to the reaction mixture dropwise at −78° C. The reaction mixture was stirred at −78° C. for 1 hour, warmed to room temperature, and stirred for an additional 20 minutes. The reaction was quenched by saturated $NH_4Cl$ at −78° C. The reaction was diluted with ethyl acetate, washed with brine, dried by $Na_2SO_4$, and concentrated to give a residue. The residue was purified by silica gel column chromatography (15% ethyl acetate in petroleum ether) to give P16-3 as a white solid (920 mg, 46%).

Step 3: Compound P16-4

Compound P16-3 (900 mg, 1.54 mmol) was dissolved in anhydrous toluene (10 mL) under argon and cooled to −78° C. in an cooling bath. Diethylaminosulfur trifluoride (DAST) (1.5 g, 9.0 mmol) was added dropwise, and the cooling bath was removed. Stirring was continued for 1.5 hours. The mixture was diluted with ethyl acetate and poured into saturated $NaHCO_3$. The organic layer was separated, washed with brine, dried by $Na_2SO_4$, and concentrated to give a residue. The residue was purified by silica gel chromatography (20% ethyl acetate in petroleum ether) to give P16-4 as a white solid (720 mg, 79%).

Step 4: Compound P16-5

A mixture of P16-4 (700 mg, 1.0 mmol) and $NH_4F$ (800 mg, 21.6 mmol) in methanol (10 mL) was refluxed for 2 hours. After cooling to room temperature, the mixture was concentrated to dryness. The resulting residue was purified by silica gel column chromatography (5−~8% MeOH in DCM) to give P16-5 as a white solid (240 mg, 58%). $^1$H NMR (DMSO-d6, 400 MHz) δ 9.55 (bs, 2H), 7.62 (s, 1H), 5.82 (d, J=7.6 Hz, 1H), 5.00 (s, 1H), 4.94 (s, 1H), 4.06-4.12 (m, 1H), 3.82 (d, J=5.2 Hz, 1H), 3.72-3.75 (m, 1H), 3.66-3.68 (m, 1H), 3.51-3.55 (m, 1H). ESI-TOF-MS: m/z 293 [M+Na]$^+$.

Step 5: Compound 16a

Compound P16-5 (150 mg, 0.56 mmol) was suspended in 2 mL of dry MeCN, and NMI (1 mL) and (2S)-isopropyl 2-((chloro(phenoxy)phosphorothioyl)amino)propanoate (536 mg, 1.68 mmol) were added. The reaction mixture was stirred for 12 hours. The solvent was evaporated, and the resulting residue was purified by HPLC (MeCN and 0.1% HCOOH in water) to give compound 16a as a white solid (a mixture of 2 P-isomers, 82 mg, 26%). $^1$H NMR (MeOD, 400 MHz) δ 7.70, 7.62 (2d, J=8.0 Hz, 1H), 7.17-7.36 (m, 5H), 6.25, 6.22 (2d, J=18.0 Hz, 1H), 5.65, 5.57 (2d, J=8.0 Hz, 1H), 4.94-4.99 (m, 1H), 4.49-4.56 (m, 1H), 4.22-4.41 (m, 2H), 4.01-4.17 (m, 2H), 3.54, 3.52 (2d, J=5.2 Hz, 1H), 1.36, 1.33 (2d, J=6.8 Hz, 3H), 1.23, 1.22 (2d, J=6.4 Hz, 6H). $^{31}$P NMR (CD$_3$OD, 162 MHz) δ 68.51, 68.43. ESI-LCMS: m/z 578.0 [M+Na]$^+$.

Example 9

Compound 18a

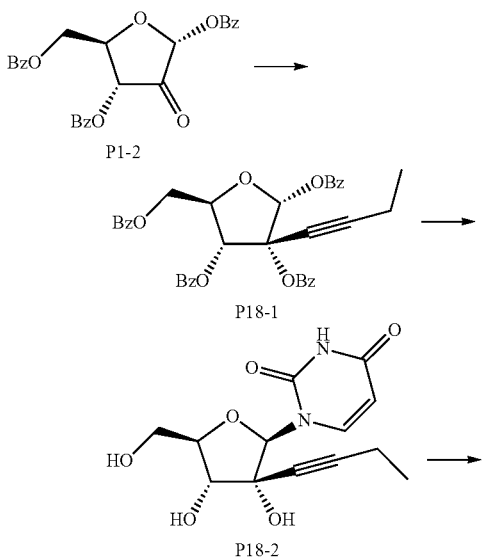

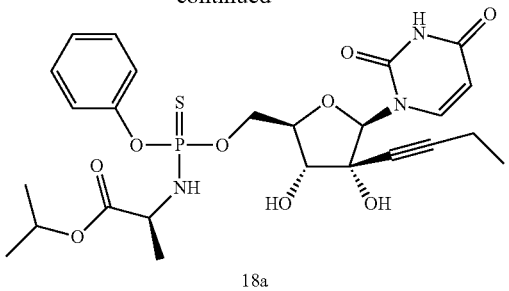

18a

Step 1: Compound P18-1

To a stirred solution of but-1-yne (2.9 g, 0.35 mol) in anhydrous THF (40 mL) was added n-BuLi (20 mL, 0.05 mol) dropwise at −78° C. The reaction mixture was stirred for 30 minutes at −78° C., and then allowed to warm to room temperature. A solution of P1-2 (5.0 g, 0.01 mol) in THF was added dropwise at −78° C. The reaction mixture was stirred for 1 hour at −78° C., and then quenched by careful addition of aqueous saturated NH$_4$Cl. The mixture was warmed to room temperature. The mixture was diluted with ethyl acetate, washed with saturated brine, dried by NaSO$_4$, and concentrated to dryness. The resulting residue was purified by column chromatography to provide a crude product. The crude product was dissolved in anhydrous DCM (50 mL), followed by addition of DMAP (2.5 g, 19.4 mmol), benzoyl chloride (4.0 g, 29.2 mmol) and Et$_3$N (3.0 g, 29.2 mmol). The reaction was stirred at room temperature for 12 hours. The reaction mixture was diluted with DCM (50 mL), and washed with saturated aqueous NaHCO$_3$ (50 mL). The combined aqueous phase was extracted with DCM (100 mL). The combined organic phase was dried with Na$_2$SO$_4$, filtered, and evaporated to dryness under reduced pressure to give a yellow oil. The oil was purified by column chromatography (5% ethyl acetate in petroleum ether) to give P18-1 (3.8 g, yield: 40%).

Step 2: Compound P18-2

To a suspension of uracil (1.9 g, 16 mmol) in 10 mL of distilled acetonitrile was added N,O-bis(trimethylsilyl)acetamide (6.9 g, 33 mmol). The resultant solution was refluxed for 30 minutes. The solution was then cooled to ambient temperature. A solution of P18-1 (3.5 g, 5.6 mmol) in 10 mL of acetonitrile was added, followed by addition of SnCl$_4$ (8.0 g, 33 mmol). The reaction mixture was refluxed overnight. The reaction mixture was cooled to room temperature, diluted with 100 mL of ethyl acetate, and washed with saturated NaHCO$_3$ and brine. The organic layer was dried with Na$_2$SO$_4$, filtered, and concentrated. The resulting residue was purified by silica gel column chromatography (ethyl acetate/hexanes 4:1) to afford the protected nucleoside intermediate (2.6 g, 80%) as a white solid. The intermediate was dissolved in methanolic ammonia (50 mL, saturated). The mixture was stirred at room temperature for 14 hours. The solvent was removed, and the resulting residue was purified by column chromatography (DCM/MeOH=30:1 to 10:1) to give P18-2 as a white solid (850 mg, 67%). $^1$H NMR (CD$_3$OD, 400 MHz) δ 8.03 (d, J=8.0 Hz, 1H), 6.01 (s, 1H), 5.68 (d, J=8.0 Hz, 1H), 4.10 (d, J=8.8 Hz, 1H), 3.47 (dd, J$_1$=2.4 Hz, J$_2$=12.4 Hz, 1H), 3.88 (ddd, J$_1$=J$_2$=2.8 Hz, J$_3$=8.8 Hz, 1H), 3.75 (dd, J$_1$=2.8 Hz, J$_2$=12.8 Hz, 1H), 2.14 (q, J=7.6 Hz, 2H), 1.02 (t, J=7.6 Hz, 3H); ESI-TOF-MS: m/z 319 [M+Na]$^+$.

Step 3: Compound 18a

Compound P18-2 (150 mg, 0.5 mmol) was suspended in 1.5 mL of dry MeCN. NMI (0.5 mL) and (2S)-isopropyl 2-((chloro(phenoxy)phosphorothioyl)amino)propanoate (478 mg, 1.5 mmol) were added. The reaction mixture was stirred for 12 hours. The solvents were evaporated, and the resulting residue was purified by RP HPLC (MeCN and 0.1% HCOOH in water) to give compound 18a (a mixture of two β isomers, 78 mg, 27%). $^1$H NMR (CD$_3$OD, 400 MHz) δ 7.77, 7.72 (2d, J=8.0 Hz, 1H), 7.15-7.36 (m, 5H), 6.04, 6.02 (2s, 1H), 5.58, 5.57 (2d, J=8.0 Hz, 1H), 4.95-5.01 (m, 1H), 4.45-4.51 (m, 1H), 4.27-4.39 (m, 1H), 4.06-4.12 (m, 3H), 2.10-2.18 (m, 2H), 1.36, 1.32 (2d, J=7.6 Hz, 3H), 1.20-1.26 (m, 6H), 0.99-1.04 (m, 3H); $^{31}$P NMR (CD$_3$OD, 162 MHz) δ 68.45, 68.22; ESI-LCMS: m/z 604 [M+Na]$^+$, 582 [M+H]$^+$.

Example 10

Compound 20a

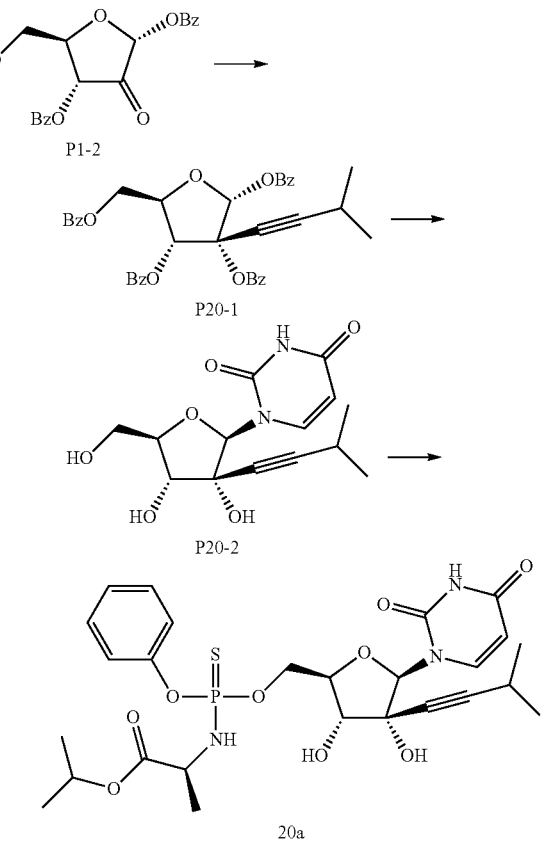

Step 1: Compound P20-1

To a solution of 3-methyl-1-butyne (3.7 g, 0.05 mol) in anhydrous THF (40 mL) was added n-BuLi (13 mL, 0.03 mol) dropwise at −78° C. The reaction mixture was stirred for 30 minutes at −78° C. A solution of P1-2 (4.8 g, 0.01 mol) in THF was added dropwise at −78° C. The reaction mixture was stirred for 1 hour at −78° C. and then quenched by addition of aqueous NH₄Cl at −78° C. The mixture was warmed to room temperature. The mixture was diluted with ethyl acetate, washed with saturated brine, dried by NaSO₄, and concentrated to dryness. The resulting residue was purified via silica gel column chromatography to give a crude product. The crude product was dissolved in anhydrous DCM (50 mL), followed by addition of DMAP (2.6 g, 21.6 mmol), benzoyl chloride (4.0 g, 30 mmol) and Et₃N (3.3 g, 32.4 mmol). The reaction mixture was stirred for 12 hours at room temperature. The reaction mixture was diluted with DCM (50 mL), and washed with saturated aqueous NaHCO₃ (50 mL). The combined aqueous phase was extracted with DCM (100 mL). The combined organic phase was dried with Na₂SO₄, filtered, and evaporated to dryness under reduced pressure to give a yellow oil. The oil was purified by column chromatography (5% ethyl acetate in petroleum ether) to give P20-1 (3.1 g, 43%) as white foam.

Step 2: Compound P20-2

To a suspension of uracil (800 mg, 6.5 mmol) in 10 mL of MeCN was added N,O-bis(trimethylsilyl)acetamide (3.0 g, 15 mmol). The mixture was refluxed for 30 minutes, and then cooled to room temperature. A solution of P20-1 (2.5 g, 3.3 mmol) in acetonitrile (10 mL) was added, followed by addition of SnCl₄ (3.5 g, 15 mmol). The reaction mixture was refluxed overnight. The reaction mixture was cooled to room temperature. The reaction mixture was diluted with 100 mL of ethyl acetate, and washed with saturated NaHCO₃ and brine. The organic layer was dried with Na₂SO₄, filtered, and concentrated. The resulting residue, was purified by silica gel column chromatography (ethyl acetate/hexanes 5:1) to afford the protected nucleoside intermediate (1.4 g, 64%) as a white solid. The protected intermediate was treated with methanolic ammonia (saturated) at room temperature for 14 hours. The solvent was removed, and the resulting residue was purified by column chromatography (DCM/MeOH=30:1 to 10:1) to give P20-2 as a white solid (510 mg, 74%). ¹H NMR (DMSO-d6, 400 MHz) δ 11.34 (br s, 1H), 7.92 (d, J=8.0 Hz, 1H), 6.01 (s, 1H), 5.94 (s, 1H), 5.87 (s, 1H), 5.63 (d, J=8.0 Hz, 1H), 5.53 (d, J=7.6 Hz, 1H), 5.18 (t, J=7.2 Hz, 1H), 3.95 (dd, J₁=J₂=8.8 Hz, 1H), 3.73-3.79 (m, 2H), 3.56-3.60 (m, 1H), 2.46 (q, J=7.2 Hz, 1H), 0.98 (t, J=7.2 Hz, 6H); Negative-ESI-TOF-MS: m/z 309 [M−H]⁺.

Step 3: Compound 20a

To a suspension of P20-2 (80 mg, 0.25 mmol) in MeCN (1.5 mL) were added NMI (0.5 mL) and (2S)-isopropyl 2-((chloro(phenoxy)phosphorothioyl)amino)propanoate (308 mg, 0.7 mmol). The reaction mixture was stirred at room temperature for 12 hours. The solvents were evaporated, and the resulting residue was purified by RP HPLC (MeCN and 0.1% HCOOH in water) to provide compound 20a (a mixture of two β isomers, 32 mg, 21%). ¹H NMR (CD₃OD, 400 MHz) δ 7.77, 7.72 (2d, J=8.0 Hz, 1H), 7.15-7.36 (m, 5H), 6.04, 6.01 (2s, 1H), 5.58, 5.57 (2d, J=8.0 Hz, 1H), 4.95-5.01 (m, 1H), 4.45-4.51 (m, 1H), 4.27-4.39 (m, 1H), 4.08-4.12 (m, 3H), 2.47-2.54 (m, 2H), 1.31-1.37 (m, 3H), 1.23, 1.22 (2d, J=6.4 Hz, 6H), 1.04-1.08 (m, 6H); ³¹P NMR (CD₃OD, 162 MHz) δ 68.515, 68.13; ESI-LCMS: m/z 618 [M+Na]⁺.

Example 11

Compound 22a

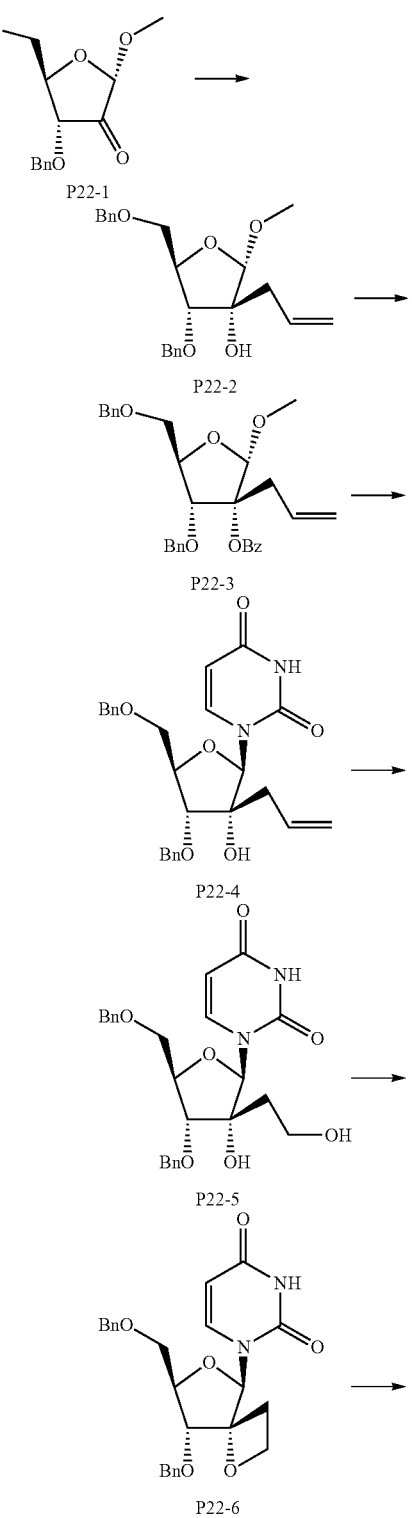

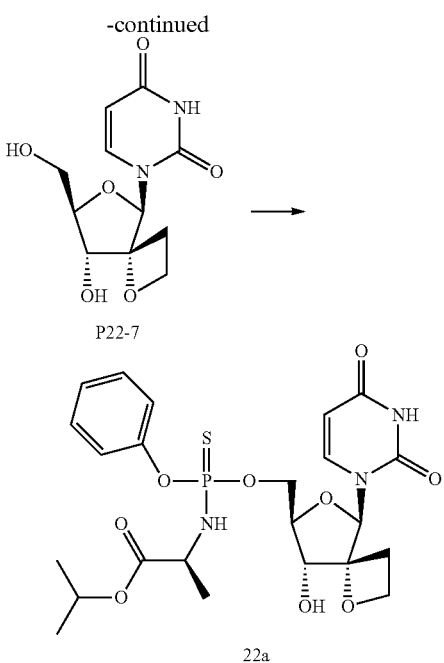

Step 1: Compound P22-2

To a solution of P22-1 (obtained as in Org. Lett., 2007, 9, 3009-3012, which is hereby incorporated by reference for the purpose of synthesizing P22-1) in dry THF (400 mL) under an argon atmosphere at −78° C., allylmagnesium bromide (400 mL, 400 mmol; 1.0 M in diethylether) is added. After stirring the reaction mixture at −78° C. for 4 hours, the reaction mixture is allowed to stir at room temperature for 2 hours. The reaction is carefully quenched with saturated aqueous ammonium chloride. The mixture is extracted with dichloromethane, and the organic layer is washed with brine. The solvent is removed, and the residue is purified by silica gel chromatography, by gradient elution with 15% to 20% ethyl acetate in hexane to give P22-2 as a colorless oil.

Step 2: Compound P22-3

To a solution of P22-2 (26.6 g, 69.2 mmol) in dry dichloromethane (500 mL) at room temperature, DMAP (2.113 g, 17.30 mmol), triethylamine (217 mL, 1557 mmol) and benzoyl chloride (18.05 mL, 156 mmol) are added. After 1 hour, additional benzoyl chloride (6 mL) and DMAP (2.1 g) are added. The mixture is stirred for 5 days. The reaction mixture is then stirred with 1 N HCl and extracted with dichloromethane. The organic layers are combined and washed with saturated aqueous NaHCO$_3$ followed by brine. After drying with MgSO$_4$, filtration and evaporation of the volatiles, the residue is purified by column chromatography (400 g silica) eluting with heptane to 15% ethyl acetate in heptane to give P22-3 as an oil (as a mixture with P22-2). The mixture is purified again with DCM as eluent. The pure fractions are collected and P22-3 is obtained as a colorless oil.

Step 3: Compound P22-4

Bis(trimethylsilyl)acetamide (BSA; 29.2 mL, 118 mmol) is added to a mixture of P22-3 (14.0 g, 23.1 mmol) and uracil (5.99 g, 53.4 mmol) in anhydrous acetonitrile (300 mL). The reaction mixture is refluxed for 1 hour and the solution is allowed to cool to room temperature. Tin chloride (11.55 mL, 99 mmol) is added dropwise at room temperature and the mixture is further stirred for 1 hour. The mixture is then stirred at reflux for 1.5 hour and again cooled to room temperature. Ethyl acetate (250 mL) is added, followed by saturated aqueous NaHCO$_3$ (250 mL) and the mixture is stirred for 15 minutes. After filtration through CELITE™, the organic layer is separated and washed with saturated aqueous NaHCO$_3$ (250 mL). The combined aqueous layer is extracted with ethyl acetate (250 mL) and the combined organic layer is dried (MgSO$_4$), filtered and evaporated to dryness under reduced pressure. The resulting yellow oil is dissolved in methanol and 25% sodium methanolate (25 mL) is added. Stirring is continued overnight. Then 25% sodium methanolate (15 mL) is added and stirring is continued overnight. Acetic acid (30 mL) is added and the solvent is removed. The residue is purified by column chromatography with heptane/ethyl acetate 50:50 to 100% ethyl acetate. Compound P22-4 is obtained as a colorless oil.

Step 4: Compound P22-5

To a stirred solution of P22-4 (7.8 g, 16.79 mmol) in a mixture of THF (10 mL) and H$_2$O (10 mL) is added sodium periodate (11.17 g, 52.2 mmol) followed by osmium(VIII) tetroxide (2 mL, 2.5 w/v % in tert-butanol, 0.168 mmol) and stirring is continued for 2 hours at room temperature. Water (100 mL) is added and extraction is performed with ethyl acetate (2×50 mL). The organic layer is washed with saturated aqueous NaHCO$_3$ (2×30 mL). The combined aqueous layer is extracted with ethyl acetate and the combined organic layer is dried over (Na$_2$SO$_4$), filtered and evaporated to dryness under reduced pressure. The oily residue obtained is dissolved in a mixture of THF (100 mL) and H$_2$O (20 mL) and sodium borohydride (1.361 g, 36.0 mmol) is added. The reaction mixture is stirred overnight at room temperature, whereupon water (100 mL) is added and extraction is performed with ethyl acetate (2×50 mL). The combined organic layer is washed with saturated aqueous NaHCO$_3$, the combined aqueous layer is extracted with ethyl acetate, and the combined organic layer is dried over (Na$_2$SO$_4$), filtered and evaporated to dryness under reduced pressure. The oily residue obtained is purified by column chromatography (0-10% (v/v) methanol in DCM then 10% isocratic) affording P22-5 as a white foam.

Step 5: Compound P22-6

Methanesulfonyl chloride (0.800 mL, 10.34 mmol) is added to P22-5 (4.32 g, 9.22 mmol) in dry pyridine (100 mL). After 1 hour and 15 minutes, 0.1 equivalents more methanesulfonyl chloride is added and the mixture is further stirred at room temperature for 45 minutes. A small amount of methanol is added and the mixture is evaporated to dryness. The residue is dissolved in ethyl acetate (100 mL) and washed with saturated NaHCO$_3$ (2×50 mL). The combined aqueous layer is extracted with ethyl acetate. The combined organic layer is then dried over Na$_2$SO$_4$ and concentrated in vacuo. The obtained residue is dissolved in dry THF and 95% NaH (932 mg, 36.9 mmol) is added at once at room temperature. After stirring for 2 hours at room temperature, the reaction mixture is poured on a saturated aqueous solution NH$_4$Cl (30 mL) followed by addition of DCM (250 mL). The separated organic layer is washed with saturated aqueous NaHCO$_3$ (2×100 mL) and the combined aqueous layer is extracted with DCM (250 mL). The combined organic layer is dried (Na$_2$SO$_4$), filtered and evaporated to dryness under reduced pressure. The residue obtained is purified by column chromatography eluting first with heptane, then with ethyl acetate to provide P22-6 as a foam.

Step 6: Compound P22-7

A mixture of P22-6 (50 mg, 0.111 mmol) in methanol (1 mL) and Pd(OH)$_2$ (8 mg) is stirred under a hydrogen atmosphere at room temperature. After 4 hours, more Pd(OH)$_2$ (30 mg) and methanol (1 mL) are added. The mixture is stirred vigorously under H$_2$-atmosphere overnight. The catalyst is removed by filtration over decalite, and the solvent is removed by evaporation. The resulting residue is purified by silica gel chromatography eluted with 10% methanol in ethyl acetate to give P22-7 as a white powder.

Step 7: Compound 22a

To a suspension of P22-7 (0.25 mmol) in MeCN are added NMI (0.5 mL) and (2S)-isopropyl 2-((chloro(phenoxy)phosphorothioyl)amino)propanoate (0.7 mmol). The reaction mixture is stirred at room temperature for 12 hours. The solvents are evaporated, and the resulting residue is purified by RP HPLC to provide compound 22a.

Example 12

Compound 6a

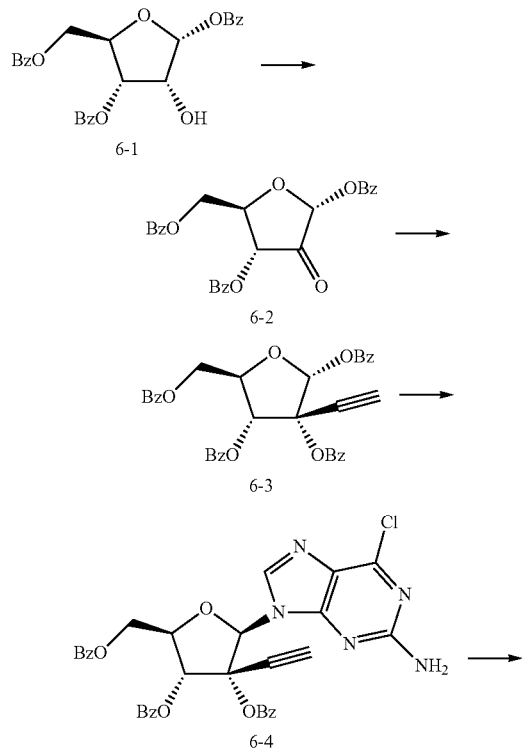

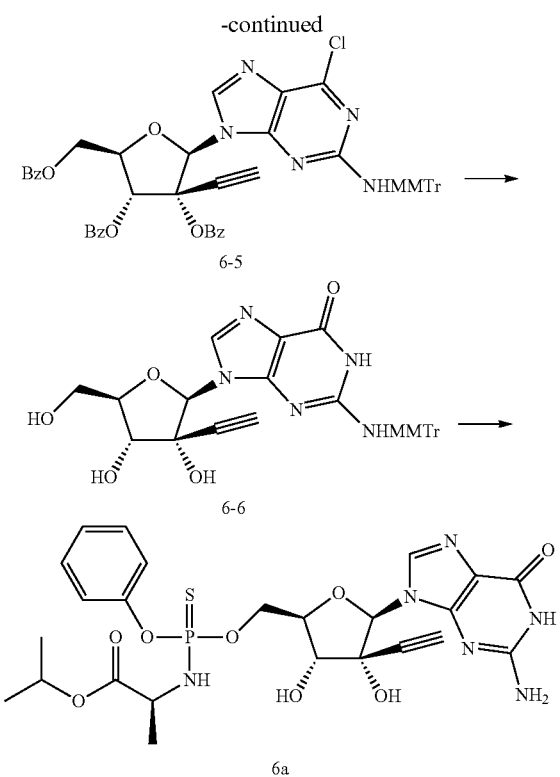

Step 1: Compound 6-2

To a solution of Dess-Martin periodinane (12.0 g, 28.1 mmol) in 500 mL of CH$_2$Cl$_2$ was added 6-1 (8.0 g, 17.3 mmol) at 0° C. The mixture was warmed to R.T. and stirred for 12 h. The solvent was removed in vacuo. The residue was triturated with TBME (150 mL) and filtered through a pad of MgSO$_4$. The filtrate was stirred with an equal volume of Na$_2$S$_2$O$_3$.5H$_2$O in 50 mL of saturated NaHCO$_3$ until the organic layer became clear (10 min). The organic layer was separated, washed with brine, dried over MgSO$_4$ and concentrated to give 6-2 (7.3 g, 91%) as a white solid.

Step 2: Compound 6-3

To a solution of 6-2 (13.0 g, 28.3 mmol) in anhydrous THF (150 mL) was added ethynylmagnesium bromide (130 mL, 65 mmol) dropwise over 20 min at −78° C. The mixture stirred for 2 h at −78° C. The ice-acetone cooling bath was removed and saturated NH$_4$Cl (200 mL) was added with stirring. After warming to R.T., the mixture was filtered through celite and washed by saturated aq. NH$_4$Cl (100 mL). The combined organic phase was dried with Na$_2$SO$_4$, filtered and concentrated to give a crude product. This reaction starting with 6-2 was repeated 2 more times to give 38.0 g of the crude product. The crude product was dissolved in anhydrous CH$_2$Cl$_2$ (200 mL), whereupon DMAP (19.1 g, 156.4 mmol), benzoyl chloride (23.5 g, 156.4 mmol) and Et$_3$N (23.7 g, 234.6 mmol) were added. After stirring for 12 h at R.T., the mixture was diluted with CH$_2$Cl$_2$ (100 mL) and then washed with saturated aq. NaHCO$_3$ (100 mL). The combined aqueous phase was extracted with DCM (100 mL). The combined organic phase was dried with Na$_2$SO$_4$, filtered and evaporated to dryness under reduced pressure to give a yellow oil, which was purified by column chromatography (5% EA in PE) to give 6-3 (18.0 g, 39%) as a white solid.

Step 3: Compound 6-4

To a stirred suspension of 6-3 (2.0 g, 3.38 mmol) and 6-chloro-9H-purin-2-amine (1.2 g, 7.10 mmol) in anhydrous MeCN (20 mL) was added DBU (3.1 g, 20.39 mmol) at 0° C. The mixture was stirred at 0° C. for 5 mins and then TMSOTf (6.0 g, 24.0 mmol) was added dropwise at 0° C. After addition, the mixture was stirred at 0° C. for 20 mins until a clear solution was achieved. The mixture was heated to 70° C. and stirred for 3 h. The reaction was monitored by LCMS. The reaction was cooled R.T. and diluted with EA. The solution was washed with saturated NaHCO$_3$ and brine in sequence. The organic layer was dried over Na$_2$SO$_4$ and concentrated. The residue was purified on a silica gel column (20-25% EA in PE) to give 6-4 (1.1 g, 57%) as light yellow foam.

Step 4: Compound 6-5

To a mixture of 6-4 (1.0 g, 1.5 mmol), AgNO$_3$ (765 mg, 4.5 mmol) and collidine (10 mL) in anhydrous pyridine (20 mL) was added MMTrCl (1.5 g, 4.5 mmol) in small portions under N$_2$. The mixture was stirred at R.T. for 12 h under N$_2$. The reaction was allowed to continue until TLC showed the reaction was completed. The mixture was filtered, and the solvent was removed under vacuum. The residue was diluted with EA, and washed with water and brine. The organic layer was separated, dried over anhydrous Na$_2$SO$_4$ and concentrated to dryness. The residue was purified on a silica gel column (5-10% EA in PE) to give 6-5 (1.2 g, 86%) as a white solid.

Step 5: Compound 6-6

To a solution of 3-Hydroxy-propionitrile (3.7 g, 52 mmol) in THF (50 mL) was added NaH (624 mg, 26 mmol) at 0° C. The mixture was stirred at R.T. for 15 mins. To the mixture was added 6-5 (1.2 g, 1.3 mmol). The mixture was then stirred at R.T. for 12 h. The mixture was concentrated to give a residue which was purified by column chromatography (1-2% MeOH in DCM) to give 6-6 (480 mg, 48%). 1H NMR (Methanol-d$_4$, 400 MHz) δ 8.04 (s, 1H), 7.18-7.34 (m, 12H), 6.84 (d, J=8.8 Hz, 2H), 5.35 (s, 1H), 4.32 (d, J=8.8 Hz, 1H), 3.82-3.89 (m, 2H), 3.76 (s, 3H), 3.67-3.71 (m, 1H), 2.61 (s, 1H).

Step 6: Compound 6a

To a mixture of 6-6 (136 mg, 0.22 mmol) and NMI (0.6 mL) in anhydrous MeCN (2 mL) was added thiophosphochloridate (224 mg, 0.70 mmol) at 0° C. The mixture was stirred at R.T. for 12 h. The mixture was then concentrated, and the residue was purified by column chromatography to give a crude protected intermediate (100 mg, 60.9%). The crude protected intermediate was dissolved in a 80% HCOOH aqueous solution (10 mL), and the mixture was stirred at R.T. for 12 h. The solvent was removed under vacuum, and the residue was purified on a silica gel column (2-5% MeOH in DCM) to give 6a (31 mg, 43.6%) as a white solid. $^1$H NMR (DMSO-d$_6$, 400 MHz) δ 8.37 (s, 1H), 7.80 (d, J=3.6 Hz, 2H), 7.16-7.37 (m, 5H), 6.38-6.73 (m, 4H), 5.84-5.99 (m, 2H), 4.79-4.86 (m, 1H), 3.93-4.38 (m, 5H), 3.32 (s, 1H), 1.10-1.27 (m, 9H). $^{31}$P NMR (DMSO-d$_6$, 162 MHz) δ 68.20, 67.68. ESI-LCMS: m/z 593.0 [M+H]$^+$.

Example 13

Compound 4a

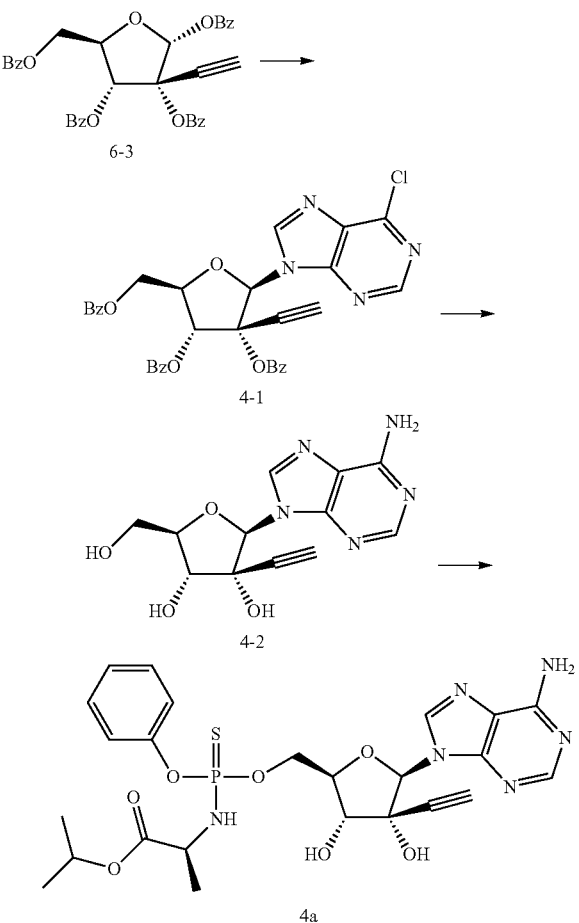

Step 1: Compound 4-1

To a stirred suspension of 6-3 (2.0 g, 3.38 mmol) and 6-chloro-9H-purine (924 mg, 6.0 mmol) in anhydrous MeCN (20 mL) was added DBU (3.1 g, 20.2 mmol) at 0° C. The mixture was stirred at 0° C. for 5 minutes and then TMSOTf (6.0 g, 24.0 mmol) was added dropwise at 0° C. After addition, the mixture was stirred at 0° C. for 20 mins until a clear solution was achieved. The mixture was heated to 70° C. and stirred for 3 h. The reaction was monitored by LCMS. The reaction was cooled to R.T. and diluted with EA. The solution was washed with saturated NaHCO$_3$ and brine in sequence. The organic layer was dried over Na$_2$SO$_4$ and then concentrated. The residue was purified on a silica gel column (10-20% EA in PE) to give 4-1 (1.1 g, 52%) as a light yellow foam.

Step 2: Compound 4-2

To a solution of 4-1 (1.1 g, 1.7 mmol) in 1,4-dioxane (10 mL) was added aqueous ammonia (30 mL) at R.T. The mixture was stirred at 100° C. in a sealed vessel for 10 h. The mixture was cooled to R.T., and the solvent was removed under reduced pressure. The residue was purified on a silica gel column (5-10% MeOH in DCM) to give 4-2 (256 mg, 80%) as a white solid. $^1$H NMR (DMSO-d$_6$, 400 MHz) δ 8.38 (s, 1H), 8.13 (s, 1H), 7.26 (s, 2H), 6.37 (s, 1H), 6.04 (s, 1H), 5.76 (d, J=7.2 Hz, 1H), 5.27 (t, J=5.2 Hz, 1H), 4.43-4.47 (m, 1H), 3.87-3.91 (m, 1H), 3.77-3.82 (m, 1H), 3.64-3.70 (m, 1H), 3.13 (s, 1H). ESI-MS: m/z 292.1 [M+H]$^+$.

Step 3: Compound 4a

To a solution of 4-2 (150 mg, 0.52 mmol) and NMI (0.6 mL) in anhydrous MeCN (2 mL) was added thiophosphochloridate (496 mg, 1.54 mmol) at 0° C. The mixture was stirred at R.T. overnight. The solvent was then evaporated, and the residue was purified by HPLC separation (0.1% HCOOH in water and MeCN) to give 4a (68 mg, 23%). $^1$H NMR (DMSO-d$_6$, 400 MHz) δ 8.38 (s, 1H), 8.21 (s, 1H), 8.14 (s, 1H), 7.16-7.37 (m, 5H), 6.49-6.66 (m, 2H), 6.07-6.09 (m, 1H), 5.97-6.03 (m, 1H), 4.71-4.86 (m, 1H), 4.59-4.60 (m, 1H), 4.21-4.38 (m, 1H), 4.10-4.17 (m, 1H), 3.90-3.93 (m, 1H), 3.21 (s, 1H), 1.04-1.24 (m, 9H). $^{31}$P NMR (DMSO-d$_6$, 162 MHz) δ 67.98, 67.95. ESI-MS: m/z 576.9 [M+H]$^+$.

Example 14

Compound 17a

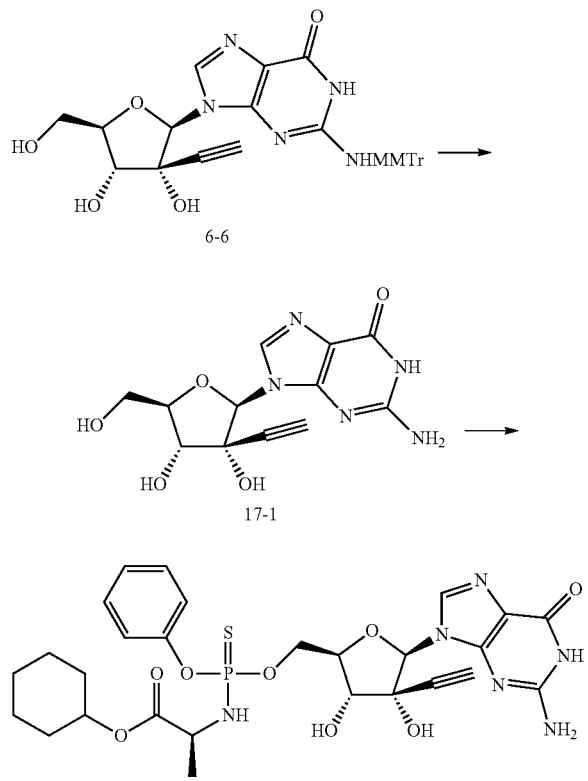

Step 1: Compound 17-1-6-6

(500 mg, 0.86 mmol) was dissolved in a 80% HCOOH solution (20 mL). The mixture was stirred at R.T. for 12 h. The solvent was removed under vacuum, and the residue was purified on a silica gel column (2-5% MeOH in DCM) to give as 17-1 (200 mg, 75.4%) as a white solid.

Step 2: Compound 17a

To a solution of 17-1 (350 mg, 1.14 mmol) and NMI (0.6 mL) in anhydrous CH$_3$CN (2 mL) was added thiophosphochloridate (649 mg, 1.8 mmol) at 0° C. The mixture was stirred at R.T. for 12 h. The solvent was then evaporated, and the residue was purified by HPLC separation (0.1% HCOOH in water and MeCN) to give 17a (90 mg, 24%) as a white solid. $^1$H NMR (Methanol-d$_4$, 400 MHz) δ 7.90 (d, J=2.4 Hz, 1H), 7.24-7.33 (m, 4H), 7.13-7.17 (m, 1H), 6.01 (d, J=12.8 Hz, 1H), 4.61-4.71 (m, 1H), 4.34-4.51 (m, 3H), 4.03-4.21 (m, 2H), 2.80 (d, J=3.2 Hz, 1H), 1.67-1.79 (m, 4H), 1.23-1.50 (m, 9H). $^{31}$P NMR (Methanol-d$_4$, 162 MHz) δ 68.41, 68.36. ESI-MS: m/z 633.1 [M+H]$^+$.

Example 15

HCV Replicon Assay

Cells

Huh-7 cells containing the self-replicating, subgenomic HCV replicon with a stable luciferase (LUC) reporter were cultured in Dulbecco's modified Eagle's medium (DMEM) containing 2 mM L-glutamine and supplemented with 10% heat-inactivated fetal bovine serum (FBS), 1% penicillin-streptomyocin, 1% nonessential amino acids, and 0.5 mg/mL G418.

Determination of Anti-HCV Activity

Determination of 50% inhibitory concentration (EC$_{50}$) of compounds in HCV replicon cells were performed by the following procedure. On the first day, 5,000 HCV replicon cells were plated per well in a 96-well plate. On the following day, test compounds were solubilized in 100% DMSO to 100× the desired final testing concentration. Each compound was then serially diluted (1:3) up to 9 different concentrations. Compounds in 100% DMSO are reduced to 10% DMSO by diluting 1:10 in cell culture media. The compounds were diluted to 10% DMSO with cell culture media, which were used to dose the HCV replicon cells in 96-well format. The final DMSO concentration was 1%. The HCV replicon cells were incubated at 37° C. for 72 hours. At 72 hours, cells were processed when the cells are still subconfluent. Compounds that reduce the LUC signal are determined by Bright-Glo Luciferase Assay (Promega, Madison, Wis.). % Inhibition was determined for each compound concentration in relation to the control cells (untreated HCV replicon) to calculate the EC$_{50}$.

Compounds of Formula (I) are active in the replicon assay. The antiviral activity of exemplary compounds is shown in Table 3, where 'A' indicates an EC$_{50}$<1 μM, 'B' indicates an EC$_{50}$≥1 μM and <10 μM, and 'C' indicates an EC$_{50}$≥10 μM and <100 μM.

TABLE 3

| # | Structure | EC$_{50}$ |
|---|---|---|
| 1a | (phenyl-O)(S=)P(NH-CH(CH$_3$)-C(=O)-O-iPr)-O-CH$_2$-[ribose with 2'-OH, 3'-OH, 3'-C≡CH]-uracil | A |
| 2a | (phenyl-O)(S=)P(NH-CH(CH$_3$)-C(=O)-O-iPr)-O-CH$_2$-[ribose with 2'-OH, 3'-OH, 3'-CH=CH$_2$]-uracil | B |
| 4a | (phenyl-O)(S=)P(NH-CH(CH$_3$)-C(=O)-O-iPr)-O-CH$_2$-[ribose with 3'-OH, 2'-OH, 2'-C≡CH]-adenine | A |
| 6a | (phenyl-O)(S=)P(NH-CH(CH$_3$)-C(=O)-O-iPr)-O-CH$_2$-[ribose with 3'-OH, 2'-OH, 2'-C≡CH]-guanine | B |
| 7a | (phenyl-O)(S=)P(NH-CH(CH$_2$CH$_2$SCH$_3$)-C(=O)-O-iPr)-O-CH$_2$-[ribose with 2'-OH, 3'-OH, 3'-C≡CH]-uracil | A |

TABLE 3-continued

| # | Structure | EC$_{50}$ |
|---|---|---|
| 8a | (structure) | C |
| 9a | (structure) | B |
| 10a | (structure) | A |
| 11a | (structure) | A |
| 12a | (structure) | A |

TABLE 3-continued

| # | Structure | EC$_{50}$ |
|---|---|---|
| 13a | 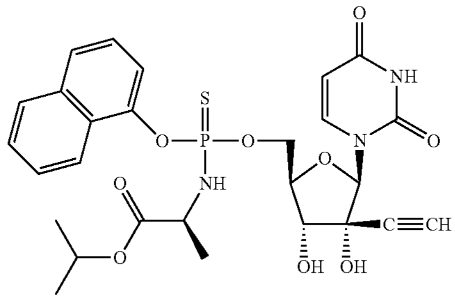 [SMILES: C#C[C@@]1(O)[C@H](O)[C@@H](COP(=S)(N[C@@H](C)C(=O)OC(C)C)Oc2cccc3ccccc23)O[C@H]1n1ccc(=O)[nH]c1=O] | A |
| 14a | 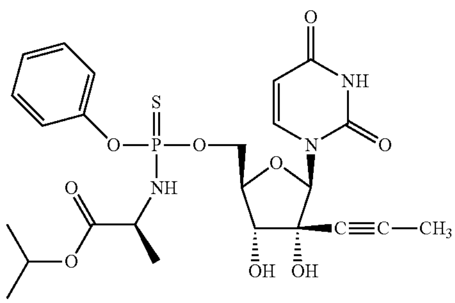 [SMILES: CC#C[C@@]1(O)[C@H](O)[C@@H](COP(=S)(N[C@@H](C)C(=O)OC(C)C)Oc2ccccc2)O[C@H]1n1ccc(=O)[nH]c1=O] | B |
| 15a | 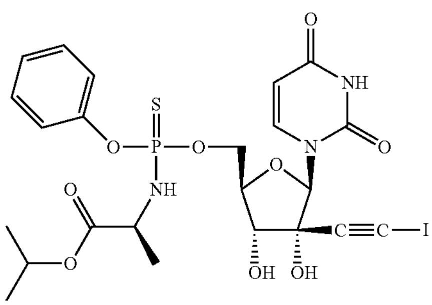 [SMILES: CC(C)OC(=O)[C@H](C)NP(=S)(OC[C@H]1O[C@@H](n2ccc(=O)[nH]c2=O)[C@@](O)(C#CI)[C@@H]1O)Oc1ccccc1] | A |
| 16a | 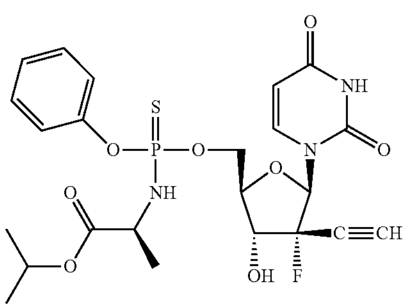 [SMILES: C#C[C@@]1(F)[C@H](O)[C@@H](COP(=S)(N[C@@H](C)C(=O)OC(C)C)Oc2ccccc2)O[C@H]1n1ccc(=O)[nH]c1=O] | B |
| 17a | 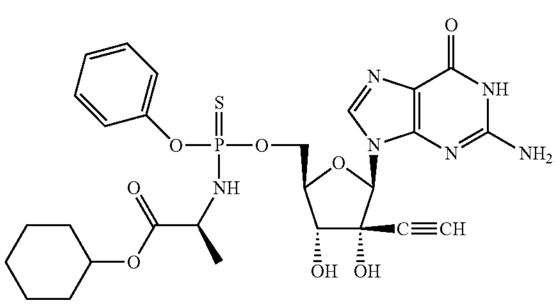 [SMILES: C#C[C@@]1(O)[C@H](O)[C@@H](COP(=S)(N[C@@H](C)C(=O)OC2CCCCC2)Oc2ccccc2)O[C@H]1n1cnc2c(=O)[nH]c(N)nc21] | B |

TABLE 3-continued
| # | Structure | EC$_{50}$ |
|---|---|---|
| 18a | 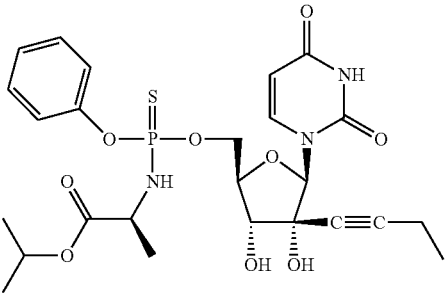 [SMILES: CCC#C[C@@]1(O)[C@H](O)[C@@H](COP(=S)(N[C@@H](C)C(=O)OC(C)C)Oc2ccccc2)O[C@H]1n1ccc(=O)[nH]c1=O] | C |
| 19a | 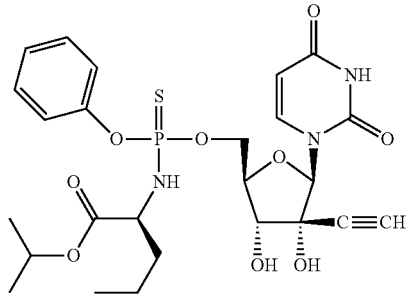 [SMILES: C#C[C@@]1(O)[C@H](O)[C@@H](COP(=S)(N[C@@H](CCC)C(=O)OC(C)C)Oc2ccccc2)O[C@H]1n1ccc(=O)[nH]c1=O] | A |
| 20a | 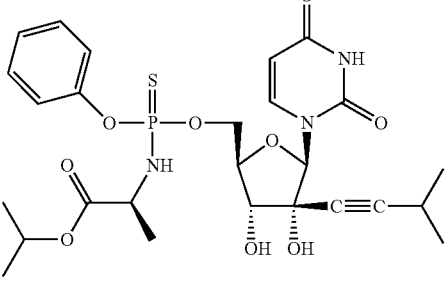 | C |
| 21a | 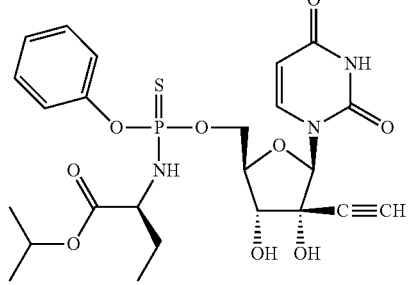 | A |
| 1aa | 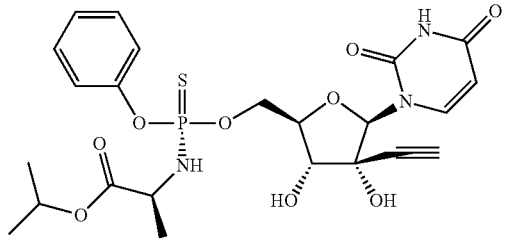 | A |

TABLE 3-continued

| # | Structure | EC$_{50}$ |
|---|---|---|
| 1ab | 1ab | A |

Example 16

Preparation of Nucleoside Thiotriphosphates 1,2,4-Triazol (42 mg, 0.6 mmol) was suspended in 1 mL of anhydrous CH$_3$CN. Triethylamine (0.088 ml, 0.63 mmol) was added and the mixture was vortexed to obtain a clear solution. After addition of PSCl$_3$ (0.01 ml, 0.1 mmol) the mixture was vortexed, followed by standing for 20 minutes, then the mixture was centrifuged. The supernatant was added to a nucleoside of Formula (A) (0.05 mmol) in trimethyl phosphate, and the mixture was kept at ambient temperature for 1 hour. Tris(tetrabutylammonium) hydrogen pyrophosphate (180 mg, 0.2 mmol) was added and the mixture was kept at room temperature for 2 hours. Under cooling with ice, the reaction was quenched with water. The resulting nucleoside 5'-triphosphate (NTP) was isolated as a mixture of diastereomers by IE chromatography on an AKTA Explorer using a HiLoad 16/10 column with Q Sepharose High Performance. Separation was done with a linear gradient of NaCl from 0 to 1N in 50 mM TRIS-buffer (pH 7.5). Fractions containing the NTP were combined, concentrated, and desalted by RP HPLC on a Synergy 4 micron Hydro-RP column (Phenominex). A linear gradient of methanol from 0 to 30% in 50 mM triethylammonium buffer was used for elution over 20 min. with a flow rate of 10 ml/min. Two separated compounds corresponding to the two Pa-diastereomers were collected.

Analytical RP HPLC was conducted using 50 mM triethylammonium acetate buffer at a pH of 7.5 and a linear gradient of acetonitrile from 0% to 25% in 7 min on a Synergy 4 micron Hydro-RP column (Phenominex). The observed retention time for each individual diastereomer is shown in Table 4 below.

TABLE 4

| Structure | | $^{31}$P NMR Pα | $^{31}$P NMR Pβ | $^{31}$P NMR Pγ | MS (M$^-$) | R.T. min |
|---|---|---|---|---|---|---|
| 23a | P(S) | 42.93 | −23.28 | −7.94 | 523.1 | 4.40 |
| 24a | P(R) | 42.69 | −22.93 | −6.22 | 523.3 | 4.67 |

R.T. = retention time

Example 17

NS5B Inhibition Assay

The enzyme activity of NS5B570-Con1 (Delta-21) was measured as an incorporation of tritiated NMP into acid-insoluble RNA products. The complementary IRES (cIRES) RNA sequence was used as a template, corresponding to 377 nucleotides from the 3'-end of HCV (−) strand RNA of the Con-1 strain, with a base content of 21% Ade, 23% Ura, 28% Cyt, and 28% Gua. The cIRES RNA was transcribed in vitro using a T7 transcription kit (Ambion, Inc.) and purified using the Qiagen RNeasy maxi kit. HCV polymerase reactions contained 50 nM NS5B570-Con1, 50 nM cIRES RNA, about 0.5 µCi tritiated NTP, 1 µm of competing cold NTP, 20 mM NaCl, 40 mm Tris-HCl (pH 8.0), 4 mm dithiothreitol, and 4 mm $MgCl_2$. Standard reactions were incubated for 2 hours at 37° C., in the presence of increasing concentration of inhibitor. At the end of the reaction, RNA was precipitated with 10% TCA, and acid-insoluble RNA products were filtered on a size exclusion 96-well plate. After washing of the plate, scintillation liquid was added and radio labeled RNA products were detected according to standard procedures with a Trilux Topcount scintillation counter. The compound concentration at which the enzyme-catalyzed rate was reduced by 50% ($IC_{50}$) was calculated by fitting the data to a non-linear regression (sigmoidal). The $IC_{50}$ values were derived from the mean of several independent experiments. Compounds of Formula (I) showed activity in this assay. A value of 'A' indicates an $IC_{50}$ of <1 µM and a value of 'B' indicates an $IC_{50}$<10 µM. Compound 23a showed A activity and Compound 24a showed B activity.

Example 18

Combination of Compounds

Combination Testing

Two or more test compounds were tested in combination with each other using an HCV genotype 1b HCV replicon harbored in Huh7 cells with a stable luciferase (LUC) reporter. Cells were cultured under standard conditions in Dulbecco's modified Eagle's medium (DMEM; Mediatech Inc, Herndon, Va.) containing 10% heat-inactivated fetal bovine serum (FBS; Mediatech Inc, Herndon, Va.) 2 mM L-glutamine, and nonessential amino acids (JRH Biosciences). HCV replicon cells were plated in a 96-well plate at a density of $10^4$ cells per well in DMEM with 10% FBS. On the following day, the culture medium was replaced with DMEM containing either no compound as a control, the test compounds serially diluted in the presence of 2% FBS and 0.5% DMSO, or a combination of compound 1a with one or more test compounds serially diluted in the presence of 2% FBS and 0.5% DMSO. The cells were incubated with no compound as a control, with the test compounds, or the combination of compounds for 72 hours. The direct effects of the combination of the test compounds were examined using a luciferase (LUC) based reporter as determined by the Bright-Glo Luciferase Assay (Promega, Madison, Wis.). Dose-response curves were determined for individual compounds and fixed ratio combinations of two or more test compounds.

The effects of test compound combinations were evaluated by two separate methods. In the Loewe additivity model, the experimental replicon data was analyzed by using CalcuSyn (Biosoft, Ferguson, Mo.), a computer program based on the method of Chou and Talalay. The program uses the experimental data to calculate a combination index (CI) value for each experimental combination tested. A CI value of <1 indicates a synergistic effect, a CI value of 1 indicates an additive effect, and a CI value of >1 indicates an antagonistic effect.

The second method utilized for evaluating combination effects used a program called MacSynergy II. MacSynergy II software was kindly provided by Dr. M. Prichard (University of Michigan). The Prichard Model allows for a three-dimensional examination of drug interactions and a calculation of the synergy volume (units: $\mu M^2\%$) generated from running the replicon assay using a checkerboard combination of two or more inhibitors. The volumes of synergy (positive volumes) or antagonism (negative volumes) represent the relative quantity of synergism or antagonism per change in the concentrations of the two drugs. Synergy and antagonism volumes are defined based on the Bliss independence model. In this model, synergy volumes of less than −25 indicate antagonistic interactions, volumes in the −25-25 range indicate additive behavior, volumes in the 25-100 range indicate synergistic behavior and volumes>100 indicate strong synergistic behavior. Determination of in vitro additive, synergistic and strongly synergistic behavior for combinations of compounds can be of utility in predicting therapeutic benefits for administering the combinations of compounds in vivo to infected patients.

The CI and synergy volume results for the combinations are provided in Table 5.

TABLE 5

| Combination Compound: | CI at $EC_{50}$ | Synergy Volume ($\mu M^2\%$) |
|---|---|---|
| 6002 | 0.69 | 29 |
| 3003 | 0.73 | 32 |
| 1001 | 0.75 | 104 |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming within the true scope and spirit of the invention.

What is claimed is:

1. A compound of Formula (I) or a pharmaceutically acceptable salt thereof:

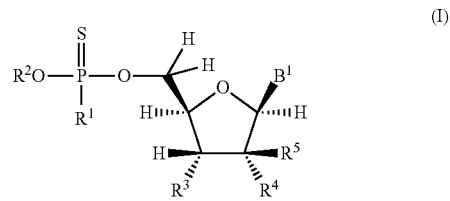

wherein:
$B^1$ is an optionally substituted heterocyclic base or an optionally substituted heterocyclic base with a protected amino group;
$R^1$ is selected from the group consisting of $O^−$, OH, an optionally substituted N-linked amino acid and an optionally substituted N-linked amino acid ester derivative;

R² is absent or selected from the group consisting of hydrogen, an optionally substituted aryl, an optionally substituted heteroaryl, an optionally substituted heterocyclyl and

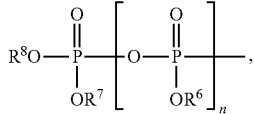

wherein R⁶, R⁷ and R⁸ are independently absent or hydrogen, and n is 0 or 1;
provided that when R¹ is O⁻ or OH, then R² is absent, hydrogen or

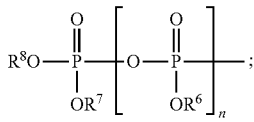

R³ is selected from the group consisting of hydrogen, halogen, —OR⁹ and —OC(=O)R¹⁰;
R⁴ is selected from the group consisting of halogen, —OR¹¹ and —OC(=O)R¹²;
or R³ and R⁴ are both oxygen atoms and linked together by a carbonyl group;
R⁵ is selected from the group consisting of an optionally substituted $C_{2-6}$ alkenyl, an optionally substituted $C_{2-6}$ alkynyl and an optionally substituted $C_{3-6}$ cycloalkyl;
or R⁴ and R⁵ together form —($C_{1-6}$ alkyl)-O— or —O—($C_{1-6}$ alkyl)—;
R⁹ and R¹¹ are independently hydrogen or an optionally substituted $C_{1-6}$ alkyl; and
R¹⁰ and R¹² are independently an optionally substituted $C_{1-6}$ alkyl or an optionally substituted $C_{3-6}$ cycloalkyl.

2. The compound of claim 1, wherein R⁵ is an optionally substituted $C_{2-6}$ alkenyl.

3. The compound of claim 1, wherein R⁵ is an optionally substituted $C_{2-6}$ alkynyl.

4. The compound of claim 1, wherein R⁵ is an optionally substituted $C_{3-6}$ cycloalkyl.

5. The compound of claim 1, wherein R⁴ is halogen.

6. The compound of claim 1, wherein R⁴ is —OR¹¹.

7. The compound of claim 1, wherein R⁴ is —OC(=O)R¹².

8. The compound of claim 1, wherein R⁴ and R⁵ together form —($C_{1-6}$ alkyl)-O— or —O—($C_{1-6}$ alkyl)-.

9. The compound of claim 1, wherein R³ is hydrogen.

10. The compound of claim 1, wherein R³ is halogen.

11. The compound of claim 1, wherein R³ is —OR⁹.

12. The compound of claim 1, wherein R³ is —OC(=O)R¹⁰.

13. The compound of claim 1, wherein R³ and R⁴ are both oxygen atoms and linked together by a carbonyl group.

14. The compound of claim 1, wherein R¹ is O⁻ or OH; and R² is absent or hydrogen.

15. The compound of claim 1, wherein R¹ is an optionally substituted N-linked α-amino acid or an optionally substituted N-linked α-amino acid ester derivative; and R² is an optionally substituted aryl.

16. The compound of claim 1, wherein R¹ is an optionally substituted N-linked α-amino acid or an optionally substituted N-linked α-amino acid ester derivative; and R² is an optionally substituted heteroaryl or an optionally substituted heterocyclyl.

17. The compound of claim 1, wherein R² is

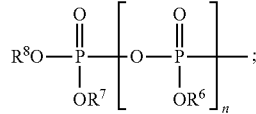

n is 0 or 1; R¹ is O⁻ or OH; and R⁶, R⁷ and R⁸ are independently absent or hydrogen.

18. The compound of claim 1, wherein B¹ is selected from the group consisting of:

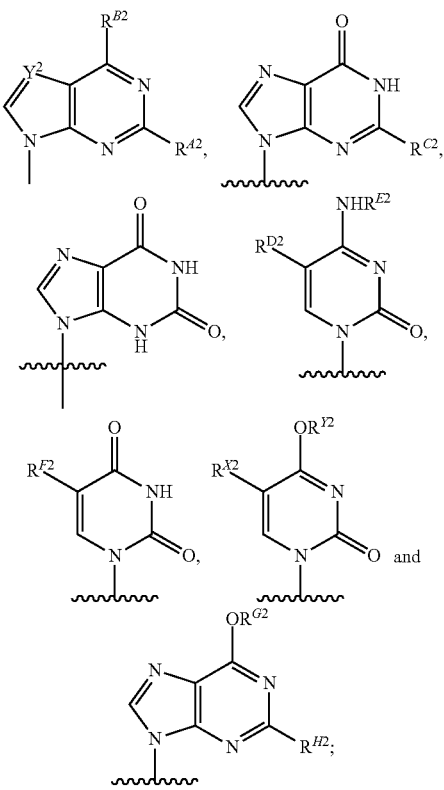

wherein:
R^{A2} is selected from the group consisting of hydrogen, halogen and NHR^{J2}, wherein R^{J2} is selected from the group consisting of hydrogen, —C(=O)R^{K2} and —C(=O)OR^{L2};

R^{B2} is halogen or NHR^{W2}, wherein R^{W2} is selected from the group consisting of hydrogen, an optionally substituted $C_{1-6}$ alkyl, an optionally substituted $C_{2-6}$ alkenyl, an optionally substituted $C_{3-8}$ cycloalkyl, —C(=O)R^{M2} and —C(=O)OR^{N2};

R^{C2} is hydrogen or NHR^{O2}, wherein R^{O2} is selected from the group consisting of hydrogen, —C(=O)R^{P2} and —C(=O)OR^{Q2};

R^{D2} is selected from the group consisting of hydrogen, halogen, an optionally substituted $C_{1-6}$ alkyl, an optionally substituted $C_{2-6}$ alkenyl and an optionally substituted $C_{2-6}$ alkynyl;

$R^{E2}$ is selected from the group consisting of hydrogen, an optionally substituted $C_{1-6}$ alkyl, an optionally substituted $C_{3-8}$ cycloalkyl, —C(═O)$R^{R2}$ and —C(═O)O$R^{S2}$;

$R^{F2}$ and $R^{X2}$ is independently selected from the group consisting of hydrogen, halogen, an optionally substituted $C_{1-6}$ alkyl, an optionally substituted $C_{2-6}$ alkenyl and an optionally substituted $C_{2-6}$ alkynyl;

$Y^2$ is N or $CR^{12}$, wherein $R^{12}$ is selected from the group consisting of hydrogen, halogen, an optionally substituted $C_{1-6}$-alkyl, an optionally substituted $C_{2-6}$-alkenyl and an optionally substituted $C_{2-6}$-alkynyl;

$R^{G2}$ is an optionally substituted $C_{1-6}$ alkyl;

$R^{H2}$ is hydrogen or $NHR^{T2}$, wherein $R^{T2}$ is independently selected from the group consisting of hydrogen, —C(═O)$R^{U2}$ and —C(═O)O$R^{V2}$, $R^{K2}$, $R^{L2}$, $R^{M2}$, $R^{N2}$, $R^{P2}$, $R^{Q2}$ $R^{R2}$, $R^{S2}$, $R^{U2}$ and $R^{V2}$ are independently selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl); and $R^{Y2}$ is an optionally substituted $C_{1-6}$-alkyl or an optionally substituted $C_{3-6}$-cycloalkyl.

19. The compound of claim 1, wherein the compound of Formula (I) is selected from the group consisting of:

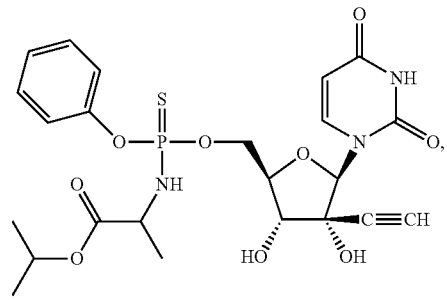

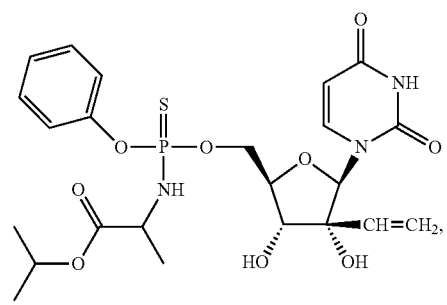

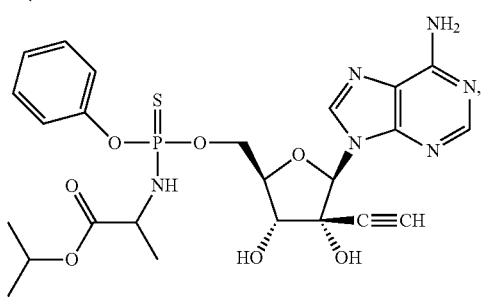

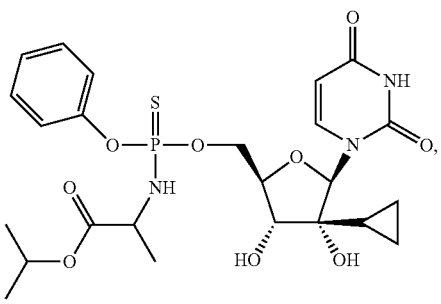

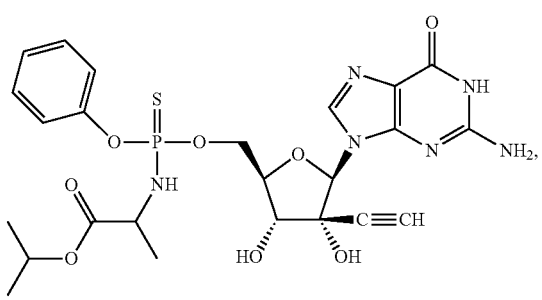

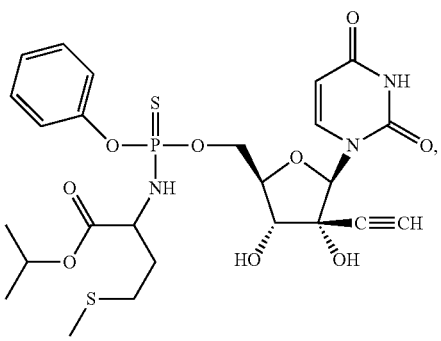

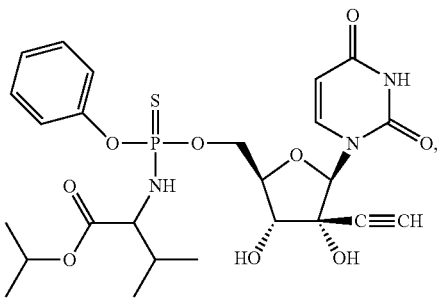

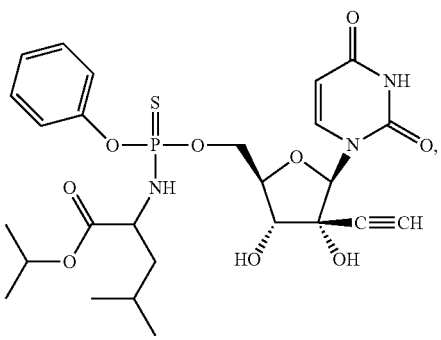

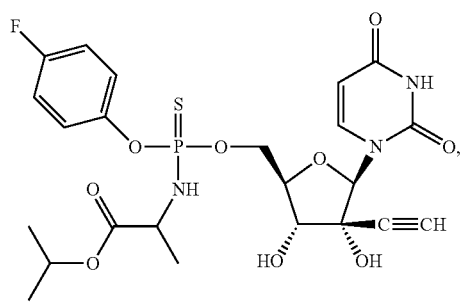
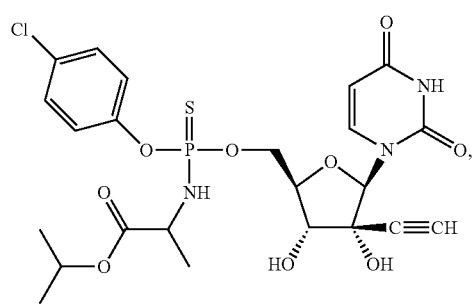
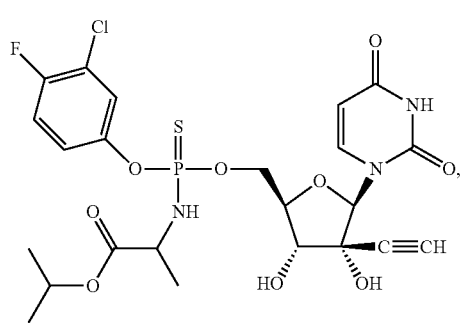
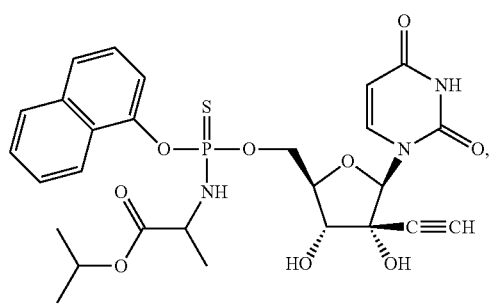
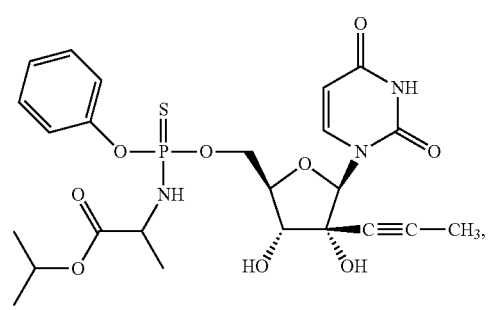
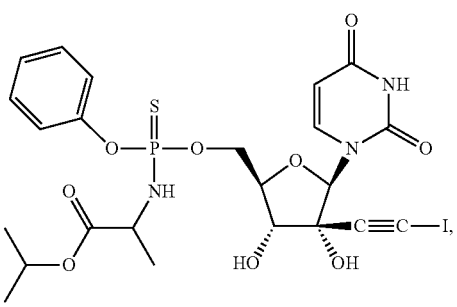
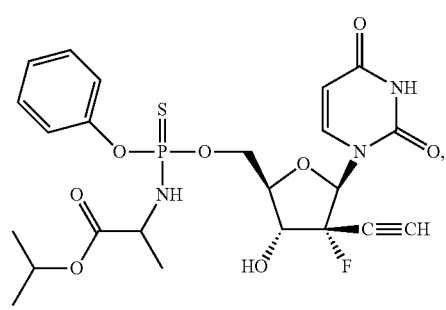
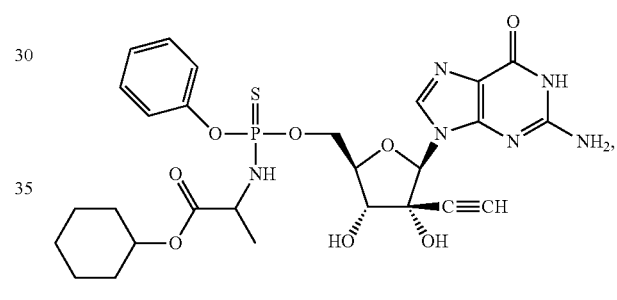
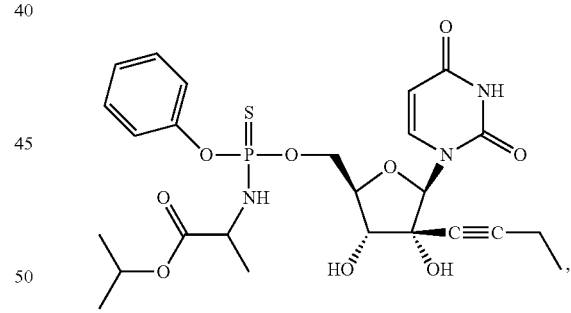
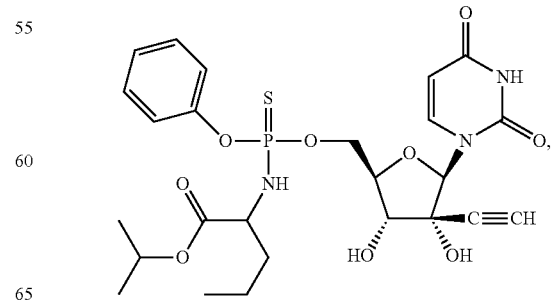

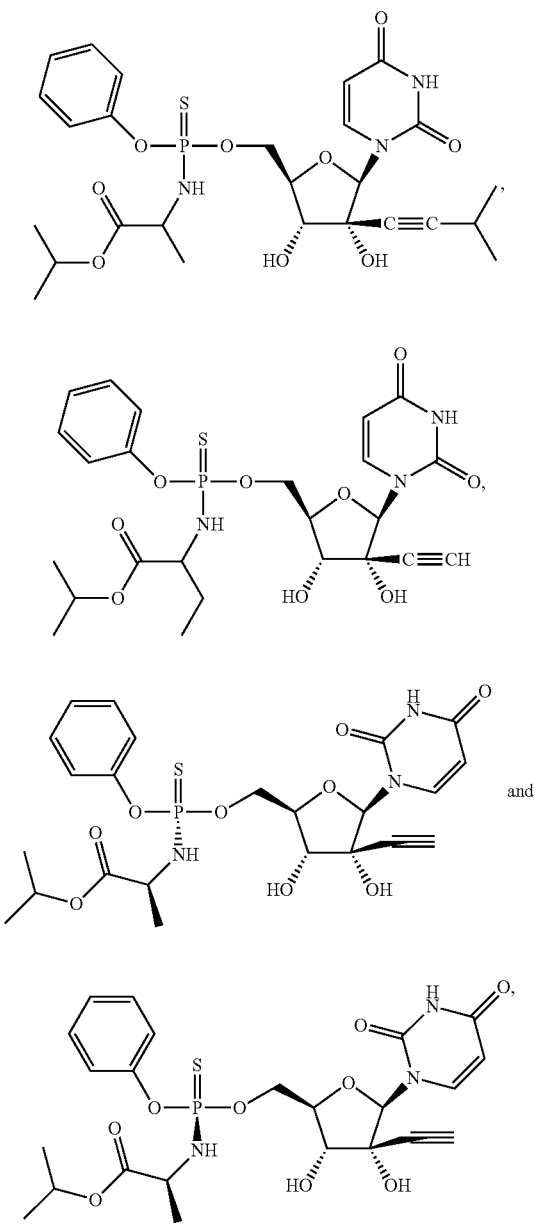

or a pharmaceutically acceptable salt of the foregoing.

20. The compound of claim 1, wherein the compound of Formula (I) is selected from:

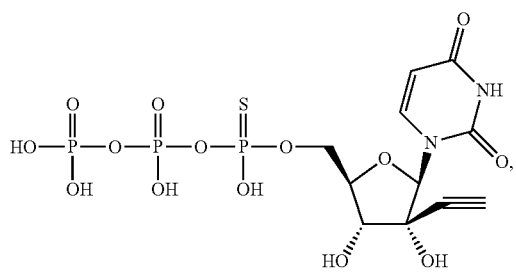

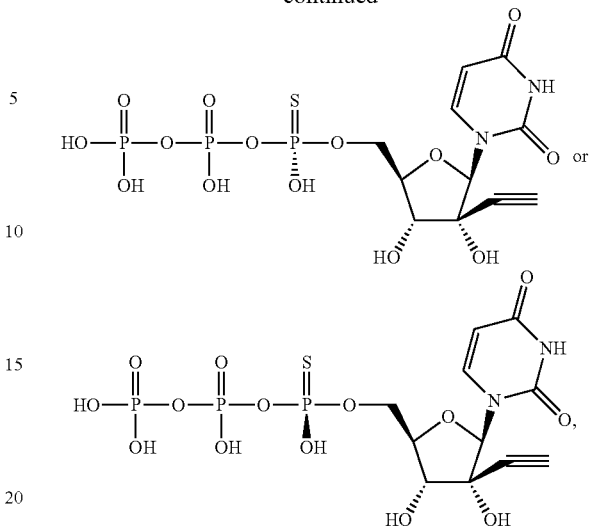

or a pharmaceutically acceptable salt of the foregoing.

21. A pharmaceutical composition comprising a therapeutically effective amount of a compound of claim 1, or a pharmaceutically acceptable salt thereof, and a pharmaceutically acceptable carrier, diluent, excipient or combination thereof.

22. A method for ameliorating or treating an HCV infection comprising administering to a subject suffering from an HCV infection a therapeutically effective amount of a compound of claim 1, or a pharmaceutically acceptable salt thereof.

23. A method of ameliorating or treating a HCV infection comprising contacting a cell infected with the HCV virus with a therapeutically effective amount of a compound of claim 1, in combination with a second anti-HCV agent selected from the group consisting of an interferon, ribavirin, a HCV protease inhibitor, a HCV polymerase inhibitor, a NS5A inhibitor, Debio-025 and a compound of Formula (CC), or a pharmaceutically acceptable salt of any of the aforementioned compounds, wherein the compound of Formula (CC), or a pharmaceutically acceptable salt thereof, has the following structure:

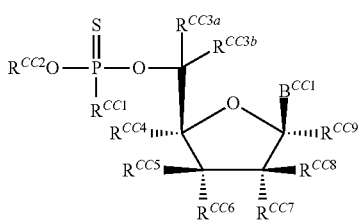

Formula (CC)

wherein:
$B^{CC1}$ is an optionally substituted heterocyclic base or an optionally substituted heterocyclic base with a protected amino group;
$R^{CC1}$ is selected from $O^-$, OH, an optionally substituted N-linked amino acid and an optionally substituted N-linked amino acid ester derivative;
$R^{CC2}$ is selected from an optionally substituted aryl, an optionally substituted heteroaryl, an optionally substituted heterocyclyl and

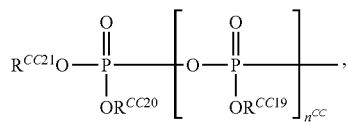

wherein $R^{CC19}$, $R^{CC20}$ and $R^{CC21}$ are independently absent or hydrogen, and $n^{CC}$ is 0 or 1; provided that when $R^{CC1}$ is O⁻ or OH, then $R^{CC2}$ is

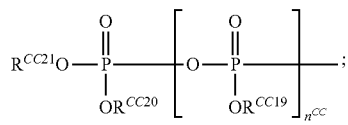

$R^{CC3a}$ and $R^{CC3b}$ are independently selected from hydrogen, deuterium, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{CC3a}$ and $R^{CC3b}$ are taken together to form an optionally substituted $C_{3-6}$ cycloalkyl;

$R^{CC4}$ is selected from hydrogen, azido, an optionally substituted $C_{1-6}$ alkyl, an optionally substituted $C_{2-6}$ alkenyl and an optionally substituted $C_{2-6}$ alkynyl;

$R^{CC5}$ is selected from hydrogen, halogen, azido, cyano, an optionally substituted $C_{1-6}$ alkyl, —OR$^{CC10}$ and —OC(=O)R$^{CC11}$;

$R^{CC6}$ is selected from hydrogen, halogen, azido, cyano, an optionally substituted $C_{1-6}$ alkyl, —OR$^{CC12}$ and —OC(=O)R$^{CC13}$;

$R^{CC7}$ is selected from hydrogen, halogen, azido, cyano, an optionally substituted $C_{1-6}$ alkyl, —OR$^{CC14}$ and —OC(=O)R$^{CC15}$; or $R^{CC6}$ and $R^{CC7}$ are both oxygen atoms and linked together by a carbonyl group;

$R^{CC8}$ is selected from hydrogen, halogen, azido, cyano, an optionally substituted $C_{1-6}$alkyl, —OR$^{CC16}$ and —OC(=O)R$^{CC17}$;

$R^{CC9}$ is selected from hydrogen, azido, cyano, an optionally substituted $C_{1-6}$ alkyl and —OR$^{CC18}$;

$R^{CC10}$, $R^{CC12}$, $R^{CC14}$, $R^{CC16}$ and $R^{CC18}$ are independently selected from hydrogen and an optionally substituted $C_{1-6}$alkyl; and $R^{CC11}$, $R^{CC13}$, $R^{CC15}$ and $R^{CC17}$ are independently selected from an optionally substituted $C_{1-6}$ alkyl and an optionally substituted $C_{3-6}$ cycloalkyl.

24. The method of claim 23, wherein the second anti-HCV agent is selected from the group consisting of pegylated interferon-alpha-2a, pegylated interferon-alpha-2b, interferon alfacon-1, pegylated interferon lambda,

1001

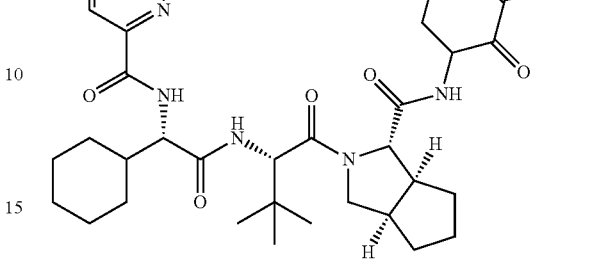

1002

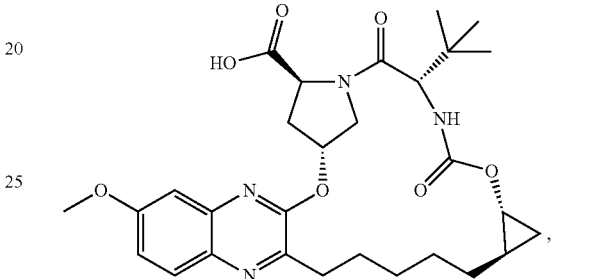

1004

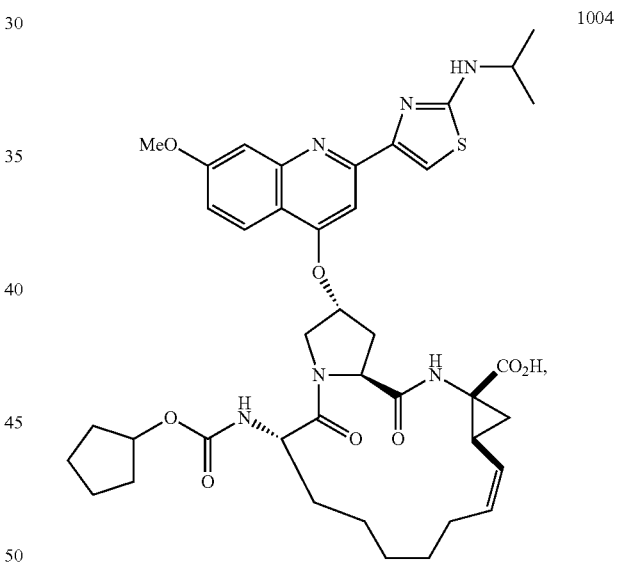

1005

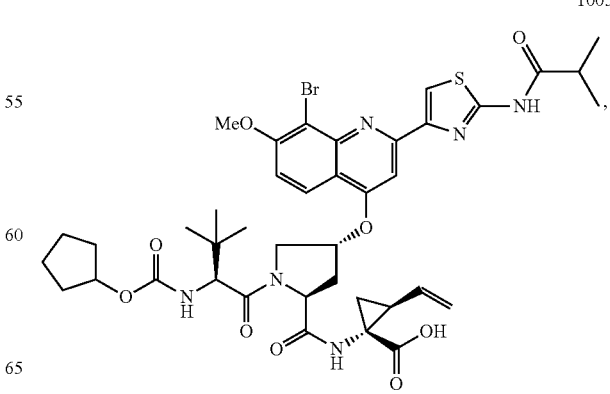

121
-continued
1006
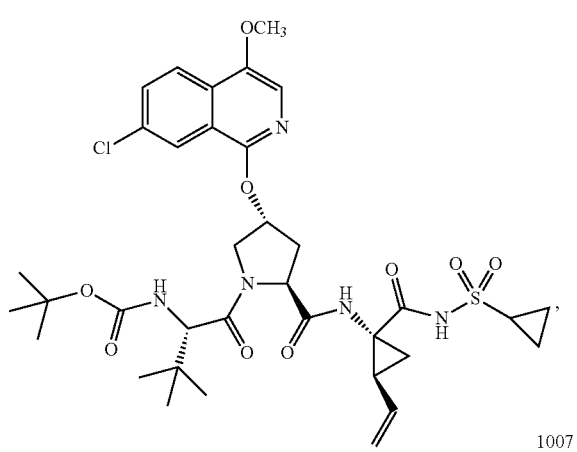
1007
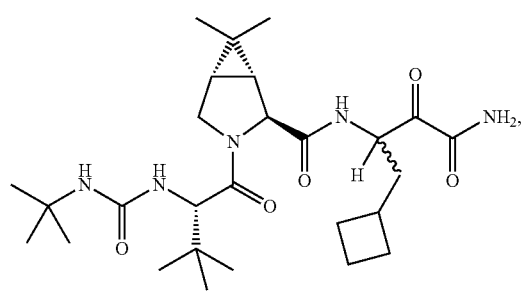
1013
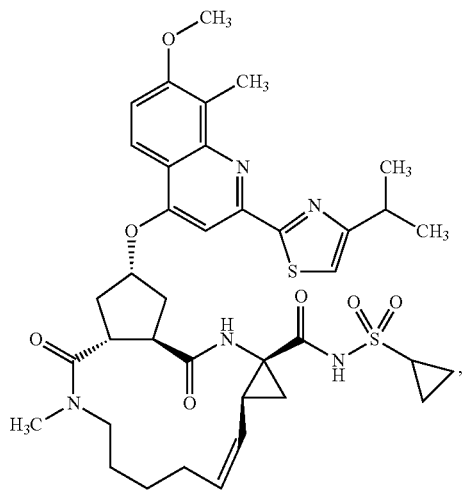
1014
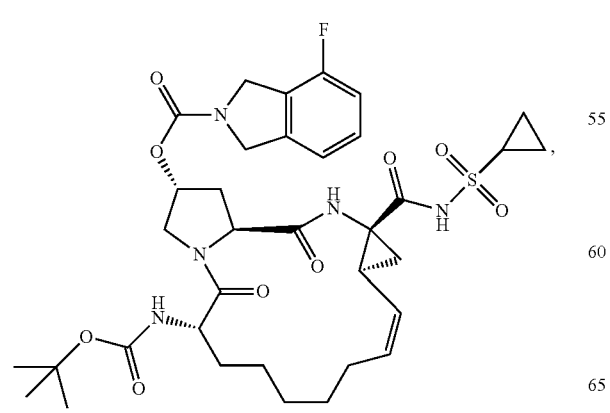
122
-continued
1015
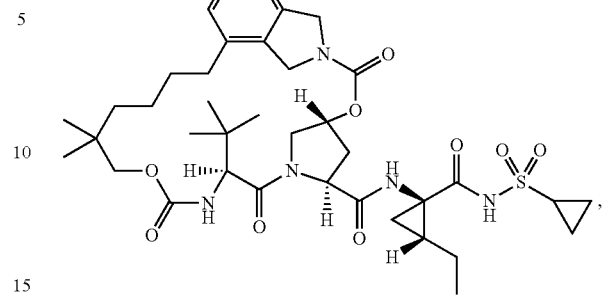
2001
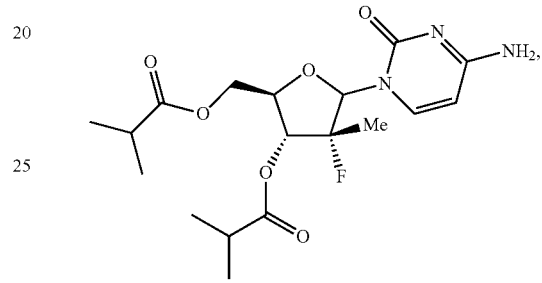
2002
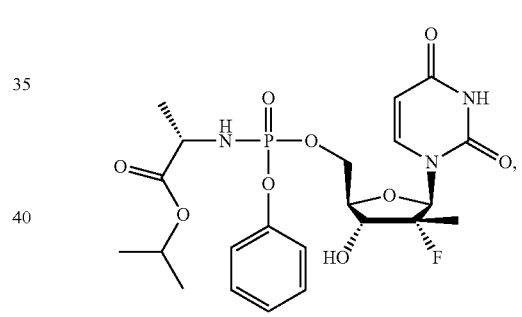
2003
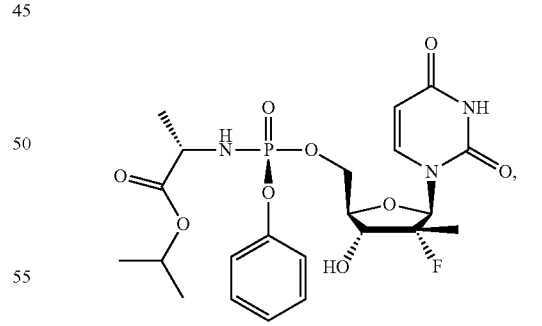
2004
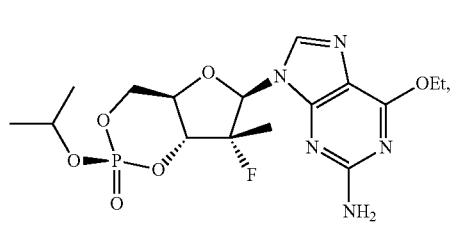

123
-continued
2005
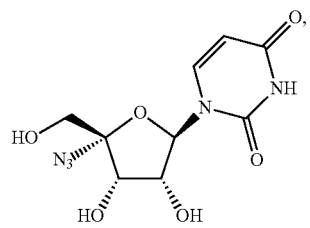
2009
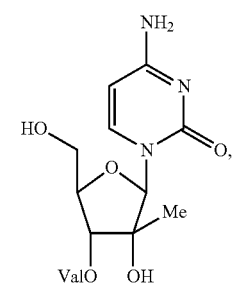
3002
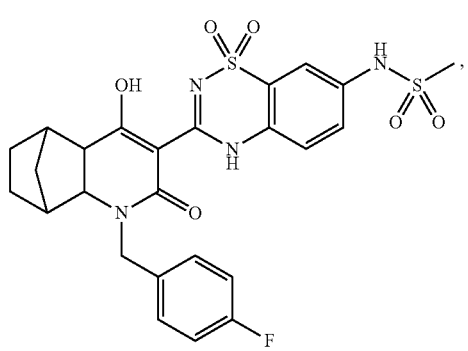
3003
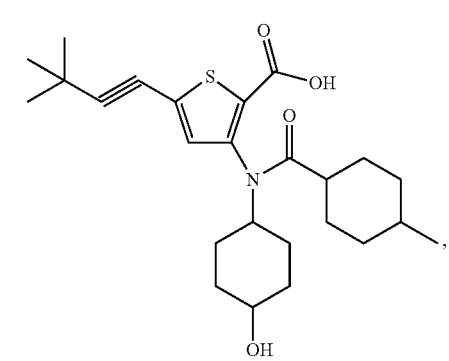
3004
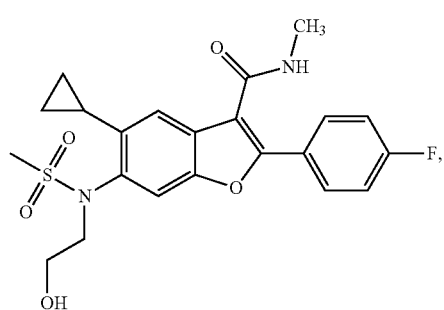
124
-continued
3006
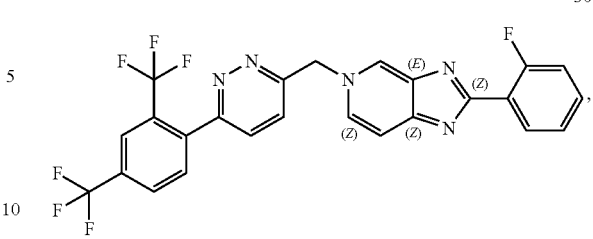
3007
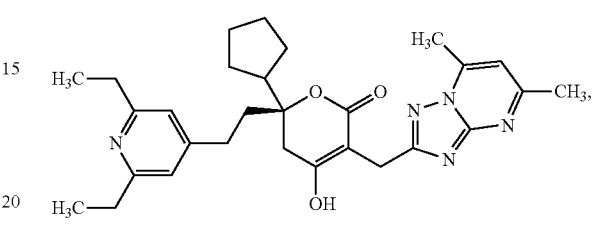
3008
4001
5008
5010
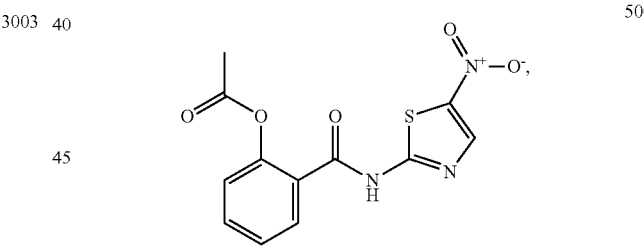
6001
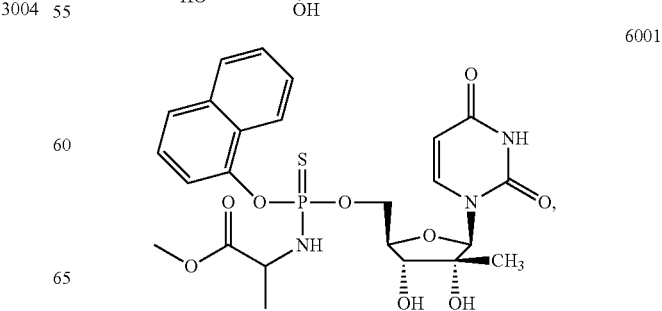

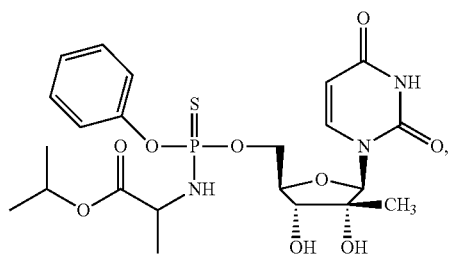
6002
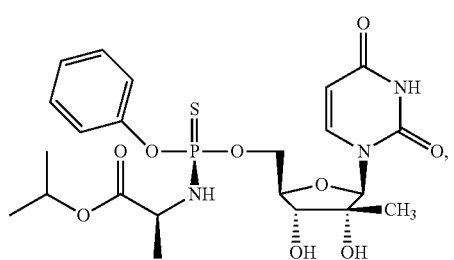
6003
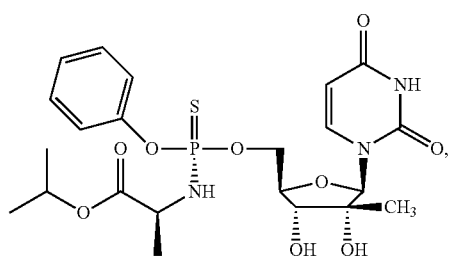
6004
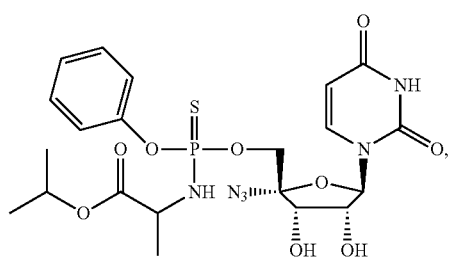
6005
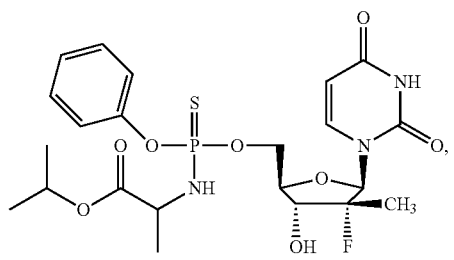
6006
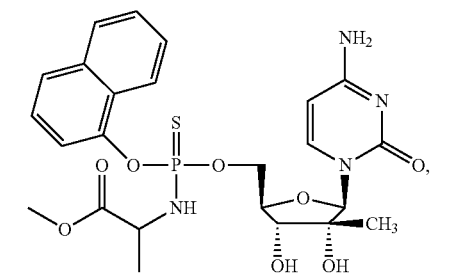
6007
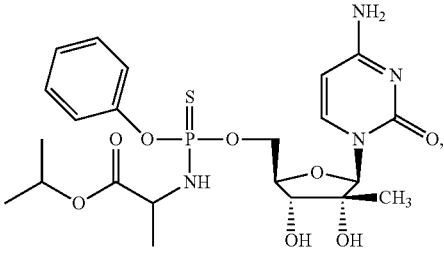
6008
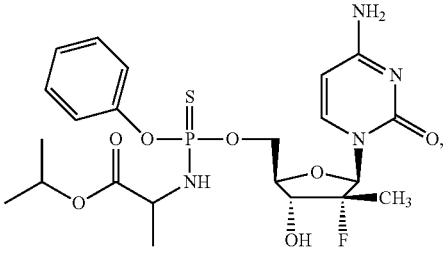
6009
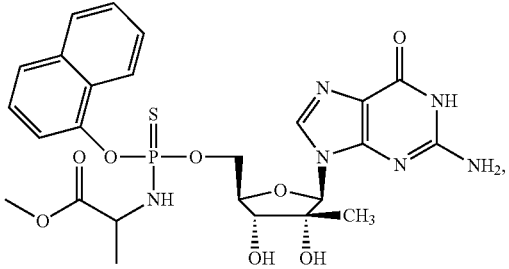
6010
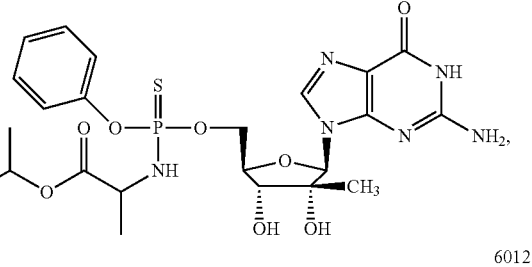
6011
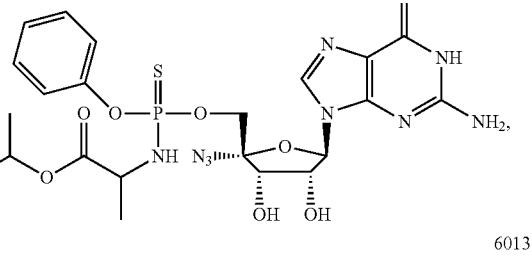
6012
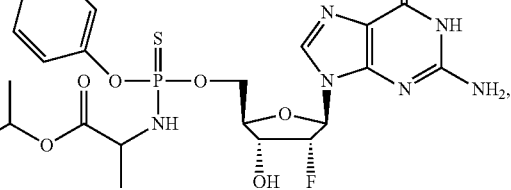
6013

127
-continued
6014
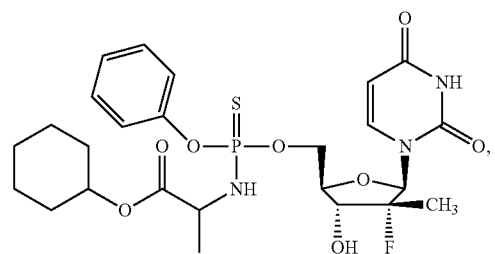
6015
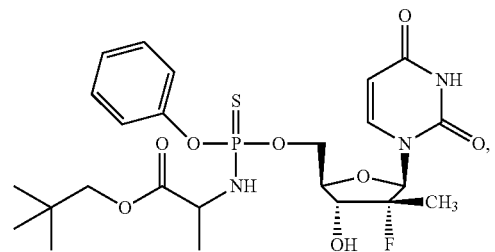
6016
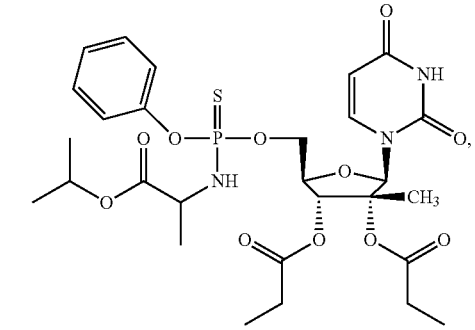
6017
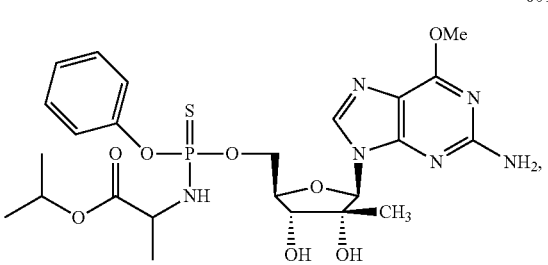
6018
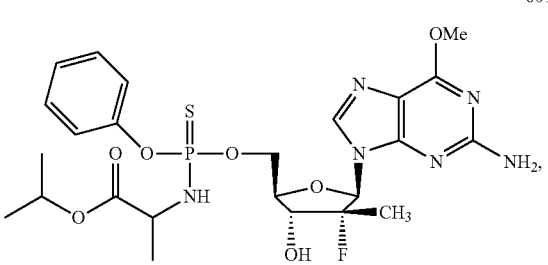
6019
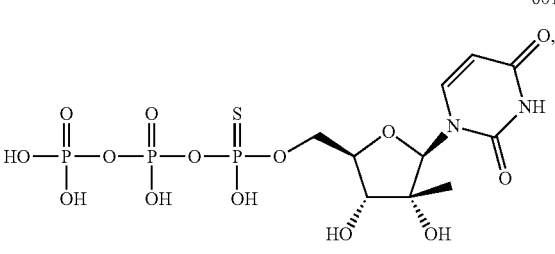
128
-continued
6020
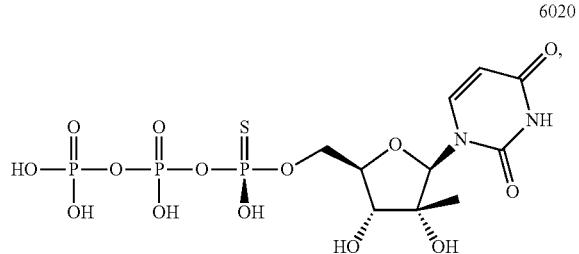
6021
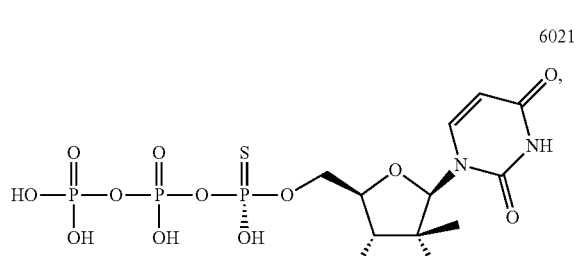
6022
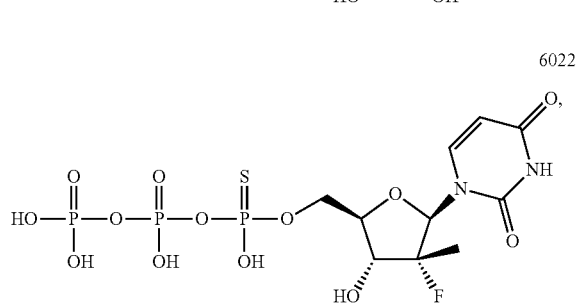
6023
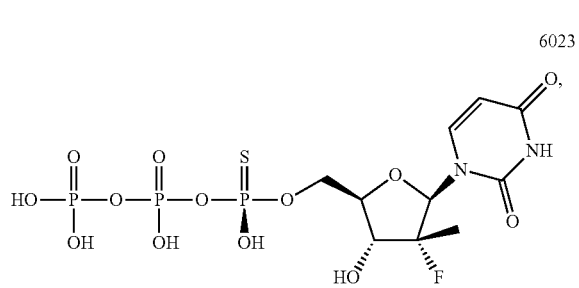
6024
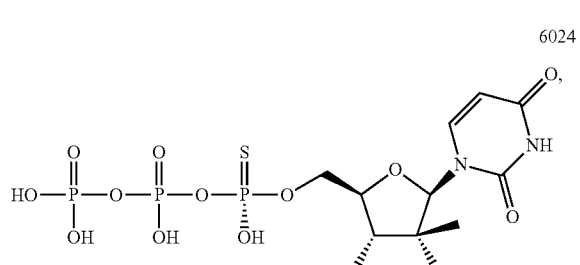
6025
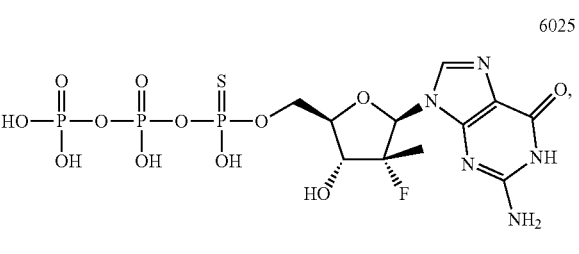

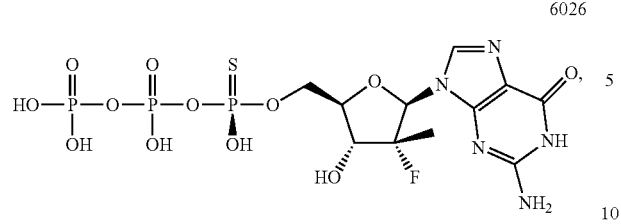
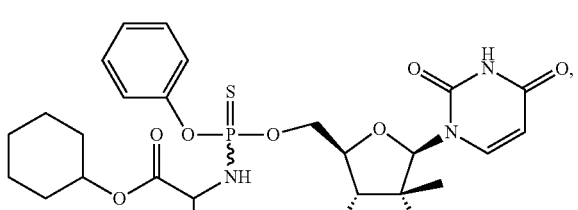
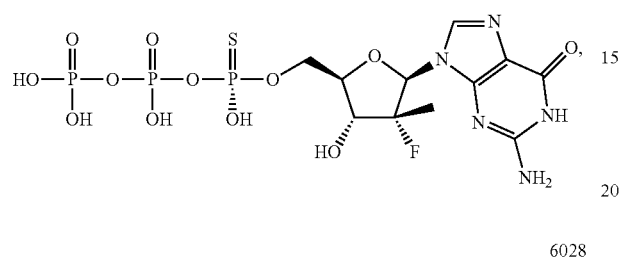
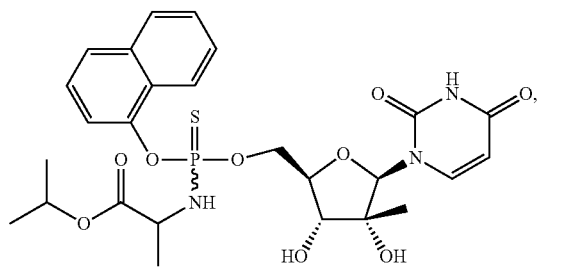
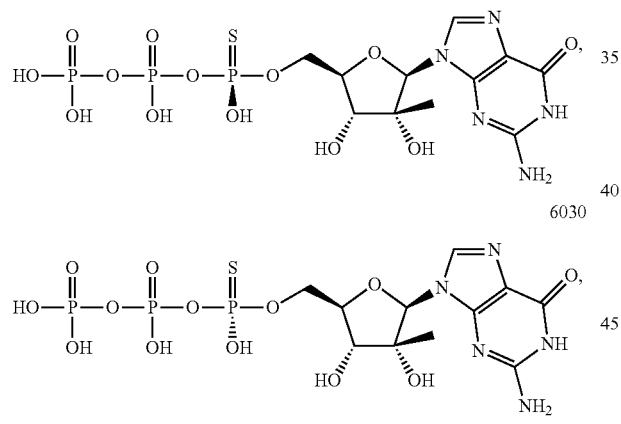
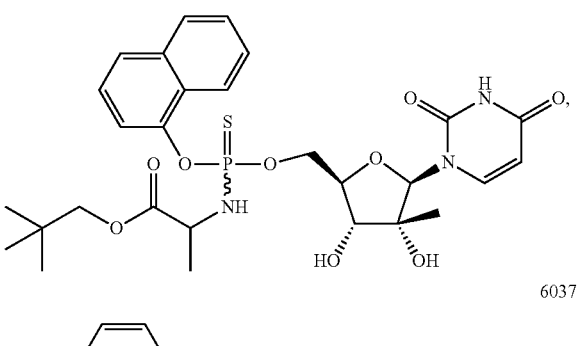
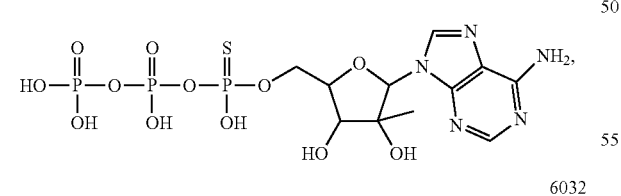
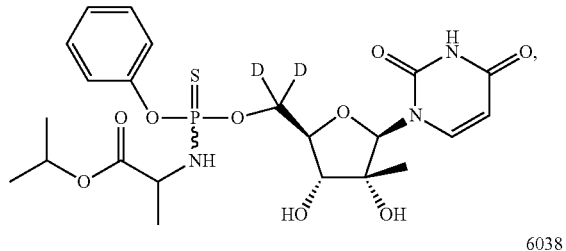
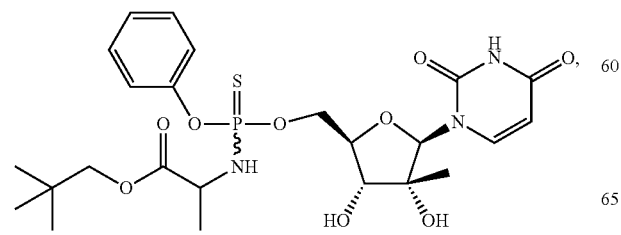
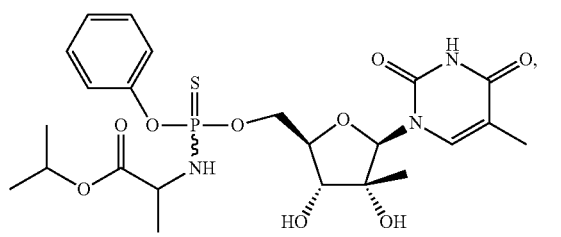

6039
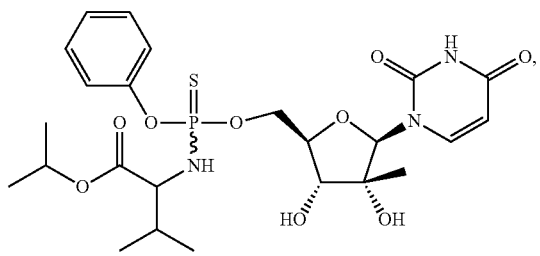
6040
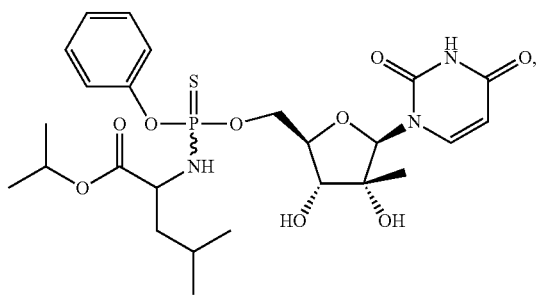
6041
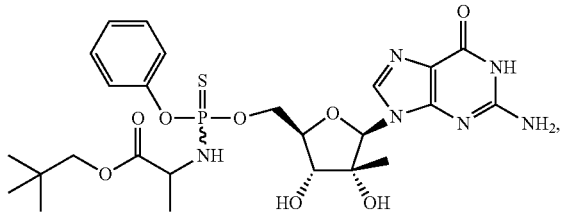
6042
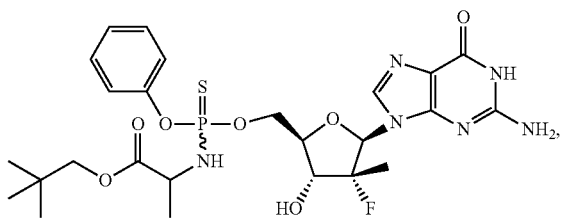
6043
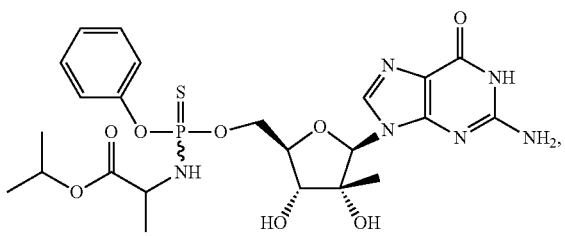
6044
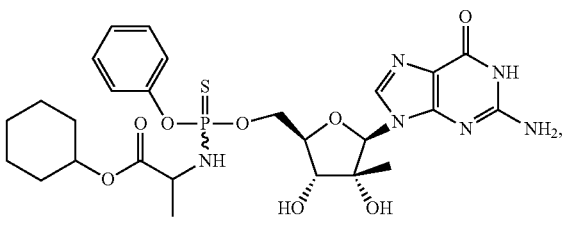
6045
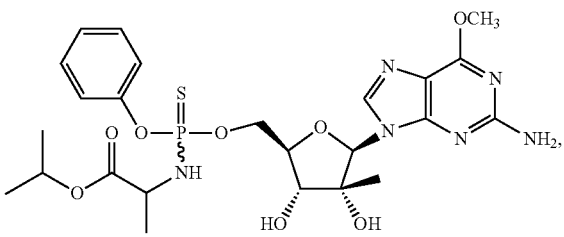
6046
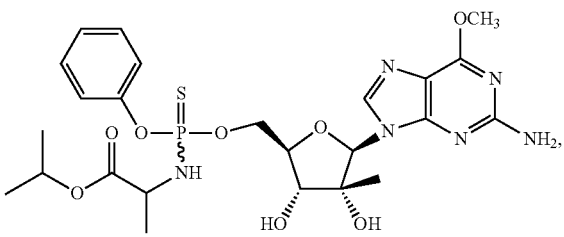
6047
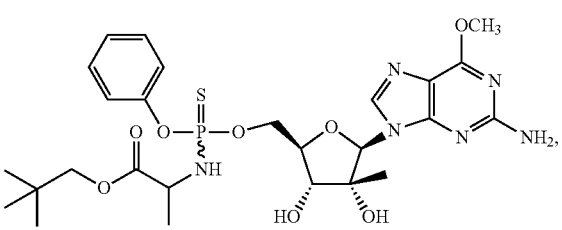
6048
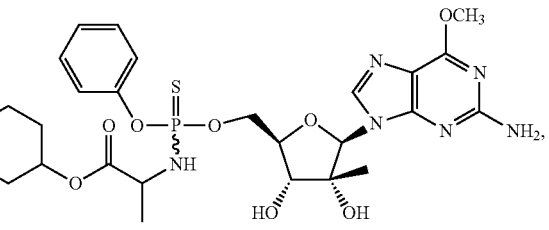
6049
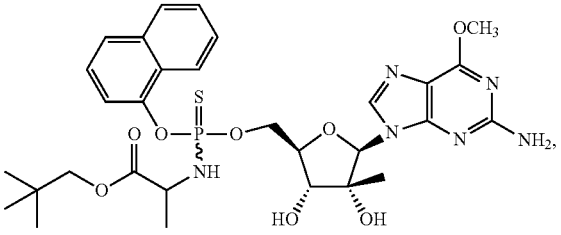
6050
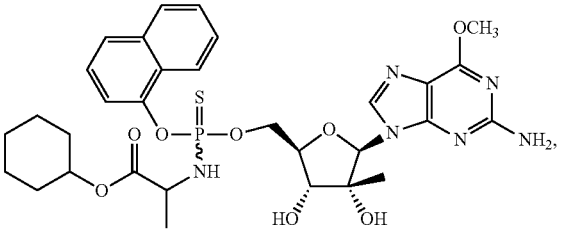

-continued
6051
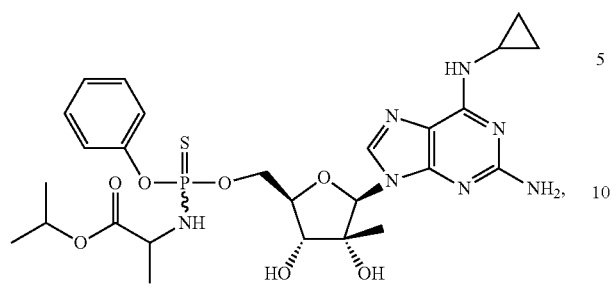
6052
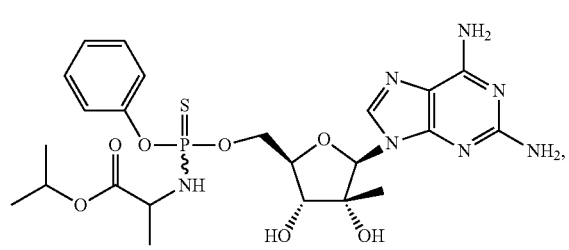
6053
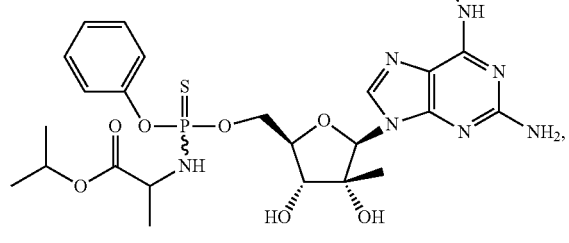
6054
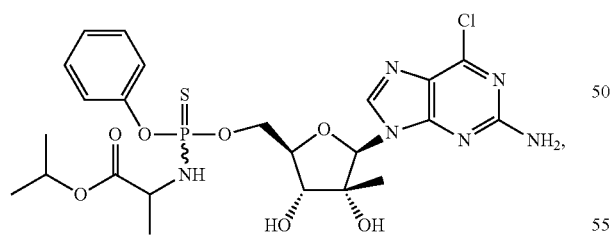
6055
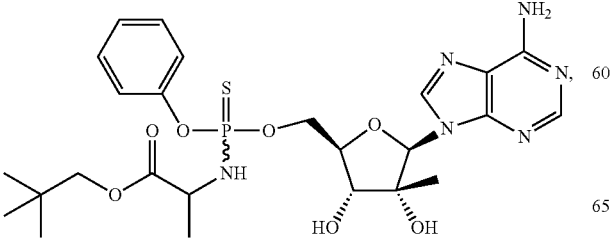
-continued
6056
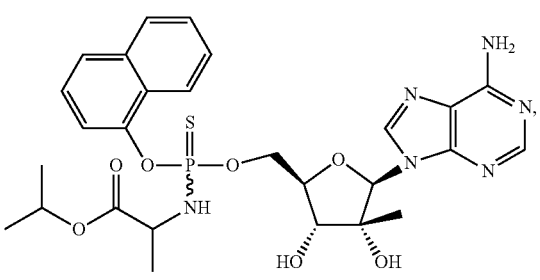
6057
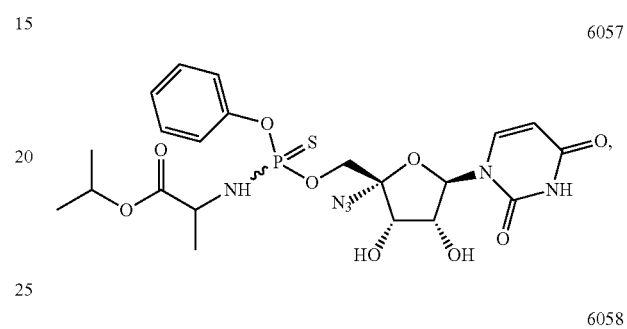
6058
6059
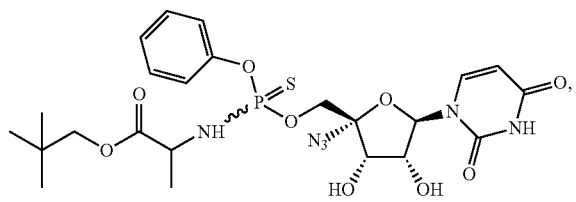
6060
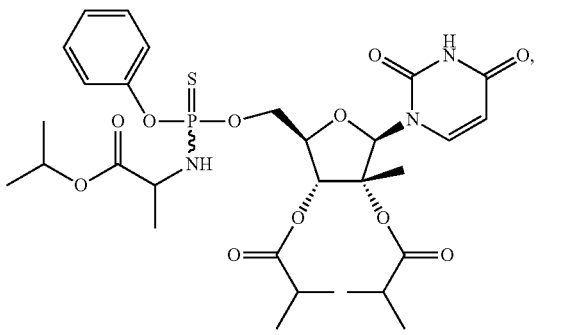

6061
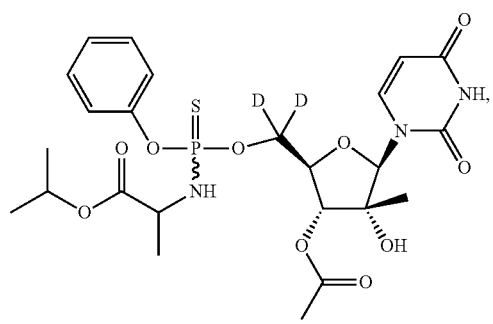
6062
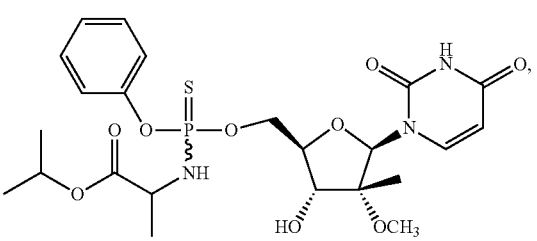
6063
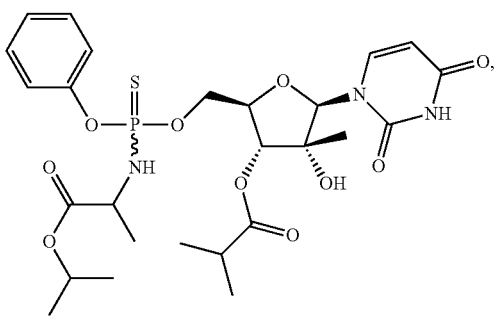
6064
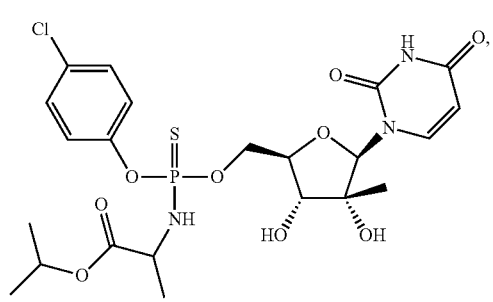
6065
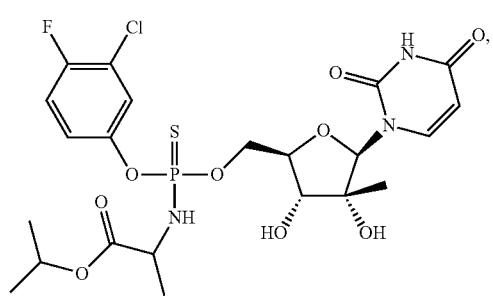
6066
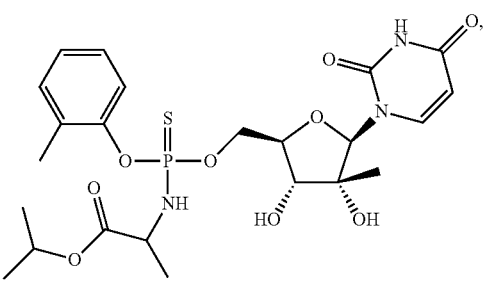
6067
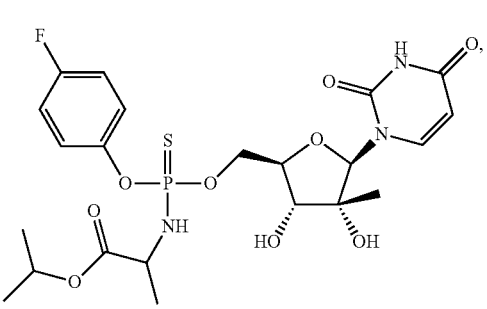
6068
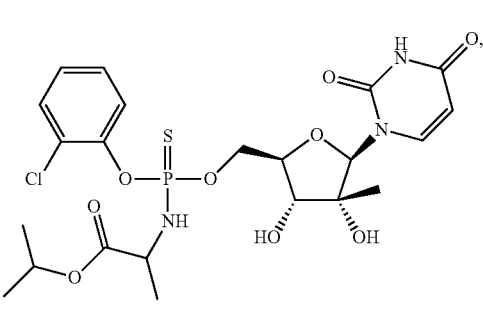
6069
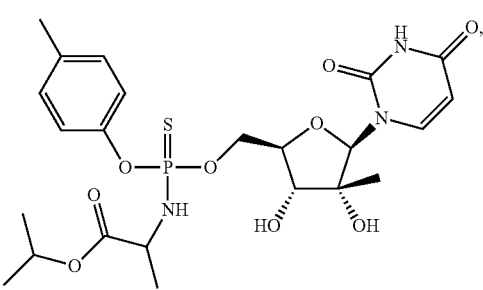
6070
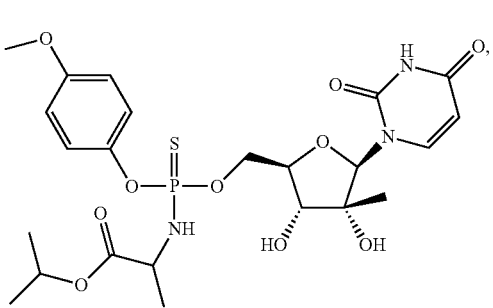

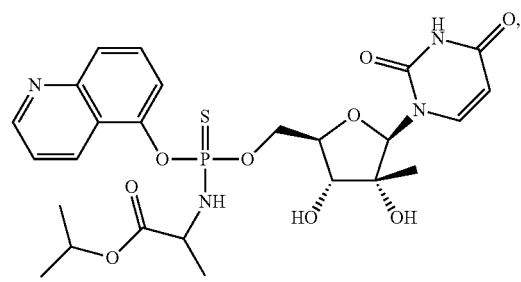
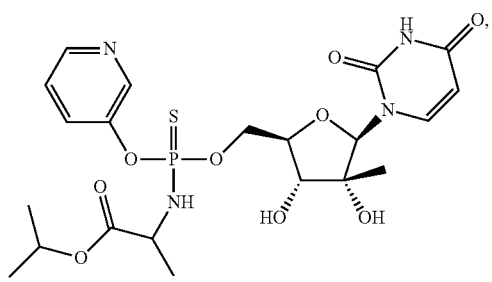
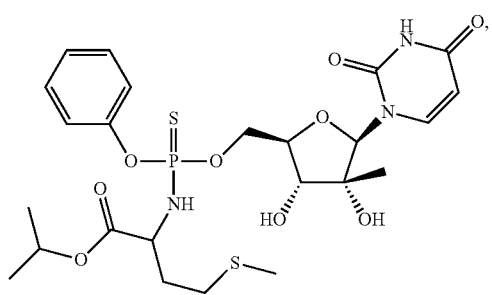
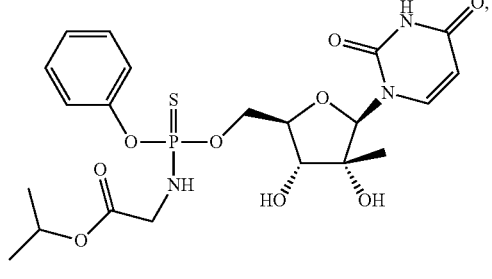
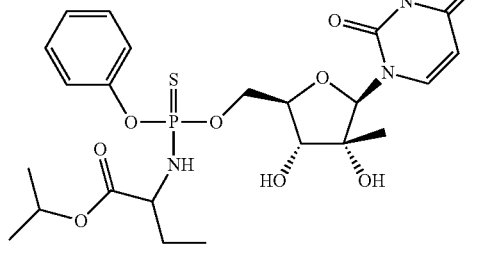
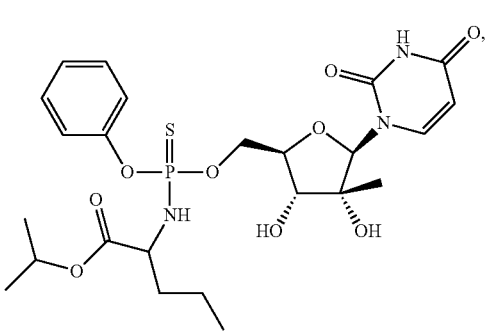
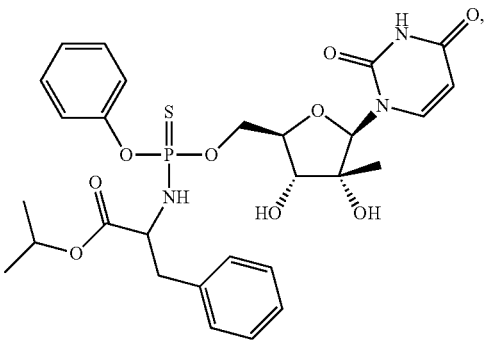
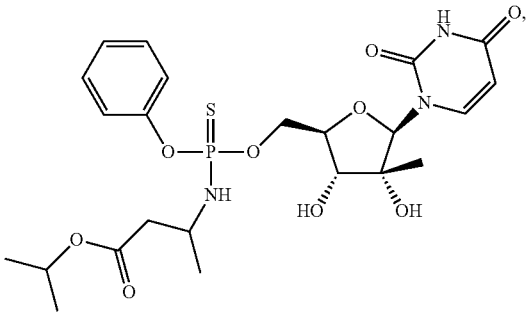
or a pharmaceutically acceptable salt of any of the aforementioned compounds.
* * * * *